United States Patent
Fujiwara et al.

(10) Patent No.: US 11,762,287 B2
(45) Date of Patent: Sep. 19, 2023

(54) ONIUM SALT COMPOUND, CHEMICALLY AMPLIFIED RESIST COMPOSITION AND PATTERNING PROCESS

(71) Applicant: Shin-Etsu Chemical Co., Ltd., Tokyo (JP)

(72) Inventors: Takayuki Fujiwara, Joetsu (JP); Kenichi Oikawa, Joetsu (JP); Tomohiro Kobayashi, Joetsu (JP); Masahiro Fukushima, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 210 days.

(21) Appl. No.: 17/087,807

(22) Filed: Nov. 3, 2020

(65) Prior Publication Data
US 2021/0149301 A1   May 20, 2021

(30) Foreign Application Priority Data
Nov. 20, 2019 (JP) .................. 2019-209432

(51) Int. Cl.
| | | |
|---|---|---|
| *G03F 7/004* | (2006.01) | |
| *G03F 7/038* | (2006.01) | |
| *G03F 7/039* | (2006.01) | |
| *C07C 69/92* | (2006.01) | |
| *C07C 381/12* | (2006.01) | |
| *C07D 333/76* | (2006.01) | |
| *C07C 25/18* | (2006.01) | |
| *C07C 69/96* | (2006.01) | |
| *C08F 220/28* | (2006.01) | |
| *C08F 220/18* | (2006.01) | |
| *C08F 212/14* | (2006.01) | |

(52) U.S. Cl.
CPC ............ *G03F 7/0045* (2013.01); *C07C 25/18* (2013.01); *C07C 69/92* (2013.01); *C07C 69/96* (2013.01); *C07C 381/12* (2013.01); *C07D 333/76* (2013.01); *C08F 212/24* (2020.02); *C08F 220/1809* (2020.02); *C08F 220/283* (2020.02); *G03F 7/0382* (2013.01); *G03F 7/0392* (2013.01); *G03F 7/0397* (2013.01); *C07C 2601/08* (2017.05); *C07C 2601/14* (2017.05); *C07C 2603/74* (2017.05)

(58) Field of Classification Search
CPC ..... G03F 7/0045; C07C 69/612; C07C 69/62; C07C 69/63; C07C 69/635; C07C 69/76; C07C 69/92
See application file for complete search history.

(56) References Cited

U.S. PATENT DOCUMENTS

| | | | |
|---|---|---|---|
| 9,221,742 B2 | 12/2015 | Ohashi et al. | |
| 10,248,020 B2 | 4/2019 | Thackeray et al. | |
| 2015/0253664 A1* | 9/2015 | Domon | G03F 7/0045 430/326 |
| 2015/0268556 A1* | 9/2015 | Domon | G03F 7/30 430/296 |
| 2017/0184964 A1* | 6/2017 | Hatakeyama | G03F 7/168 |
| 2022/0091508 A1* | 3/2022 | Nishikori | G03F 7/0045 |

FOREIGN PATENT DOCUMENTS

| | | |
|---|---|---|
| JP | 2014-142620 A | 8/2014 |
| JP | 5904180 B2 | 4/2016 |
| JP | 2018-135326 A | 8/2018 |

* cited by examiner

*Primary Examiner* — Amanda C. Walke
*Assistant Examiner* — Anna Malloy
(74) *Attorney, Agent, or Firm* — WHDA, LLP

(57) ABSTRACT

An onium salt having formula (1) serving as an acid diffusion inhibitor and a chemically amplified resist composition comprising the acid diffusion inhibitor are provided. When processed by lithography, the resist composition exhibits dissolution contrast, acid diffusion suppressing effect, and excellent lithography performance factors such as CDU, LWR and sensitivity.

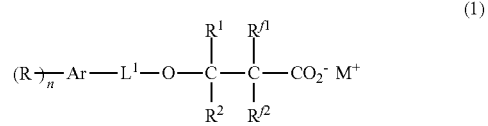

19 Claims, No Drawings

ONIUM SALT COMPOUND, CHEMICALLY AMPLIFIED RESIST COMPOSITION AND PATTERNING PROCESS

CROSS-REFERENCE TO RELATED APPLICATION

This non-provisional application claims priority under 35 U.S.C. § 119(a) on Patent Application No. 2019-209432 filed in Japan on Nov. 20, 2019, the entire contents of which are hereby incorporated by reference.

TECHNICAL FIELD

This invention relates to an onium salt compound, a chemically amplified resist composition, and a pattern forming process.

BACKGROUND ART

To meet the demand for higher integration and operating speeds in LSIs, further miniaturization of the pattern rule is desired. The requirement to form resist patterns of high resolution necessitates not only to improve lithography properties as typified by pattern profile, contrast, mask error factor (MEF), depth of focus (DOF), critical dimension uniformity (CDU), and line width roughness (LWR), but also to minimize defects on the resist pattern after development.

One means for improving lithography performance is the modification or structural optimization of acid diffusion inhibitors, specifically onium salts of weak acids such as sulfonium salts of weak acids for suppressing the diffusion of generated acid and adjusting their solvent solubility. Also an attempt is made to improve contrast by endowing additive components other than the base polymer with a function to change solubility in a developer under the action of an acid. It is expected that the contrast is improved by introducing tertiary ester groups or acetal groups into the additive components, for example, photoacid generator and acid diffusion inhibitor components. For example, Patent Document 1 describes a photoacid generator having an acid labile group in the sulfonium cation. Patent Document 2 discloses an acid diffusion inhibitor having an acetal group as the acid labile group in the anion. When acid labile groups are introduced into the additive components as described above, not only a contrast improvement due to a polarity switch is achieved, but also the acid diffusion is controlled by polar groups which result from elimination of acid labile groups. Thus improvements in various lithography factors are expectable.

As the acid diffusion inhibitor featuring minimal defects and improved LWR, Patent Document 3 discloses an onium salt of the following formula.

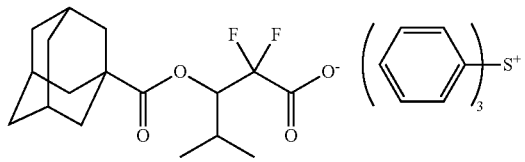

When this onium salt is used as an acid diffusion inhibitor, there are obtained no results satisfying various lithography factors and defectiveness for the current generation where ultrafine processing using ArF or EUV lithography is required.

CITATION LIST

Patent Document 1: JP-A 2014-142620 (U.S. Pat. No. 10,248,020)
Patent Document 2: JP-A 2018-135326
Patent Document 3: JP 5904180 (U.S. Pat. No. 9,221,742)

DISCLOSURE OF INVENTION

While resist patterns of high resolution are recently required, resist compositions comprising conventional acid diffusion inhibitors do not always meet lithography performance factors such as sensitivity, CDU, and LWR and defectiveness in resist patterns as developed. Although the resist compositions using compounds structured to undergo a polarity switch under the action of acid as the photoacid generator or acid diffusion inhibitor are effective for improving LWR and CDU, the results of other lithography factors are still unsatisfactory.

An object of the invention is to provide a chemically amplified resist composition which when processed by lithography using high-energy radiation such as KrF or ArF excimer laser, EB or EUV, is improved in dissolution contrast, acid diffusion suppression, and lithography performance factors such as sensitivity, CDU, and LWR. Another object is to provide an acid diffusion inhibitor used in the resist composition and a pattern forming process using the resist composition.

The inventors have found that a chemically amplified resist composition comprising an onium salt compound having an anion containing a specific acid labile group in its partial structure as an acid diffusion inhibitor exhibits improved lithography performance factors such as sensitivity, CDU, and LWR, forms a pattern with minimal defects after development, and is suited for high accuracy micropatterning.

In one aspect, the invention provides an onium salt compound having the formula (1).

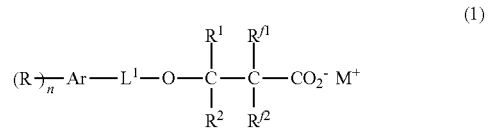

Herein $R^1$ and $R^2$ are each independently hydrogen or a $C_1$-$C_{10}$ hydrocarbyl group which may contain a heteroatom, $R^1$ and $R^2$ may bond together to form a ring with the carbon atom to which they are attached. $R^{f1}$ and $R^{f2}$ are each independently hydrogen, fluorine or trifluoromethyl, at least one thereof being fluorine or trifluoromethyl. $L^1$ is a single bond or carbonyl group. Ar is a (n+1)-valent $C_3$-$C_{15}$ aromatic group which may have a substituent, n is an integer of 1 to 5. $M^+$ is an ammonium, sulfonium or iodonium cation. R is a group having the following formula (R-1), (R-2), (R-3), (R-4) or (R-5).

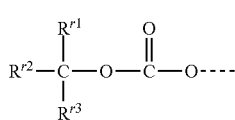
(R-2)

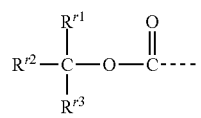
(R-3)

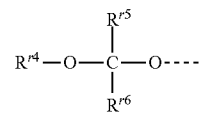
(R-4)

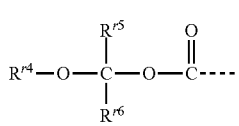
(R-5)

Herein $R^{r1}$, $R^{r2}$, $R^{r3}$ and $R^{r4}$ are each independently a $C_1$-$C_{10}$ hydrocarbyl group, $R^{r1}$ and $R^{r2}$ may bond together to form a ring with the carbon atom to which they are attached; $R^{r5}$ and $R^{r6}$ are each independently hydrogen or a $C_1$-$C_5$ hydrocarbyl group, any two of $R^{r4}$, $R^{r5}$ and $R^{r6}$ may bond together to form a ring with the atom to which they are attached; the broken line designates a valence bond to Ar in formula (1).

Preferably the onium salt compound has the formula (2).

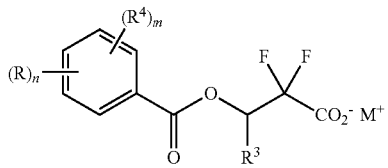
(2)

Herein R and M are as defined above; n is an integer of 1 to 5, m is an integer of 0 to 4, n+m is from 1 to 5; $R^3$ is hydrogen or a $C_1$-$C_{10}$ hydrocarbyl group which may contain a heteroatom; $R^4$ is hydrogen, fluorine, iodine, hydroxyl, or a $C_1$-$C_{10}$ hydrocarbyl group which may contain a heteroatom, a constituent —$CH_2$— in the hydrocarbyl group may be replaced by an ether bond or carbonyl moiety, with the proviso that when m is 2 or more, a plurality of $R^4$ may be the same or different, or two $R^4$ may bond together to form a ring with the carbon atoms to which they are attached.

More preferably, $R^3$ is hydrogen, isopropyl, adamantyl or optionally substituted phenyl.

Also preferably, R is a group having formula (R-1) or (R-2).

In a preferred embodiment, $M^+$ is a cation having any one of the following formulae (M-1) to (M-4).

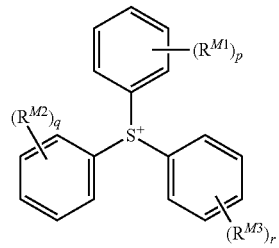
(M-1)

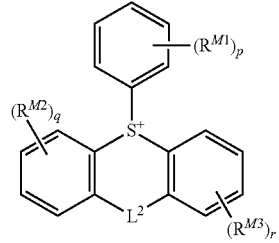
(M-2)

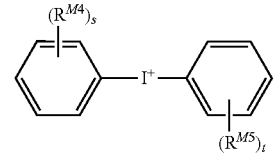
(M-3)

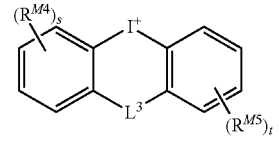
(M-4)

Herein $R^{M1}$, $R^{M2}$, $R^{M3}$, $R^{M4}$, and $R^{M5}$ are each independently hydrogen, halogen, hydroxyl, or a $C_1$-$C_{15}$ hydrocarbyl group which may contain a heteroatom, —$CH_2$— in the hydrocarbyl group may be replaced by an ether bond, carbonyl moiety or sulfonyl moiety. $L^2$ and $L^3$ are each independently a single bond methylene group, ether bond, thioether bond, carbonyl group, sulfinyl group, sulfonyl group or —N($R^N$). N is hydrogen or a $C_1$-$C_{10}$ hydrocarbyl group which may contain a heteroatom, —$CH_2$— in the hydrocarbyl group may be replaced by an ether bond, carbonyl moiety or sulfonyl moiety. The subscripts p, q, r, s and t are each independently an integer of 0 to 5: when p is 2 or more, a plurality of $R^{M1}$ may be the same or different, and two $R^{M1}$ may bond together to form a ring with the carbon atoms on the benzene ring to which they are attached, when q is 2 or more, a plurality of $R^{M1}$ may be the same or different, and two $R^{M2}$ may bond together to form a ring with the carbon atoms on the benzene ring to which they are attached, when r is 2 or more, a plurality of $R^{M2}$ may be the same or different, and two $R^{M3}$ may bond together to form a ring with the carbon atoms on the benzene ring to which they are attached, when s is 2 or more, a plurality of $R^{M4}$ may be the same or different, and two $R^{M4}$ may bond together to form a ring with the carbon atoms on the benzene ring to which they are attached, when t is 2 or more, a plurality of $R^{M5}$ may be the same or different, and two $R^{M5}$ may bond together to form a ring with the carbon atoms on the benzene ring to which they are attached.

Further preferably, the onium salt compound has the following formula (3) or (4).

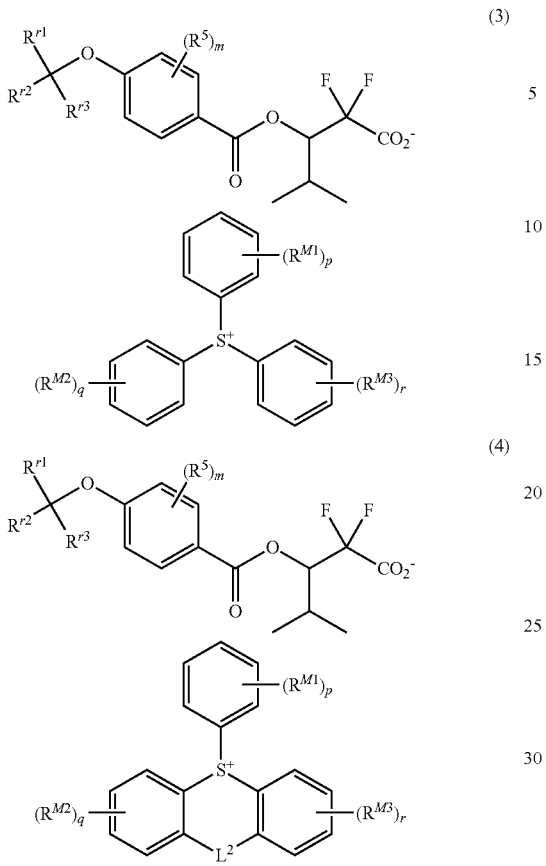

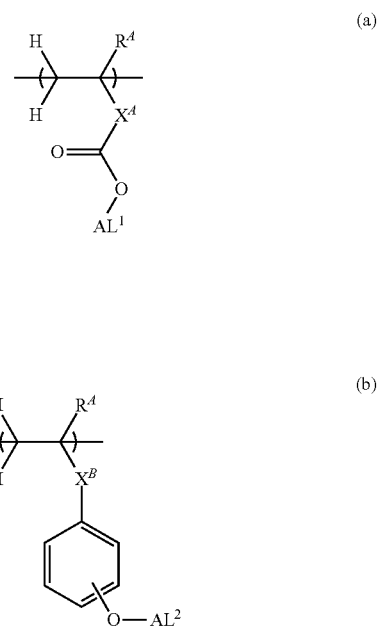

Herein $R^A$ is each independently hydrogen or methyl, $X^A$ is a single bond, phenylene group, naphthylene group or (backbone)-C(=O)—O—$X^{A1}$—, $X^{A1}$ is a $C_1$-$C_{15}$ hydrocarbylene group which may contain a hydroxyl moiety, ether bond, ester bond or lactone ring, $X^B$ is a single bond or ester bond, $AL^1$ and $AL^2$ are each independently an acid labile group.

Preferably, the acid labile group has the formula (L1), (L2) or (L3):

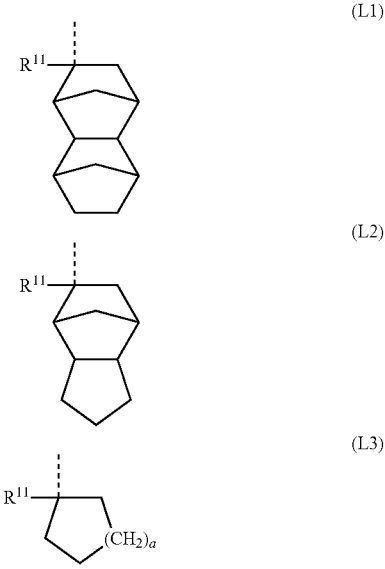

Herein $R^{r1}$, $R^{r2}$, $R^{r3}$, $R^{M1}$, $R^{M2}$, $R^{M3}$, $L^2$, p, q, r, and m are as defined above. $R^5$ is hydrogen, fluorine, hydroxyl, or a $C_1$-$C_5$ hydrocarbyl group in which —$CH_2$— may be replaced by an ether bond or carbonyl moiety, and when m is 2 or more, a plurality of $R^5$ may be the same or different, and two $R^5$ may bond together to form a ring with the carbon atoms to which they are attached.

In another aspect, the invention provides an acid diffusion inhibitor comprising the onium salt compound defined above.

In a further aspect, the invention provides a chemically amplified resist composition comprising (A) a base polymer adapted to change its solubility in a developer under the action of an acid, (B) a photoacid generator, (C) an acid diffusion inhibitor comprising the onium salt compound defined above, and (D) an organic solvent; or a chemically amplified resist composition comprising (A') a base polymer adapted to change its solubility in a developer under the action of an acid, the base polymer comprising recurring units having a function of generating an acid upon exposure to light, (C) an acid diffusion inhibitor comprising the onium salt compound defined above, and (D) an organic solvent.

In a preferred embodiment, the base polymer comprises recurring units having the formula (a) or recurring units having the formula (b).

wherein $R^{11}$ is each independently a $C_1$-$C_7$ hydrocarbyl group in which —$CH_2$— may be replaced by an ether bond, a is 1 or 2, and the broken line designates a valence bond.

S Preferably, the base polymer comprises recurring units having the formula (c):

(c)

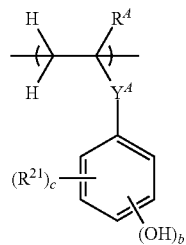

wherein $R^A$ is hydrogen or methyl, $Y^A$ is a single bond or ester bond, $R^{21}$ is fluorine, iodine or a $C_1$-$C_{10}$ hydrocarbyl group in which —$CH_2$— may be replaced by an ether bond or carbonyl moiety, b is an integer of 1 to 5, c is an integer of 0 to 4, and b+c is 1 to S.

Preferably, the recurring units having a function of generating an acid upon exposure to light are units of at least one type selected from the formulae (d1) to (d4).

(d1)

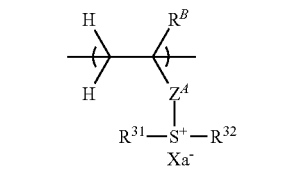

(d2)

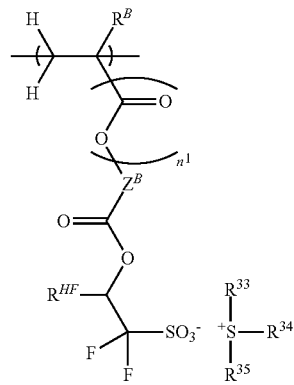

(d3)

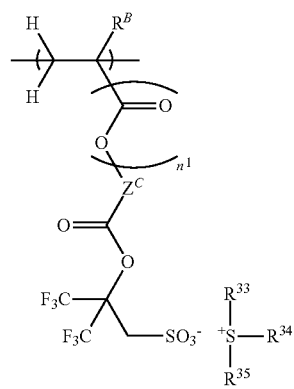

(d4)

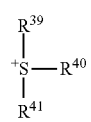

Herein $R^B$ is each independently hydrogen, fluorine, methyl or trifluoromethyl; $Z^A$ is a single bond, phenylene group, —O—$Z^{A1}$—, —C(=O)—O—$Z^{A1}$— or —C(=O)—NH—$Z^{A1}$—, $Z^{A1}$ is a $C_1$-$C_{20}$ hydrocarbylene group which may contain a heteroatom; $Z^B$ and $Z^C$ are each independently a single bond or a $C_1$-$C_{20}$ hydrocarbylene group which may contain a heteroatom; $Z^D$ is a single bond, methylene, ethylene, phenylene, fluorinated phenylene, —O—$Z^{D1}$—, —C(=O)—$Z^{D1}$— or —C(=O)—NH—$Z^{D1}$—, $Z^{D1}$ is an optionally substituted phenylene group; $R^3$ to $R^4$ are each independently a $C_1$-$C_{20}$ hydrocarbyl group which may contain a heteroatom, any two of $Z^A$, $R^{31}$ and $R^{32}$ may bond together to form a ring with the sulfur atom to which they are attached, any two of $R^{33}$, $R^{34}$ and $R^{35}$, any two of $R^{36}$, $R^{37}$ and $R^{38}$, and any two of $R^{39}$, $R^{40}$ and $R^{41}$ may bond together to form a ring with the sulfur atom to which they are attached, $R^{HF}$ is hydrogen or trifluoromethyl; $n^1$ is 0 or 1, $n^1$ is 0 when $Z^B$ is a single bond, $n^2$ is 0 or 1, $n^2$ is 0 when $Z^C$ is a single bond; and Xa⁻ is a non-nucleophilic counter ion.

In a further aspect, the invention provides a pattern forming process comprising the steps of applying the chemically amplified resist composition defined above to form a resist film on a substrate, exposing a selected region of the resist film to KrF excimer laser, ArF excimer laser, EB or EUV, and developing the exposed resist film in a developer.

In one preferred embodiment, the developing step uses an alkaline aqueous solution as the developer, thereby forming a positive pattern in which an exposed region of the resist film is dissolved away and an unexposed region of the resist film is not dissolved.

In another preferred embodiment, the developing step uses an organic solvent as the developer, thereby forming a negative pattern in which an unexposed region of the resist film is dissolved away and an exposed region of the resist film is not dissolved.

The organic solvent is typically at least one solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

Advantageous Effects of Invention

When the inventive chemically amplified resist composition comprising the onium salt compound as an acid diffusion inhibitor is processed by lithography, a resist pattern with minimal defects and exhibiting improved lithography performance factors such as sensitivity, CDU, and LWR can be formed.

DESCRIPTION OF THE PREFERRED EMBODIMENTS

The singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. The terms "group" and "moiety" are interchangeable. In chemical formulae, the broken line denotes a valence bond; Me stands for methyl, tBu for tert-butyl. Ac for acetyl, and Ph for phenyl. It is understood that for some structures represented by chemical formulae, there can exist enantiomers and diastereomers because of the presence of asymmetric carbon atoms. In such a case, a single formula collectively represents all such isomers. The isomers may be used alone or in admixture.

The abbreviations have the following meaning.
EB: electron beam
EUV: extreme ultraviolet
GPC: gel permeation chromatography
Mw: weight average molecular weight
Mw/Mn: molecular weight dispersity
PAG: photoacid generator
PEB: post-exposure bake
LWR: line width roughness
CDU: critical dimension uniformity
Onium Salt The invention provides an onium salt compound having the formula (1).

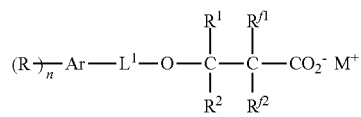
(1)

In formula (1), $R^1$ and $R^2$ are each independently hydrogen or a $C_1$-$C_{10}$ hydrocarbyl group which may contain a heteroatom, $R^1$ and $R^2$ may bond together to form a ring with the carbon atom to which they are attached.

The $C_1$-$C_{10}$ hydrocarbyl group may be saturated or unsaturated and straight, branched or cyclic. Examples include alkyl groups such as methyl, ethyl, propyl, isopropyl, n-butyl, sec-butyl, tert-butyl, n-pentyl, n-hexyl, n-octyl, n-nonyl, and n-decyl; cyclic saturated hydrocarbyl groups such as cyclopentyl, cyclohexyl, and adamantyl; aryl groups such as phenyl; and combinations thereof. In these groups, some hydrogen may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate bond, lactone ring, sultone ring, carboxylic anhydride or haloalkyl moiety. When $R^1$ and $R^2$ bond together to form a ring with the carbon atom to which they are attached, exemplary rings include cyclopentane, cyclohexane and adamantane rings. It is preferred from the aspects of lithography performance and ease of synthesis that one of $R^1$ and $R^2$ be hydrogen. It is believed that when one of $R^1$ and $R^2$ is hydrogen, the space around the carboxylate site becomes sterically empty so that the onium salt compound acts efficiently as an acid diffusion inhibitor.

In formula (1), $R^{f1}$ and $R^{f2}$ are each independently hydrogen, fluorine or trifluoromethyl, at least one thereof being fluorine or trifluoromethyl. Most preferably, both $R^{f1}$ and $R^{f2}$ are fluorine.

In formula (1), $L^1$ is a single bond or carbonyl group, preferably carbonyl group.

In formula (1), Ar is a (n+1)-valent $C_3$-$C_{15}$ aromatic group which may have a substituent. The aromatic group is obtained by removing (n+1) number of hydrogen atoms on aromatic ring from a $C_3$-$C_{15}$ aromatic compound. Examples of the $C_3$-$C_{15}$ aromatic compound include benzene, naphthalene, furan, thiophene, benzothiophene, indole, and oxazole. Of these, groups derived from benzene are preferred from the aspects of solubility, storage stability, and sensitivity. The groups derived from benzene are effective for properly suppressing acid diffusion and maintaining a high sensitivity. The aromatic group may have a substituent(s). Suitable substituents include fluorine, hydroxyl, and $C_1$-$C_{10}$ hydrocarbyl groups in which a constituent —$CH_2$— may be replaced by an ether bond or carbonyl moiety.

In formula (1), n is an integer of 1 to 5, preferably 1 or 2, most preferably 1. When n is 1 or 2, the proportion of R left unreacted after acid elimination reaction is low enough to establish a dissolution contrast efficiently.

In formula (1), R is a group having the following formula (R-1), (R-2), (R-3), (R-4) or (R-5).

(R-1)

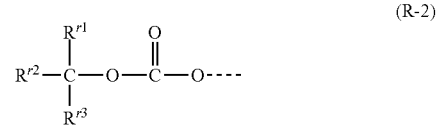
(R-2)

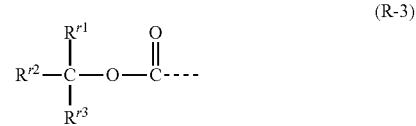
(R-3)

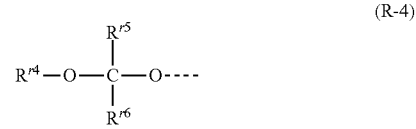
(R-4)

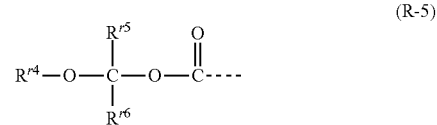
(R-5)

In formulae (R-1) to (R-5), the broken line designates a valence bond to Ar in formula (1). $R^{r1}$, $R^{r2}$, $R^{r3}$ and $R^{r4}$ are each independently a $C_1$-$C_{10}$ hydrocarbyl group. $R^{r1}$ and $R^{r2}$ may bond together to form a ring with the carbon atom to which they are attached. $R^{r5}$ and $R^{r6}$ are each independently hydrogen or a $C_1$-$C_5$ hydrocarbyl group. Any two of $R^{r4}$, $R^{r5}$ and $R^{r6}$ may bond together to form a ring with the atom(s) to which they are attached. Examples of the hydrocarbyl group are as exemplified above for $R^1$ and $R^2$.

Examples of the group having formula (R-1) are given below, but not limited thereto.

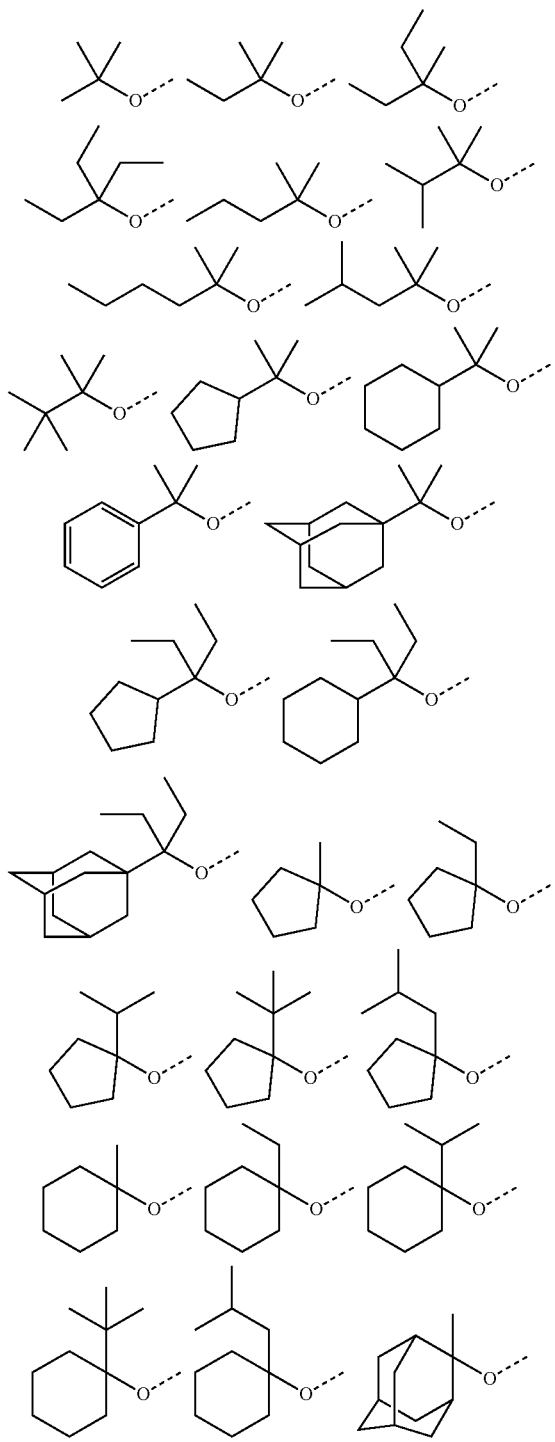

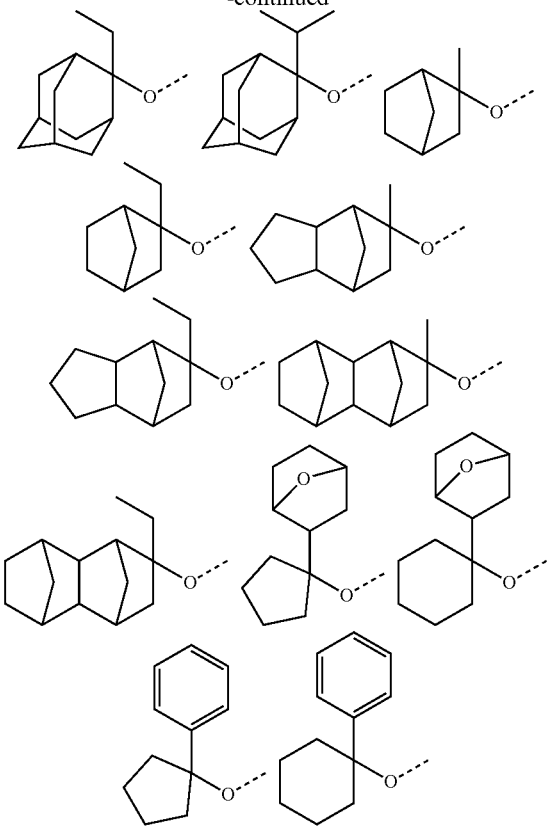

Examples of the group having formula (R-2) are given below, but not limited thereto.

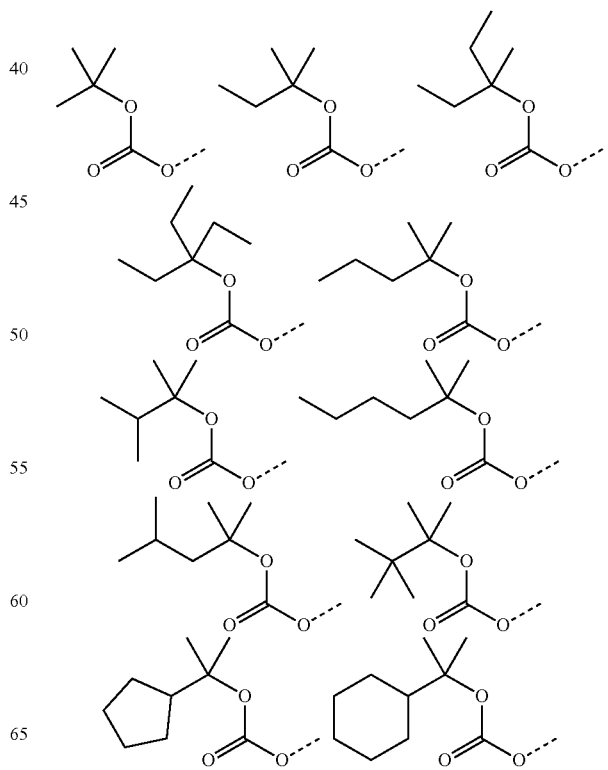

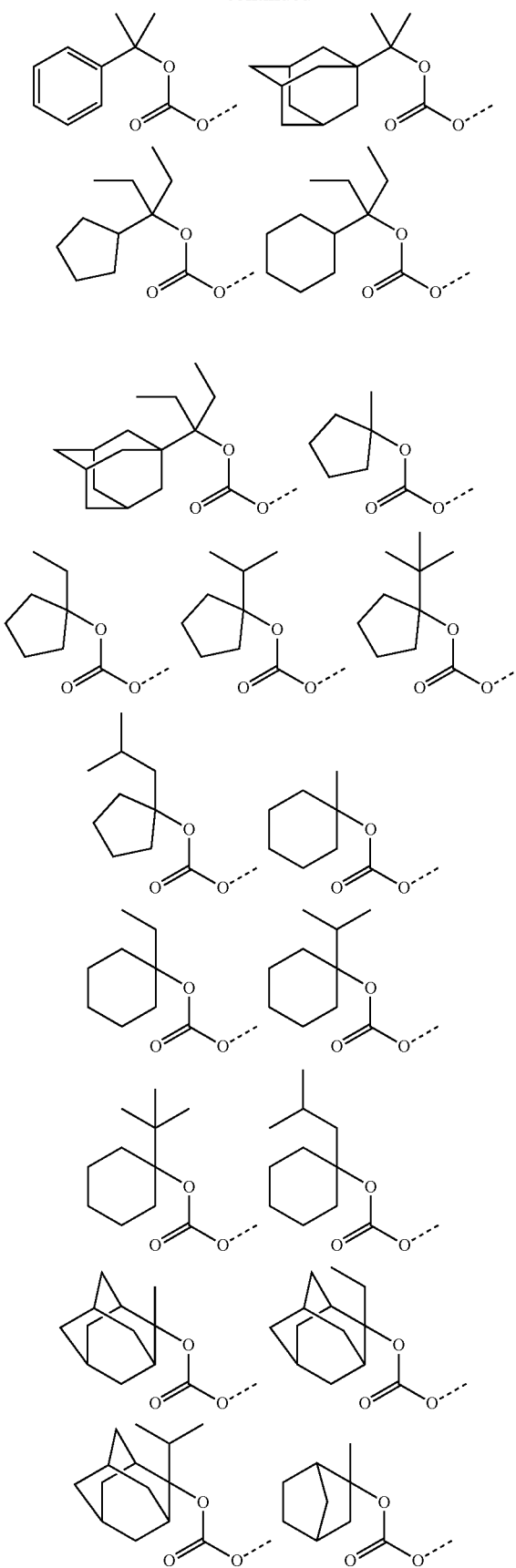
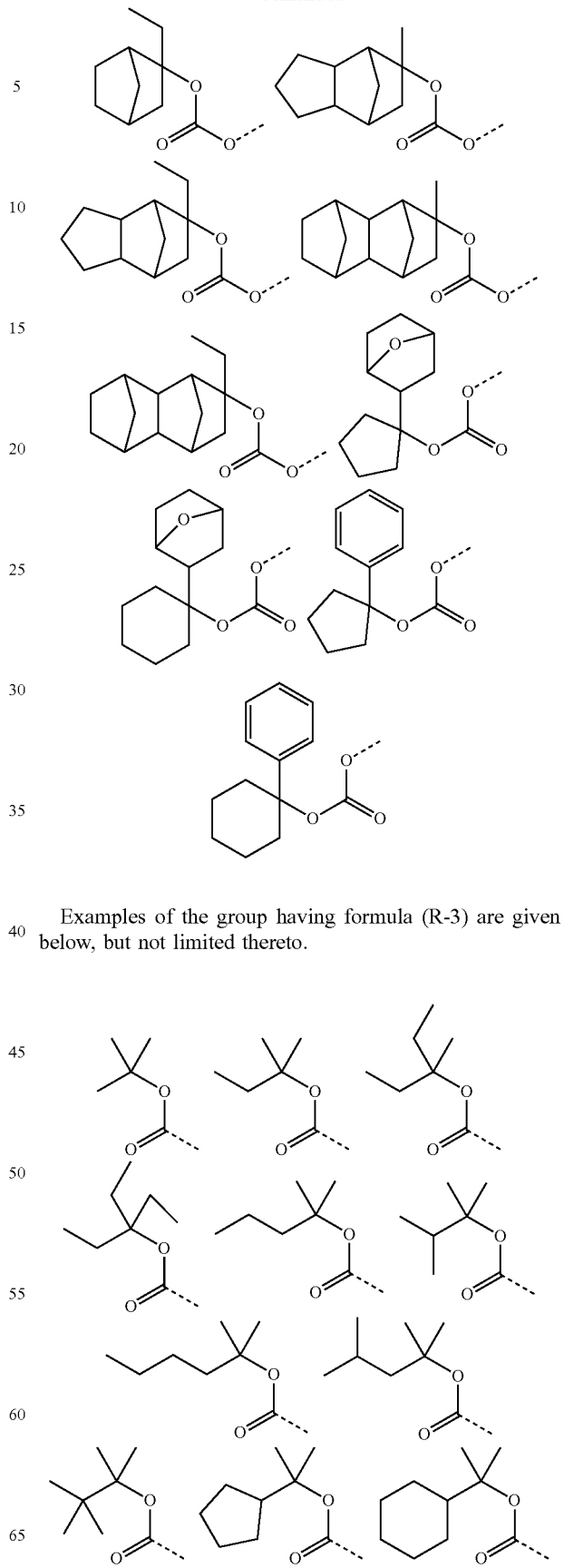
Examples of the group having formula (R-3) are given below, but not limited thereto.

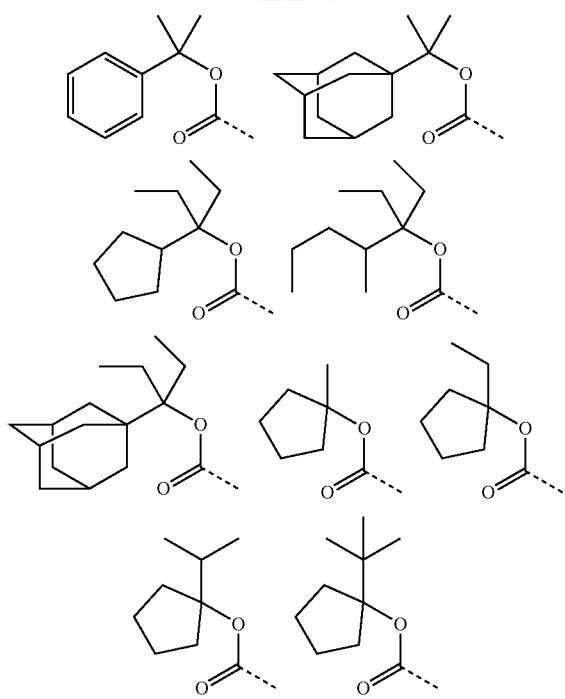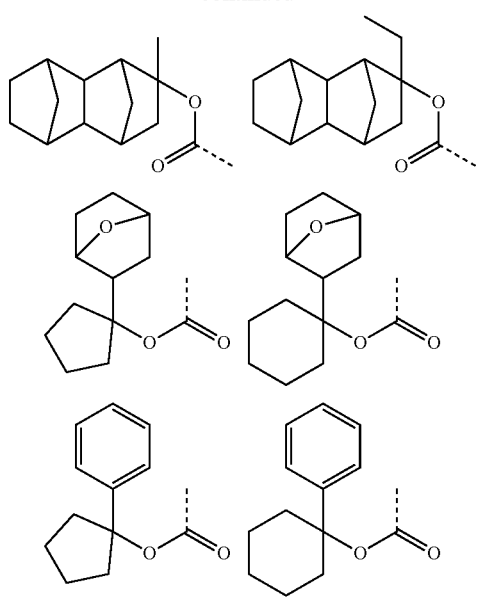
Examples of the group having formula (R-4) are given below, but not limited thereto.
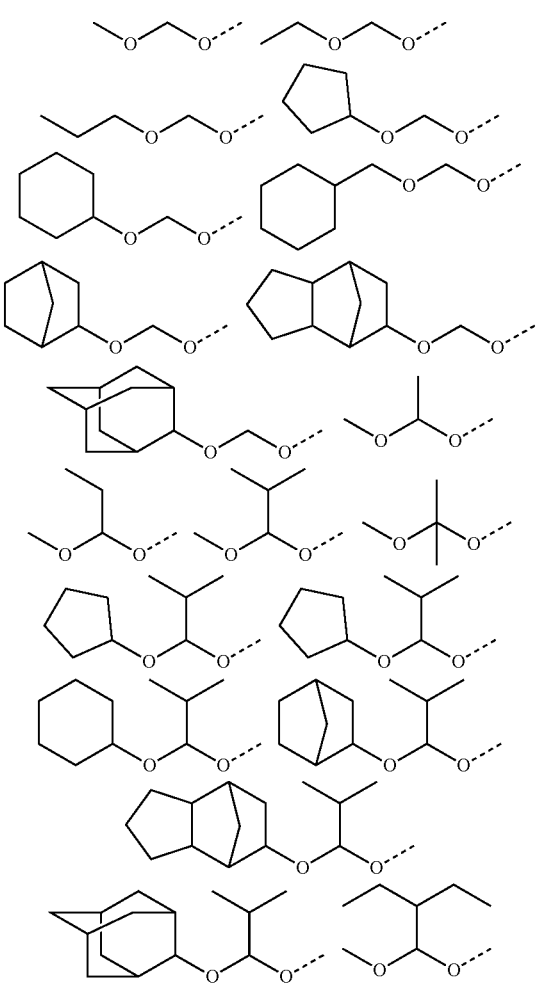

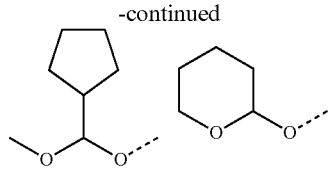

Examples of the group having formula (R-5) are given below, but not limited thereto.

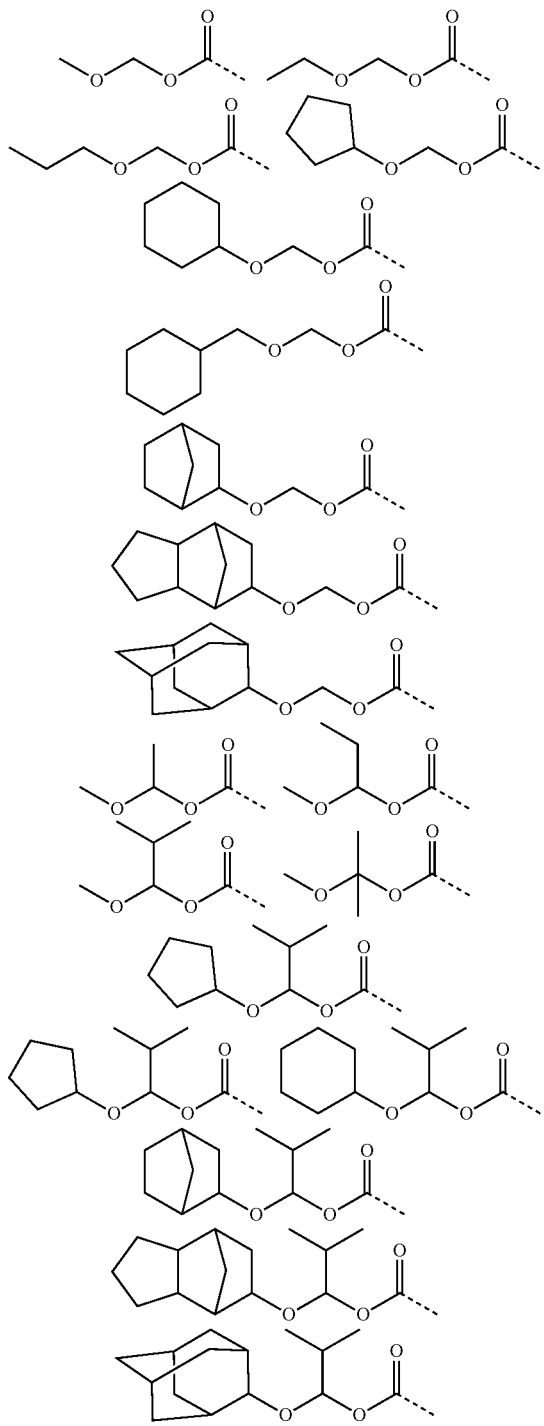

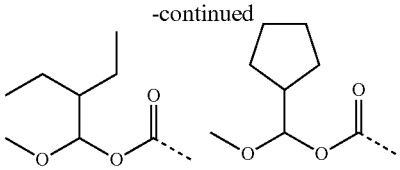

Preferably R is a group having formula (R-1) or (R-2). Since the group of formula (R-1) or (R-2) has an adequate acid eliminating ability, the onium salt compound alone or the resist composition comprising the onium salt compound has a satisfactory long-term storage stability.

More preferably R is selected from groups having the following formulae. Though the mechanism is not well understood, it is presumed that when R is a group of any one of these formulae, the anion has a good balance between lipophilicity and acid eliminating ability, from which improvements in lithography performance factors such as LWR and CDU are expectable.

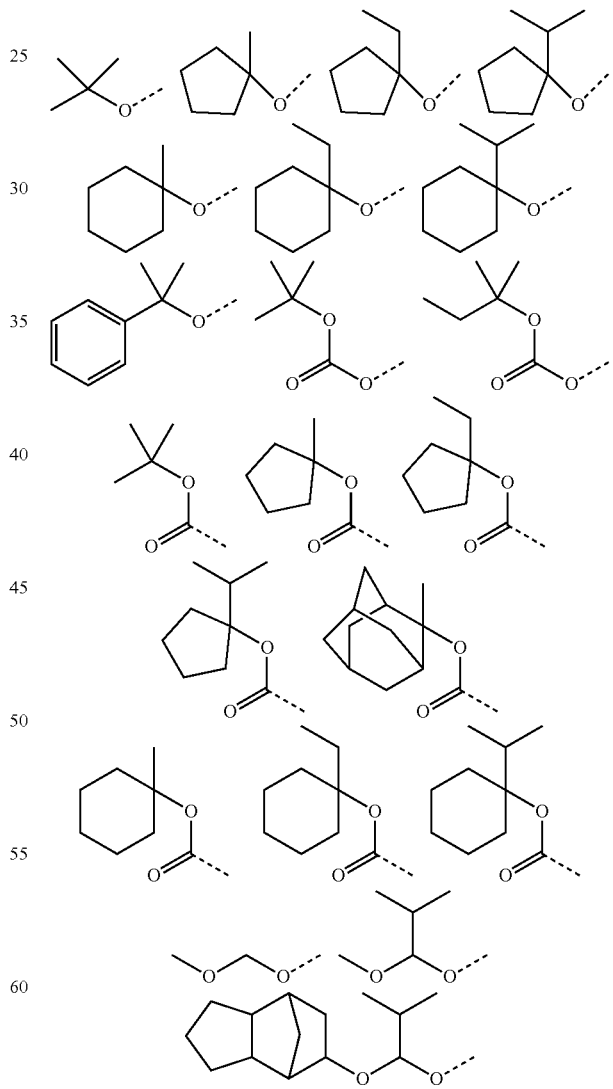

Of the onium salt compounds of formula (1), compounds of the following formula (2) as preferred.

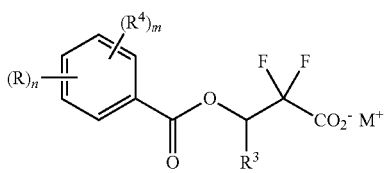

(2)

Herein R and M⁺ are as defined above.

In formula (2), n is an integer of 1 to 5, m is an integer of 0 to 4, and n+m is from 1 to 5; n is preferably 1 or 2, most preferably 1, and m is preferably 0, 1 or 2.

In formula (2), $R^3$ is hydrogen or a $C_1$-$C_{10}$ hydrocarbyl group which may contain a heteroatom. The hydrocarbyl group may be saturated or unsaturated and straight, branched or cyclic. Examples include alkyl groups such as methyl, ethyl, propyl, isopropyl, n-butyl, sec-butyl, tert-butyl, n-pentyl, n-hexyl, n-octyl, n-nonyl, and n-decyl; cyclic saturated hydrocarbyl groups such as cyclopentyl, cyclohexyl, and adamantyl: aryl groups such as phenyl; and combinations thereof. In these groups, some hydrogen may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate bond, lactone ring, sultone ring, carboxylic anhydride or haloalkyl moiety. Preferably $R^3$ is hydrogen, propyl, isopropyl, cyclohexyl, adamantyl, phenyl, 4-fluorophenyl, 4-trifluoromethylphenyl, 4-iodophenyl or 4-methoxyphenyl. More preferably $R^3$ is hydrogen, isopropyl, adamantyl, phenyl or 4-iodophenyl.

In formula (2), $R^4$ is hydrogen, fluorine, iodine, hydroxyl, or a $C_1$-$C_{10}$ hydrocarbyl group which may contain a heteroatom. The hydrocarbyl group may be saturated or unsaturated and straight, branched or cyclic. Examples include alkyl groups such as methyl, ethyl, propyl, isopropyl, n-butyl, sec-butyl, tert-butyl, n-pentyl, n-hexyl, n-octyl, n-nonyl, and n-decyl; cyclic saturated hydrocarbyl groups such as cyclopentyl, cyclohexyl, and adamantyl; aryl groups such as phenyl; and combinations thereof. A constituent —$CH_2$— in the hydrocarbyl group may be replaced by an ether bond or carbonyl moiety. The constituent —$CH_2$— in the hydrocarbyl group may be one bonding to a carbon atom in the benzene ring in formula (2). Examples of the substituted hydrocarbyl group include methoxy, ethoxy, propoxy, butoxy, phenoxy, 2-methoxyethoxy, acetyl, ethylcarbonyl, hexylcarbonyl, acetoxy, ethylcarbonyloxy, propylcarbonyloxy, pentylcarbonyloxy, hexylcarbonyloxy, heptylcarbonyloxy, methoxycarbonyloxy, (2-methoxyethoxy)methylcarbonyloxy, methyloxycarbonyl, ethyloxycarbonyl, hexyloxycarbonyl, phenyloxycarbonyl, acetoxymethyl, phenoxymethyl, and methoxycarbonyloxy.

When m is 2 or more, a plurality of $R^4$ may be the same or different, or two $R^4$ may bond together to form a ring with the carbon atoms to which they are attached. Examples of the ring are shown below, but not limited thereto. The broken line designates a point of attachment to the carbonyl group in formula (2).

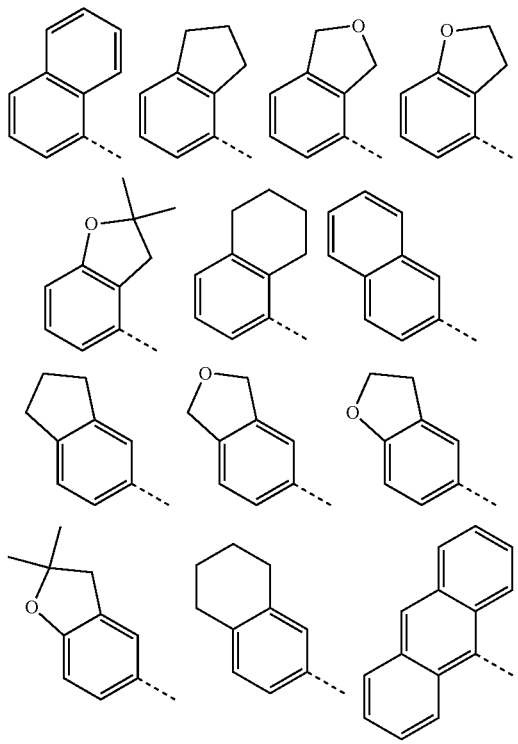

In formulae (1) and (2), M⁺ is an ammonium, sulfonium or iodonium cation. Preferably M⁺ is a sulfonium or iodonium cation having at least one aromatic ring.

Examples of the ammonium cation include tetramethylammonium, tetraethylammonium, tetrabutylammonium, triethylphenylammonium, trimethylbenzylammonium, triethylbenzylammonium, and triethylammonium cations.

Of the sulfonium cations, cations having the following formulae (M-1) and (M-2) are preferred. Of the iodonium cations, cations having the following formulae (M-3) and (M-4) are preferred.

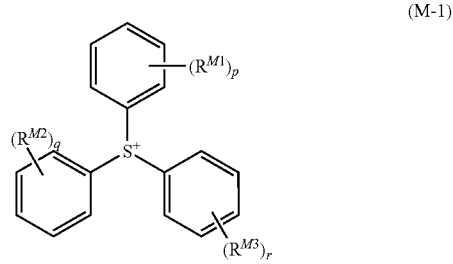

(M-1)

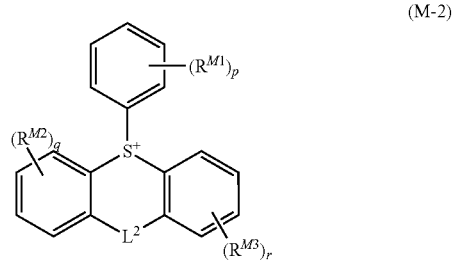

(M-2)

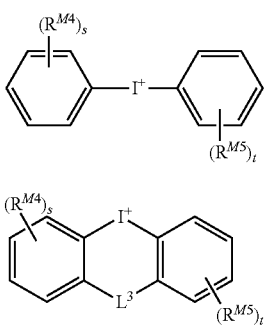

(M-3)

(M-4)

In formulae (M-1) to (M-4), $R^{M1}$, $R^{M2}$, $R^{M3}$, $R^{M4}$, and $R^{M5}$ are each independently hydrogen, halogen, hydroxyl, or a $C_1$-$C_{15}$ hydrocarbyl group which may contain a heteroatom, —$CH_2$— in the hydrocarbyl group may be replaced by an ether bond, carbonyl moiety or sulfonyl moiety. The constituent —$CH_2$— in the hydrocarbyl group may be one bonding to a carbon atom on the benzene ring in formulae (M-1) to (M-4). Examples of the hydrocarbyl group and substituted hydrocarbyl group are as exemplified above for $R^4$.

In formulae (M-2) and (M-4), $L^2$ and $L^3$ are each independently a single bond, methylene group, ether bond, thioether bond, carbonyl group, sulfinyl group, sulfonyl group or N($R^N$). $R^N$ is hydrogen or a $C_1$-$C_{10}$ hydrocarbyl group which may contain a heteroatom, —$CH_2$— in the hydrocarbyl group may be replaced by an ether bond, carbonyl moiety or sulfonyl moiety.

In formulae (M-1) to (M-4), p, q, r, s and t are each independently an integer of 0 to 5. When p is 2 or more, a plurality of $R^{M1}$ may be the same or different, and two $R^{M1}$ may bond together to form a ring with the carbon atoms on the benzene ring to which they are attached. When q is 2 or more, a plurality of $R^2$ may be the same or different, and two $R^{M2}$ may bond together to form a ring with the carbon atoms on the benzene ring to which they are attached. When r is 2 or more, a plurality of $R^{M3}$ may be the same or different, and two $R^{M4}$ may bond together to form a ring with the carbon atoms on the benzene ring to which they are attached. When s is 2 or more, a plurality of $R^{M4}$ may be the same or different, and two $R^{M4}$ may bond together to form a ring with the carbon atoms on the benzene ring to which they are attached. When t is 2 or more, a plurality of $R^{M5}$ may be the same or different, and two $R^{M5}$ may bond together to form a ring with the carbon atoms on the benzene ring to which they are attached.

Examples of the sulfonium cation having formula (M-1) are given below, but not limited thereto.

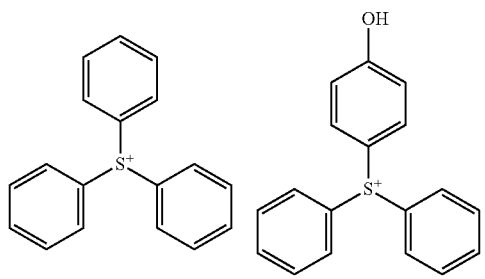

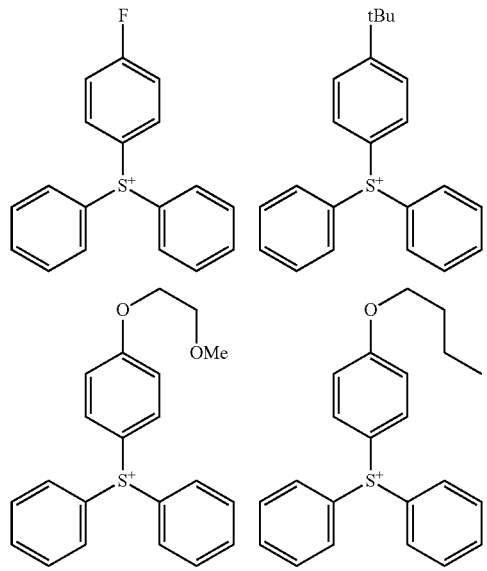

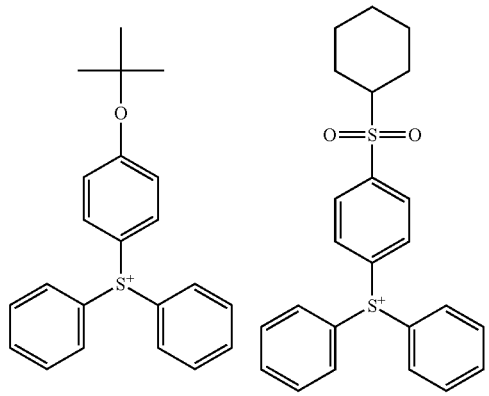

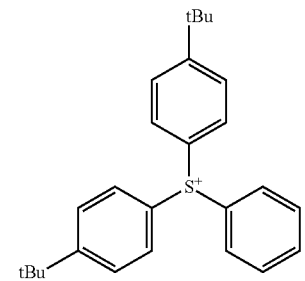

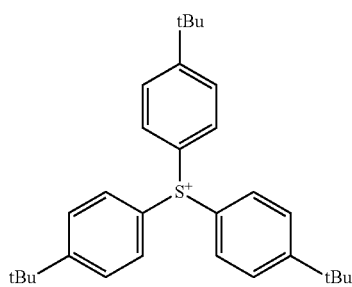

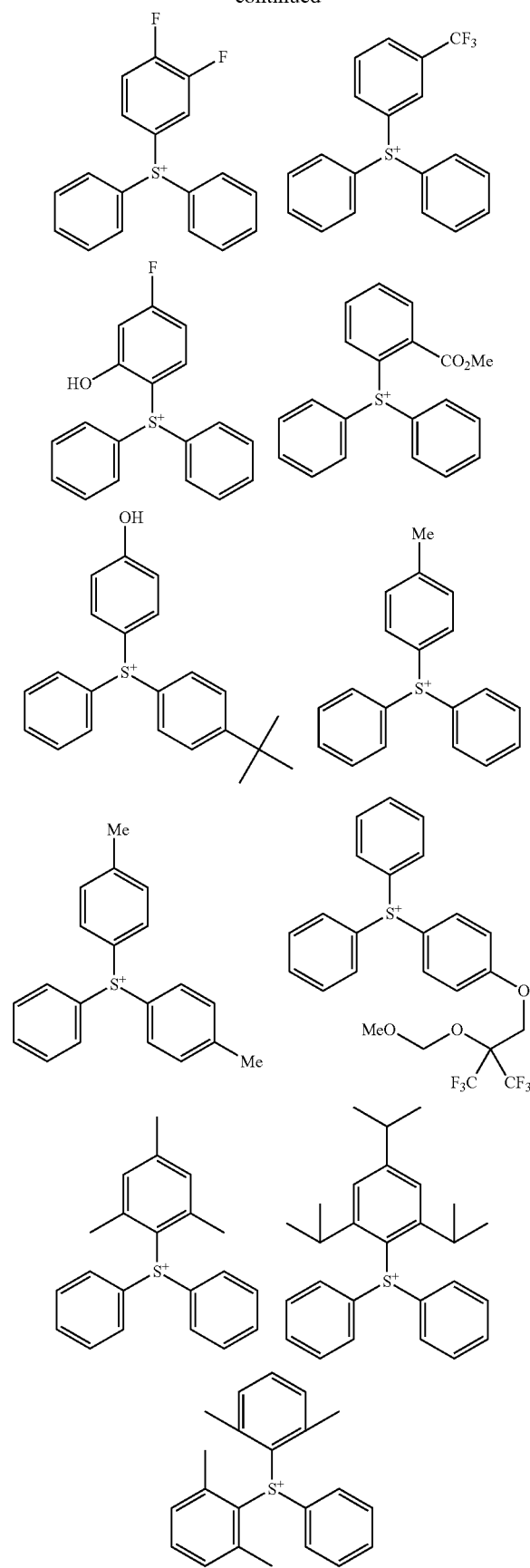
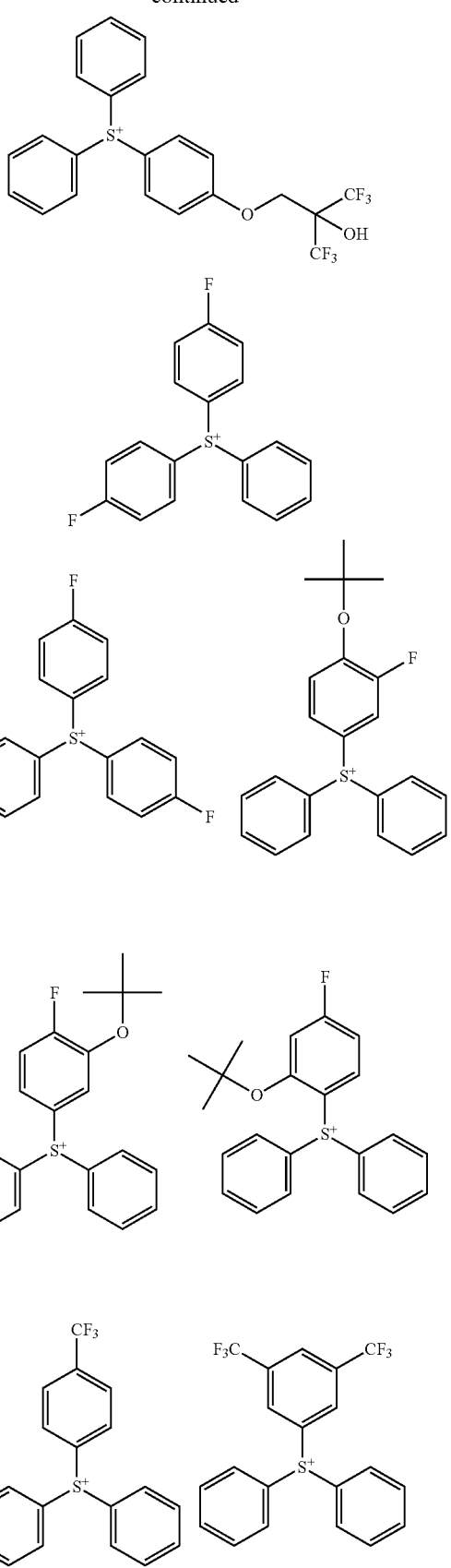

-continued
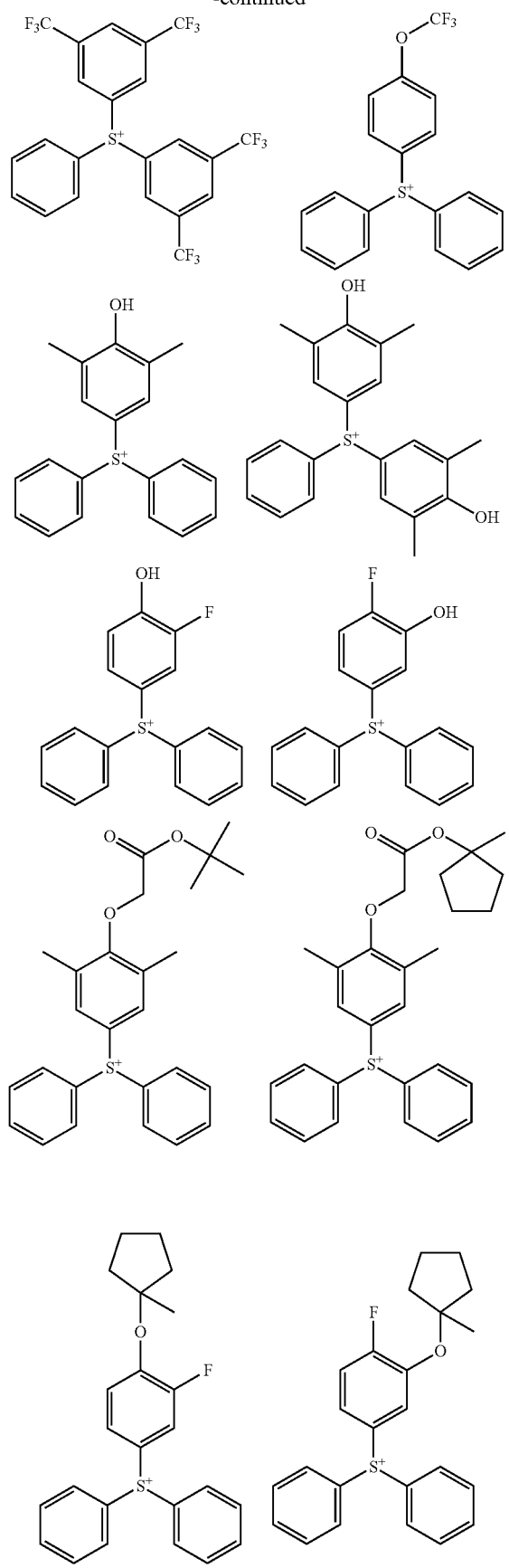
-continued
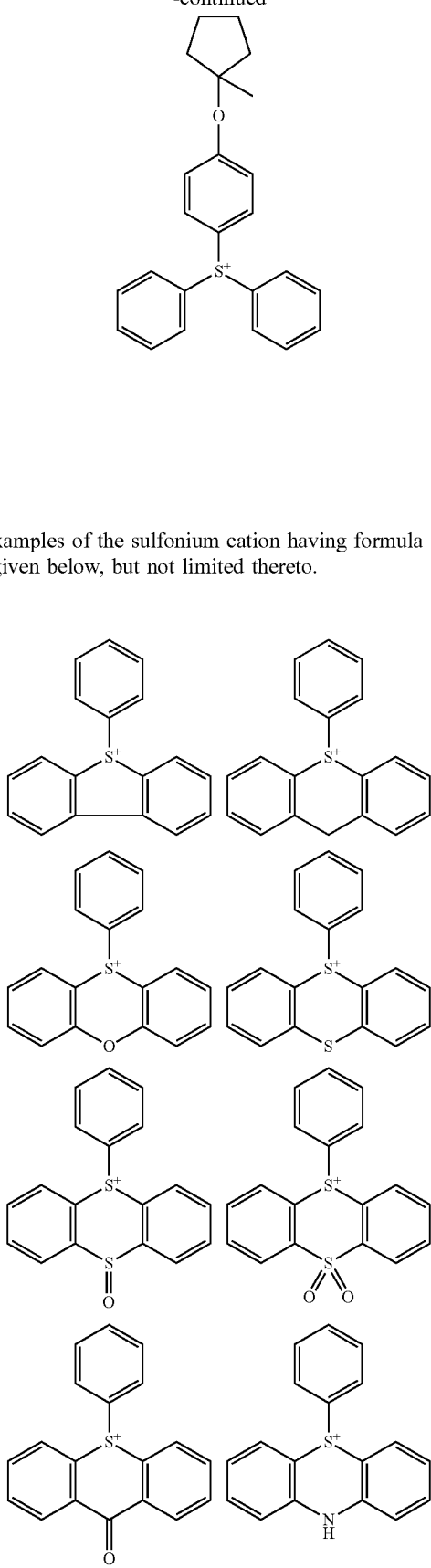
Examples of the sulfonium cation having formula (M-2) are given below, but not limited thereto.

-continued
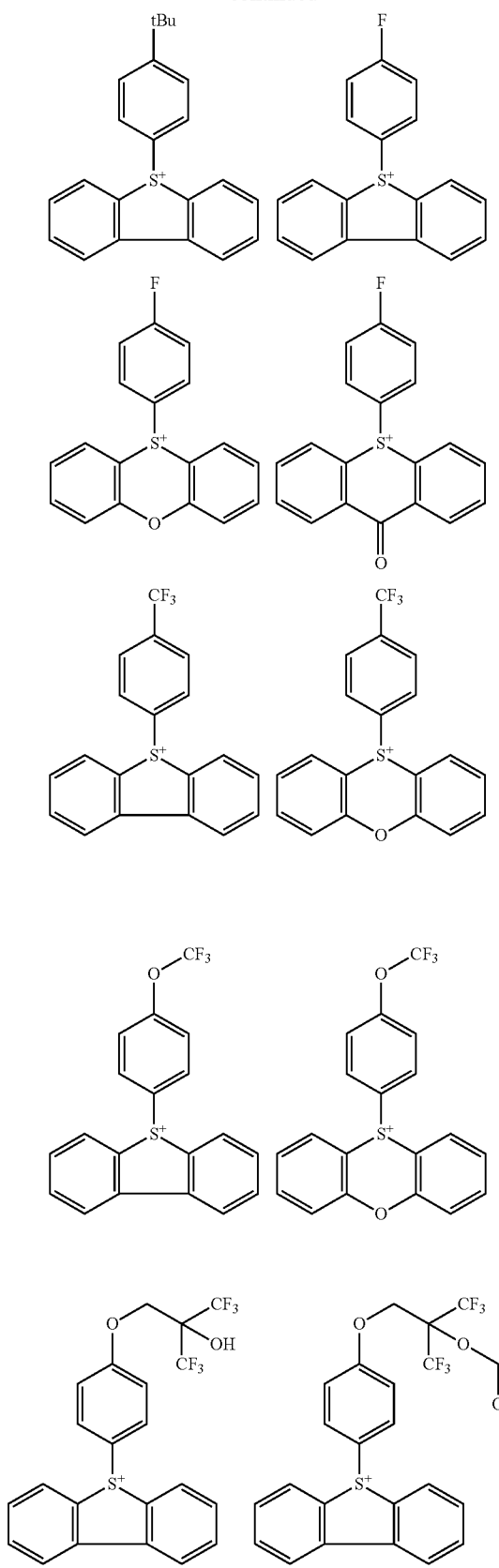
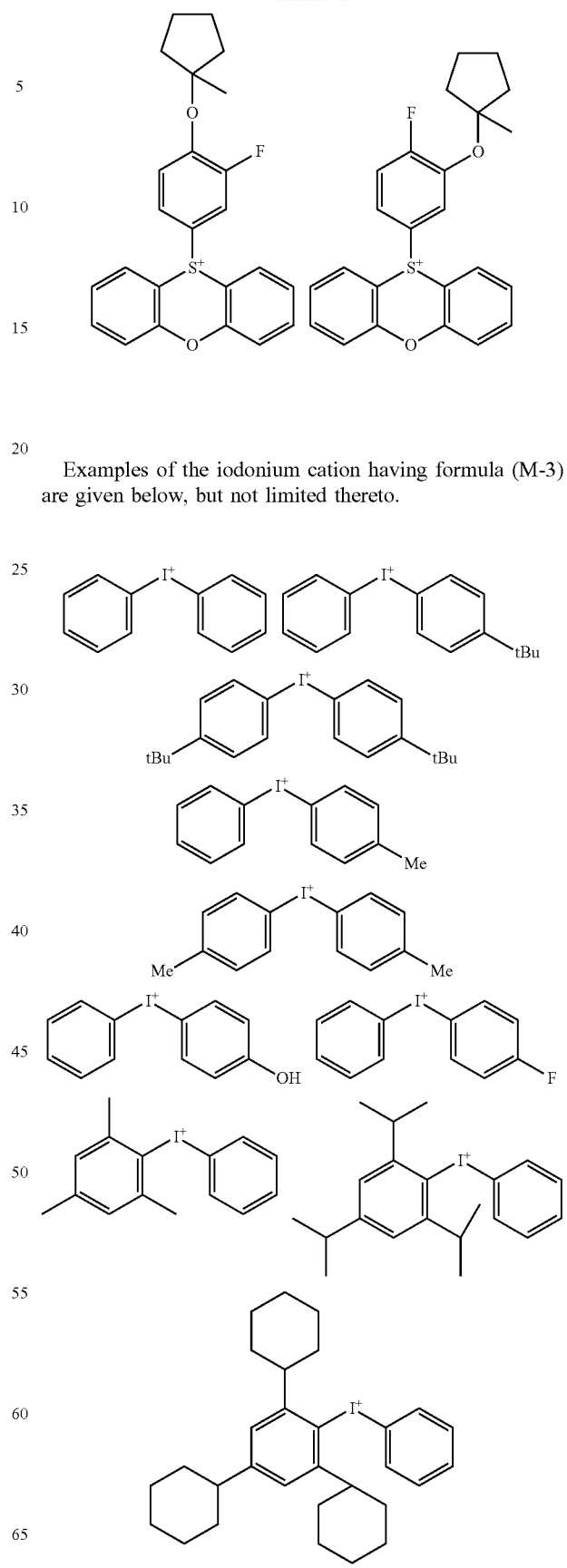
Examples of the iodonium cation having formula (M-3) are given below, but not limited thereto.

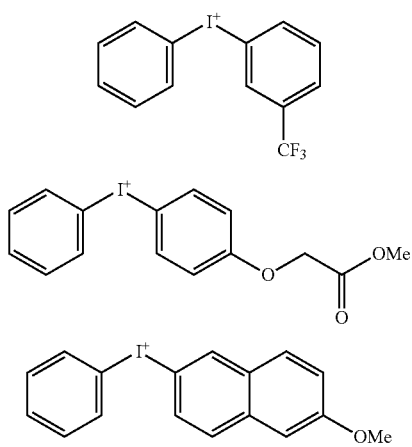
Examples of the iodonium cation having formula (M-4) are given below, but not limited thereto.
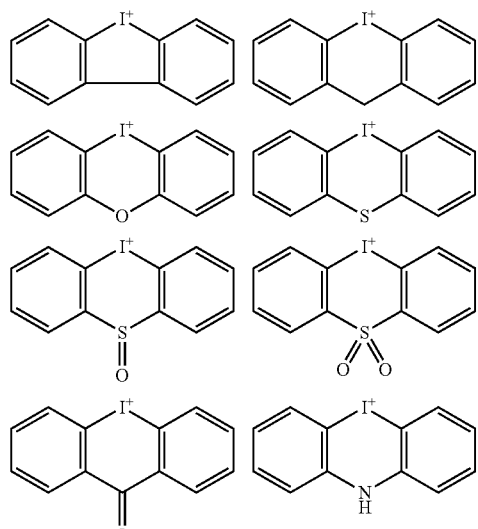
Suitable sulfonium cations other than the sulfonium cations having formulae (M-1) and (M-2) are given below, but not limited thereto.
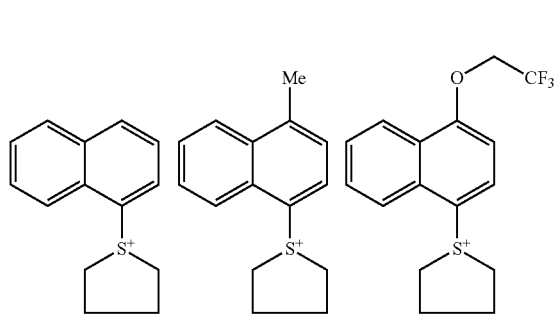
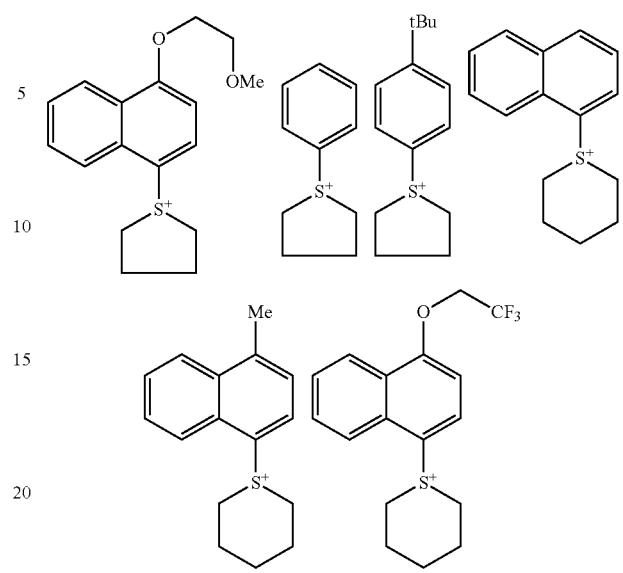
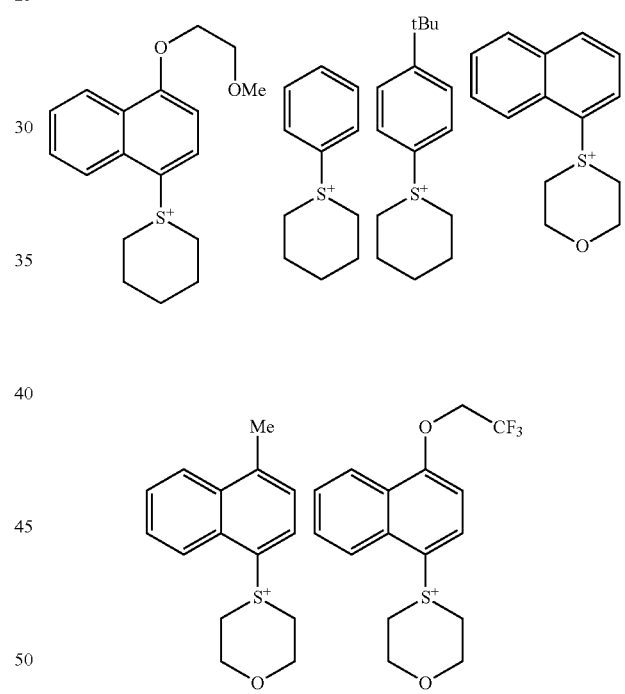
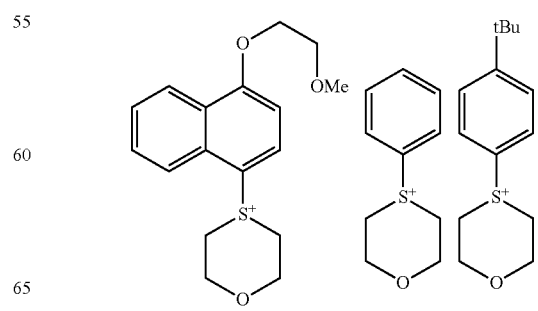

31
-continued

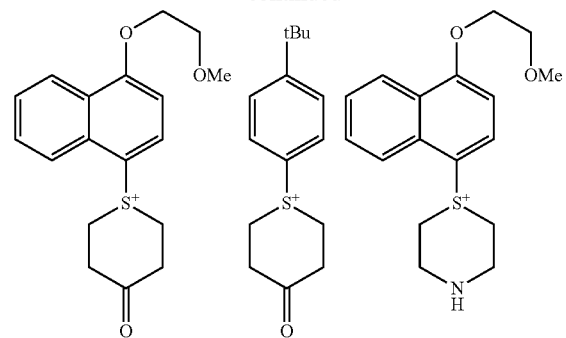
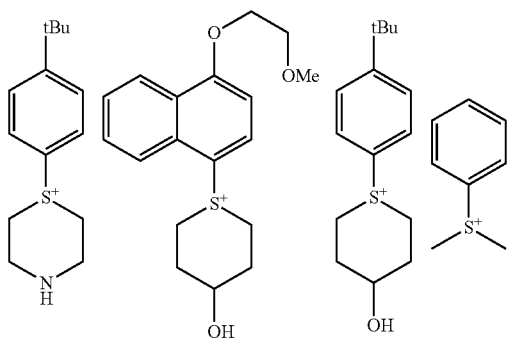
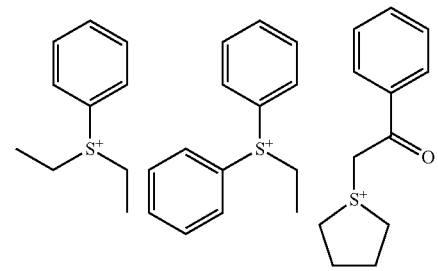
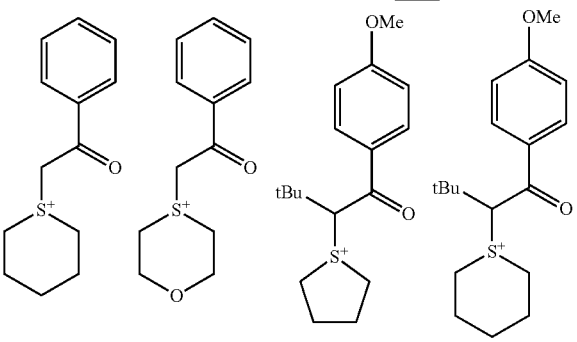
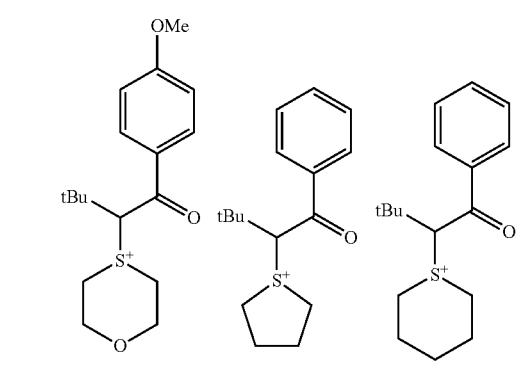

32
-continued

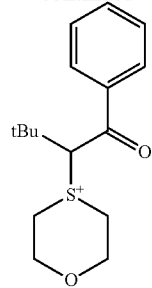

Of the compounds having formula (2), compounds having the following formulae (3) and (4) are more preferred.

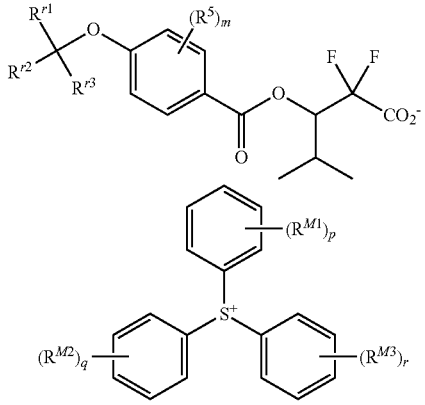

(3)

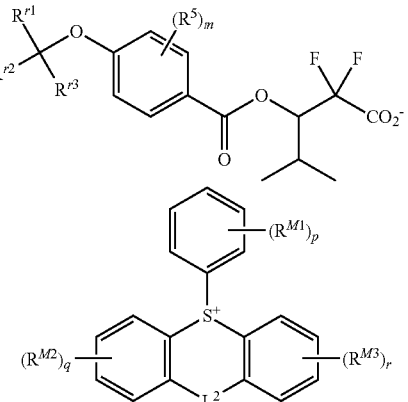

(4)

Herein $R^{r1}$, $R^{r2}$, $R^{r3}$, $R^{M1}$, $R^{M2}$, $R^{M3}$, $L^2$, p, q, r, and m are as defined above.

In formulae (3) and (4), $R^5$ is hydrogen, fluorine, hydroxyl, or a $C_1$-$C_5$ hydrocarbyl group in which —$CH_2$— may be replaced by an ether bond or carbonyl moiety. The constituent —$CH_2$— in the hydrocarbyl group may be one bonding to a carbon atom on the benzene ring in formula (3) or (4). When m is 2 or more, a plurality of $R^5$ may be the same or different, and two $R^5$ may bond together to form a ring with the carbon atoms to which they are attached.

Examples of the hydrocarbyl group and substituted hydrocarbyl group, represented by $R^5$, are as exemplified above for $R^4$, but of 1 to 5 carbon atoms. Illustrative examples include methyl, ethyl, propyl, isopropyl, butyl, sec-butyl, tert-butyl, pentyl, methoxy, ethoxy, propoxy, butoxy, methoxyethoxy, acetoxy, acetyl, and trifluoromethyl, but are not limited thereto. Examples of the ring formed by $R^5$ are as exemplified above for the ring that two $R^4$, taken together, form with the carbon atoms to which they are attached.
Examples of the anion in the onium salt compound having formula (1) are shown below, but not limited thereto.
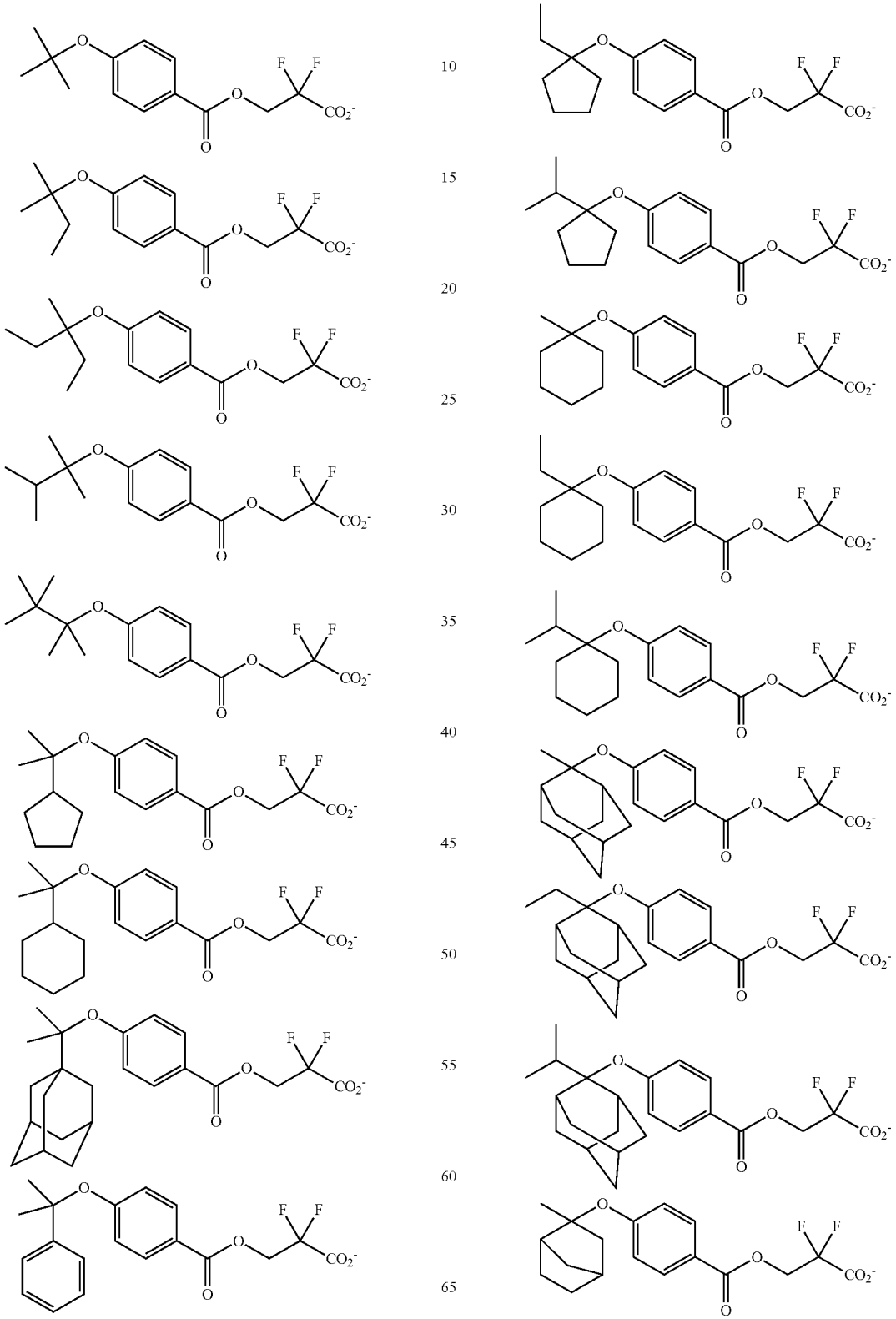

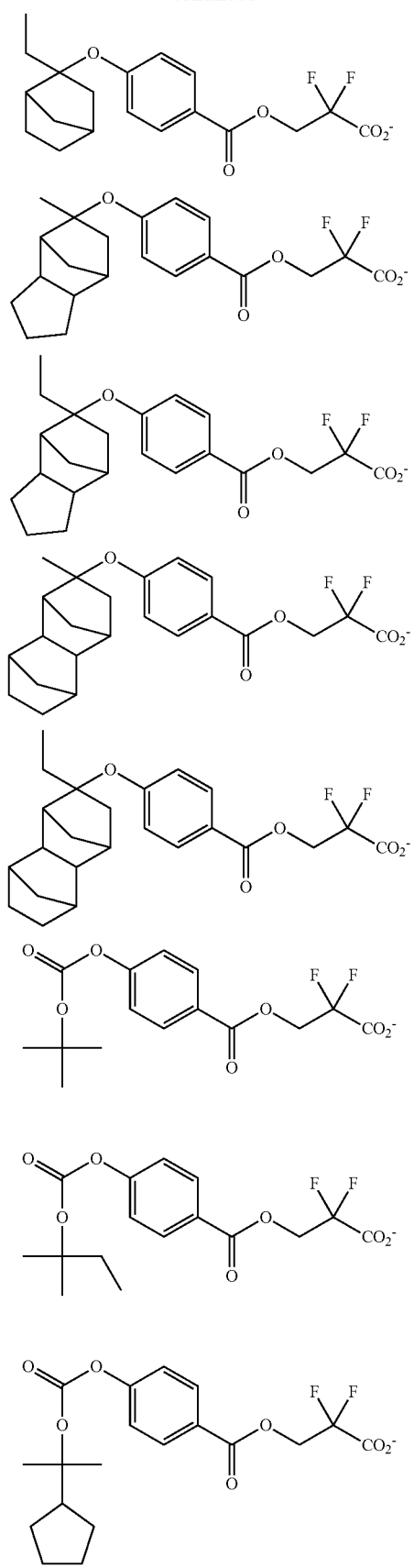
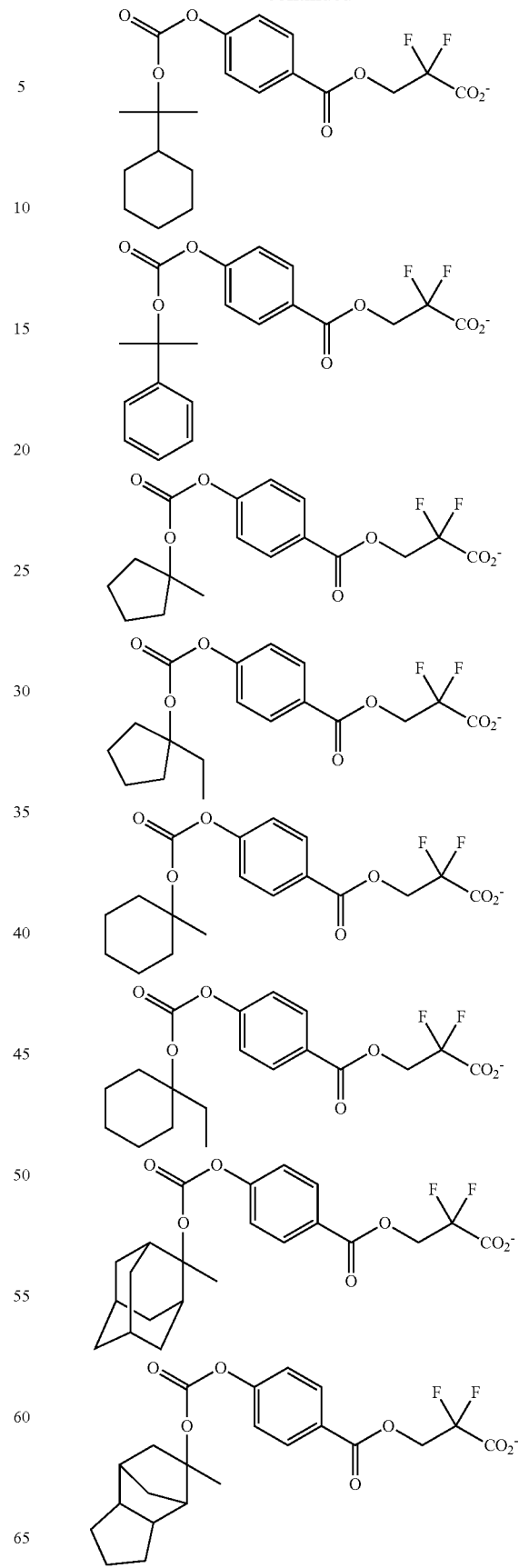

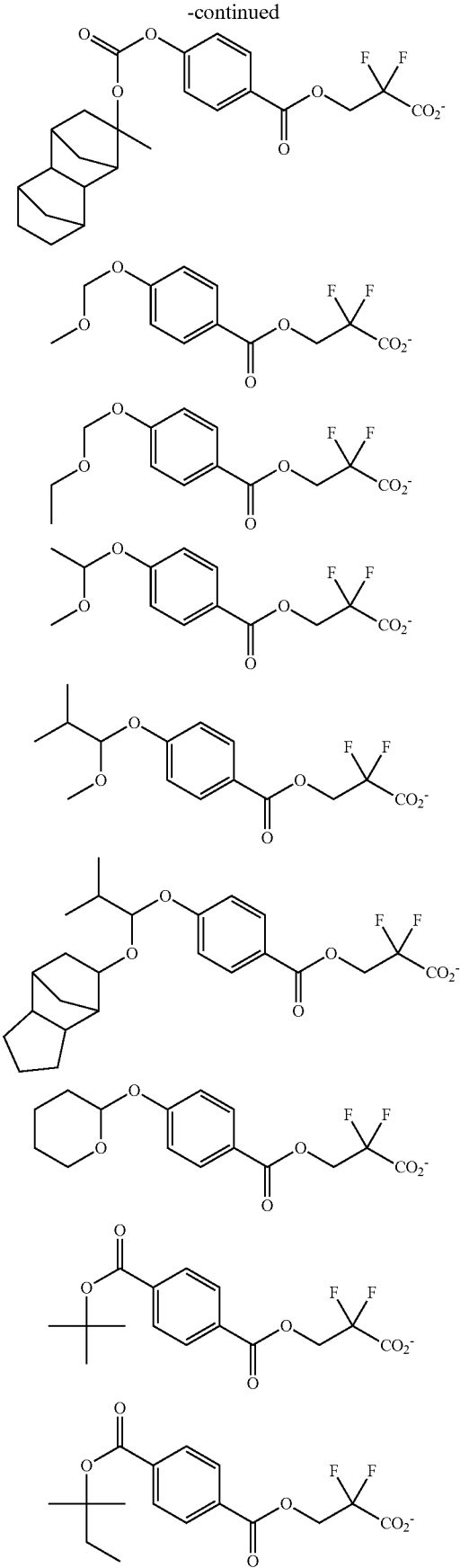
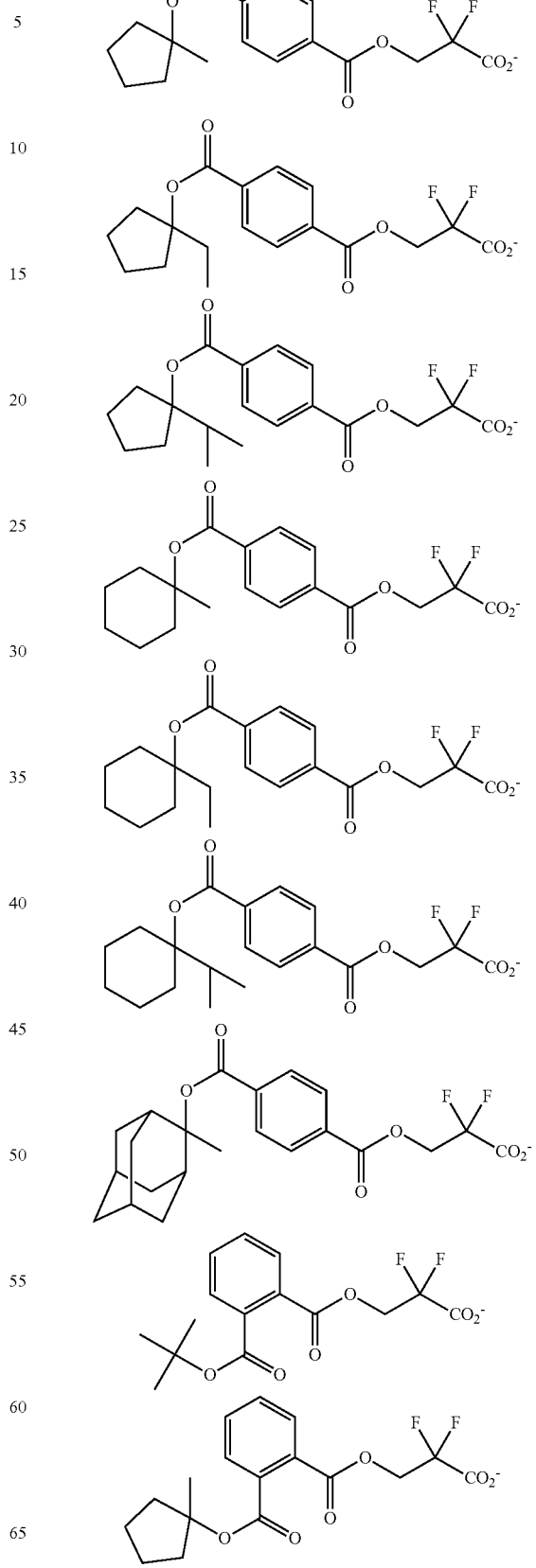

39
-continued
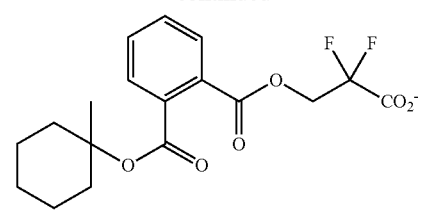
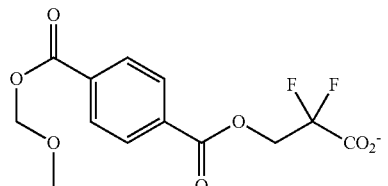
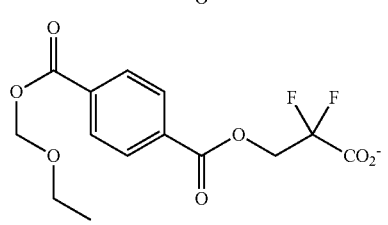
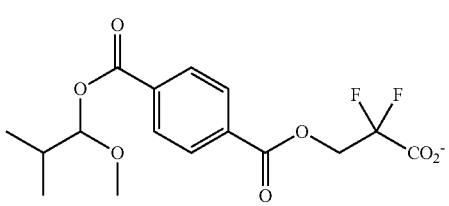
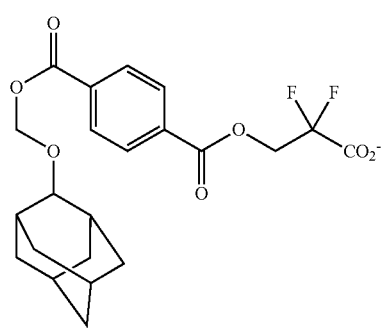
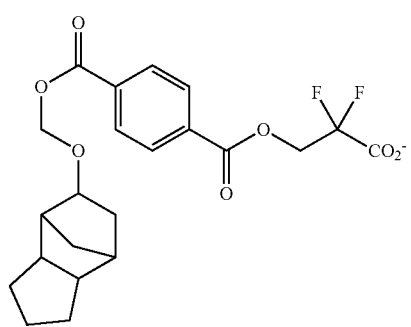
40
-continued
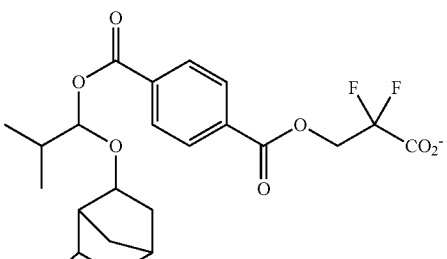
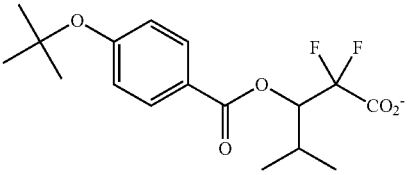
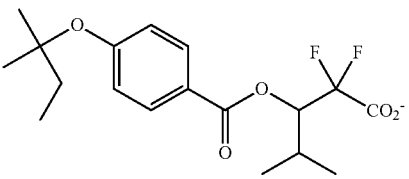
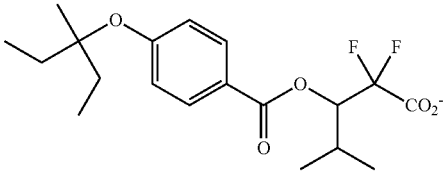
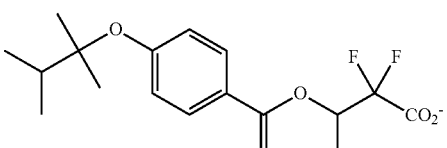
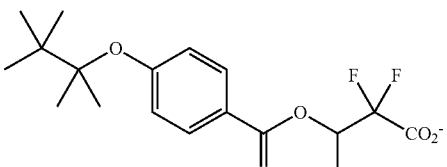
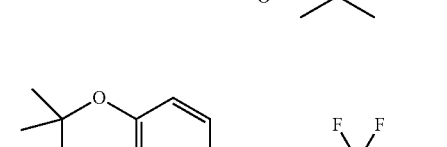
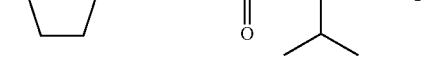
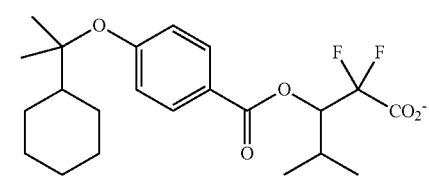

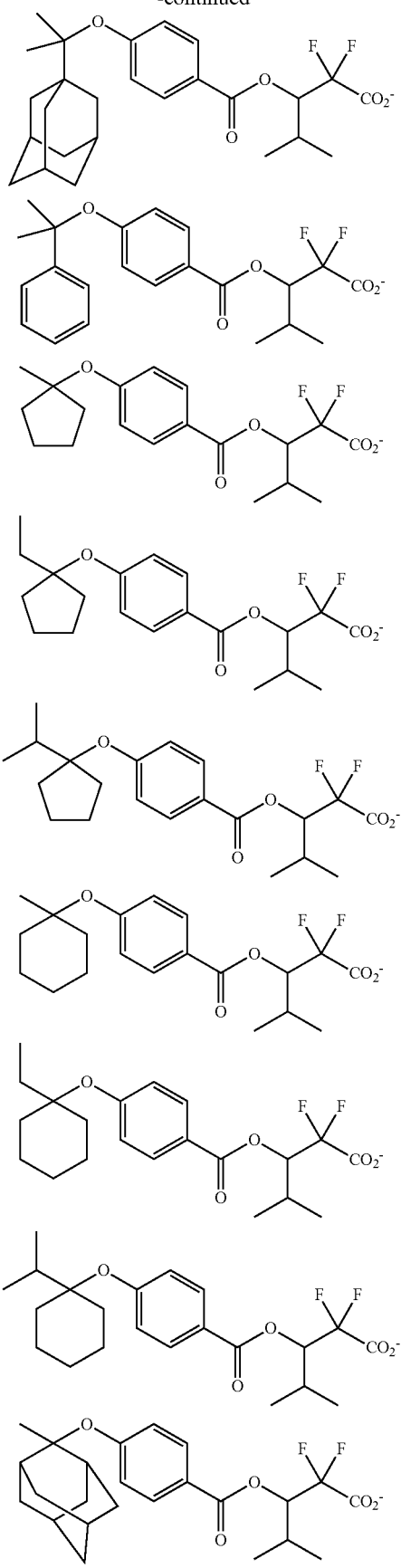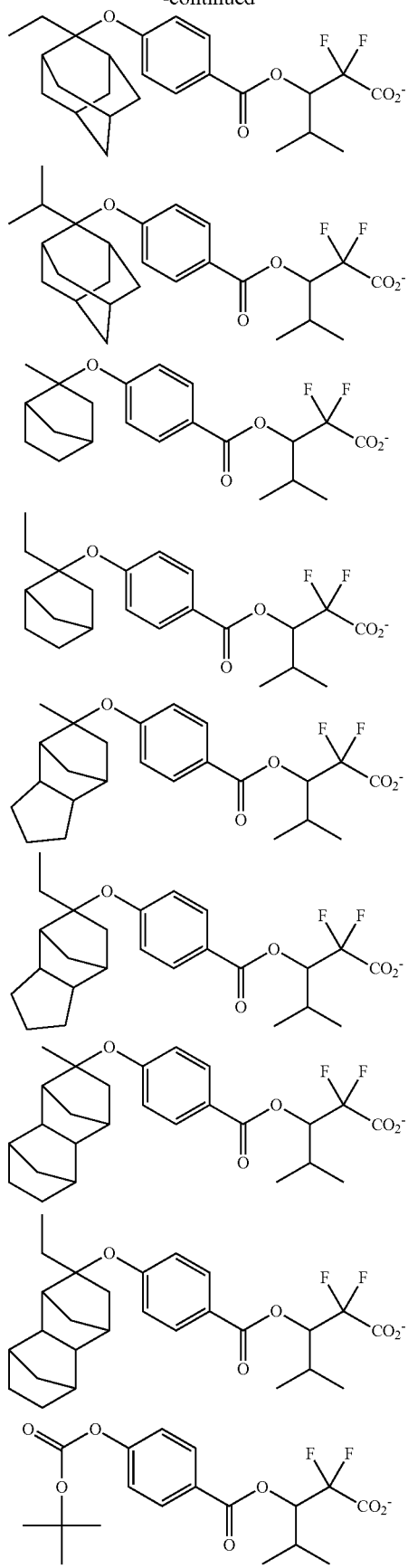

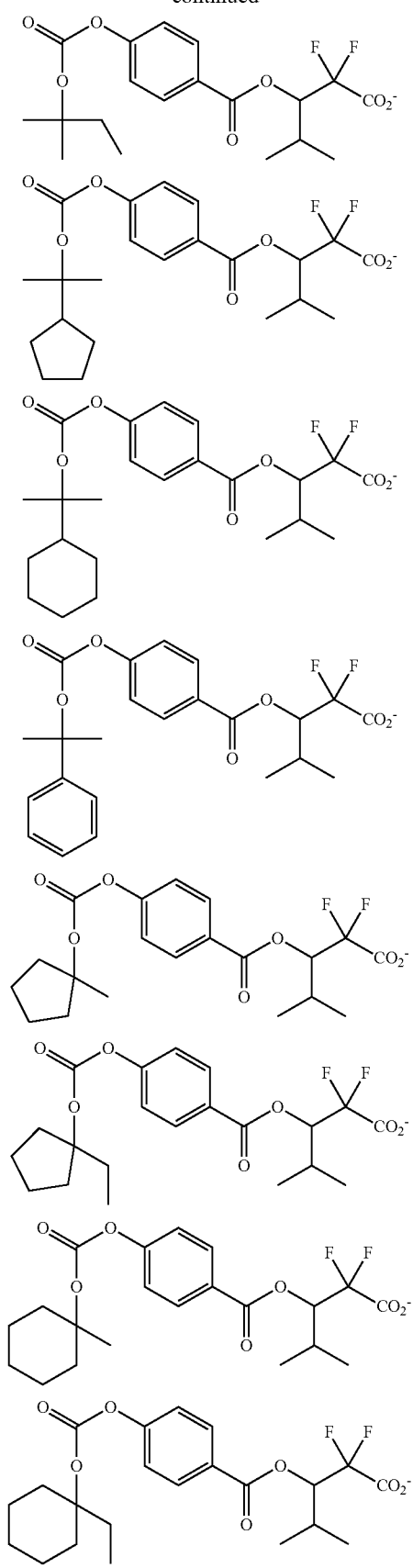
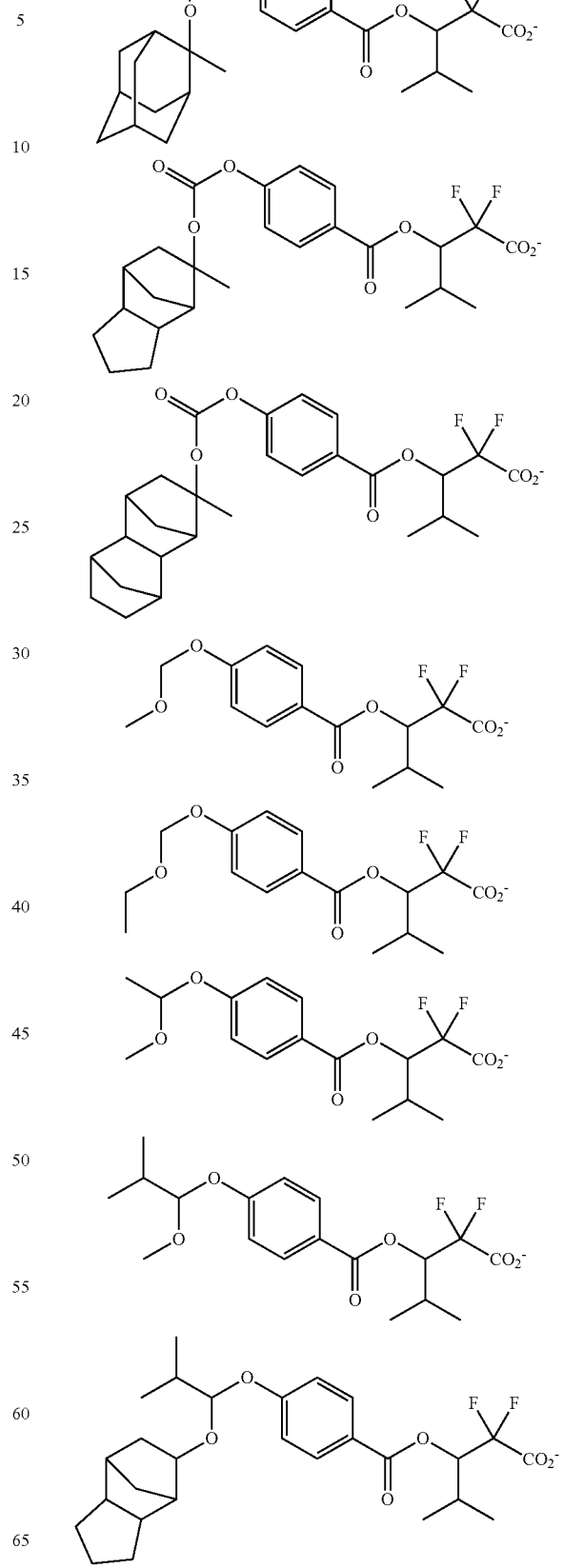

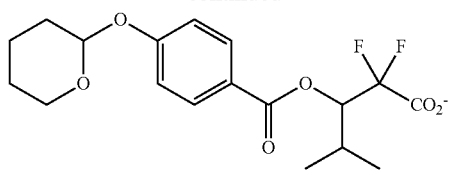
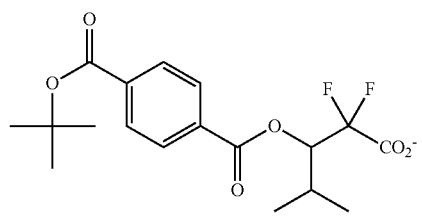
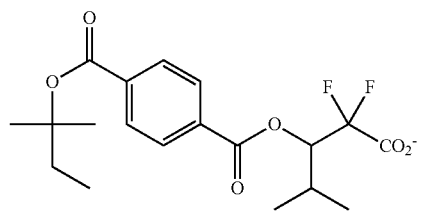
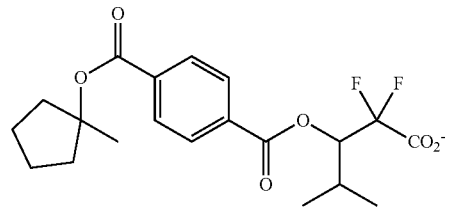
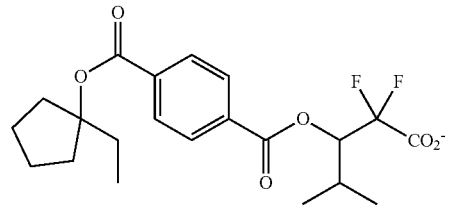
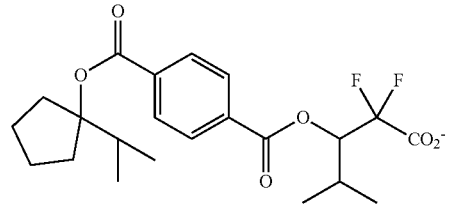
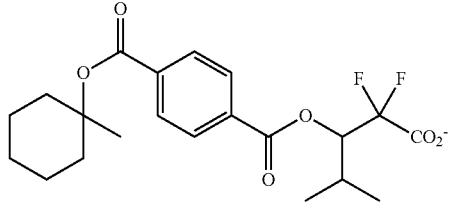
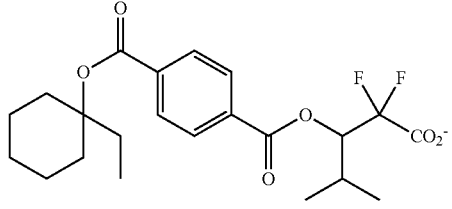
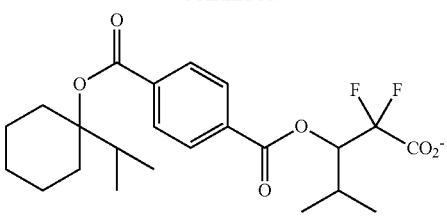
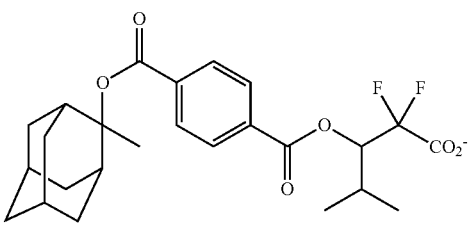
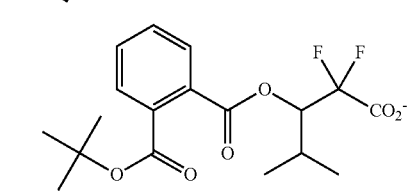
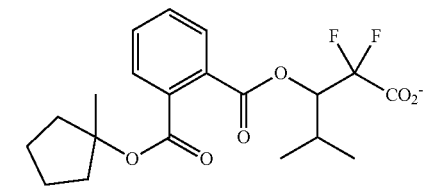
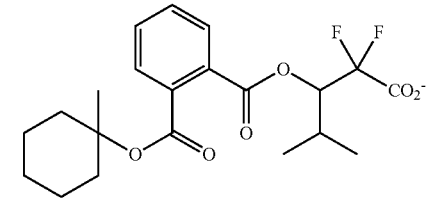
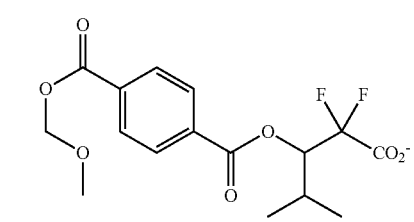
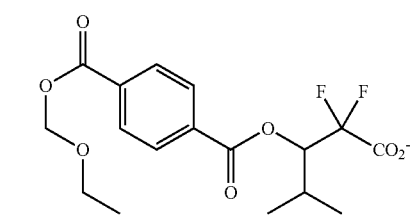
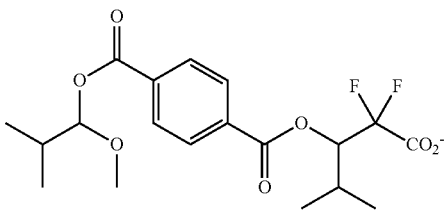

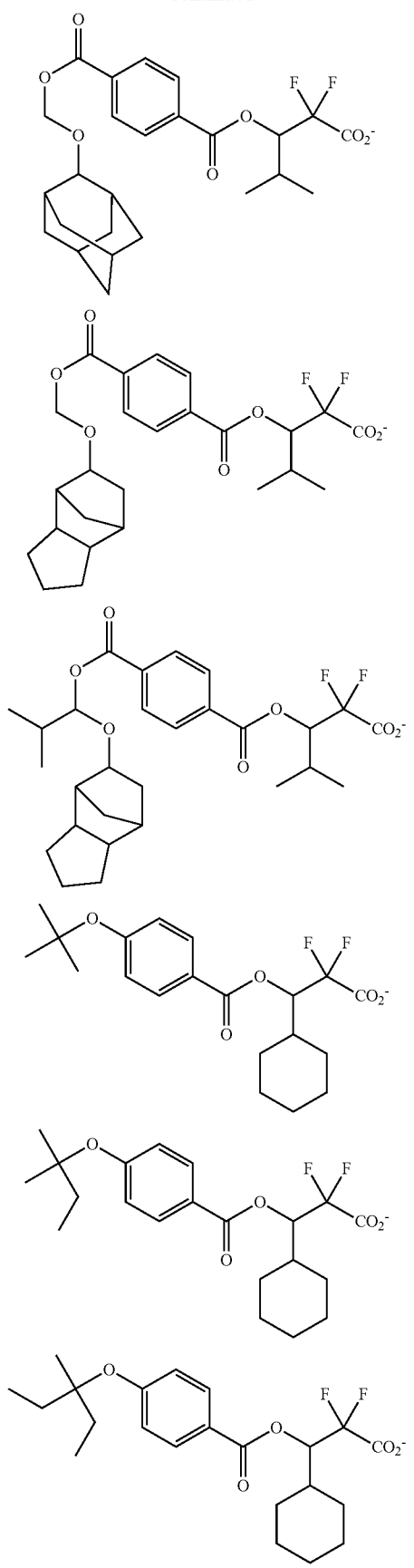
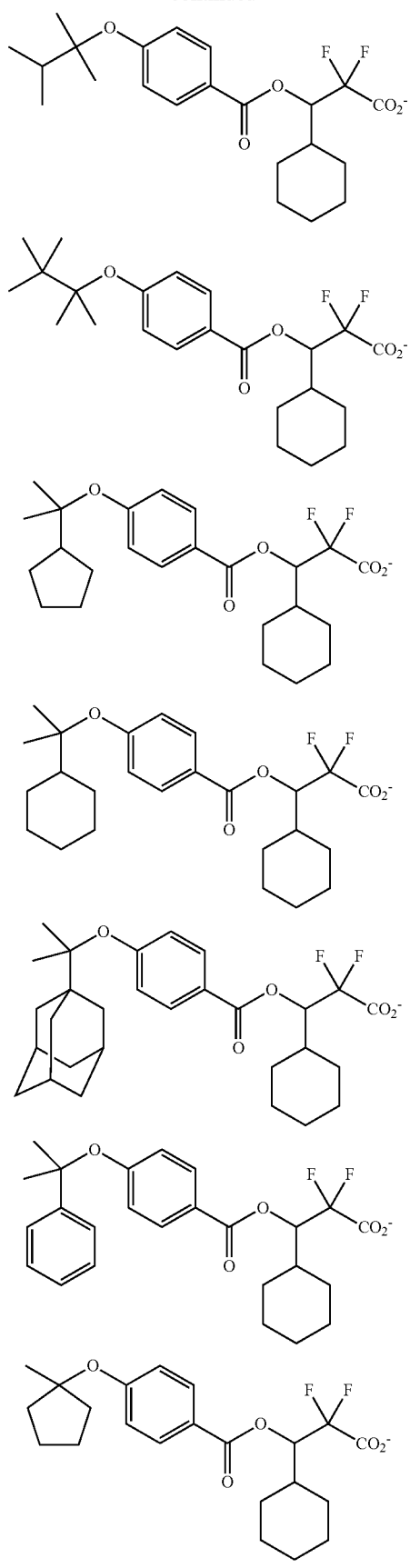

-continued
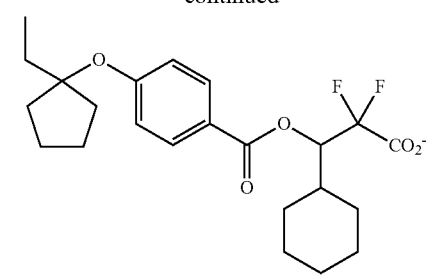
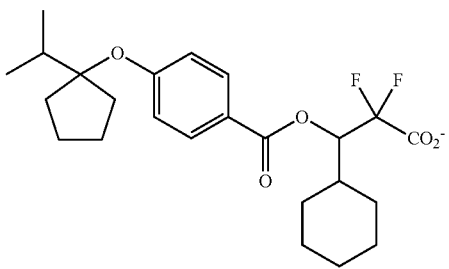
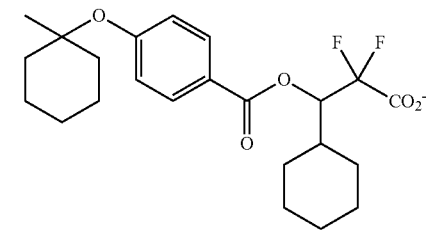
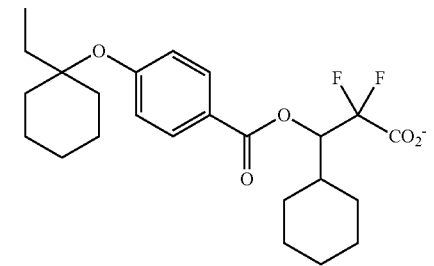
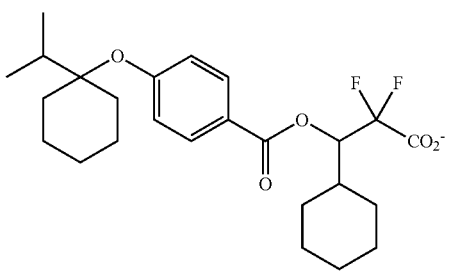
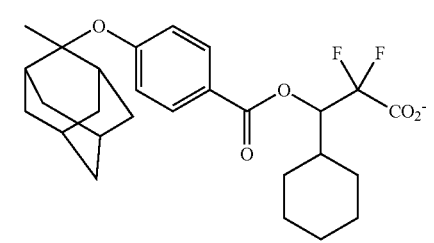
-continued
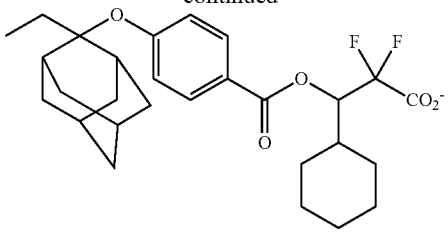
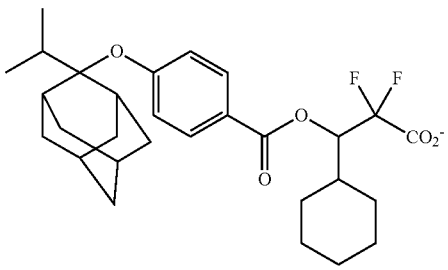
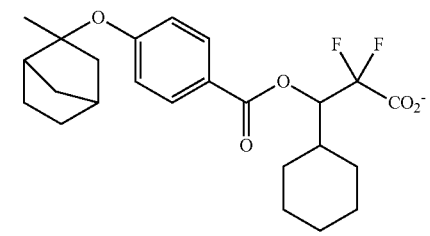
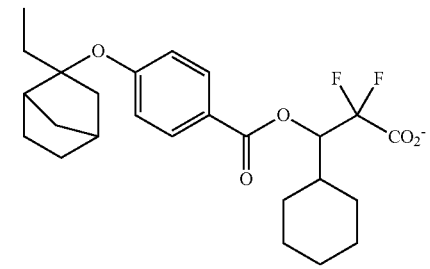
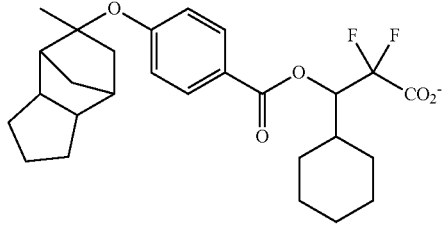
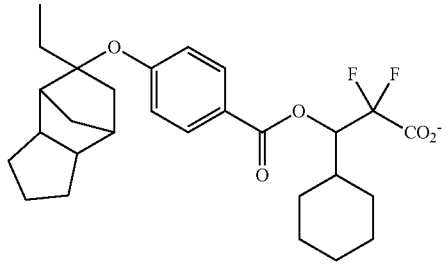
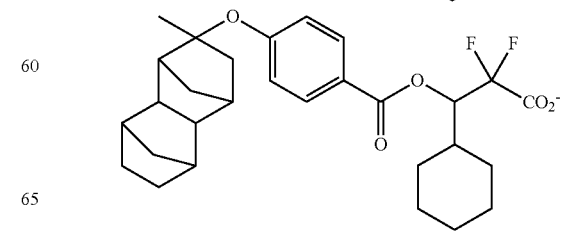

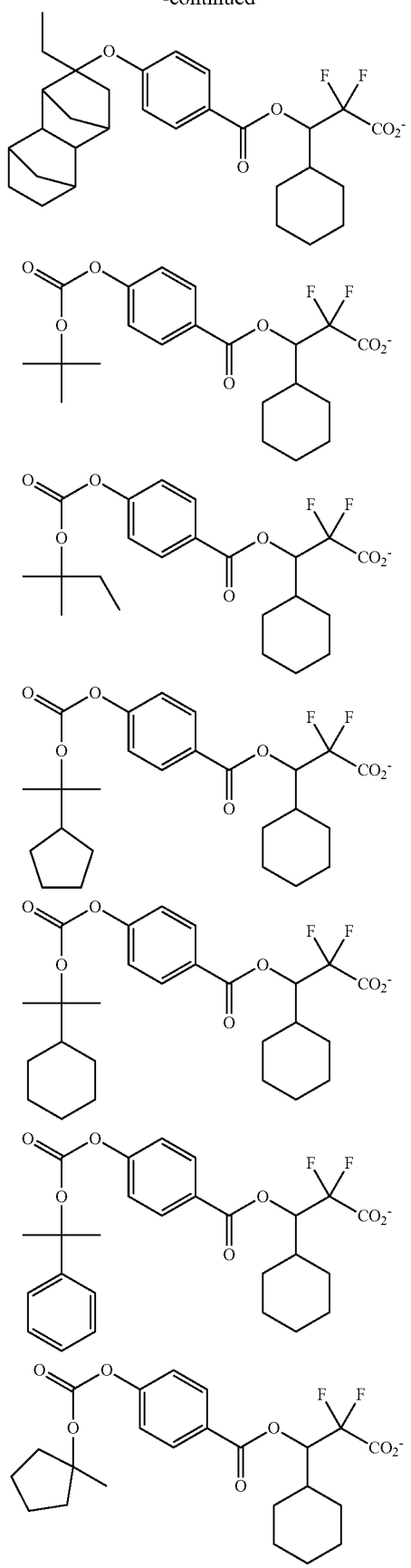
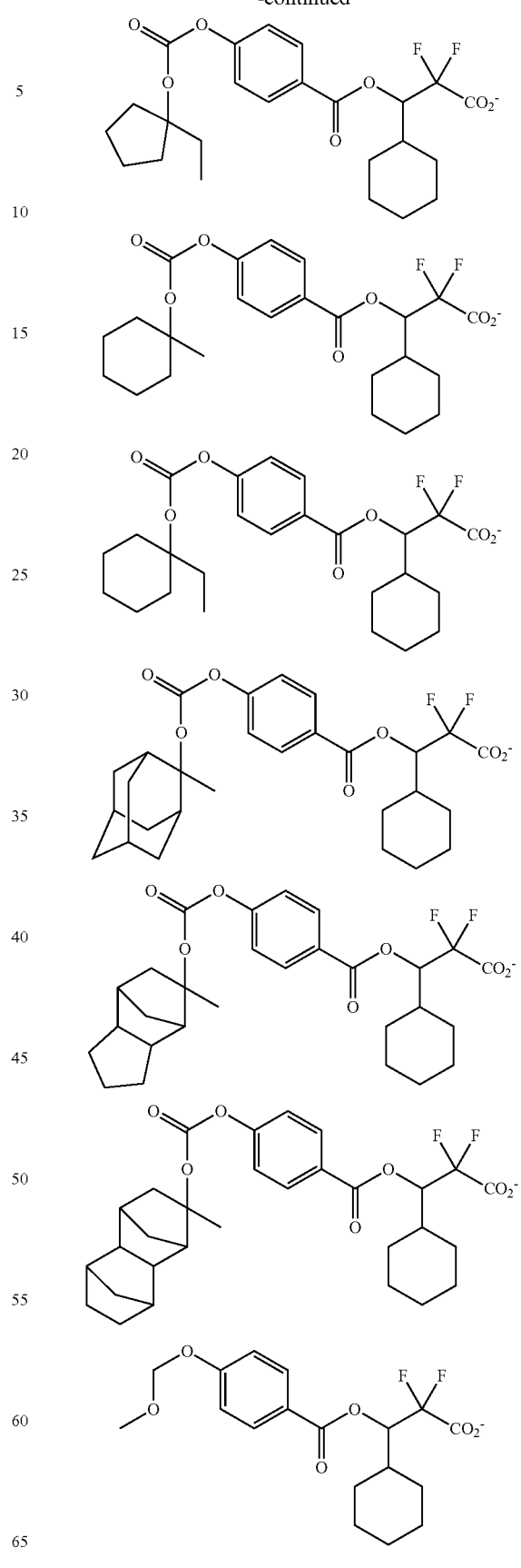

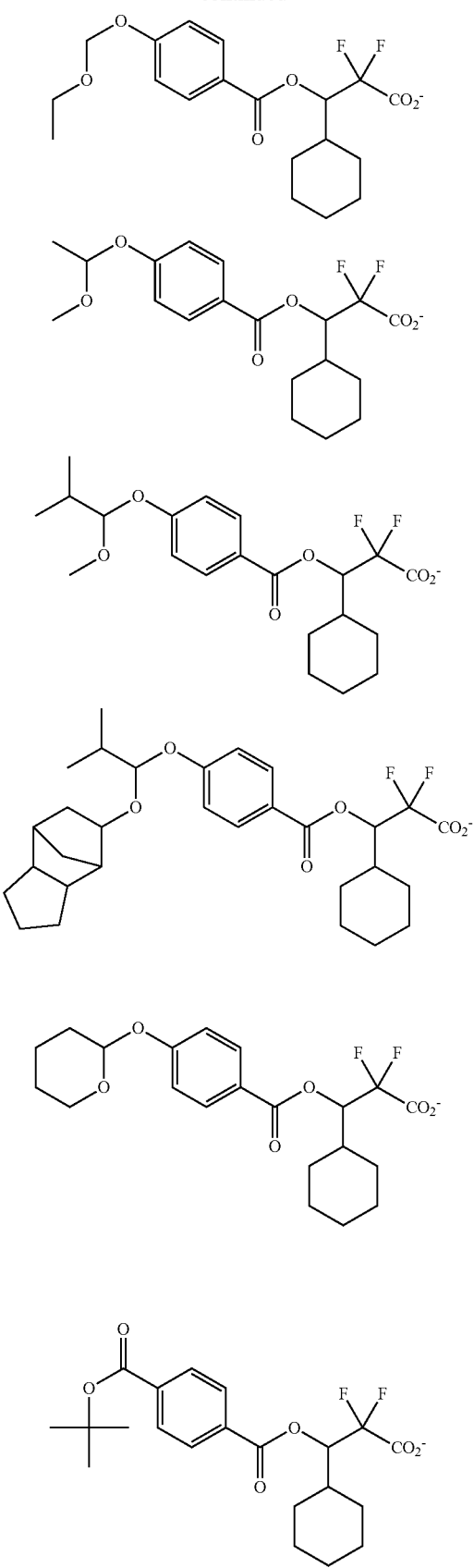
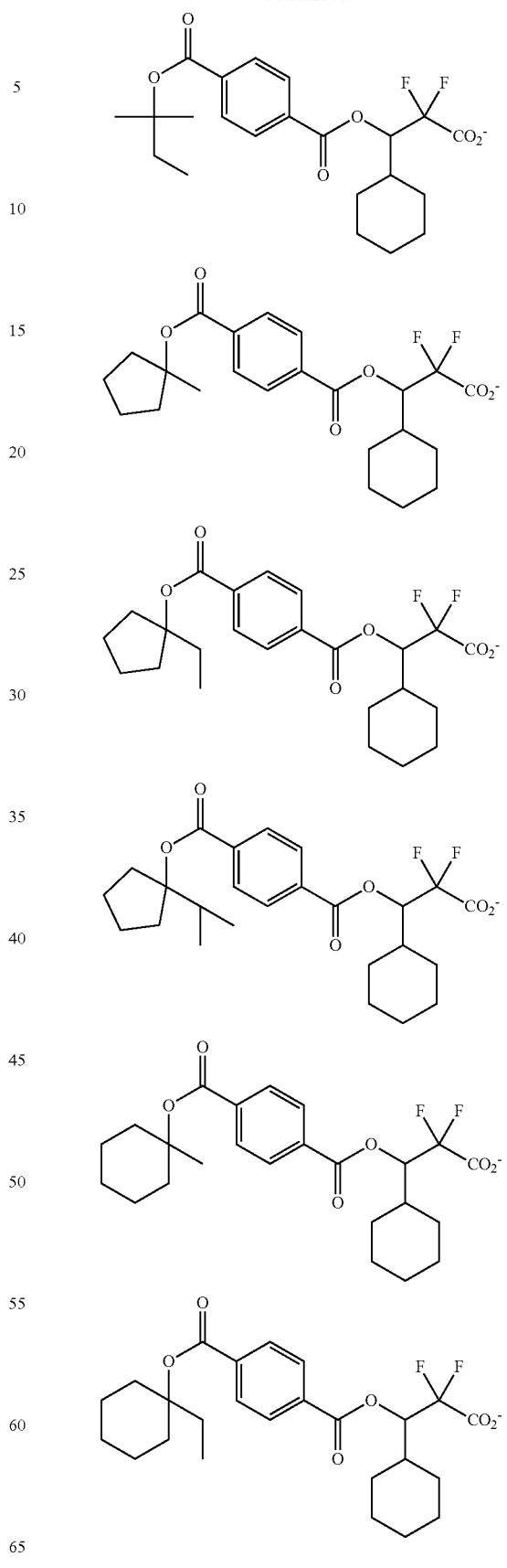

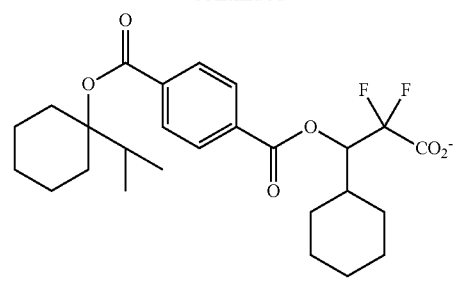
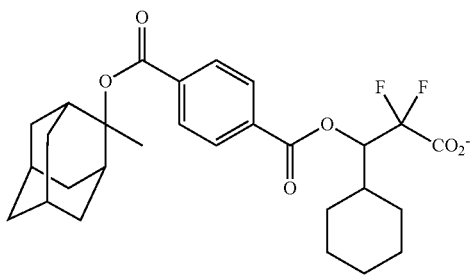
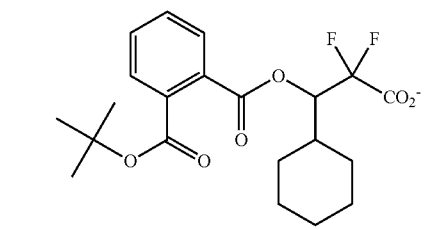
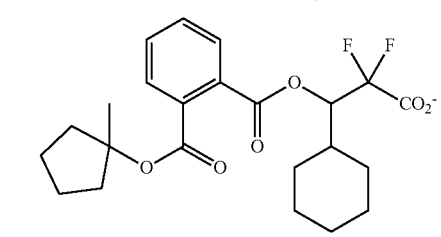
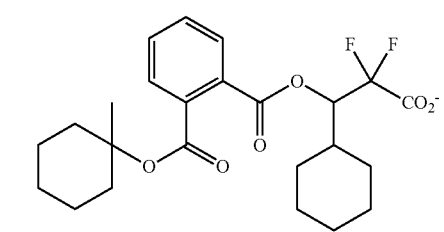
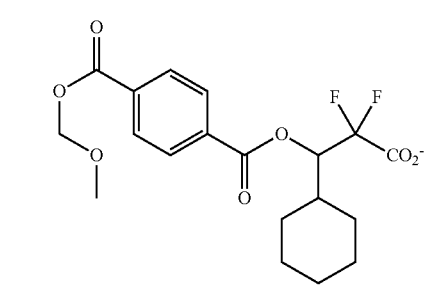
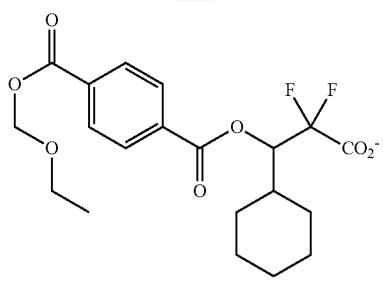
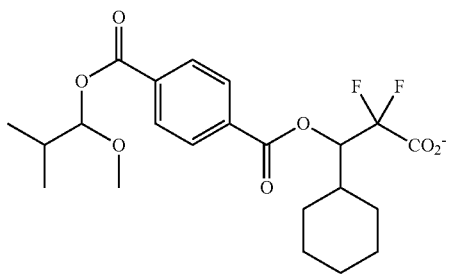
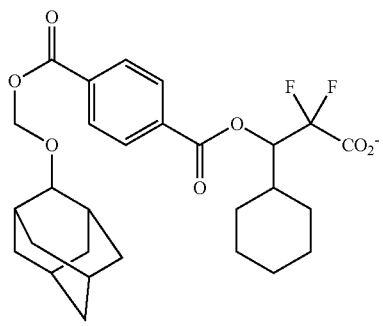
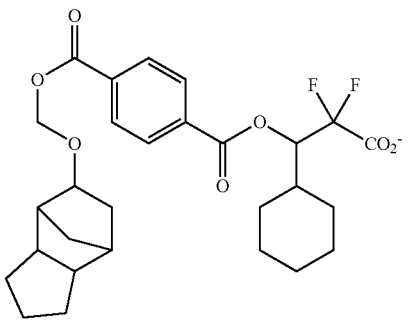
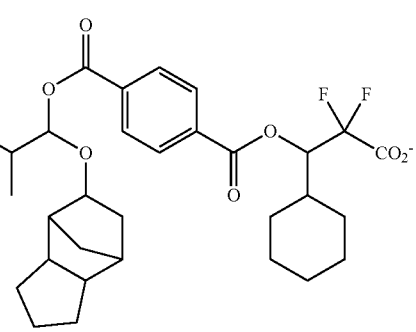

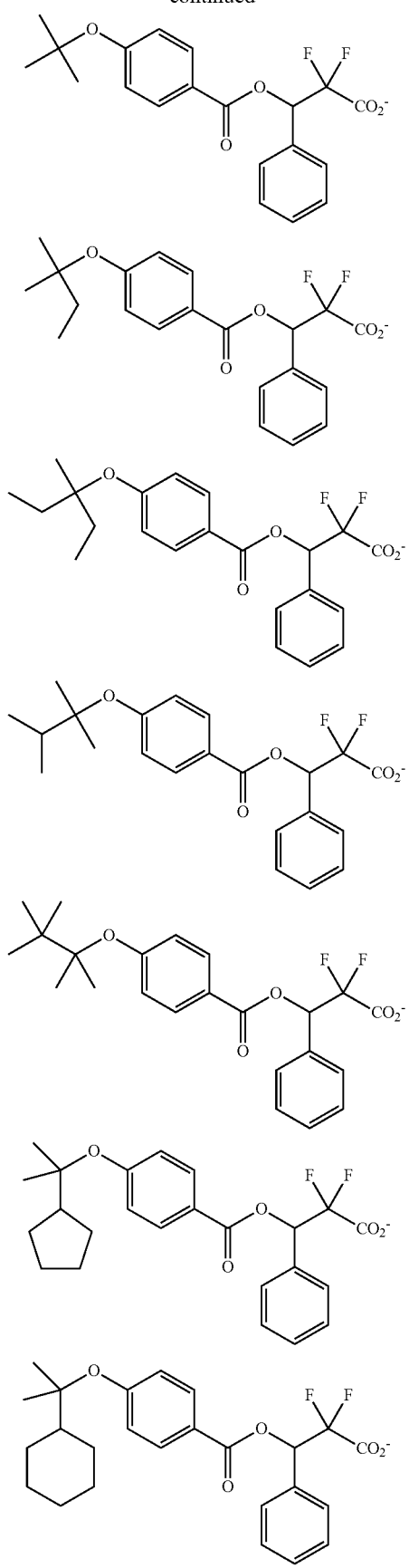
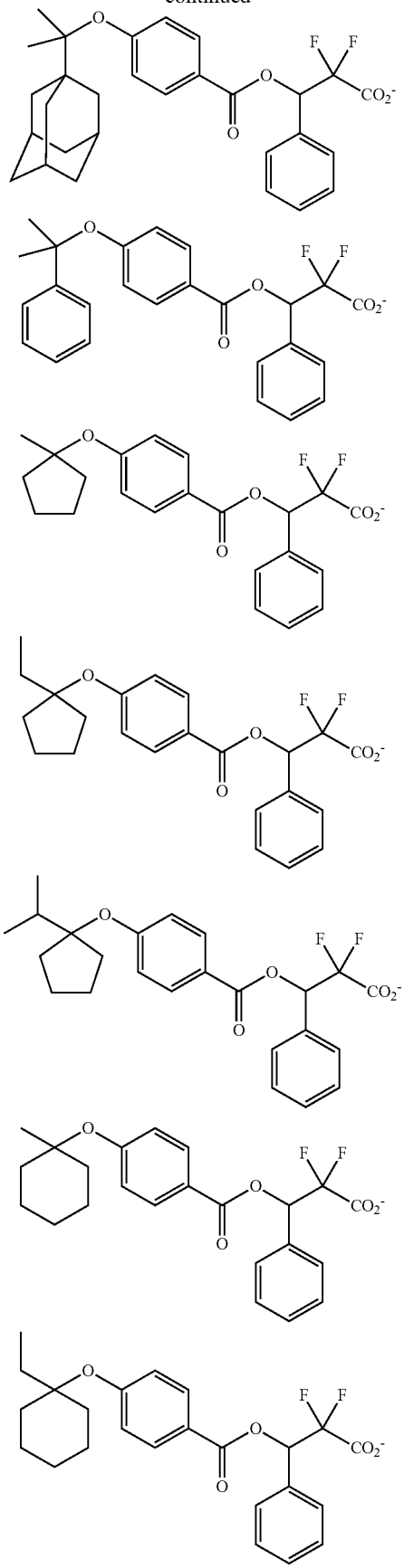

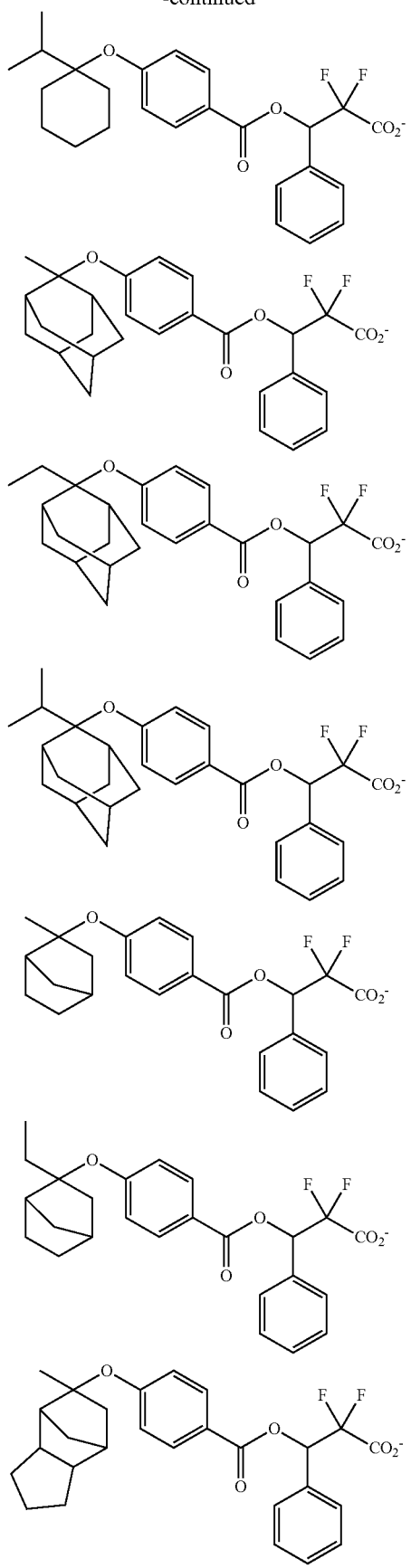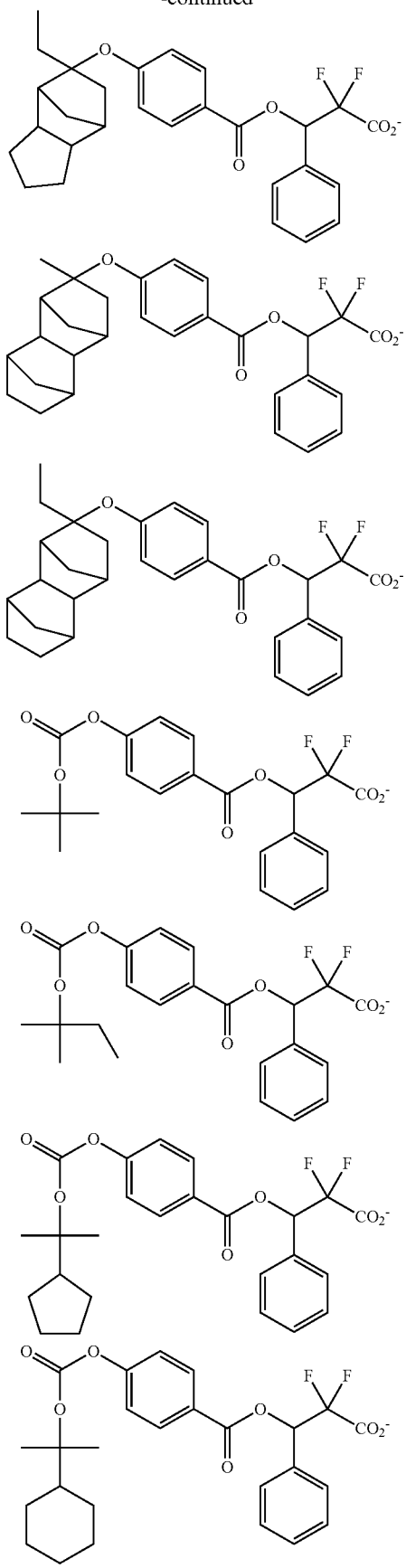

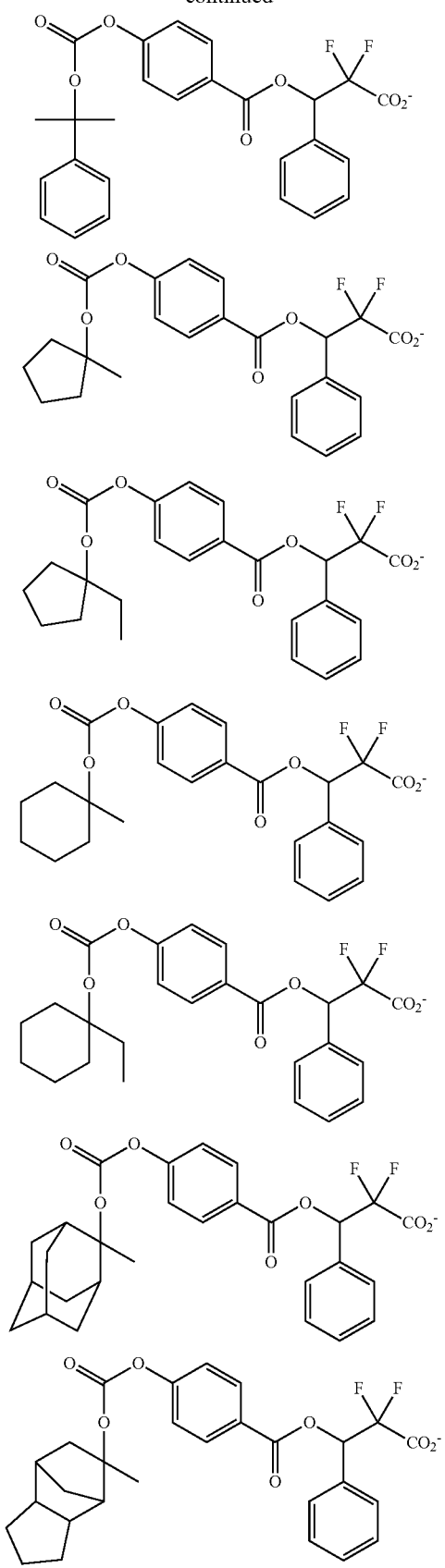
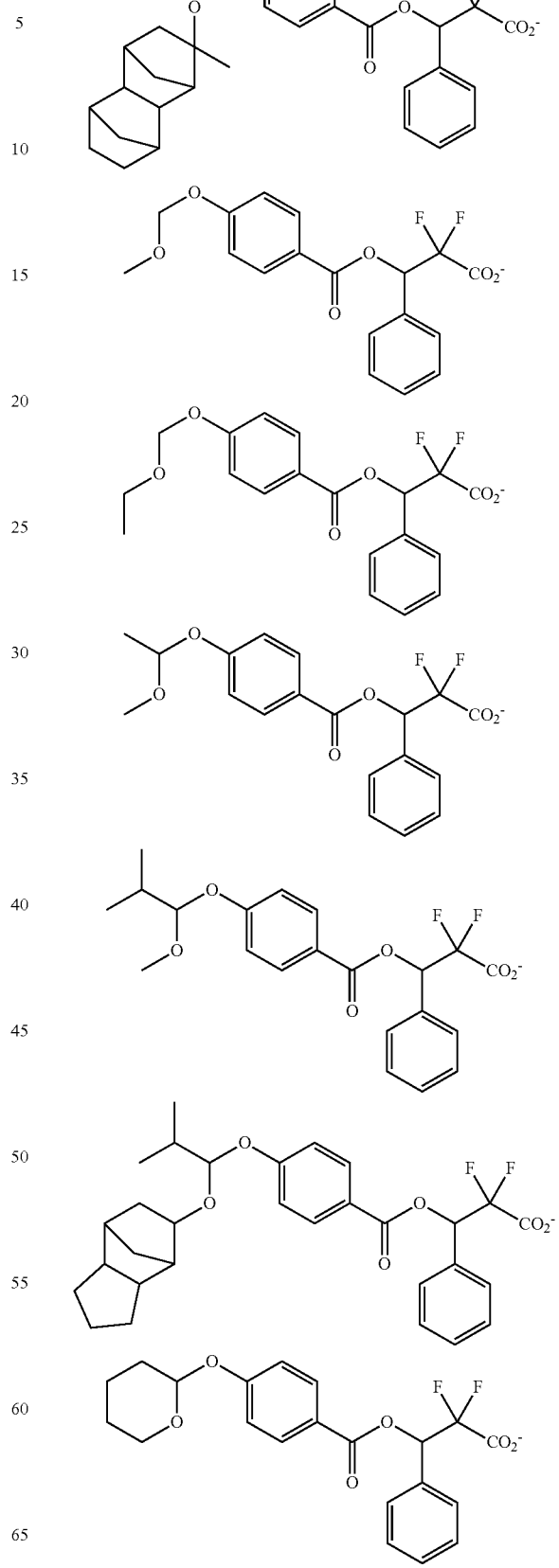

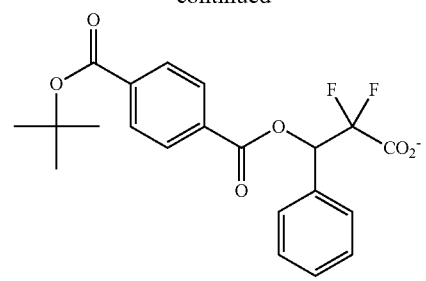
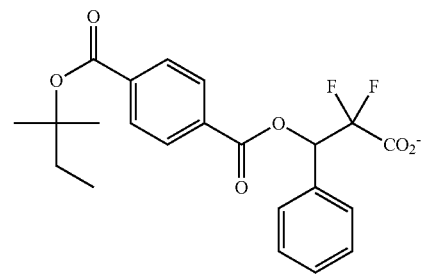
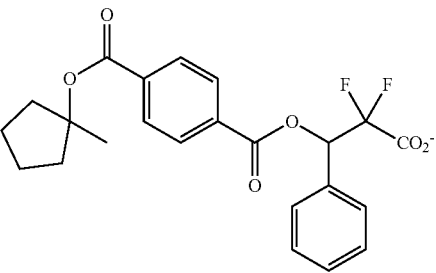
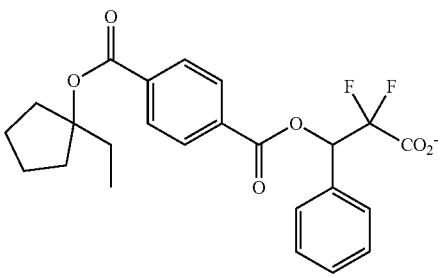
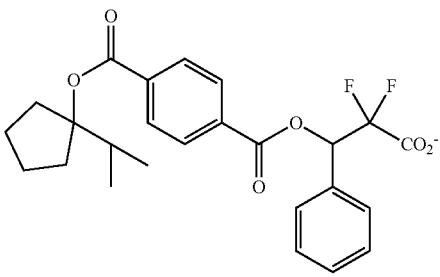
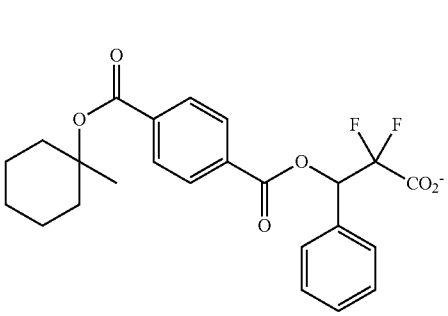
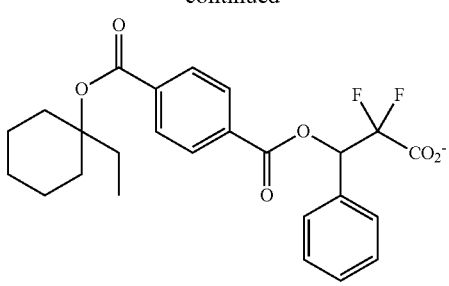
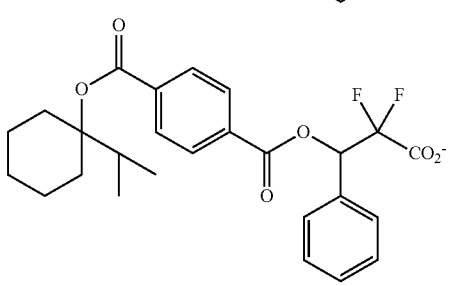
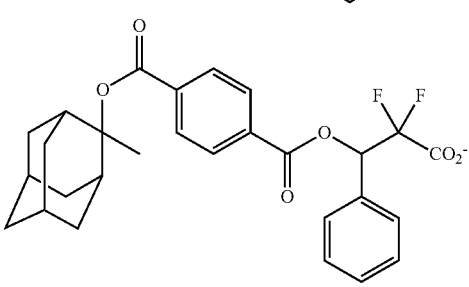
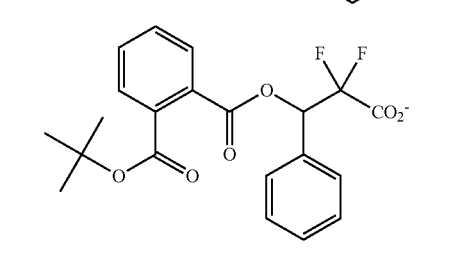
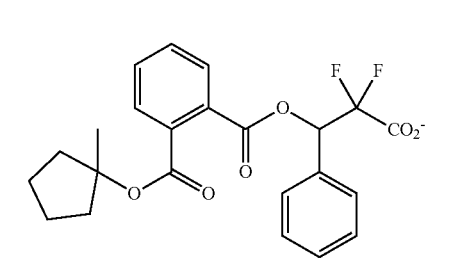

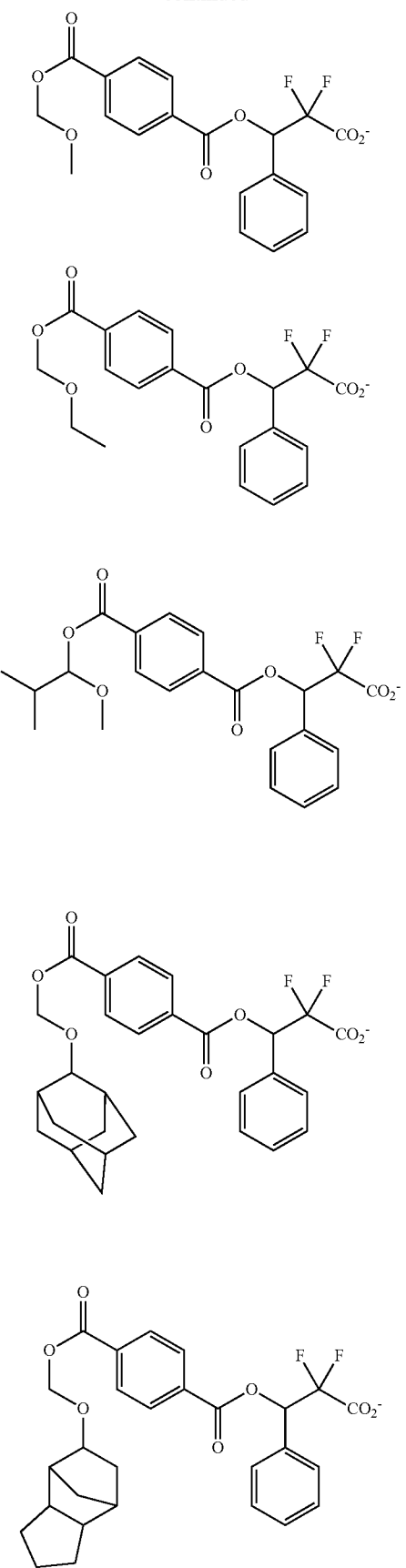
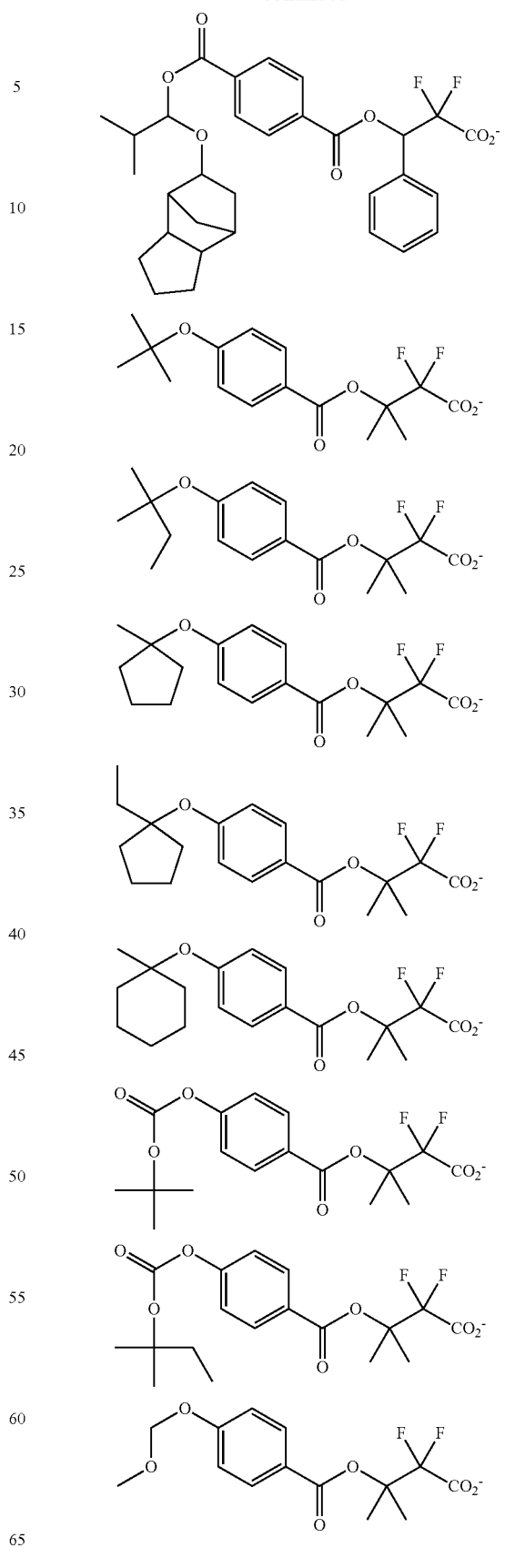

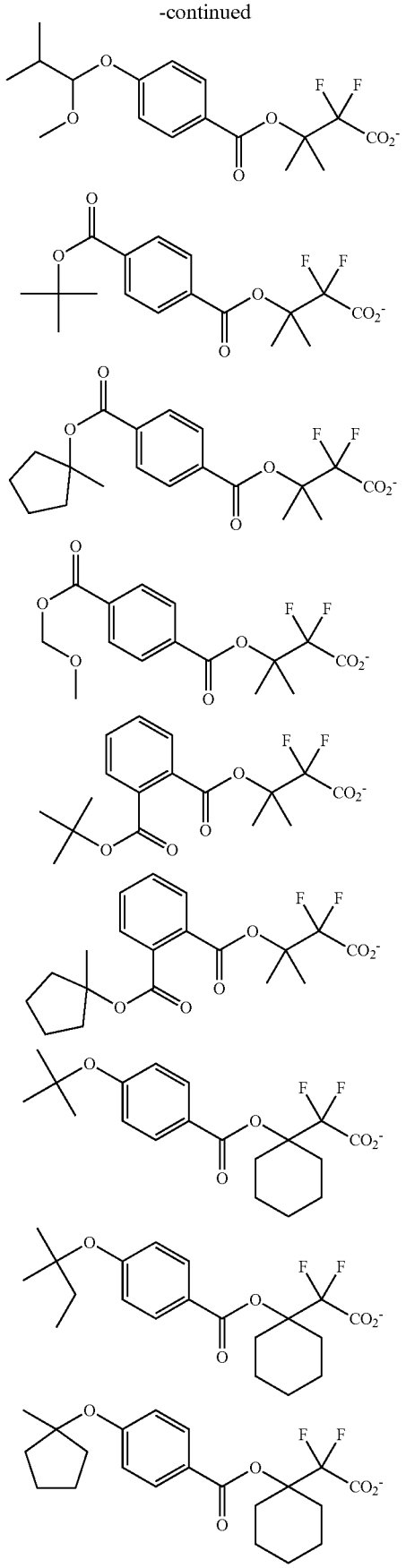
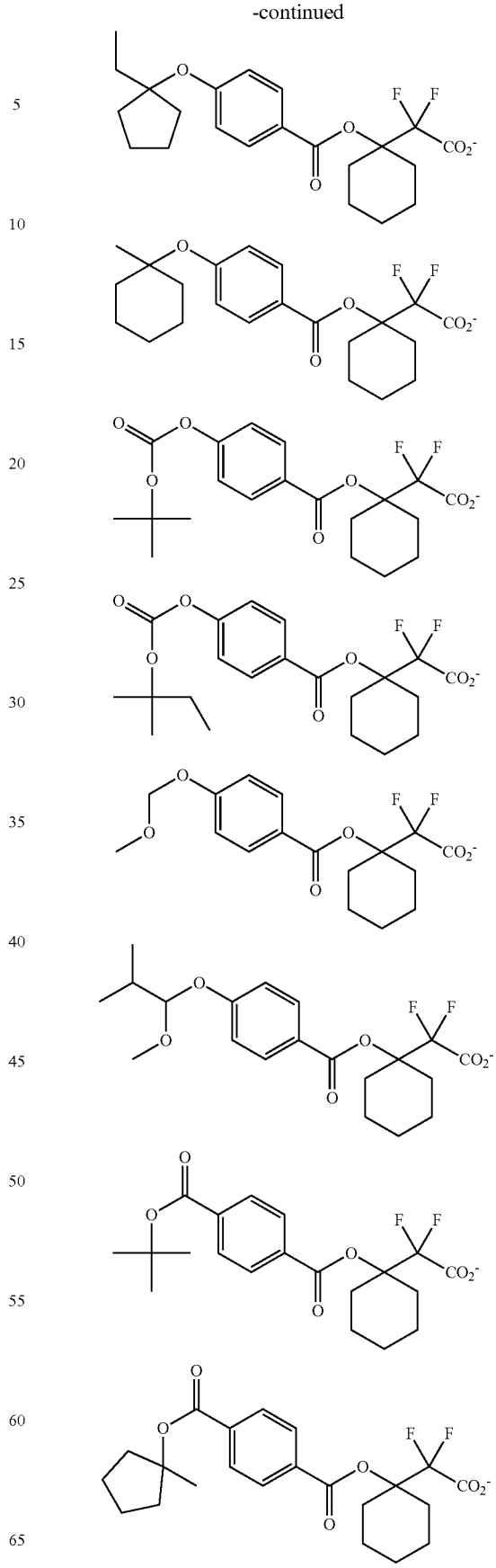

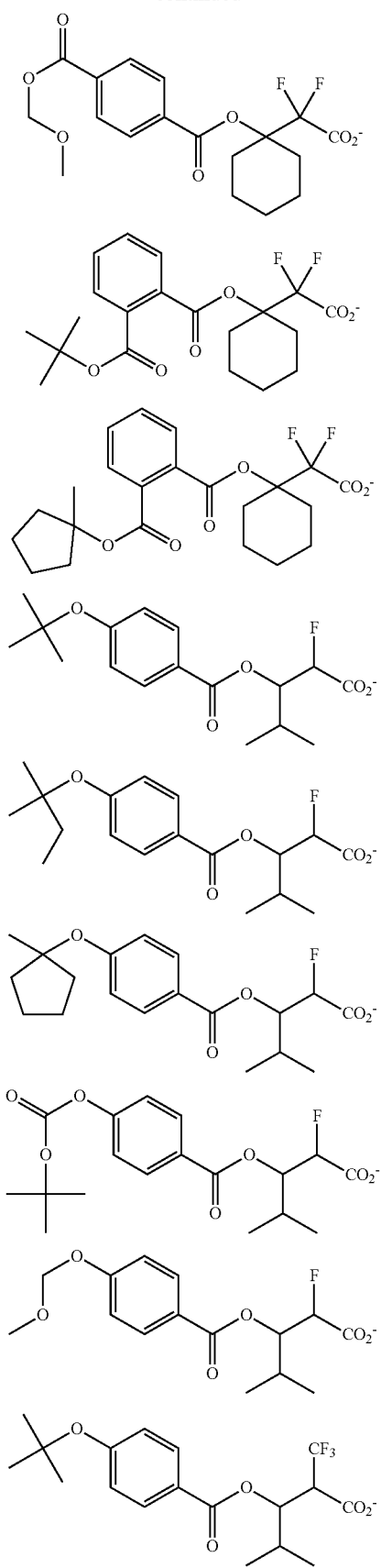
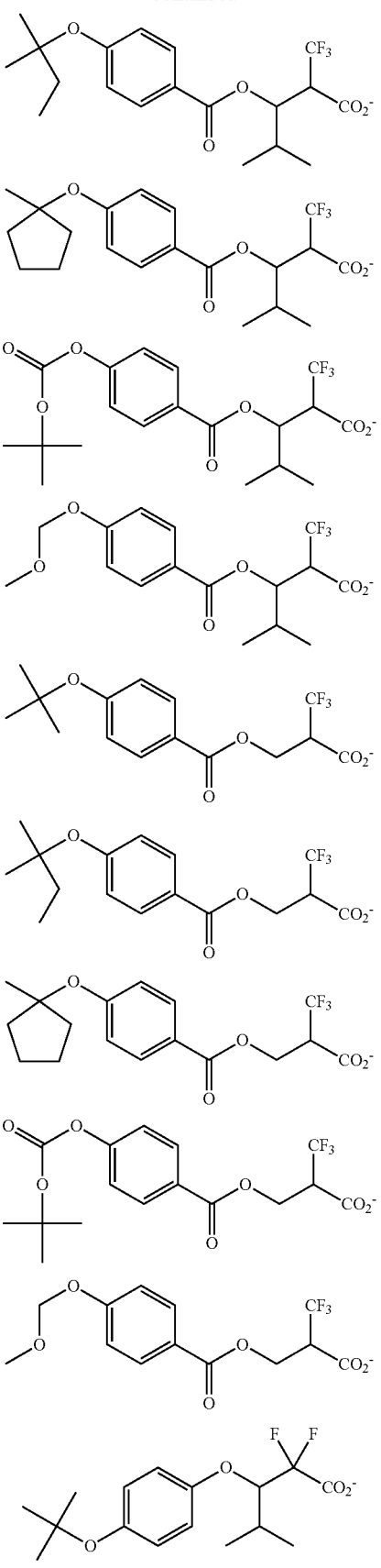

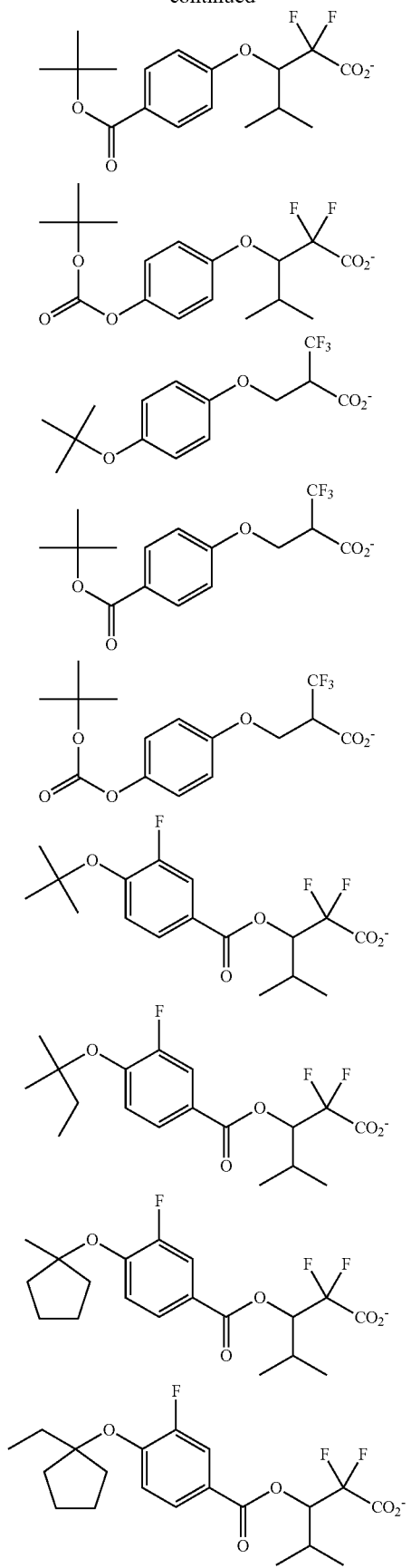
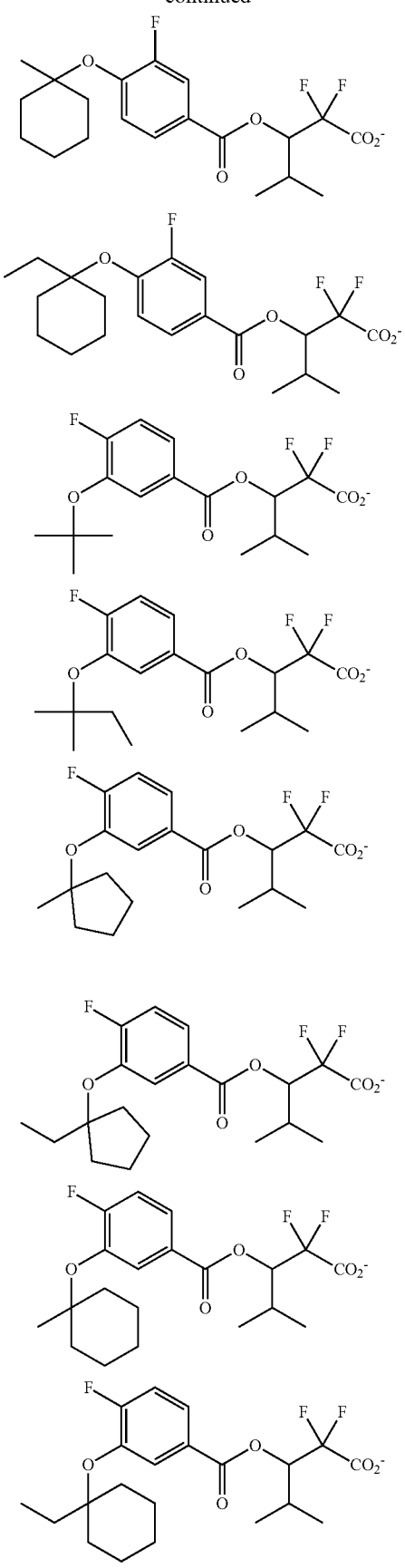

73
-continued
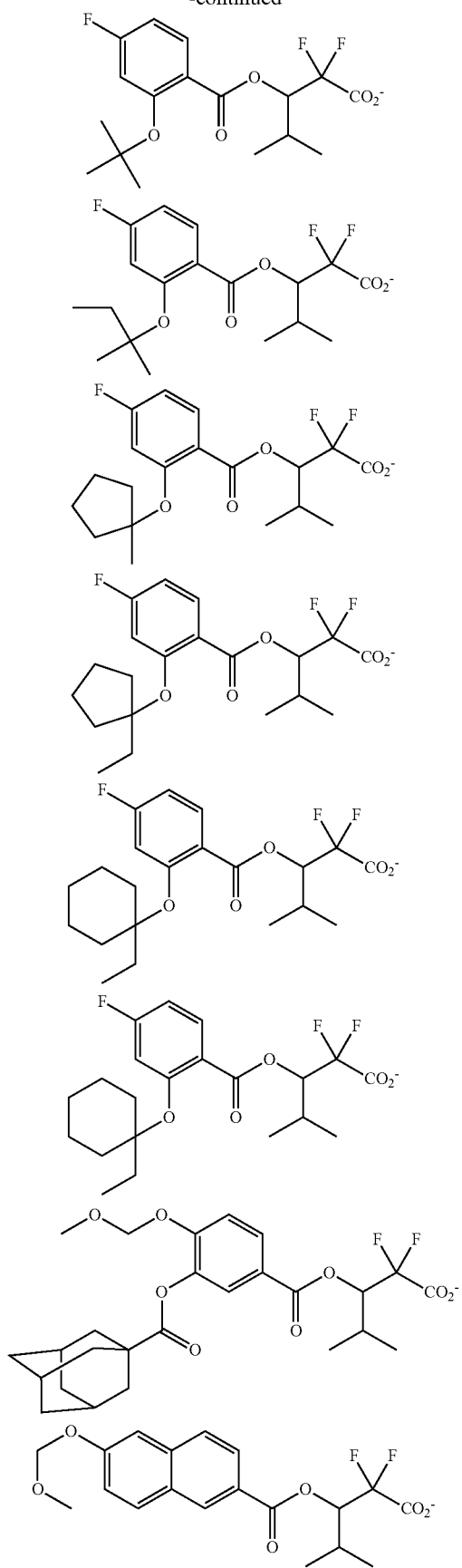
74
-continued
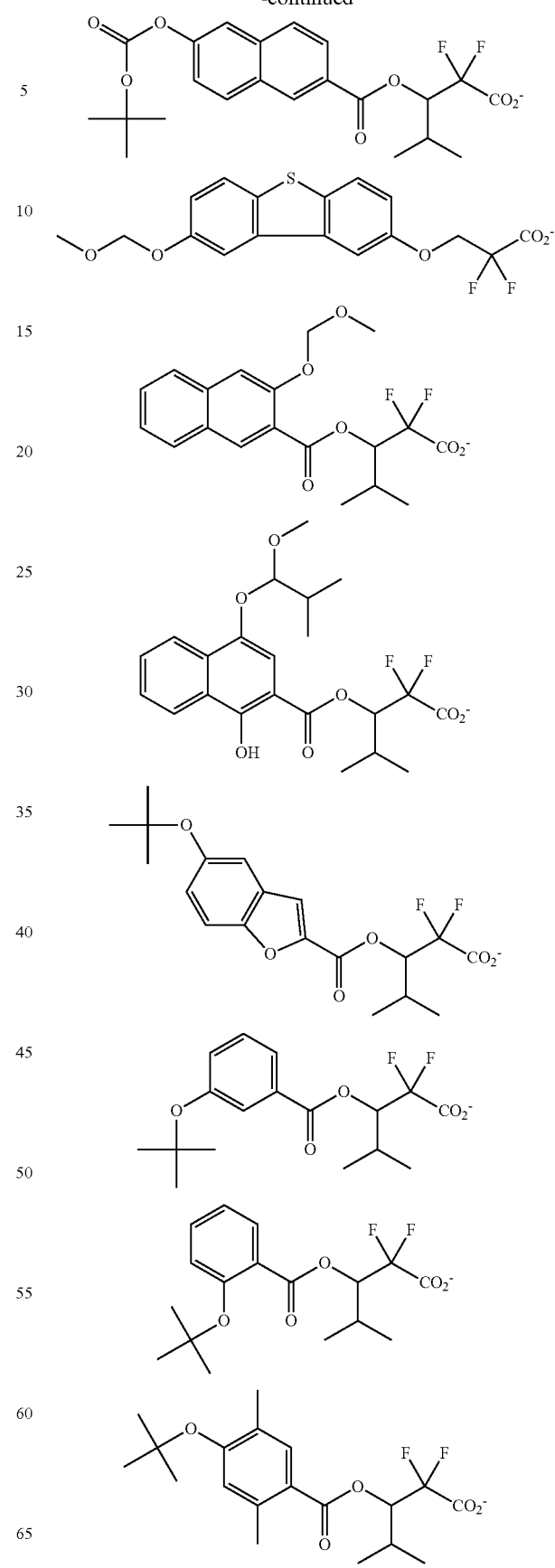

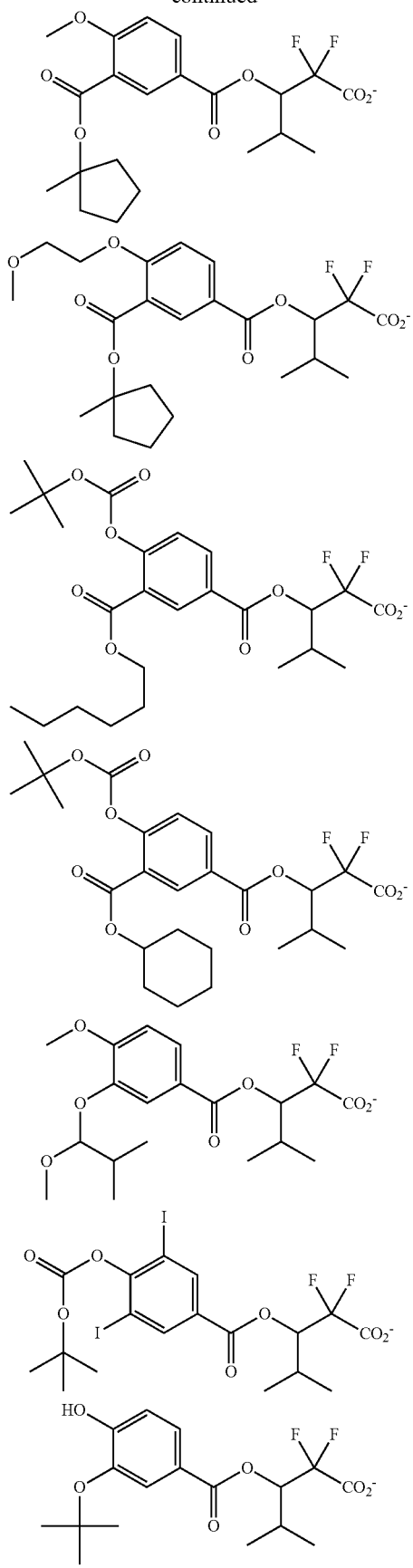
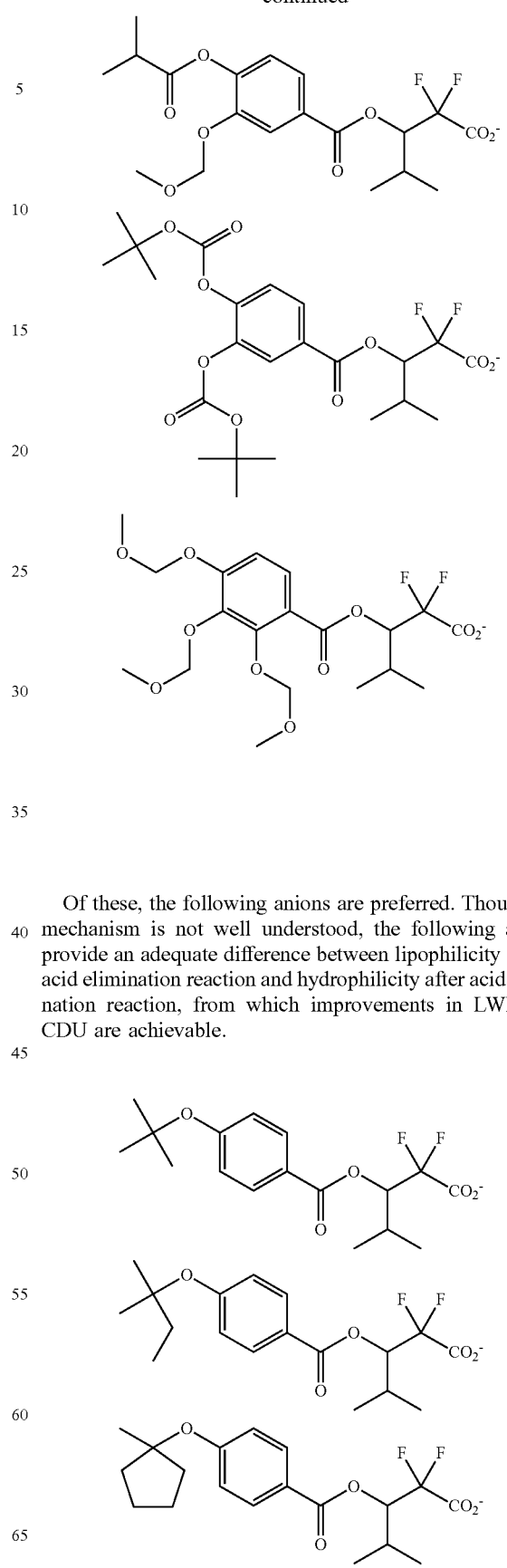
Of these, the following anions are preferred. Though the mechanism is not well understood, the following anions provide an adequate difference between lipophilicity before acid elimination reaction and hydrophilicity after acid elimination reaction, from which improvements in LWR and CDU are achievable.

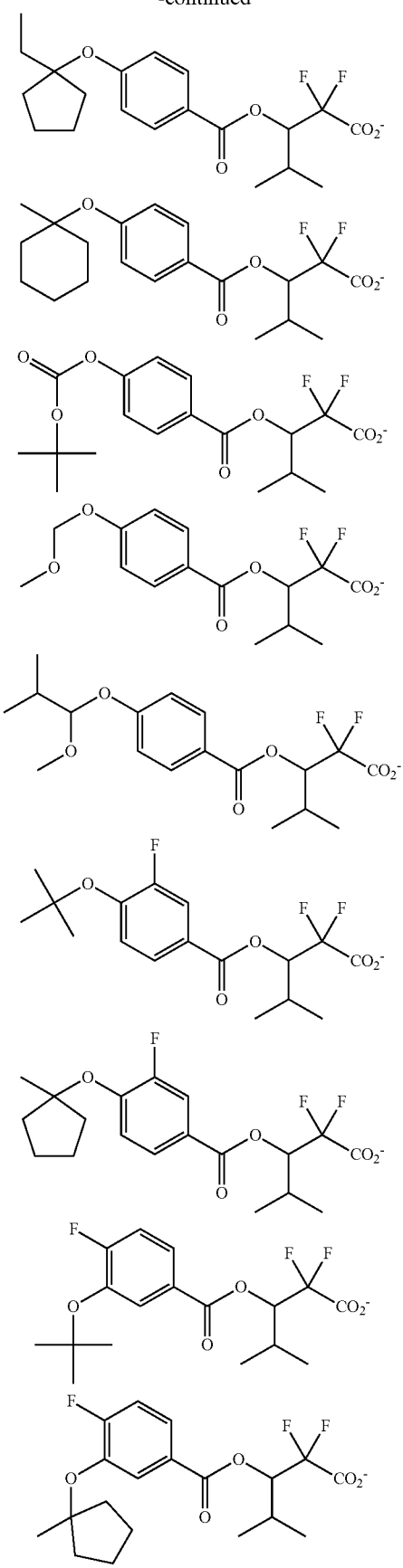

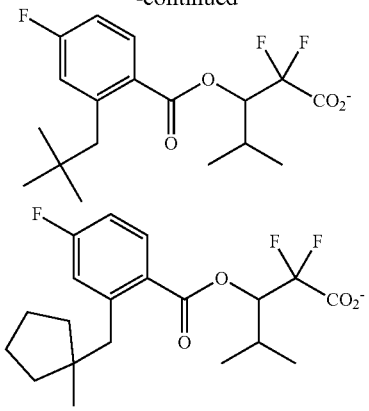

Exemplary structures for the onium salt compound of the invention include arbitrary combinations of cations with anions, both as exemplified above.

The onium salt compound of formula (1) wherein $L^1$ is carbonyl may be synthesized, for example, according to the following Scheme A.

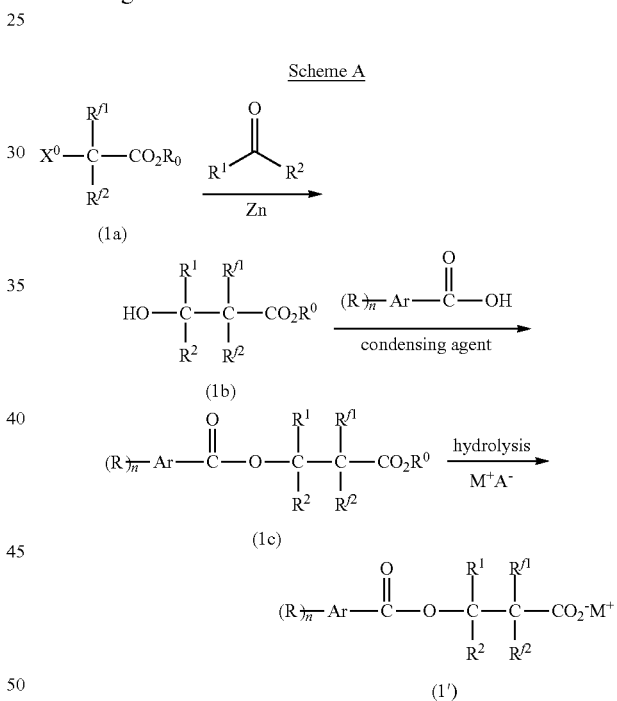

Herein $R^1$, $R^2$, $R^{f1}$, $R^{f2}$, R, Ar, n, and $M^+$ are as defined above. $X^0$ is chlorine, bromine or iodine. $R^0$ is a $C_1$-$C_5$ hydrocarbyl group. $A^-$ is an anion.

In the first step, an α-haloacetate (1a) is reacted with a carbonyl compound in the presence of zinc to synthesize an intermediate compound (1b). Those compounds (1a) wherein $X^0$ is chlorine or bromine and $R^0$ is methyl or ethyl are commercially available.

In the second step, intermediate compound (1b) is condensed or esterified with a carboxylic acid to synthesize an intermediate compound (1c). For the esterification reaction, a condensing agent such as 1-ethyl-3-(3-dimethylaminopropyl)carbodiimide hydrochloride may be used. When a carboxylic acid having an acid labile group is used in the reaction, it is recommended to use the condensing agent because of difficult preparation of acid chloride under acidic conditions. It is possible to introduce an acid labile group after the esterification although this deviates from Scheme A. In this case, besides the reaction with acid chloride, well-known organic chemistry reactions such as reaction with acid anhydride may be used for the esterification.

In the third step, intermediate compound (1c) is hydrolyzed in a standard way to cleave the ester moiety $R^0$. The resulting carboxylate or carboxylic acid is subjected to salt exchange with an onium salt of the desired cation having the formula: $M^+A^-$, whereby the desired onium salt compound (1') is synthesized. It is noted that $A^-$ is preferably a chloride, bromide, iodide, methylsulfate or methanesulfonate anion because exchange reaction takes place in a quantitative manner. The salt exchange in the third step is readily accomplished by any well-known method, for example, with reference to JP-A 2007-145797.

Alternatively, the onium salt compound of formula (1) may be synthesized, for example, according to the following Scheme B.

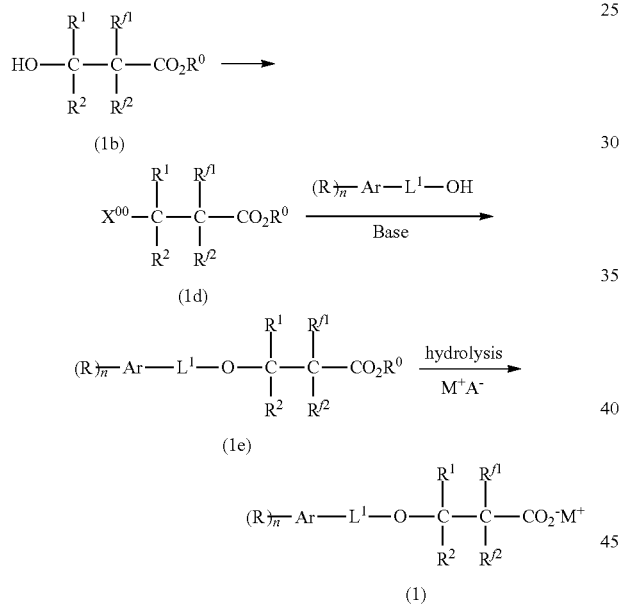

Herein $R^1$, $R^2$, $R^{/1}$, $R^{/2}$, R, $R^0$, Ar, $L^1$, n, $M^+$, and $A^-$ are as defined above. $X^{00}$ is a leaving group.

Once intermediate compound (1b) is synthesized according to Scheme A, it is converted to an intermediate compound (1d) by replacing the hydroxyl group by a leaving group $X^{00}$. The leaving group may be a methanesulfonate or p-toluenesulfonate. The conversion may be achieved by any well-known organic chemistry reaction. The intermediate compound (1d) is then reacted with a phenol or benzenecarboxylic acid under basic conditions, to synthesize an intermediate compound (1e) via nucleophilic substitution reaction. Examples of the base used herein include amines such as triethylamine and diisopropylethylamine, and strong bases such as sodium carbonate, potassium carbonate, sodium hydroxide, potassium hydroxide, and sodium hydride. The final conversion from intermediate compound (1e) to the onium salt compound (1) may be conducted by the same method as in Scheme A.

The synthesis methods mentioned above are merely exemplary and the method is not limited thereto.

Chemically Amplified Resist Composition

Another embodiment of the invention is a chemically amplified resist composition comprising (A) a base polymer adapted to change its solubility in a developer under the action of an acid, (B) a photoacid generator, (C-1) an acid diffusion inhibitor comprising the inventive onium salt compound, and (D) an organic solvent as essential components, and if necessary, (C-2) an acid diffusion inhibitor other than the inventive onium salt compound, (E) a surfactant, and (F) other components.

A further embodiment of the invention is a chemically amplified resist composition comprising (A') a base polymer adapted to change its solubility in a developer under the action of an acid, the base polymer comprising recurring units having a function of generating an acid upon exposure to light, (C-1) an acid diffusion inhibitor comprising the inventive onium salt compound, and (D) an organic solvent as essential components, and if necessary, (B) a photoacid generator, (C-2) an acid diffusion inhibitor other than the inventive onium salt compound, (E) a surfactant, and (F) other components.

(A) Base Polymer

Component (A) is a base polymer adapted to change its solubility in a developer under the action of an acid. It is preferably a polymer comprising recurring units having the formula (a) or recurring units having the formula (b), which are also referred to as recurring units (a) and (b), respectively.

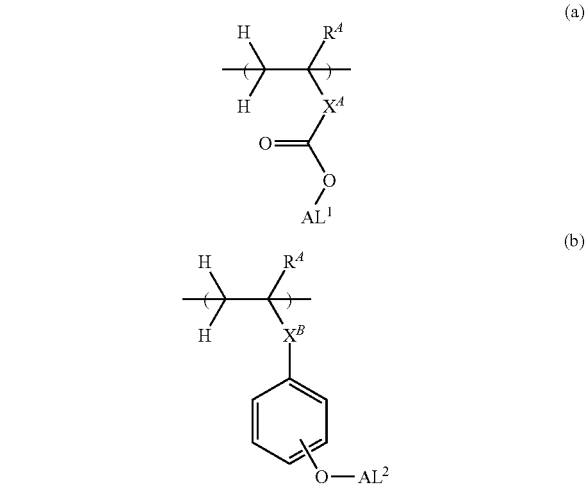

In formulae (a) and (b), $R^A$ is each independently hydrogen or methyl. $X^A$ is a single bond, phenylene group, naphthylene group or (backbone)-C(=O)-O-$X^{A1}$-, wherein $X^{A1}$ is a $C_1$-$C_{15}$ hydrocarbylene group which may contain a hydroxyl moiety, ether bond, ester bond or lactone ring. $X^B$ is a single bond or ester bond. $AL^1$ and $AL^2$ are each independently an acid labile group. The hydrocarbylene group may be saturated or unsaturated and straight, branched or cyclic.

While the acid labile groups represented by $AL^1$ and $AL^2$ are not particularly limited, suitable acid labile groups include $C_4$-$C_{20}$ tertiary hydrocarbyl groups, trialkylsilyl groups in which each alkyl moiety has 1 to 6 carbon atoms, and $C_4$-$C_{20}$ oxoalkyl groups. With respect to the structure of these acid labile groups, reference should be made to U.S. Pat. No. 9,164,384 (JP-A 2014-225005, paragraphs [0016]-[0035]).

Acid labile groups having the following formulae (L1) to (L3) are preferred as $AL^1$ and $AL^2$.

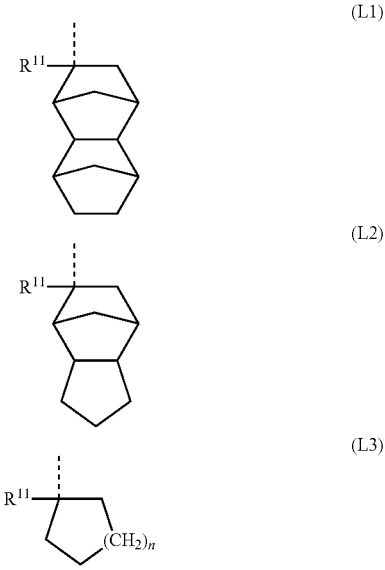

(L1)

(L2)

(L3)

In formulae (L1) to (L3), $R^{11}$ is each independently a $C_1$-$C_7$ hydrocarbyl group in which —$CH_2$— may be replaced by an ether bond, and "a" is 1 or 2.

Of the acid labile groups $AL^1$ and $AL^2$, the following groups are most preferred.

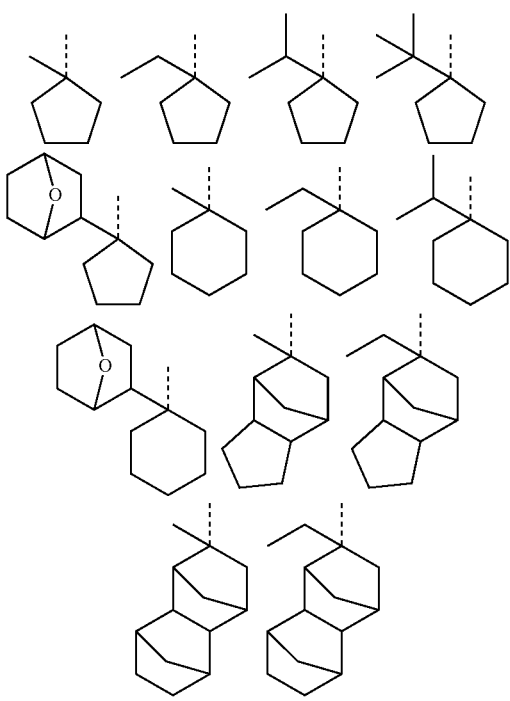

A resist composition comprising a base polymer containing recurring units (a) or (b) having an acid labile group and the inventive onium salt compound is improved in lithography performance. Although the detail is not well understood, the following reason is presumed, when a tertiary alicyclic hydrocarbyl group having formula (L1), (L2) or (L3) is bonded to the ester site, the group becomes more acid labile or decomposable due to steric repulsion than other chainlike tertiary alkyl groups such as tert-butyl and tert-pentyl. Also, as compared with acid labile groups having adamantane ring, the acid labile group having formula (L1), (L2) or (3) allows for easy progress of acid-aided elimination reaction, tending to provide a high sensitivity. Therefore, when a tertiary alicyclic hydrocarbyl group is incorporated in the polarity switch unit of the base polymer in a resist composition, the dissolution contrast between exposed and unexposed regions is increased. While the inventive onium salt compound serves as an acid diffusion inhibitor, the carboxylic acid generated after quenching of a strong acid has a relatively high acidity. When the inventive onium salt compound is used in combination with acid labile group units having high reactivity, the acid generated after quenching promotes elimination reaction, though to a slight extent, leading to an improvement in contrast. As a result, lithography performance is improved. Although the acid labile group of tertiary ether type as represented by formula (b) is typically low in acid elimination reactivity, the acid elimination reaction is promoted in the co-presence of a protonic hydroxyl group having high acidity like phenol. As a result, there are obtained similar effects to the aforementioned tertiary ester type.

While examples of the structure having formula (a) wherein $X^A$ is a variant include the structures described in U.S. Pat. No. 9,164,384 (JP-A 2014-225005, paragraph [0015]). Of these, preferred structures are shown below. Herein $R^A$ and $AL^1$ are as defined above.

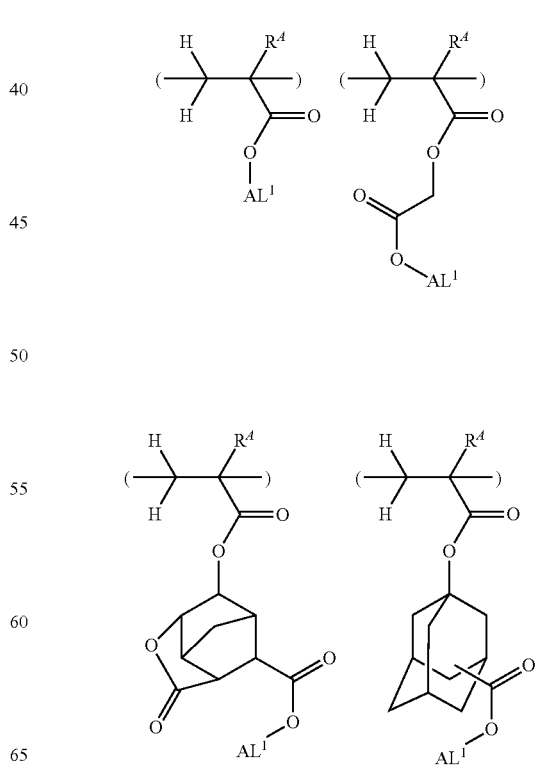

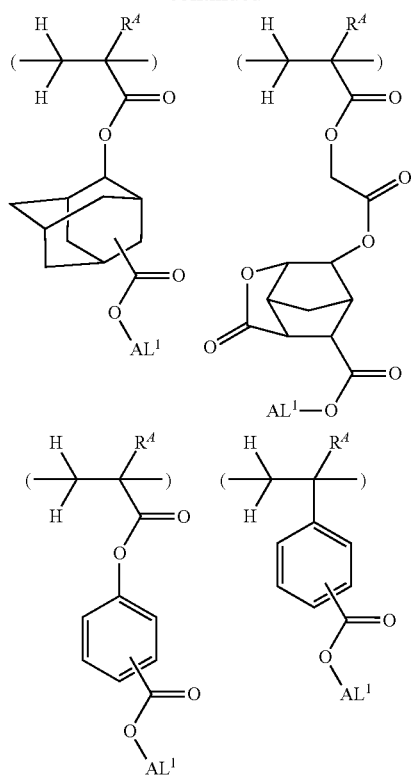
Examples of the recurring unit (a) are given below, but not limited thereto. Herein $R^A$ is as defined above.
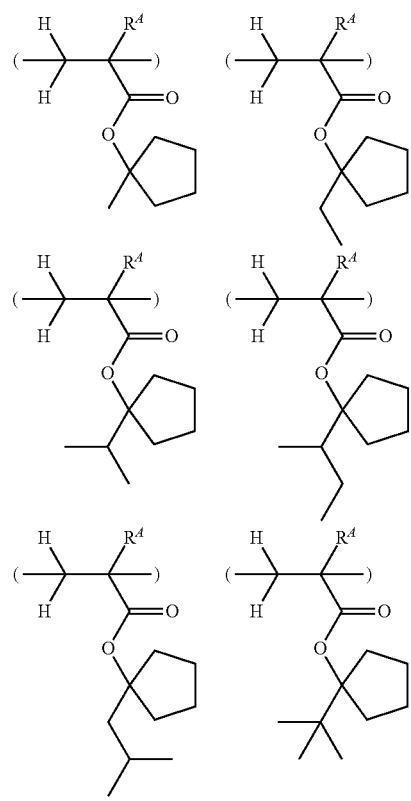
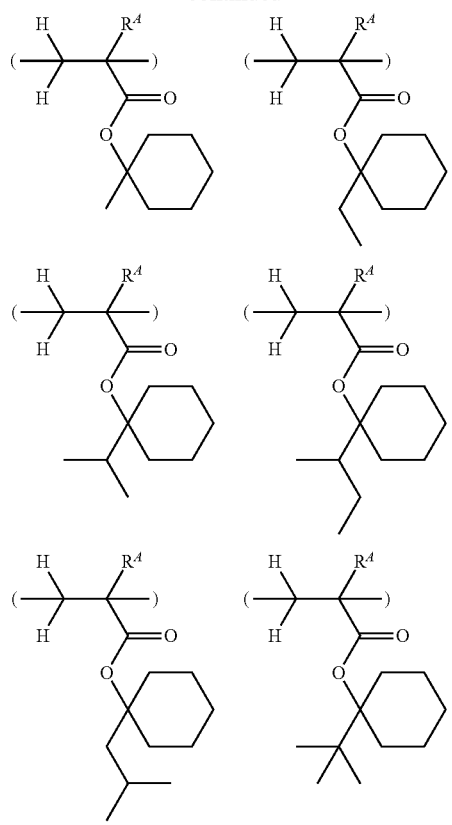

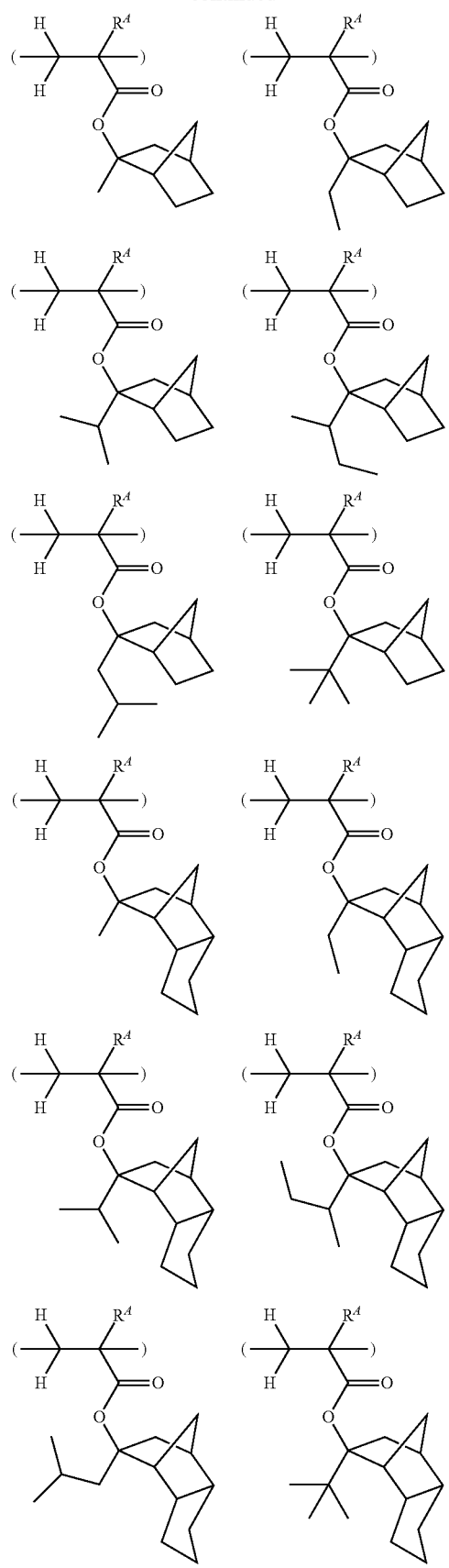
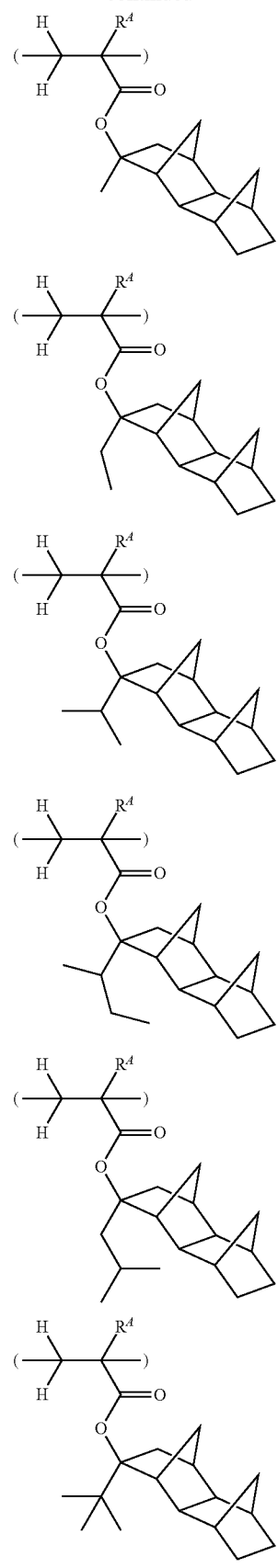

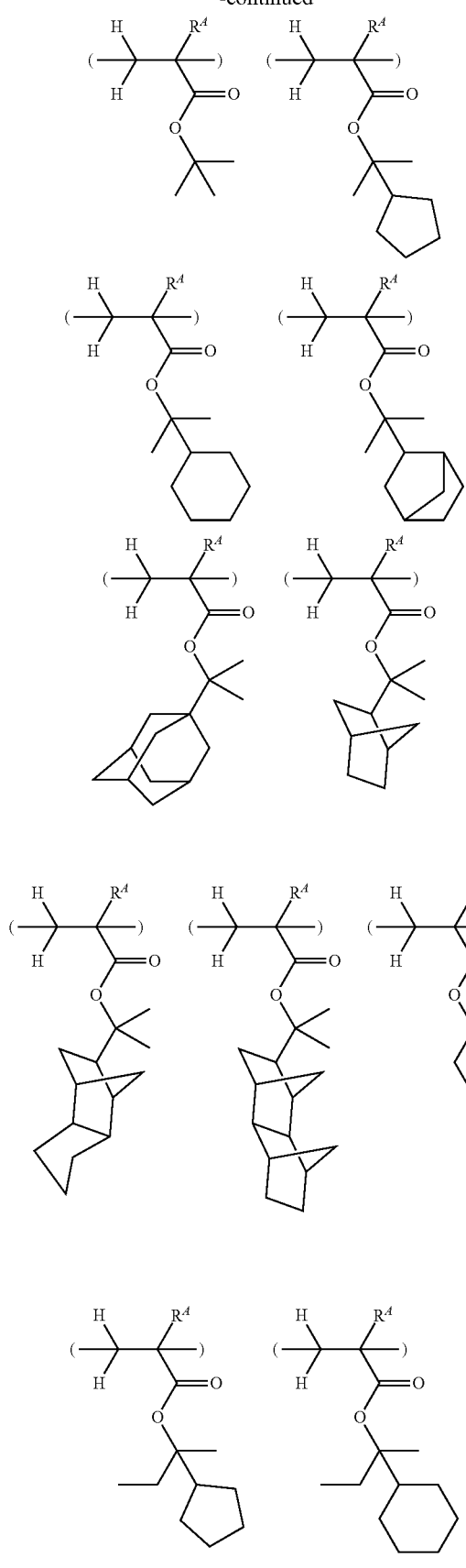
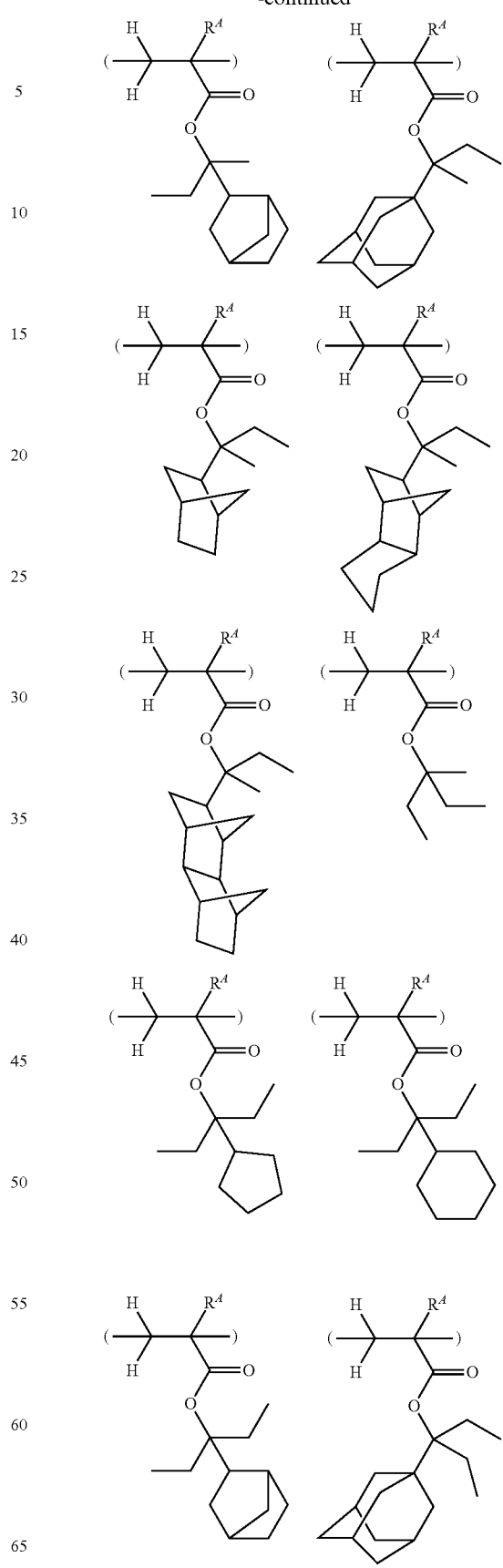

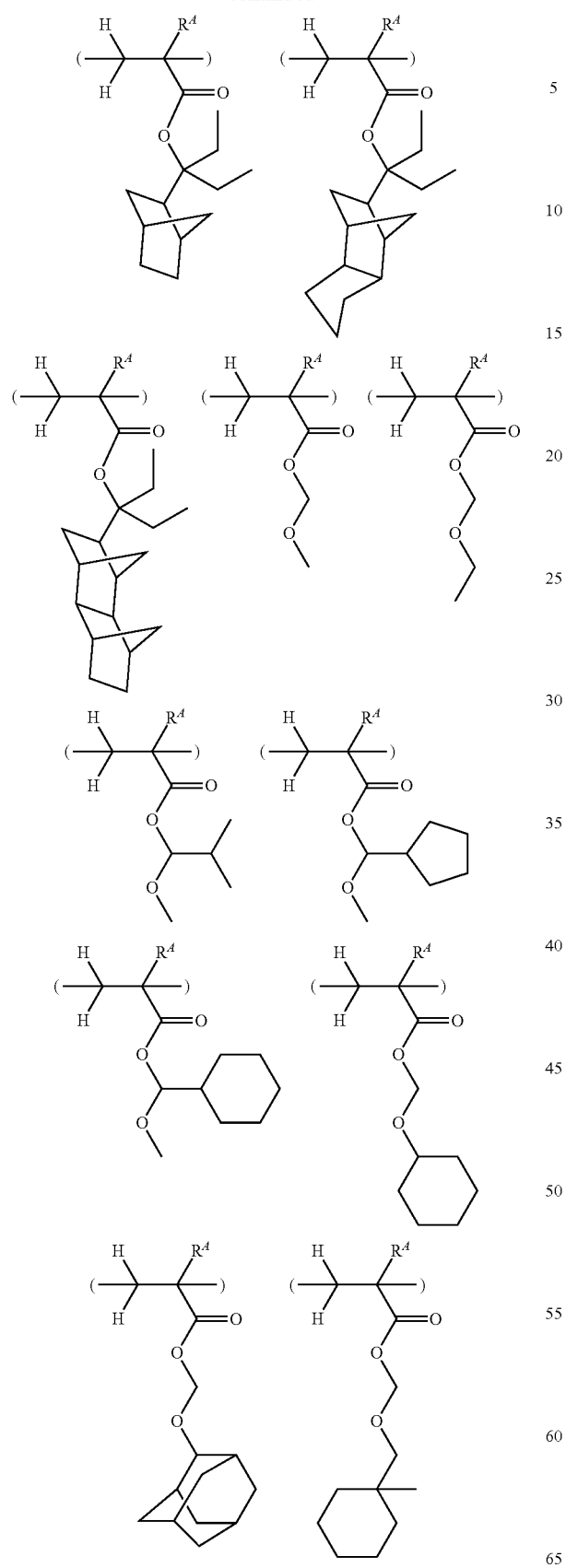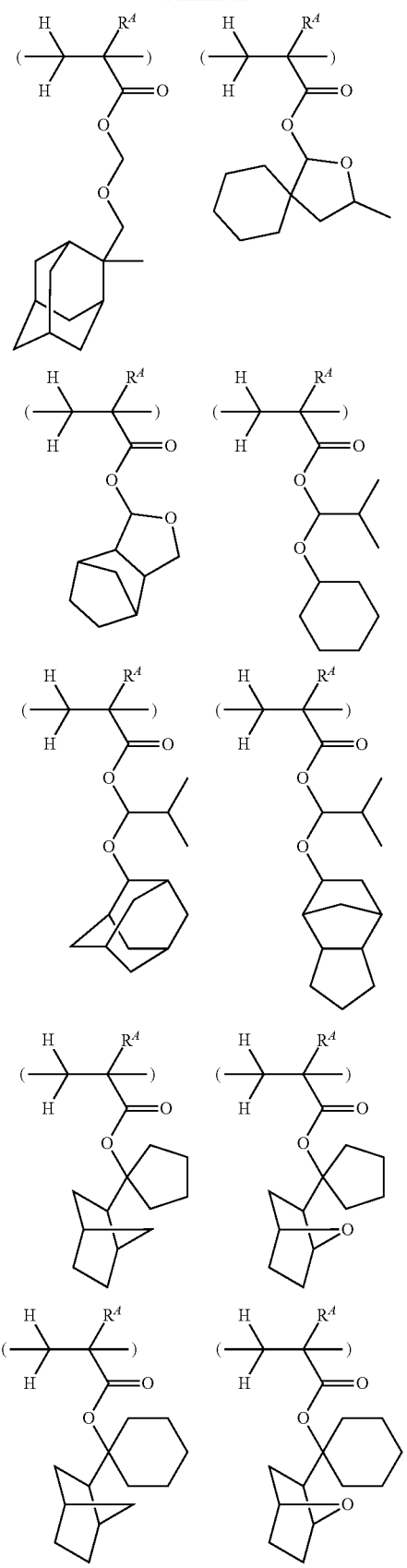

-continued
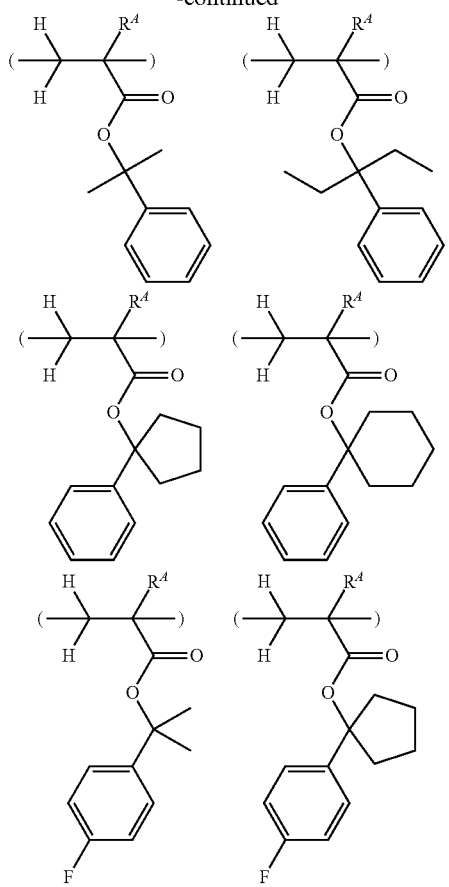
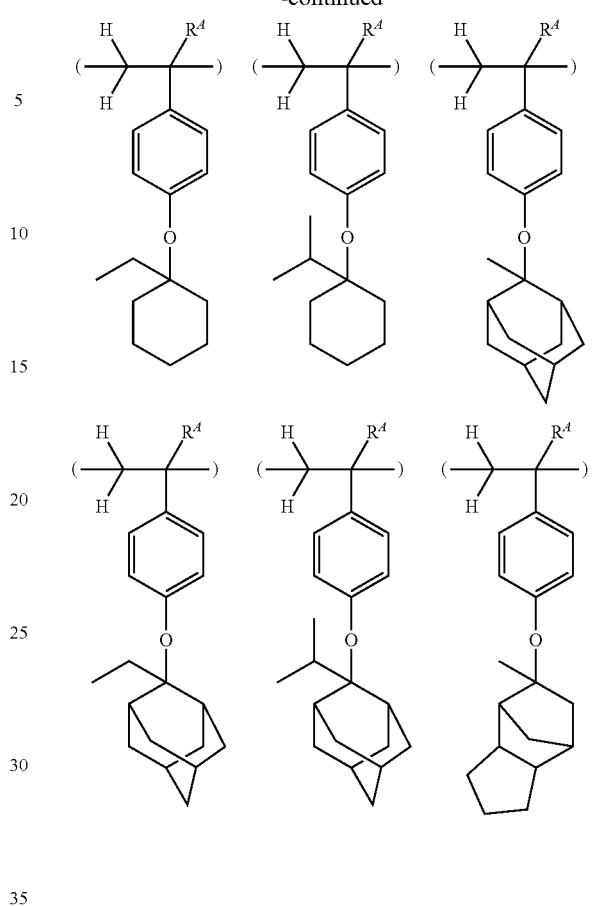
Examples of the recurring unit (b) are given below, but not limited thereto. Herein $R^A$ is as defined above.
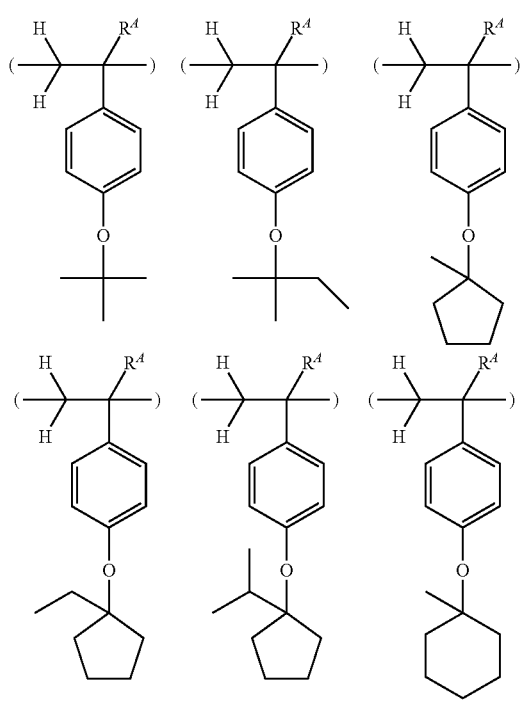
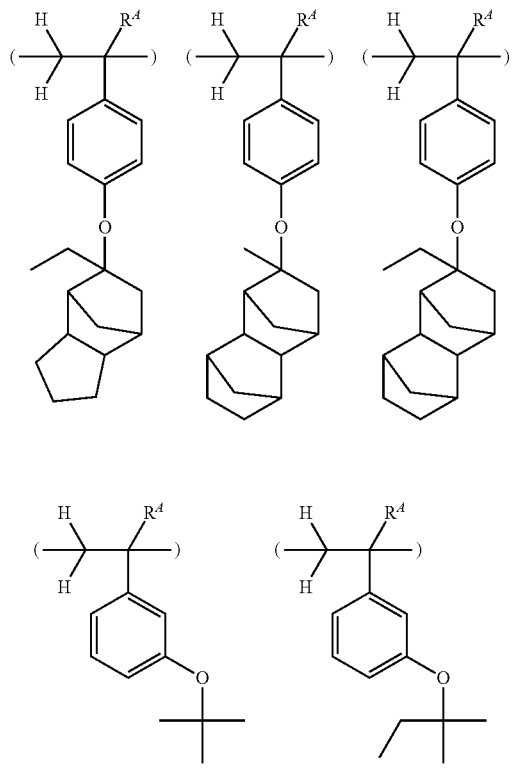

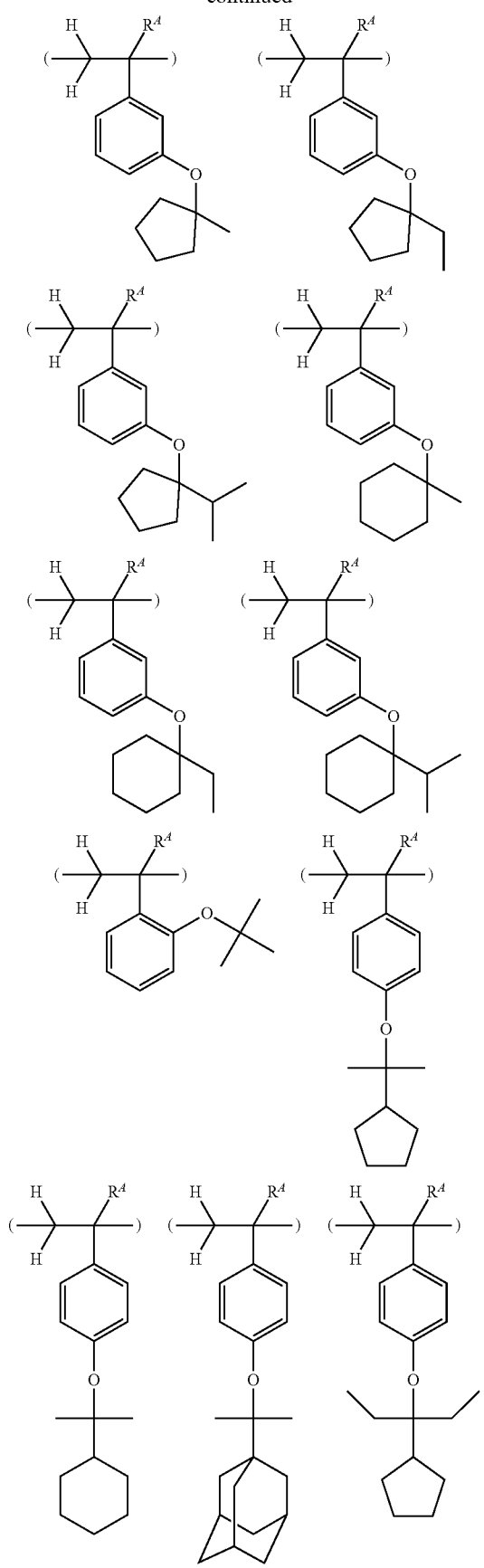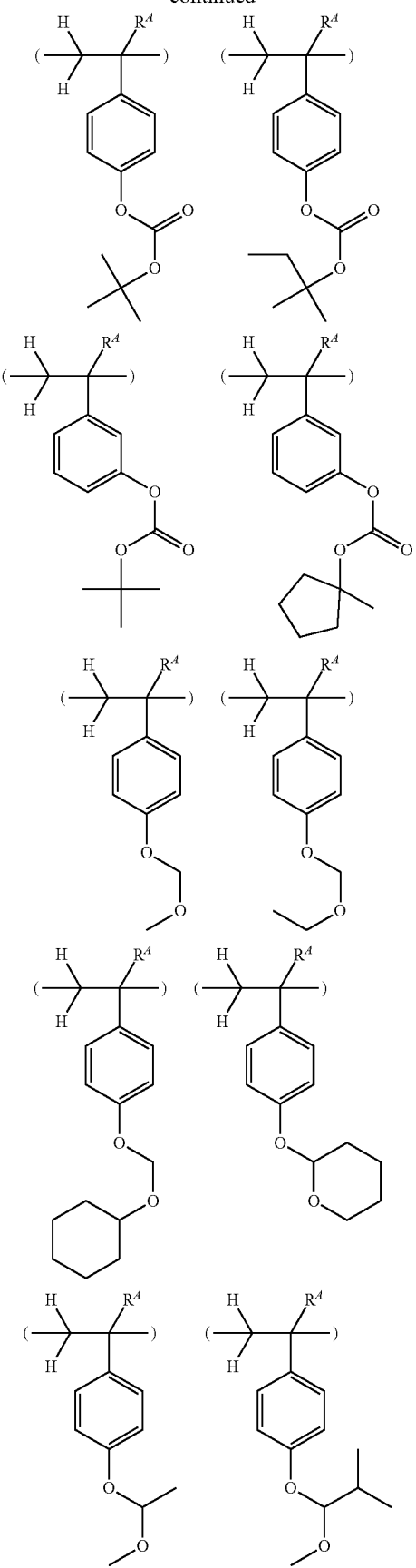

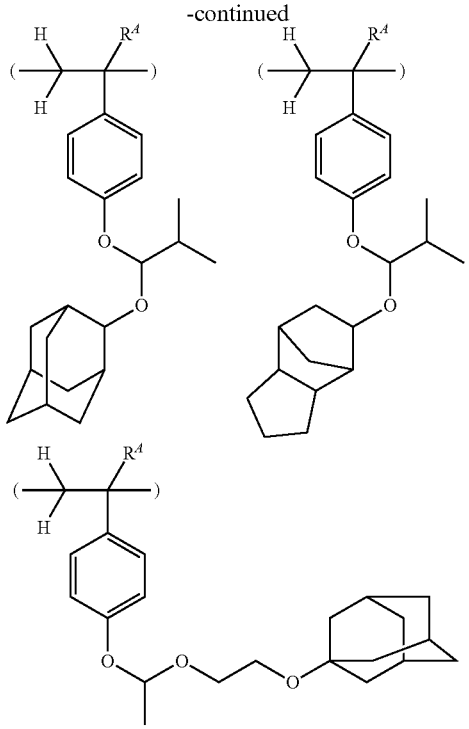

Although the above examples correspond to the unit wherein $X^A$ or $X^B$ is a single bond, combinations with similar acid labile groups are possible where $X^A$ or $X^B$ is other than a single bond. Examples of the units wherein $X^A$ is other than a single bond are as exemplified above. Examples of the units wherein $X^B$ is an ester bond correspond to the above-exemplified units wherein the single bond between the backbone and the benzene ring is replaced by an ester bond.

The base polymer may further comprise recurring units having the formula (c), which are also referred to as recurring units (c).

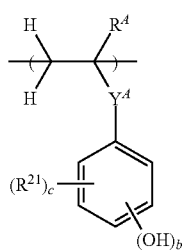

(c)

In formula (c), $R^A$ is hydrogen or methyl. $Y^A$ is a single bond or ester bond.

In formula (c), $R^{21}$ is fluorine, iodine or a $C_1$-$C_{10}$ hydrocarbyl group. The hydrocarbyl group may be saturated or unsaturated and straight, branched or cyclic. Examples include alkyl groups such as methyl, ethyl, propyl, isopropyl, n-butyl, sec-butyl, tert-butyl, n-pentyl, n-hexyl, n-octyl, n-nonyl, and n-decyl: cyclic saturated hydrocarbyl groups such as cyclopentyl, cyclohexyl, and adamantyl: aryl groups such as phenyl; and combinations thereof.

A constituent —$CH_2$— in the hydrocarbyl group may be replaced by an ether bond or carbonyl group. The constituent —$CH_2$— in the hydrocarbyl group may be one bonding to a carbon atom on the benzene ring in formula (c). Examples of the substituted hydrocarbyl group include, but are not limited to, methoxy, ethoxy, propoxy, butoxy, phenoxy, 2-methoxyethoxy, acetyl, ethylcarbonyl, hexylcarbonyl, acetoxy, ethylcarbonyloxy, propylcarbonyloxy, pentylcarbonyloxy, hexylcarbonyloxy, heptylcarbonyloxy, methoxymethylcarbonyloxy, (2-methoxyethoxy)methylcarbonyloxy, methyloxycarbonyl, ethyloxycarbonyl, hexyloxycarbonyl, phenyloxycarbonyl, acetoxymethyl, phenoxymethyl, and methoxycarbonyloxy. Preferably $R^{21}$ is fluorine, iodine, methyl, acetyl or methoxy.

In formula (c), b is an integer of 1 to 5, c is an integer of 0 to 4, and b+c is 1 to 5. Preferably b is 1, 2 or 3, and c is 0, 1 or 2.

The recurring unit (c) serves to improve the adhesion to the substrate or the underlay film. Since the recurring unit (c) has a phenolic hydroxyl group with high acidity, it promotes the action of an acid generated upon exposure, contributing to a higher sensitivity, and becomes a proton source to the acid generated upon EUV exposure, from which an improvement in sensitivity is expectable.

Examples of the recurring unit (c) are given below, but not limited thereto. Herein $R^A$ is as defined above.

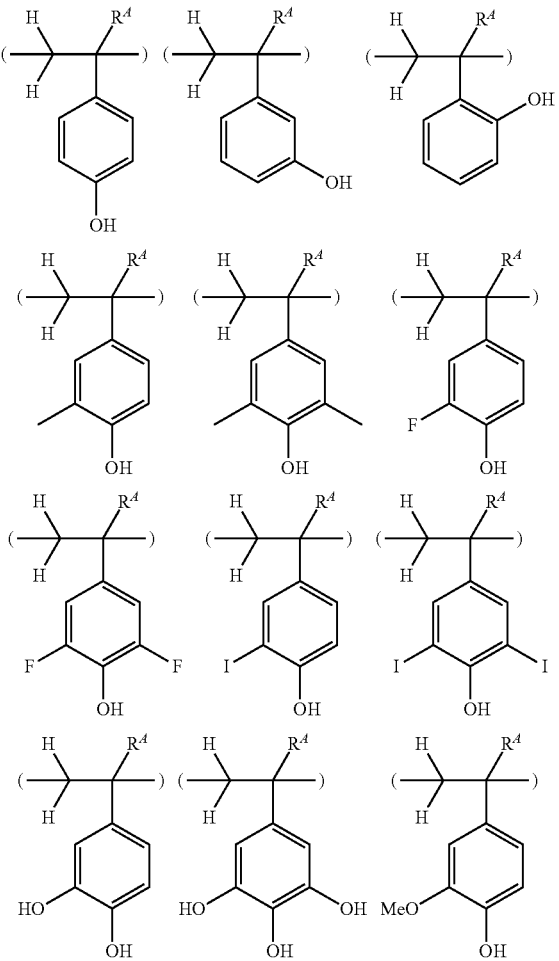

-continued
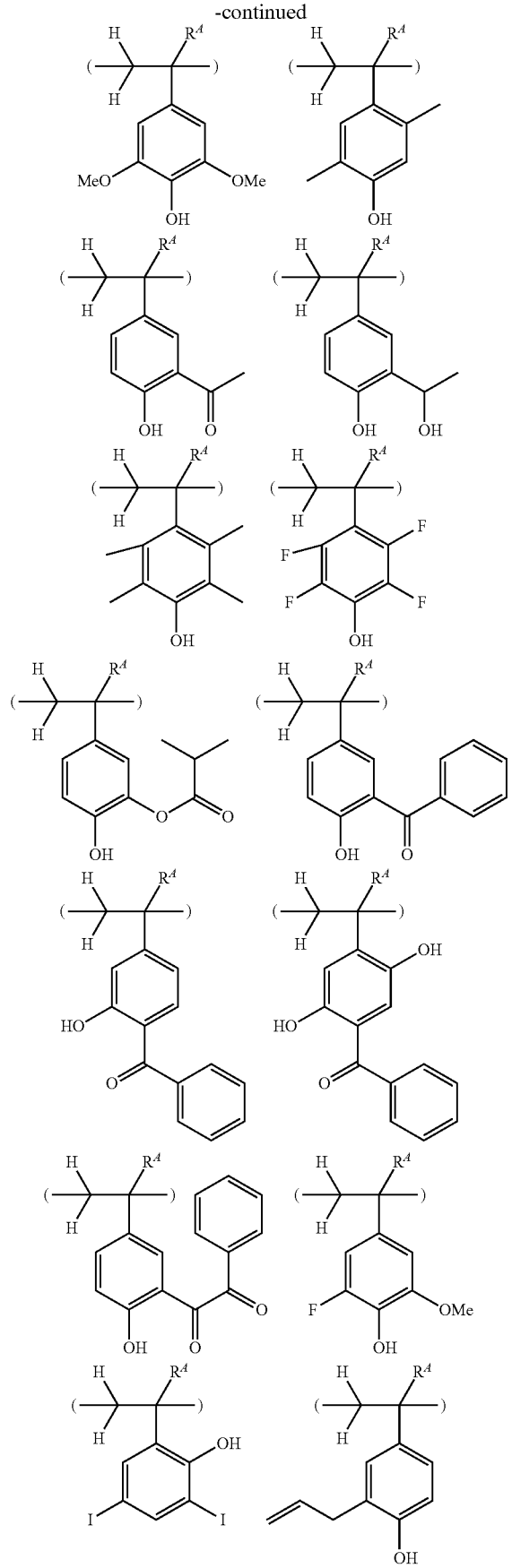
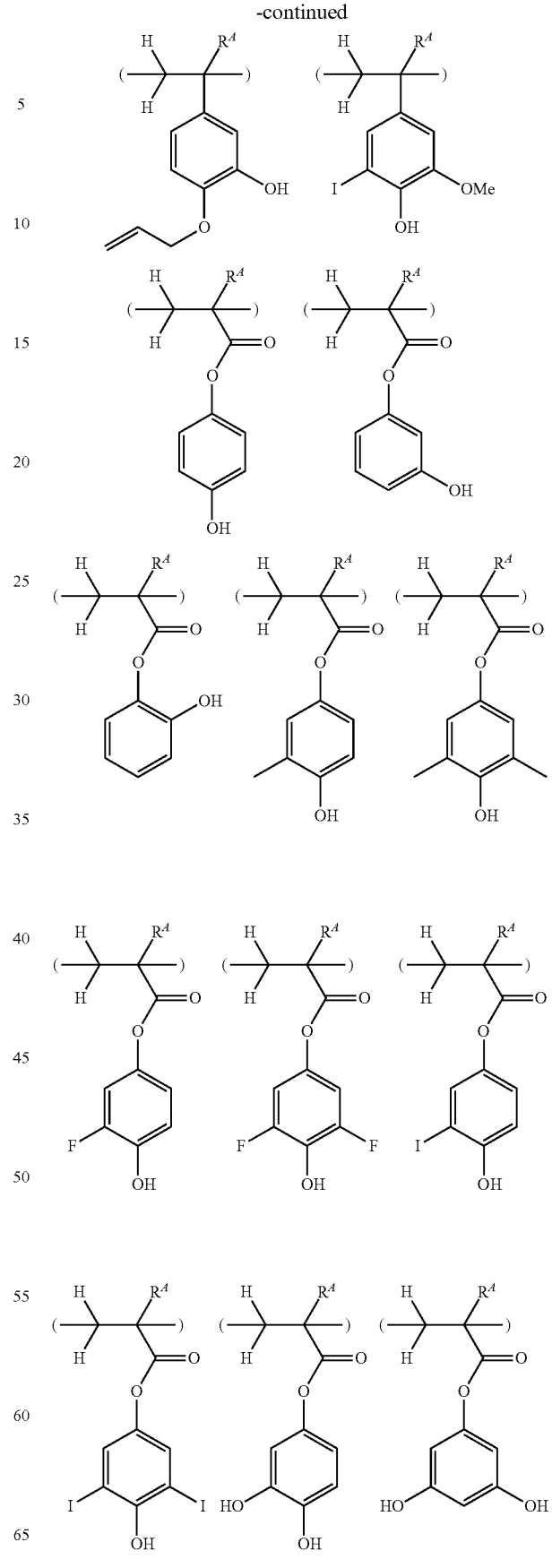

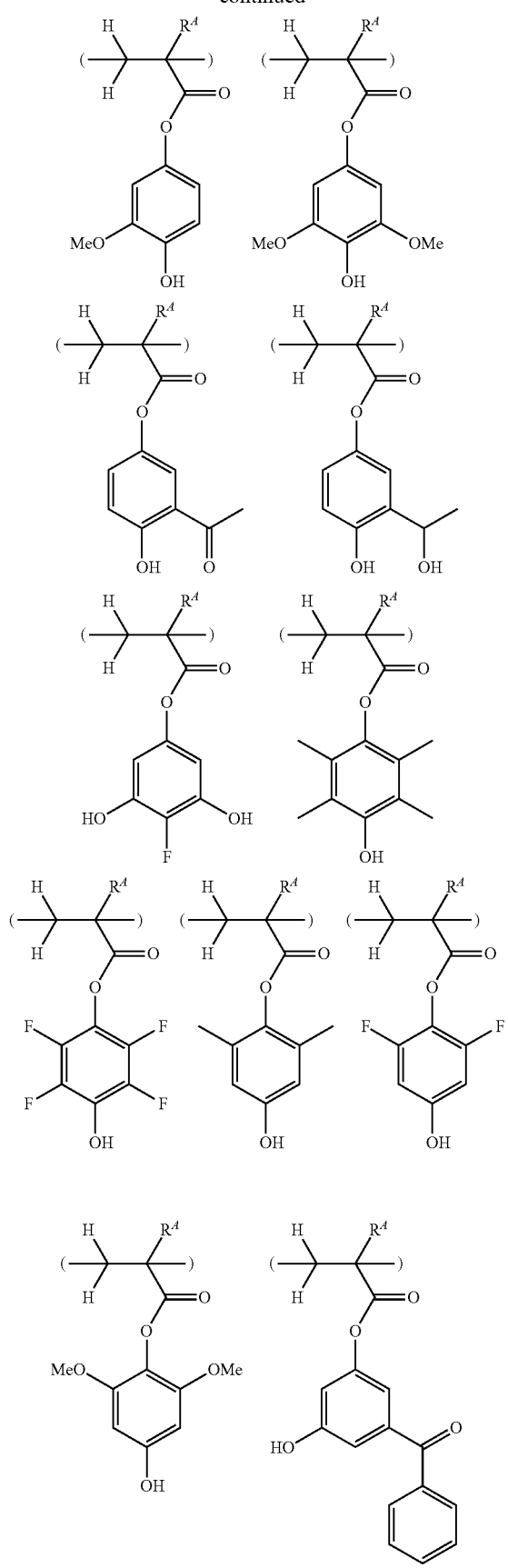
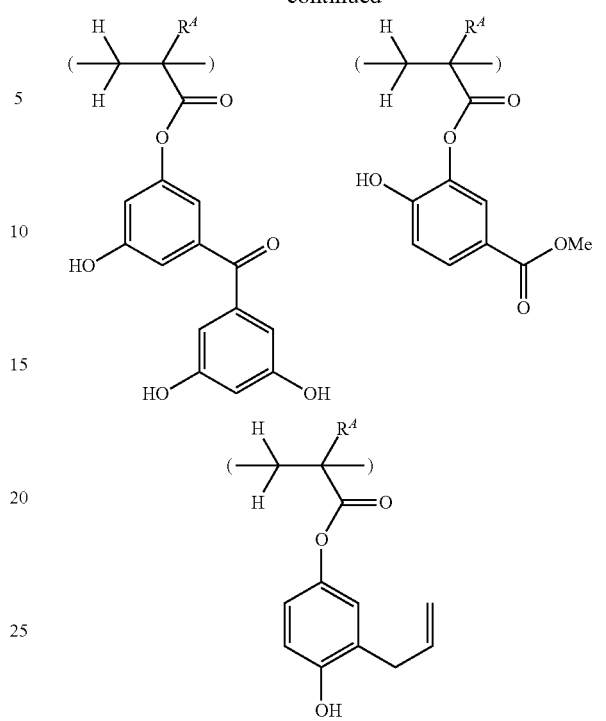
Of the above recurring units (c), the following units are preferred. Herein $R^A$ is as defined above.
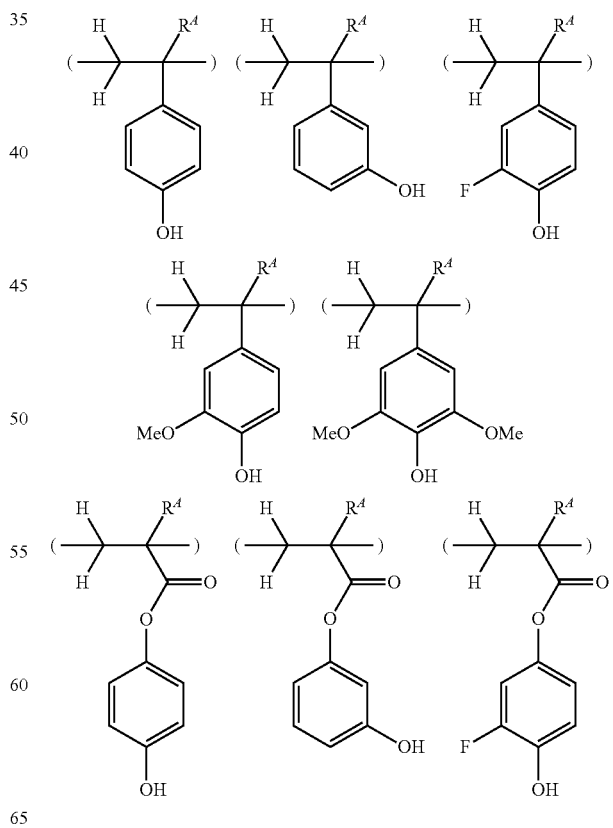

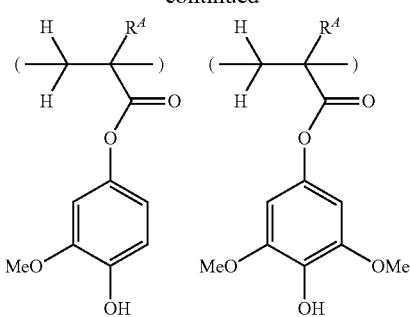

The base polymer may further comprise recurring units having the formula (d1), (d2), (6) or (d4), which are also referred to as recurring units (d1) to (d4), respectively.

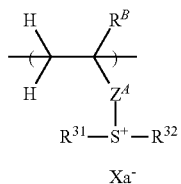
(d1)

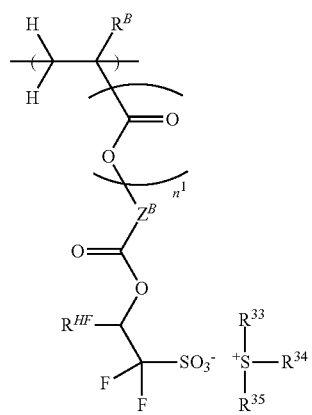
(d2)

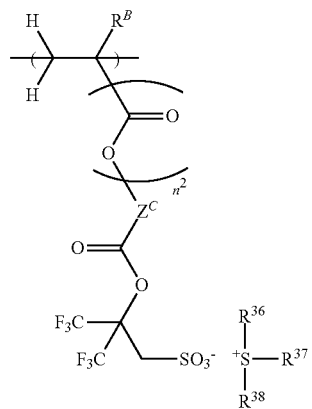
(d3)

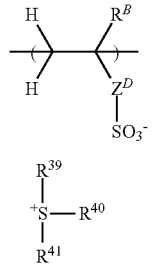
(d4)

In formulae (d1) to (d4), $R^B$ is each independently hydrogen, fluorine, methyl or trifluoromethyl. $Z^A$ is a single bond, phenylene, $-O-Z^{41}-$, $-C(=O)-O-Z^{41}-$ or $-C(=O)-NH-Z^{41}-$, wherein $Z^{41}$ is a $C_1$-$C_{20}$ hydrocarbylene group which may contain a heteroatom. $Z^B$ and $Z^C$ are each independently a single bond or a $C_1$-$C_{20}$ hydrocarbylene group which may contain a heteroatom. $Z^D$ is a single bond methylene, ethylene, phenylene, fluorinated phenylene, $-O-Z^{D1}-$, $-C(=O)-O-Z^{D1}-$ or $-C(=O)-NH-Z^{D1}-$, wherein $Z^{D1}$ is an optionally substituted phenylene group.

The hydrocarbylene group represented by $Z^{41}$ may be saturated or unsaturated and straight, branched or cyclic. Examples thereof include alkanediyl groups such as methylene, ethane-1,1-diyl, ethane-1,2-diyl, propane-1,2-diyl, propane-2,2-diyl, propane-1,3-diyl, 2-methylpropane-1,3-diyl, butane-1,3-diyl, butane-2,3-diyl, butane-1,4-diyl, pentane-1,3-diyl, pentane-1,4-diyl, 2,2-dimethylpropane-1,3-diyl, pentane-1,5-diyl, and hexane-1,6-diyl; cyclic saturated hydrocarbylene groups such as cyclopentane-1,2-diyl, cyclopentane-1,3-diyl, cyclohexane-1,6-diyl, and adamantane-1,3-diyl: alkenediyl groups such as ethene-1,2-diyl, 1-propene-1,3-diyl, 2-butene-1,4-diyl, and 1-methyl-1-butene-1,4-diyl; unsaturated alicyclic hydrocarbylene groups such as 2-cyclohexene-1,4-diyl; aromatic hydrocarbylene groups such as phenylene, and combinations thereof. In these groups, some hydrogen may be substituted by a moiety containing a heteroatom such as oxygen, sulfur, nitrogen or halogen, and some carbon may be replaced by a moiety containing a heteroatom such as oxygen, sulfur or nitrogen, so that the group may contain a hydroxy moiety, cyano moiety, carbonyl moiety, ether bond, ester bond, sulfonic acid ester bond, carbonate bond, lactone ring, sultone ring, carboxylic anhydride or haloalkyl moiety.

The hydrocarbylene groups represented by $Z^B$ and $Z^C$ may be saturated or unsaturated and straight, branched or cyclic. Examples thereof are as exemplified above for the hydrocarbylene group $Z^{41}$.

In formulae (d1) to (d4), $R^{31}$ to $R^{41}$ are each independently a $C_1$-$C_{20}$ hydrocarbyl group which may contain a heteroatom. The hydrocarbyl group may be saturated or unsaturated and straight, branched or cyclic. Examples include alkyl groups such as methyl, ethyl, n-propyl, isopropyl, n-butyl, and tert-buty, cyclic saturated hydrocarbyl groups such as cyclopropyl, cyclopentyl, cyclohexyl, cyclopropylmethyl, 4-methylcyclohexyl, cyclohexylmethyl, norbornyl, and adamantyl, alkenyl groups such as vinyl, allyl, propenyl, butenyl, and hexenyl, unsaturated alicyclic hydrocarbyl groups such as cyclohexenyl, aryl groups such as phenyl and naphthyl, heteroaryl groups such as thienyl, aralkyl groups such as benzyl, 1-phenylethyl and 2-phenylethyl, and combinations thereof. Inter alia, aryl groups are preferred. In these groups, some hydrogen may be substituted by a moiety containing a heteroatom such as oxygen, sulfur, nitrogen or halogen, and some carbon may be replaced by a moiety containing a heteroatom such as oxygen, sulfur or nitrogen, so that the group may contain a hydroxyl moiety, cyano moiety, carbonyl moiety, ether bond, ester bond, sulfonic acid ester bond, carbonate bond, lactone ring, sultone ring, caboxylic anhydride or haloalkyl moiety.

$Z^A$ and $R^{31}$ to $R^{41}$ are preferably of a structure containing a phenyl group which is bonded to $S^+$ in the formula.

Any two of $Z^A$, $R^{31}$ and $R^{32}$ may bond together to form a ring with the sulfur atom to which they are attached, any two of $R^{33}$, $R^{34}$ and $R^{35}$, any two of $R^{36}$, $R^{37}$ and $R^{38}$, or any two of $R^{39}$, $R^{40}$ and $R^{41}$ may bond together to form a ring with the sulfur atom to which they are attached.

In formula (d2), $R^{HF}$ is hydrogen or trifluoromethyl.

In formula (d2), $n^1$ is 0 or 1, n is 0 when $Z^B$ is a single bond. In formula (d3), $n^2$ is 0 or 1, $n^2$ is 0 when $Z^C$ is a single bond.

In formula (d1), Xa⁻ is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bistrifluoromehysulfonyl)imide, bis(perfluoroethylsulfonyl)imide and bis(perfluorobutylsulfonyl)imide; and methide ions such as tris(trifluoromethylsulfony)methide and tris(perfluoroethylsulfonyl)methide. Preferred are anions having the formulae (d1-1) and (d1-2).

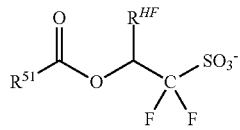

(d1-1)

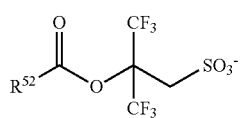

(d1-2)

In formulae (d1-1) and (d1-2), $R^{51}$ and $R^{52}$ are each independently a $C_1$-$C_{40}$ hydrocarbyl group which may contain a heteroatom, and $R^{HF}$ is hydrogen or trifluoromethyl.

Examples of the anion having formula (d1-1) include the anions described in JP-A 2014-177407, paragraphs [0100]-[0101] and the anions shown below, but are not limited thereto. Herein $R^{HF}$ is as defined above.

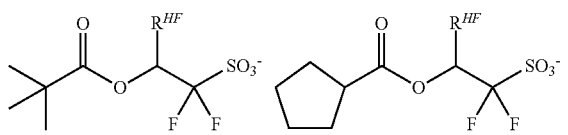

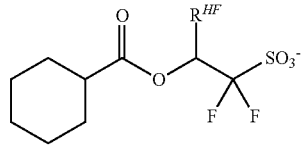

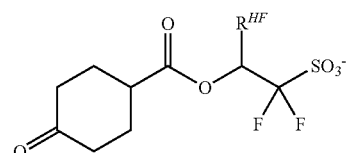

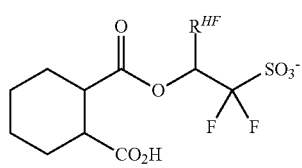

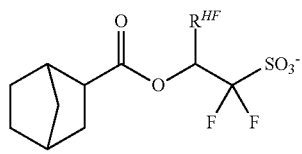

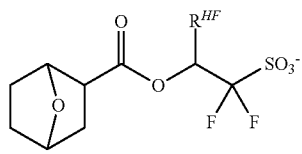

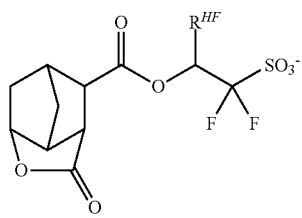

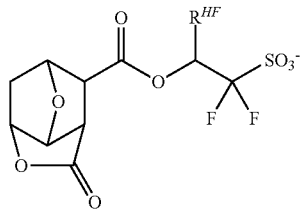

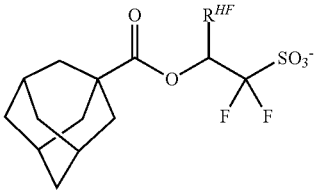

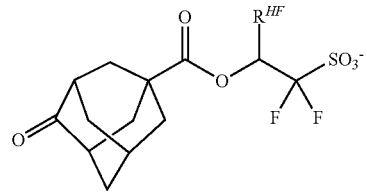

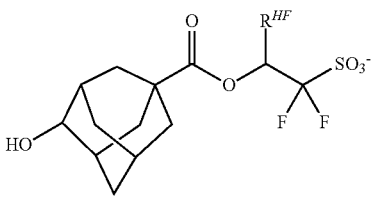

-continued
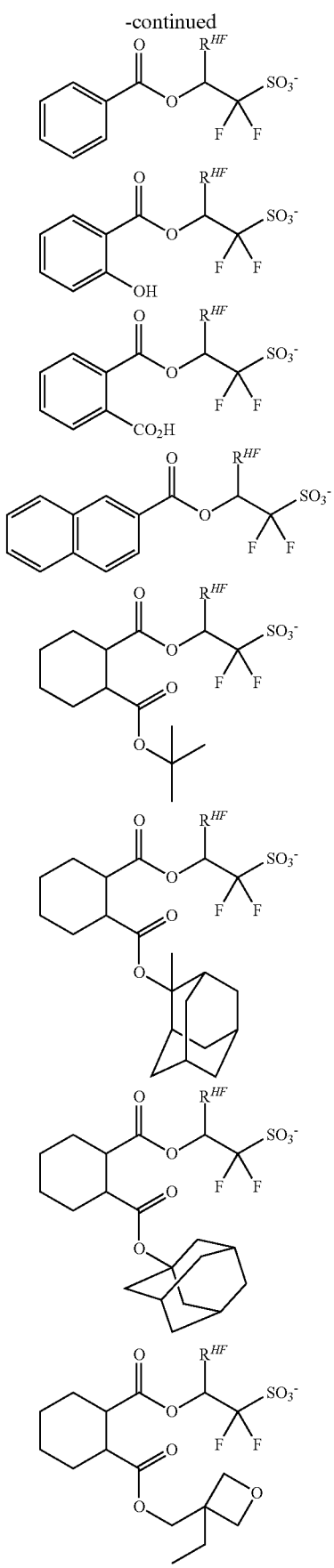
-continued
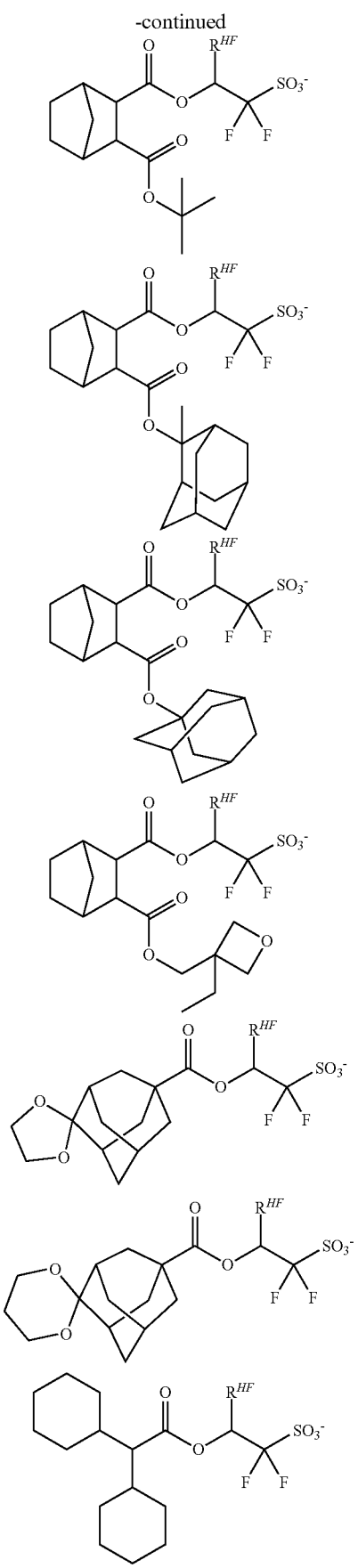

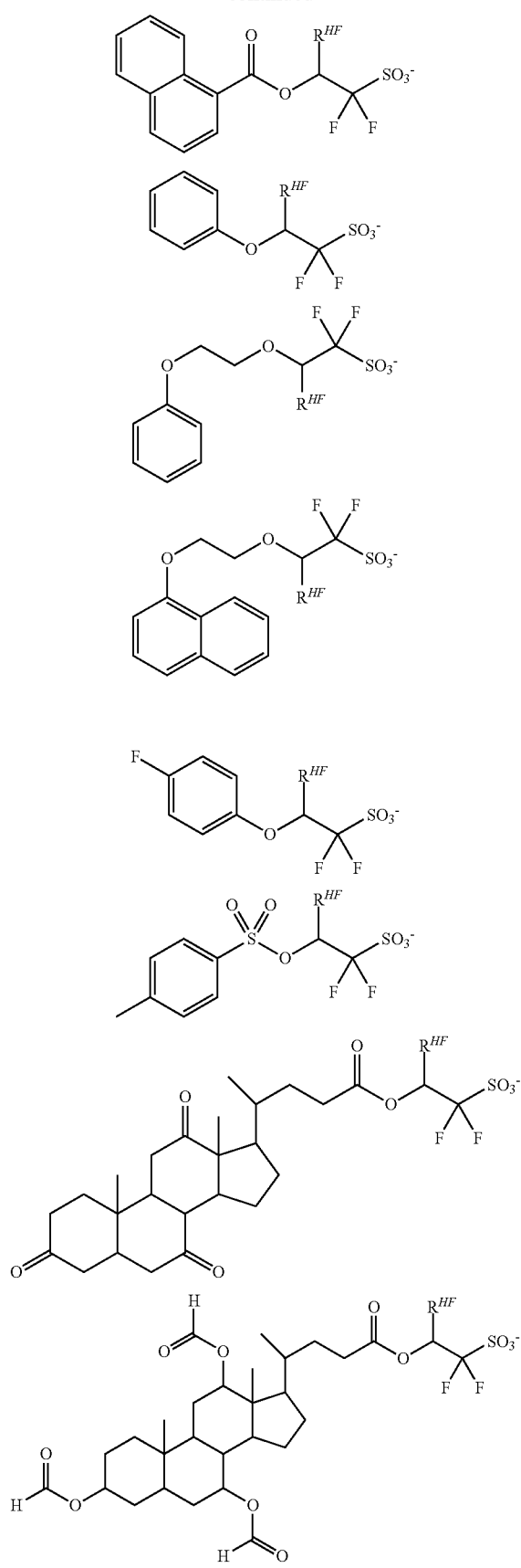
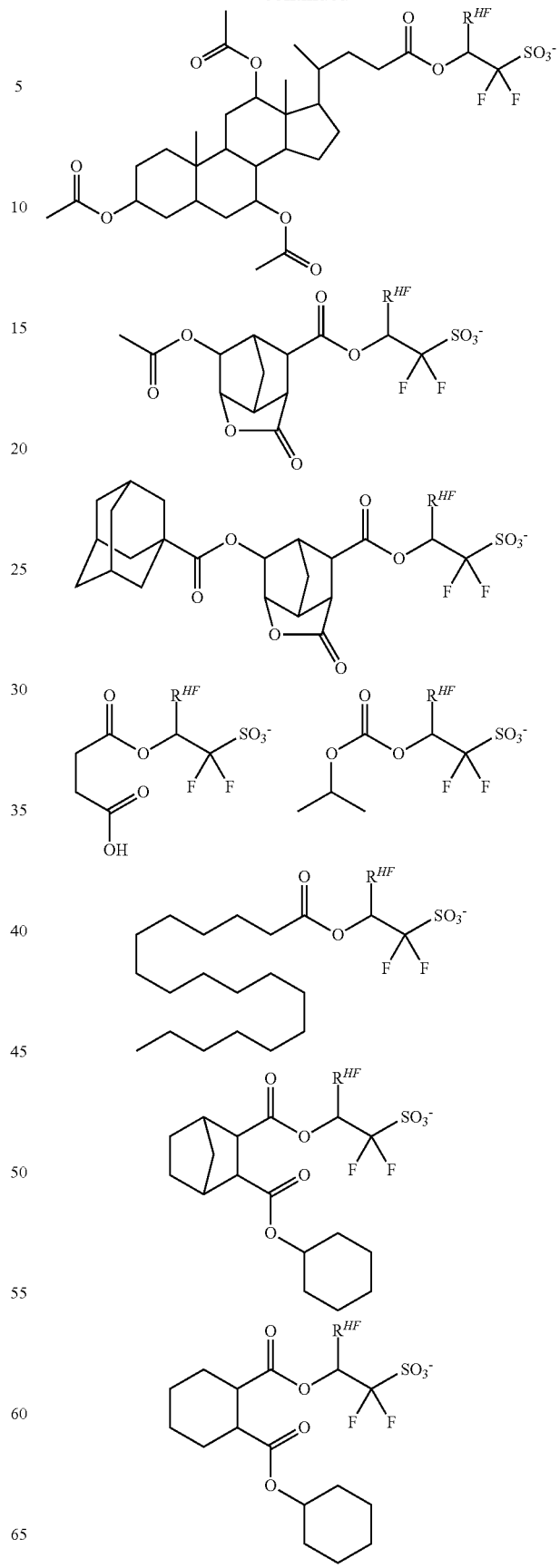

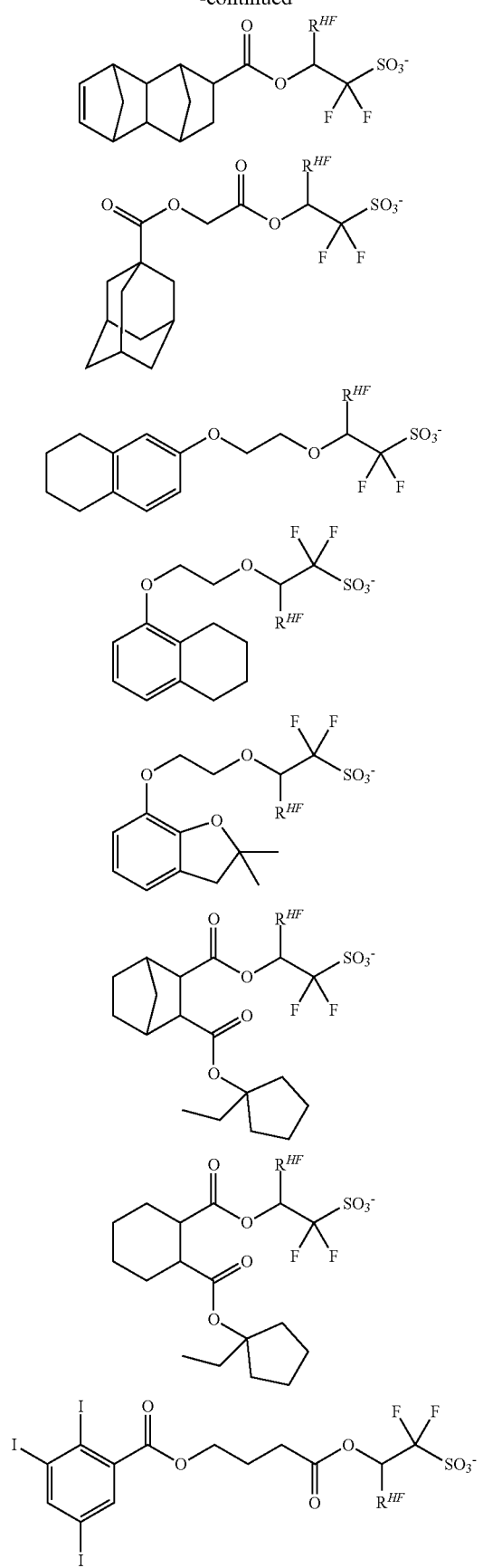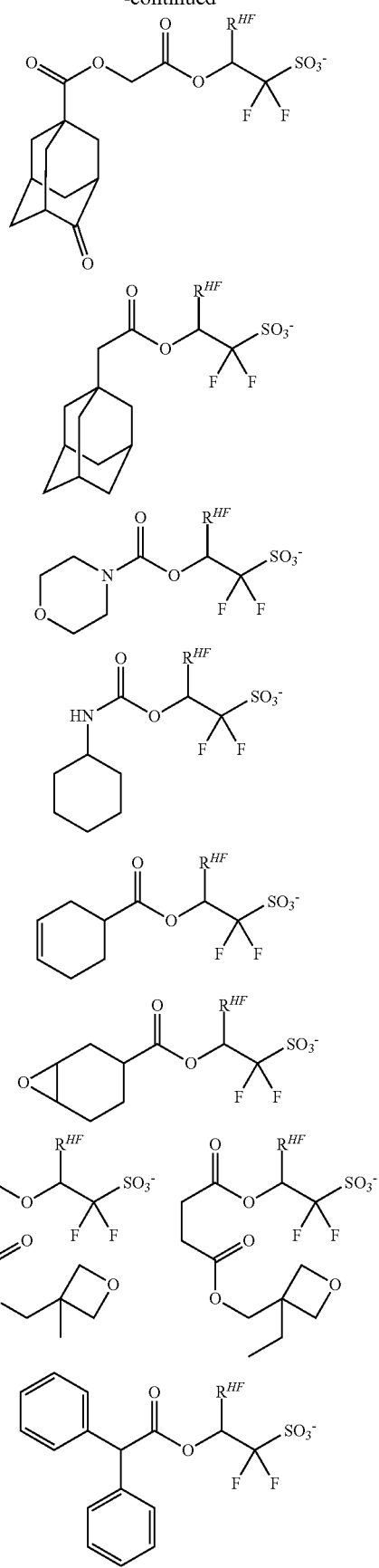

111
-continued
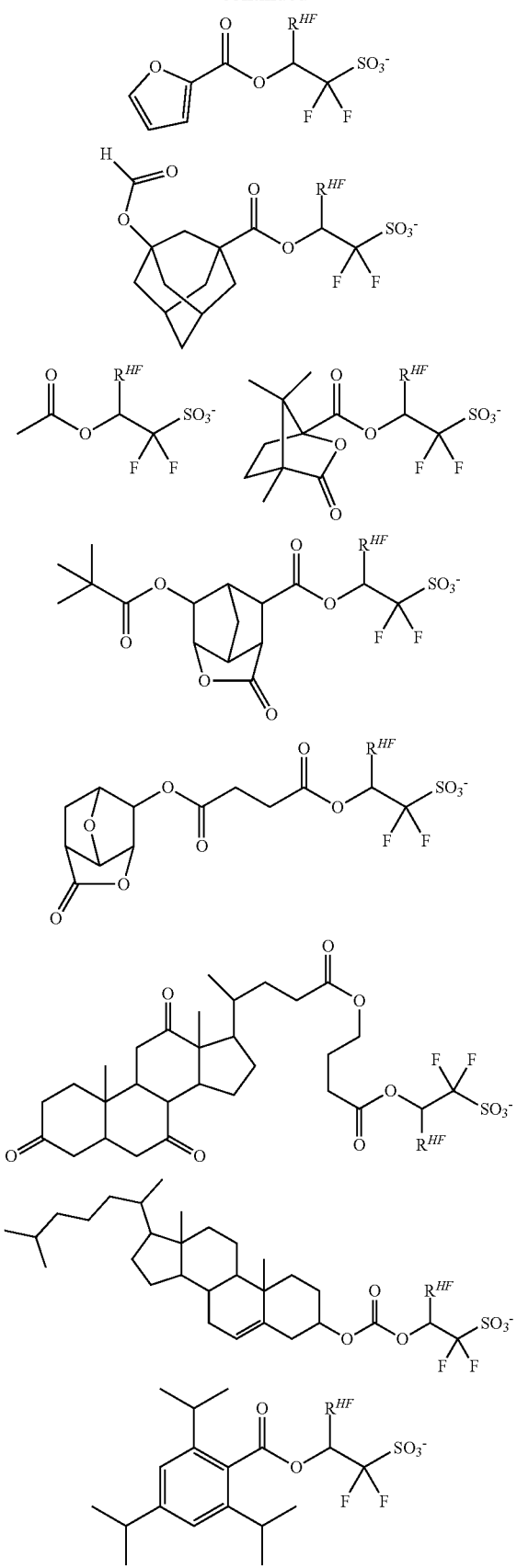
112
-continued
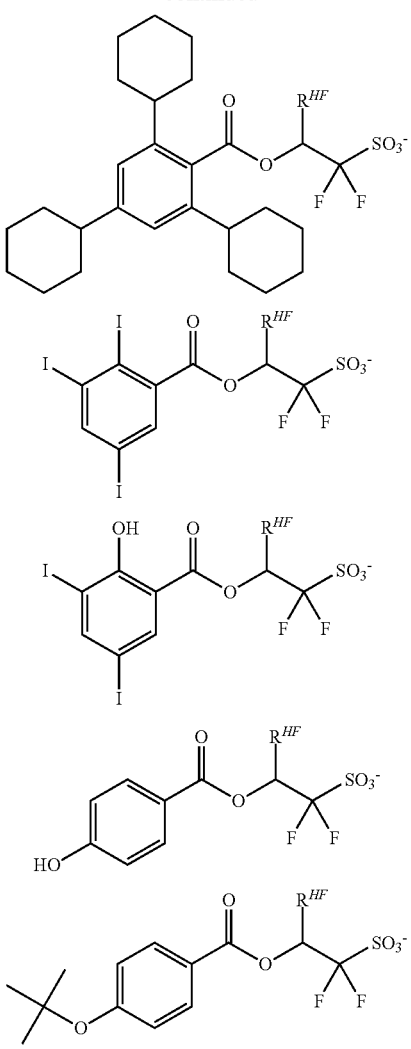
Examples of the anion having formula (d1-2) include the anions described in JP-A 2010-215608, paragraphs [0080]-[0081] and the anions shown below, but are not limited thereto.
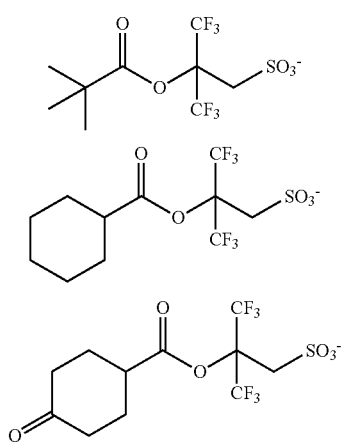

113
-continued
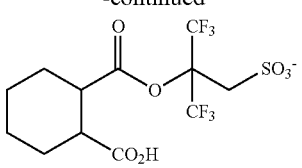
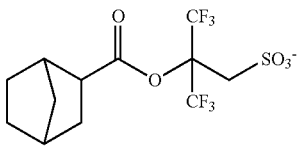
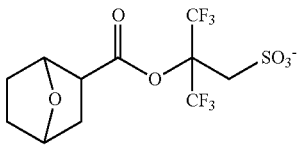
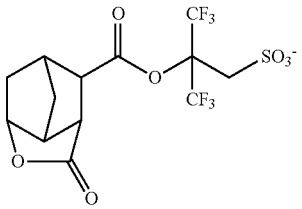
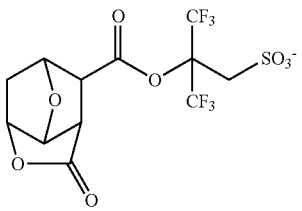
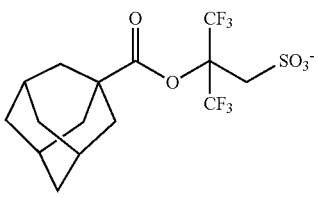
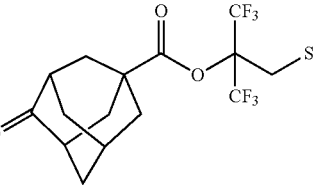
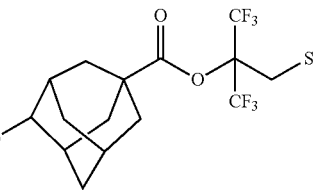
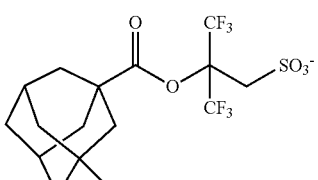
114
-continued
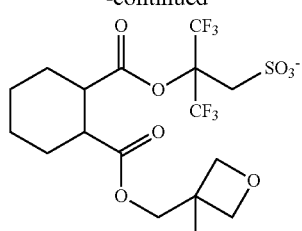
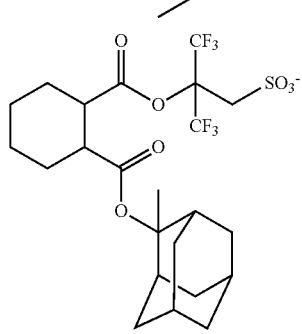
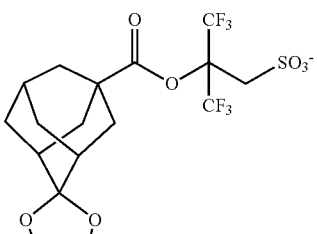
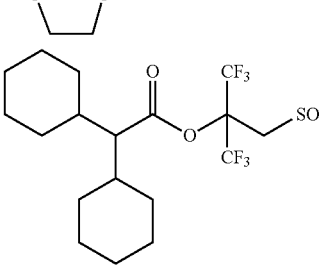
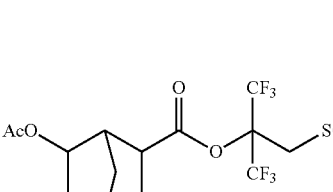
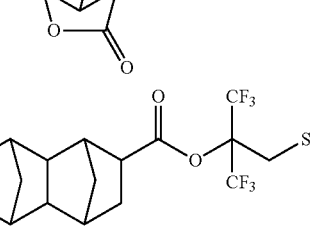
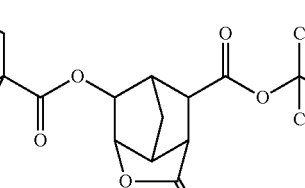

115
-continued

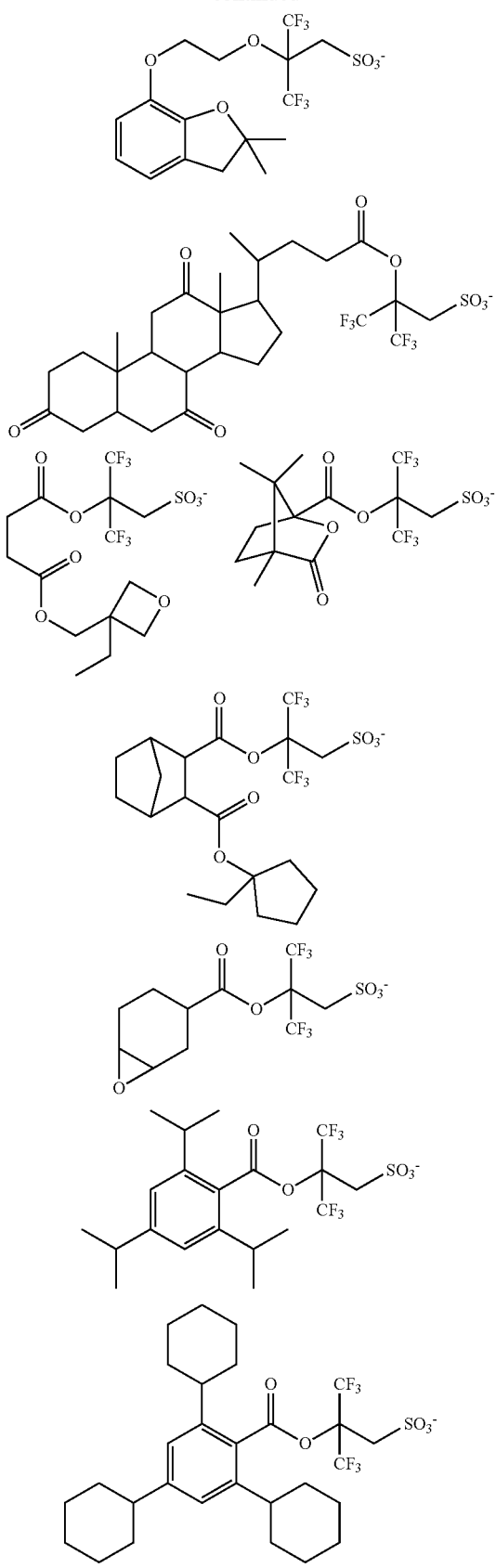

116
-continued

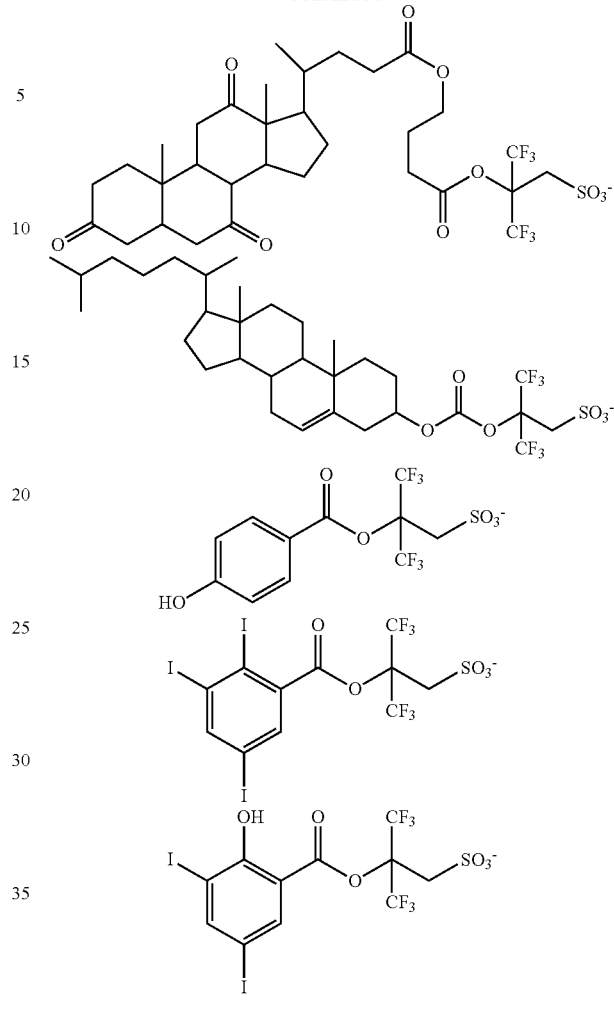

Examples of the anion in recurring unit (d2) include the anions described in JP-A 2014-177407, paragraphs [0021]-[0026]. Exemplary structures of the anion wherein $R^{HF}$ is hydrogen include the anions described in JP-A 2010-116550, paragraphs [0021]-[0028]. Exemplary structures of the anion wherein $R^{HF}$ is trifluoromethyl include the anions described in JP-A 2010-077404, paragraphs [0021]-[0027].

Examples of the anion in recurring unit (d3) correspond to the examples of the anion in recurring unit (d2) wherein —CH($R^{HF}$)CF$_2$SO$_3^-$ is replaced by —C(CF$_3$)$_2$CH$_2$SO$_3^-$.

Preferred examples of the anion in recurring units (d2) to (d4) are given below, but not limited thereto. Herein $R^B$ is as defined above.

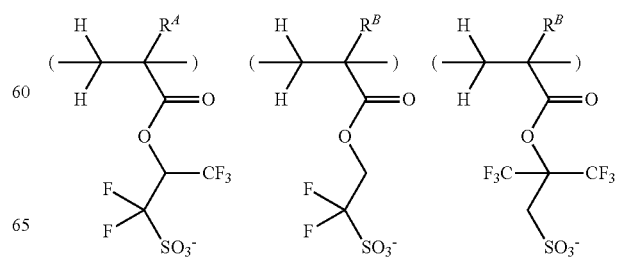

117
-continued
118
-continued
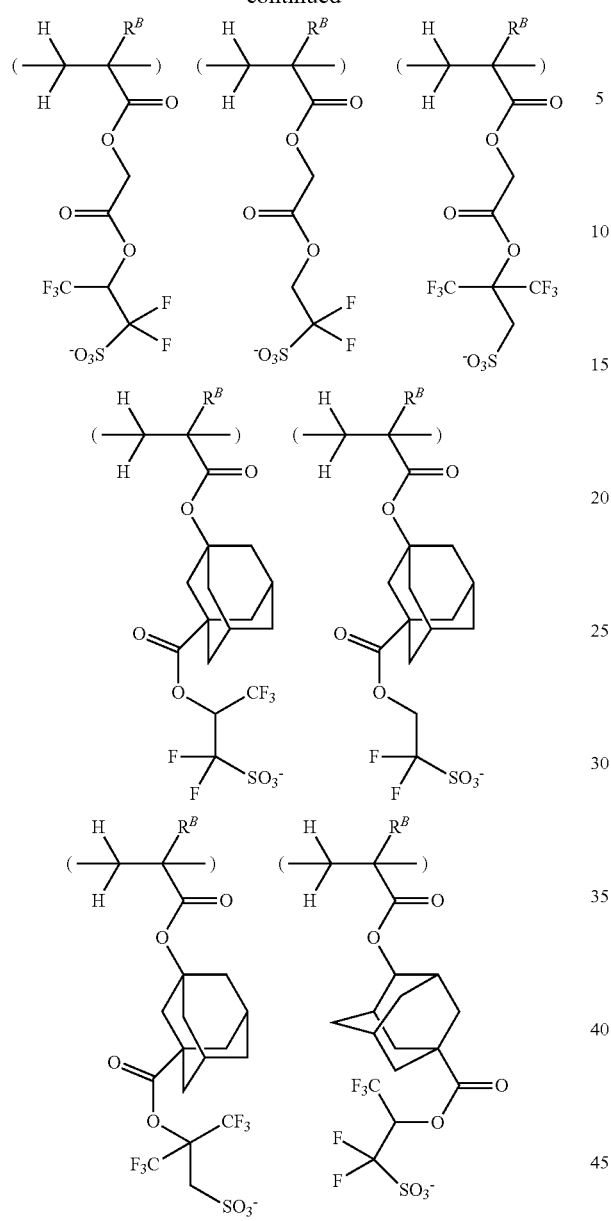
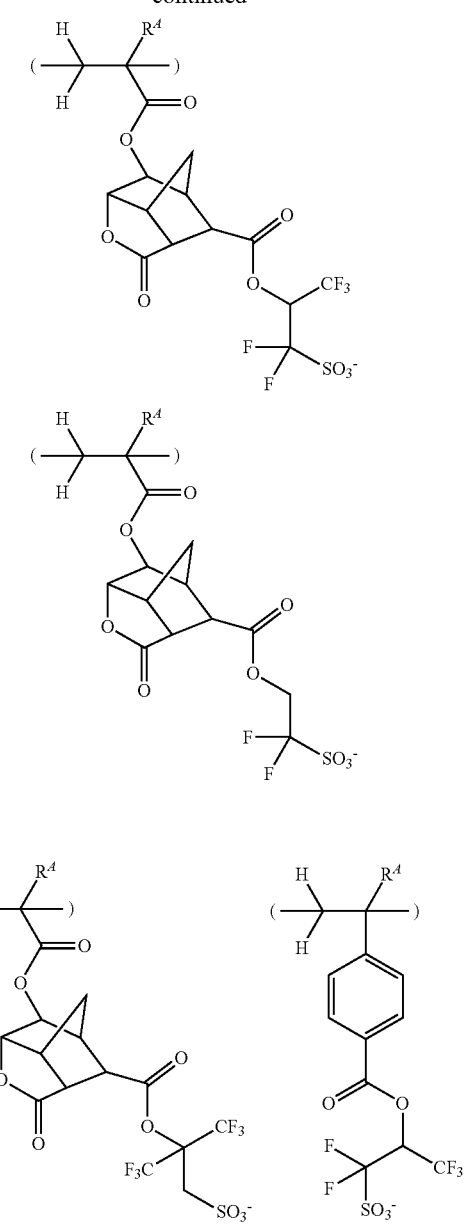

119
-continued
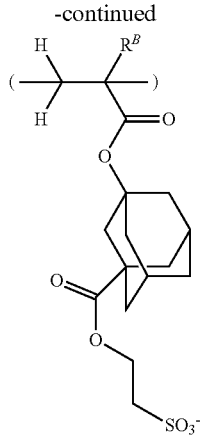
Examples of the sulfonium cation in recurring units (d2) to (d4) include those described in JP-A 2008-158339, paragraph [0223] as well as those exemplified above for the sulfonium cation M⁺ in formula (1). Of these, the preferred cations are given below, but not limited thereto.
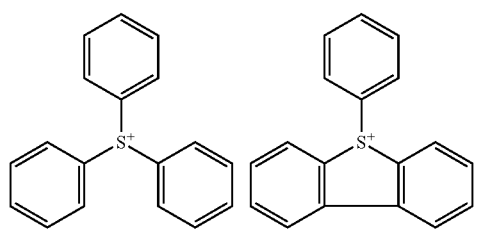
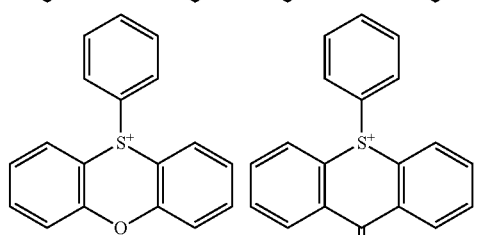
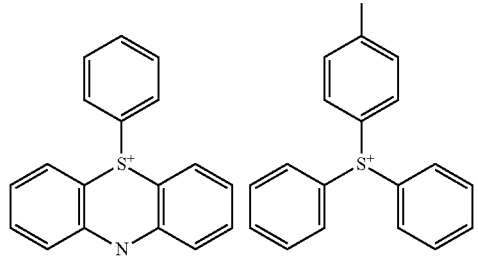
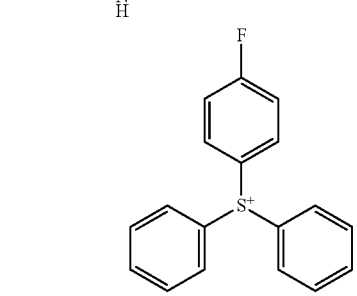
120
-continued
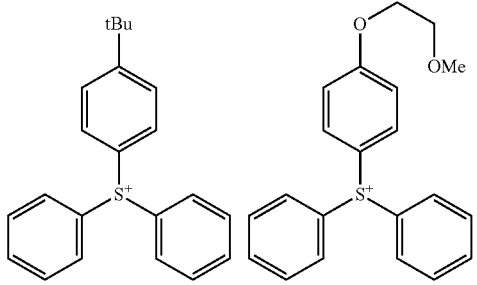
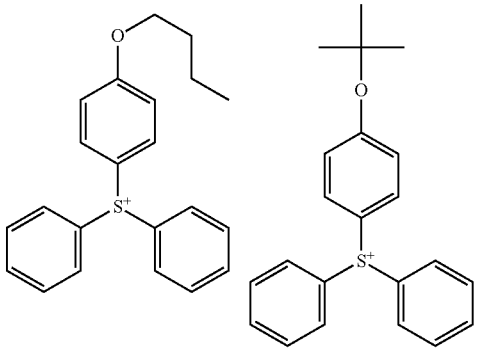
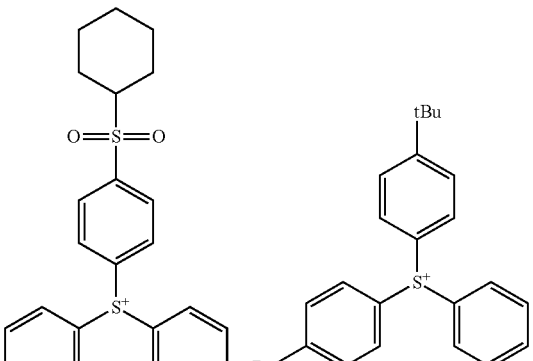
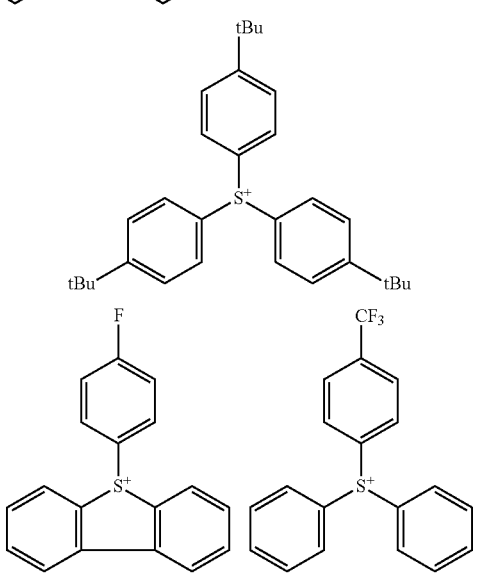

-continued

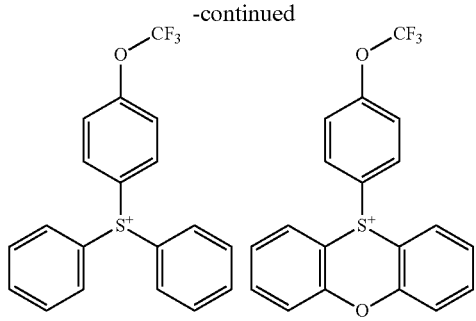

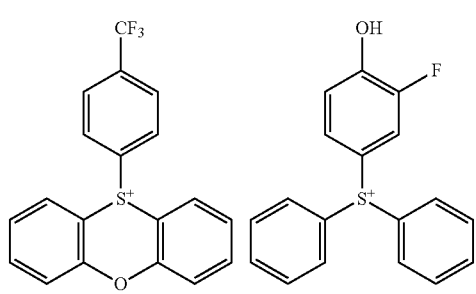

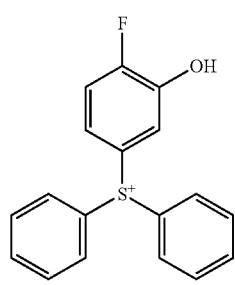

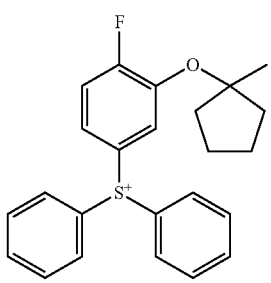

The recurring units (d1) to (d4) have the function of a photoacid generator. On use of a base polymer comprising recurring units (d1) to (d4), a photoacid generator of addition type to be described later may be omitted.

The base polymer may further comprise recurring units (e) containing a hydroxyl group (other than phenolic hydroxyl group), lactone ring, ether bond, ester bond, carbonyl group, cyano group or carboxyl group as another adhesive group.

Examples of the recurring units (e) are given below, but not limited thereto. Herein $R^A$ is as defined above.

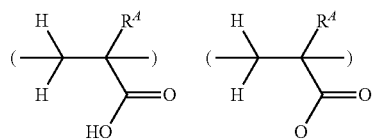

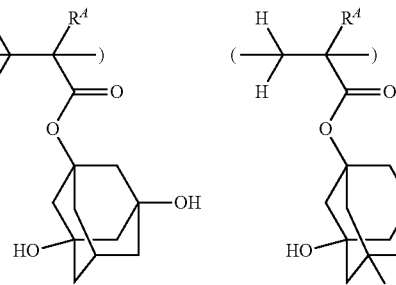

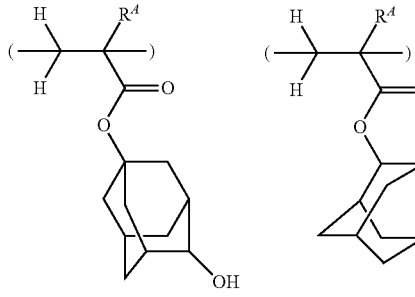

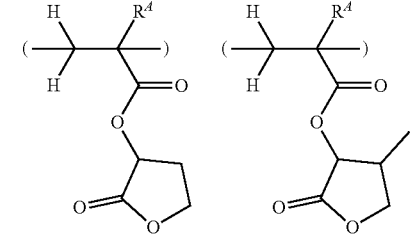

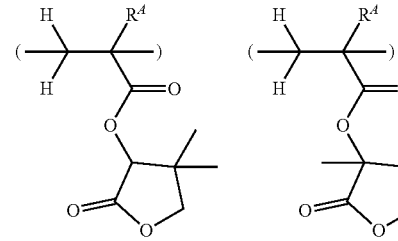

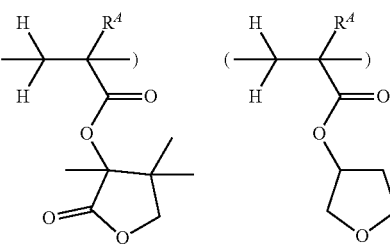

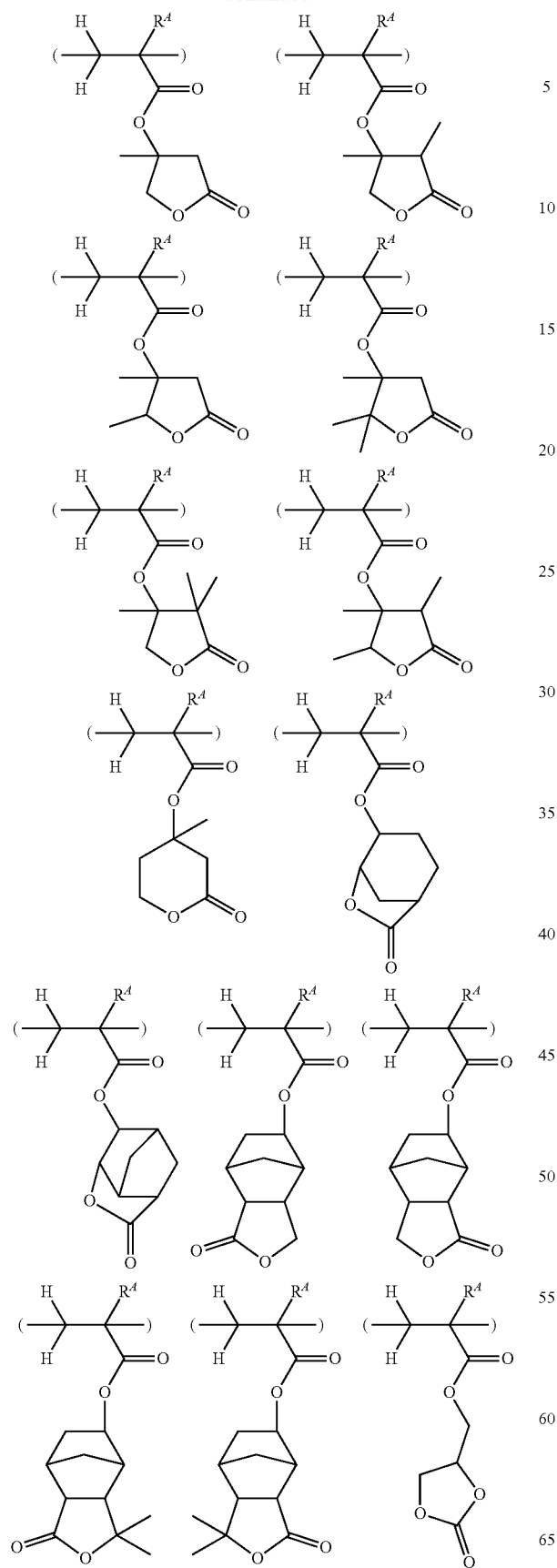
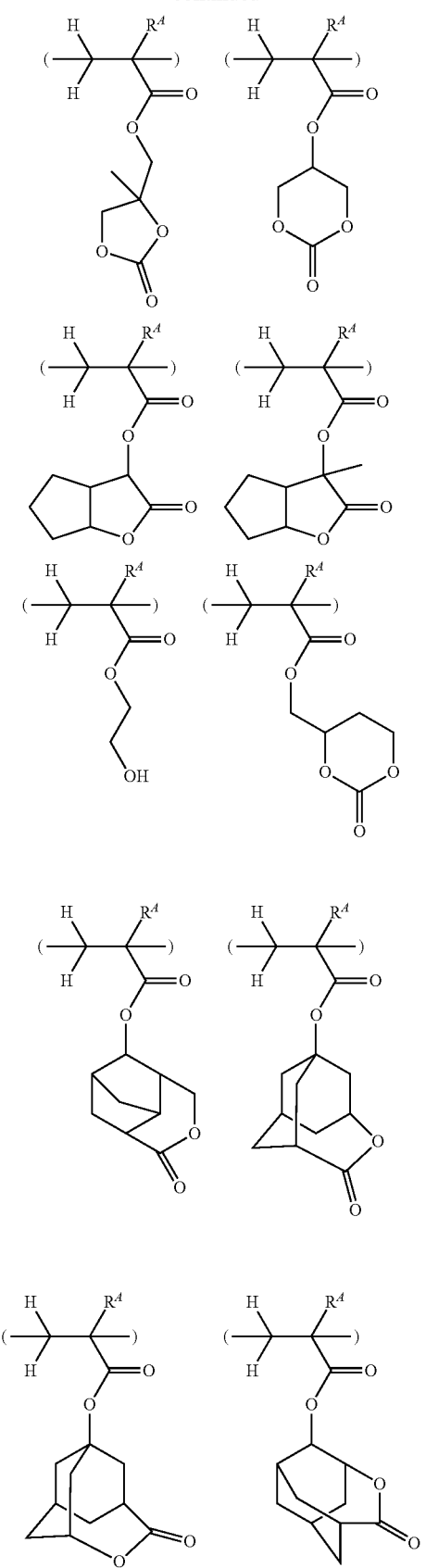

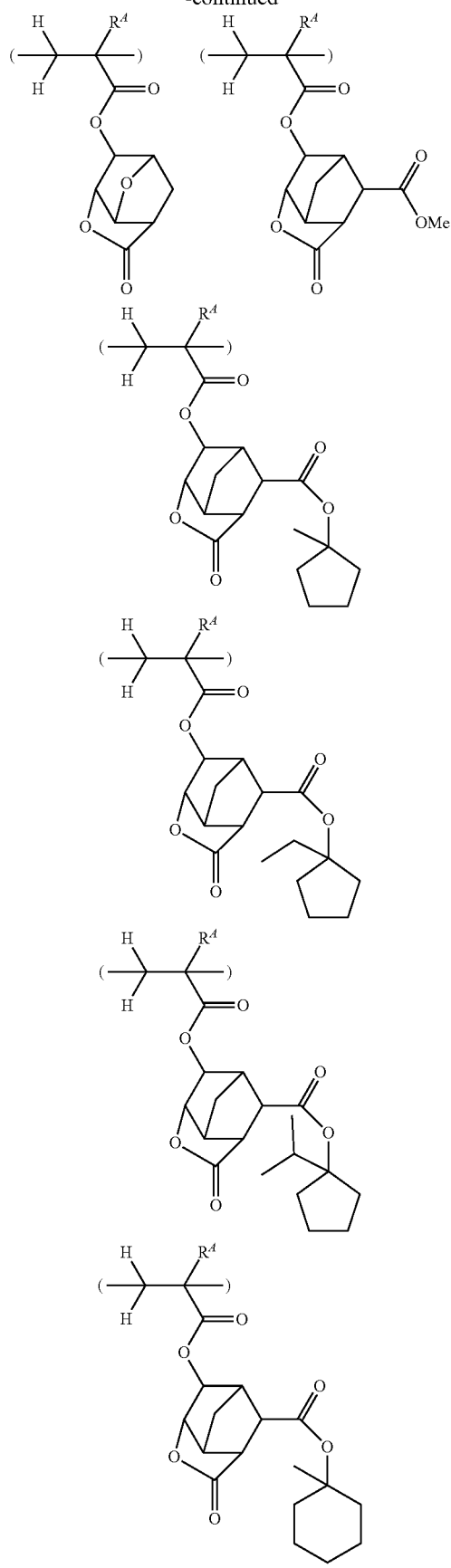
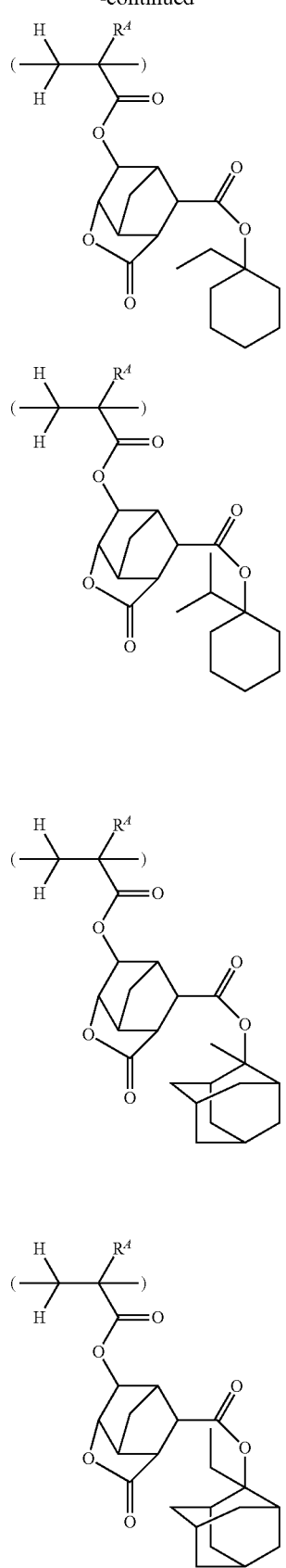

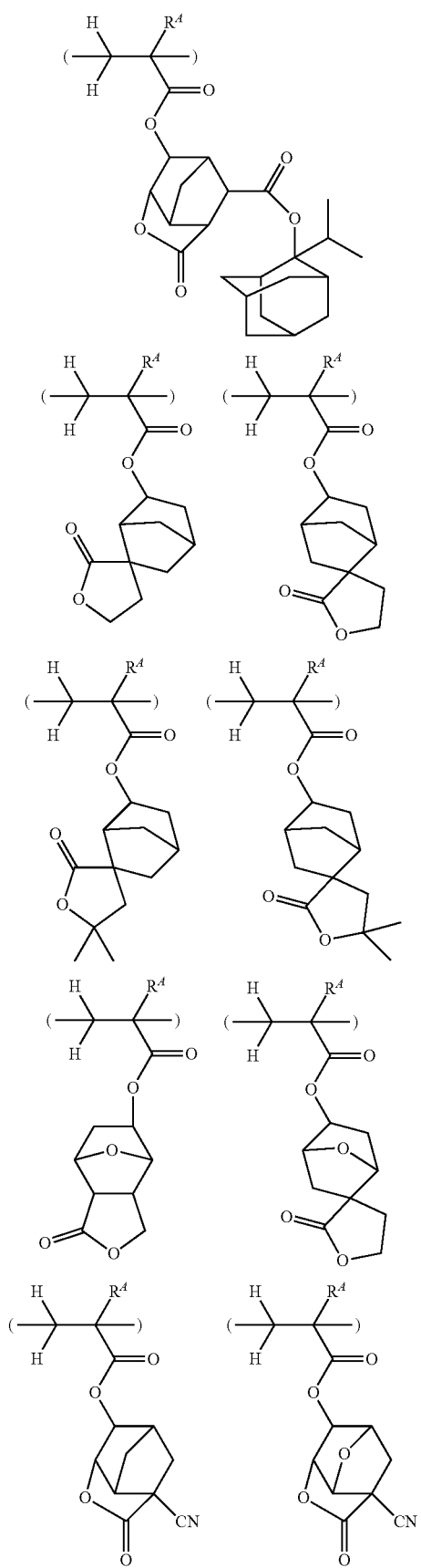
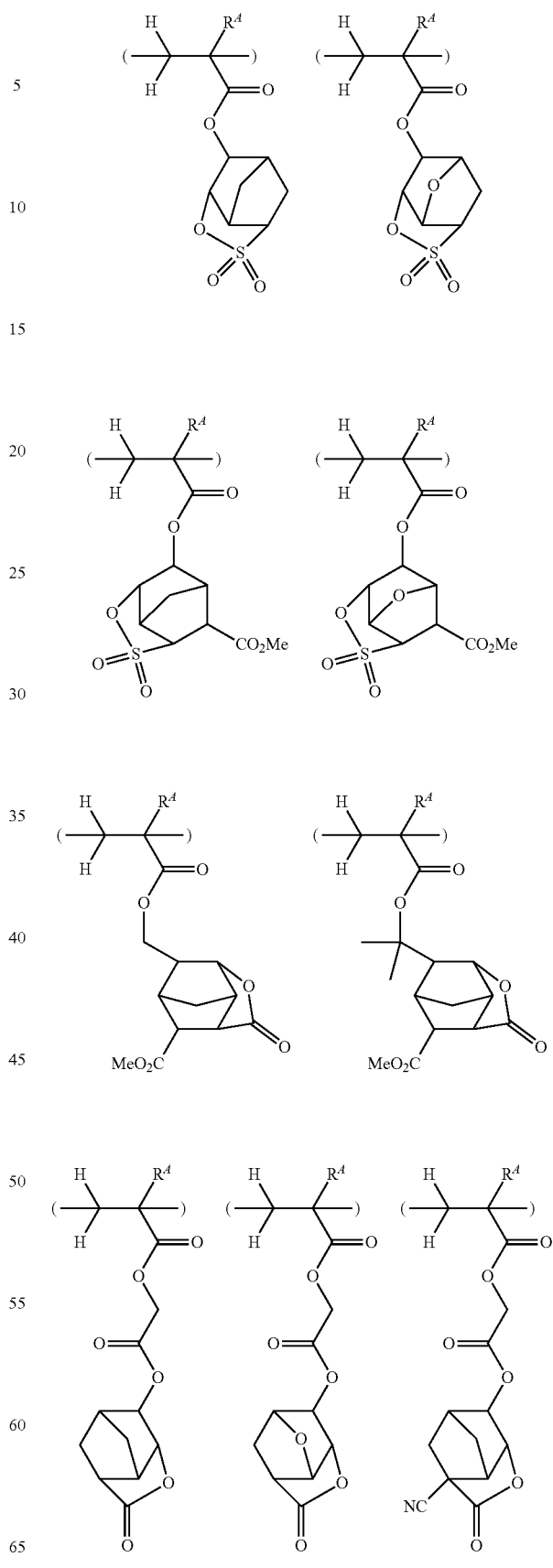

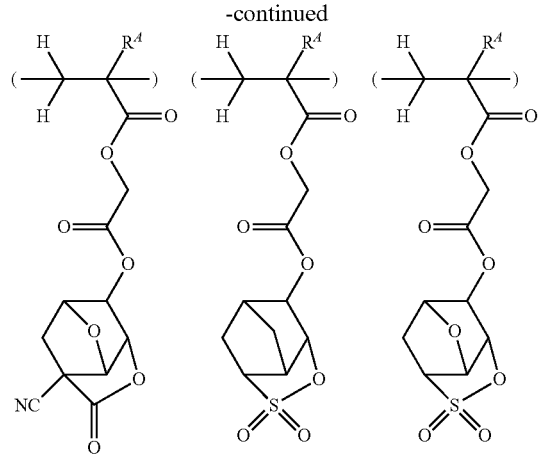
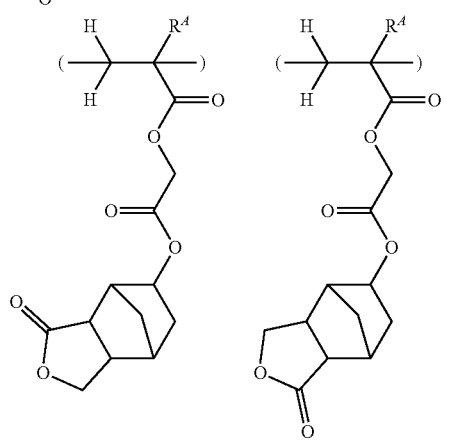
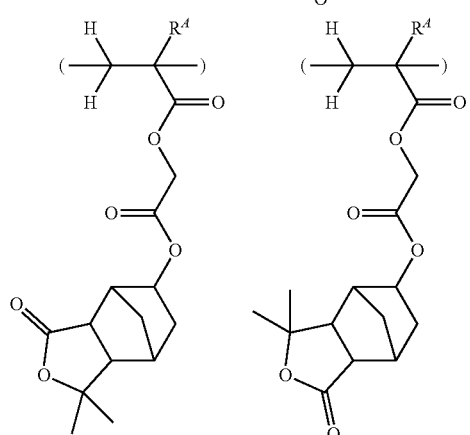
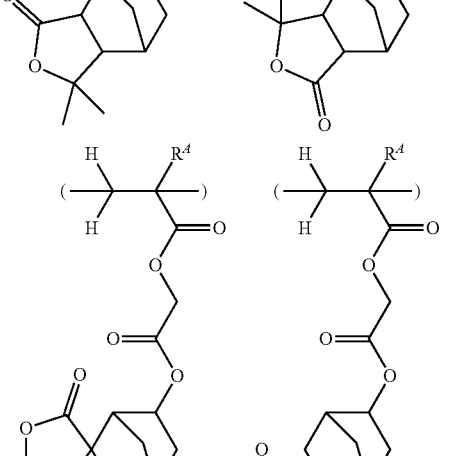
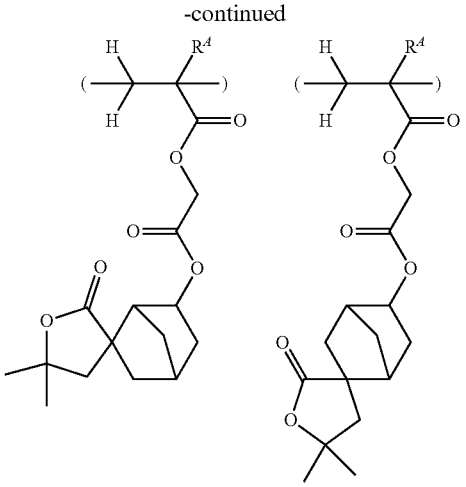
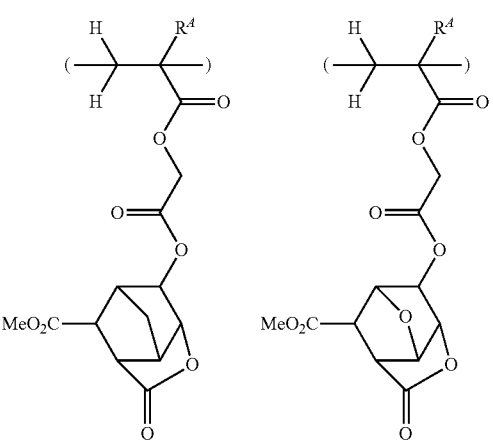
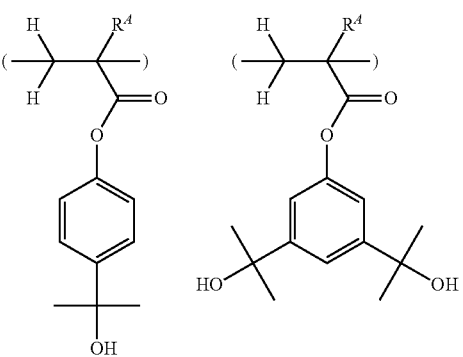
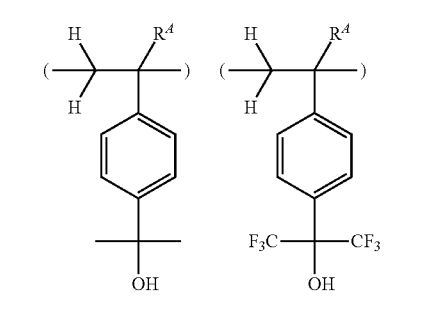

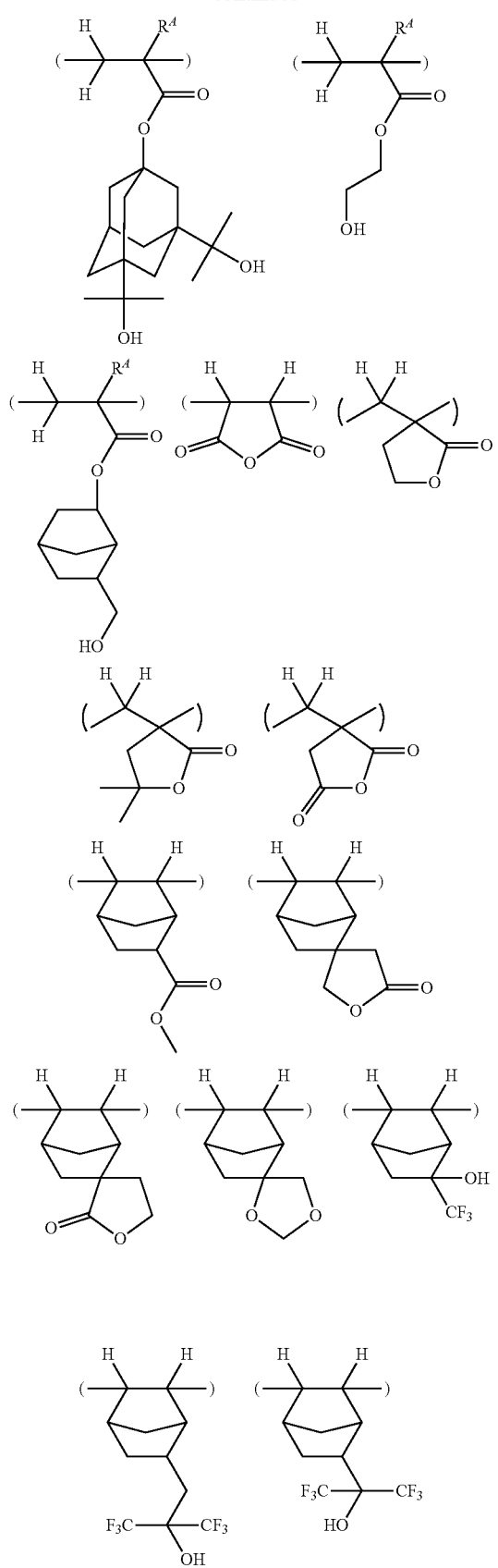
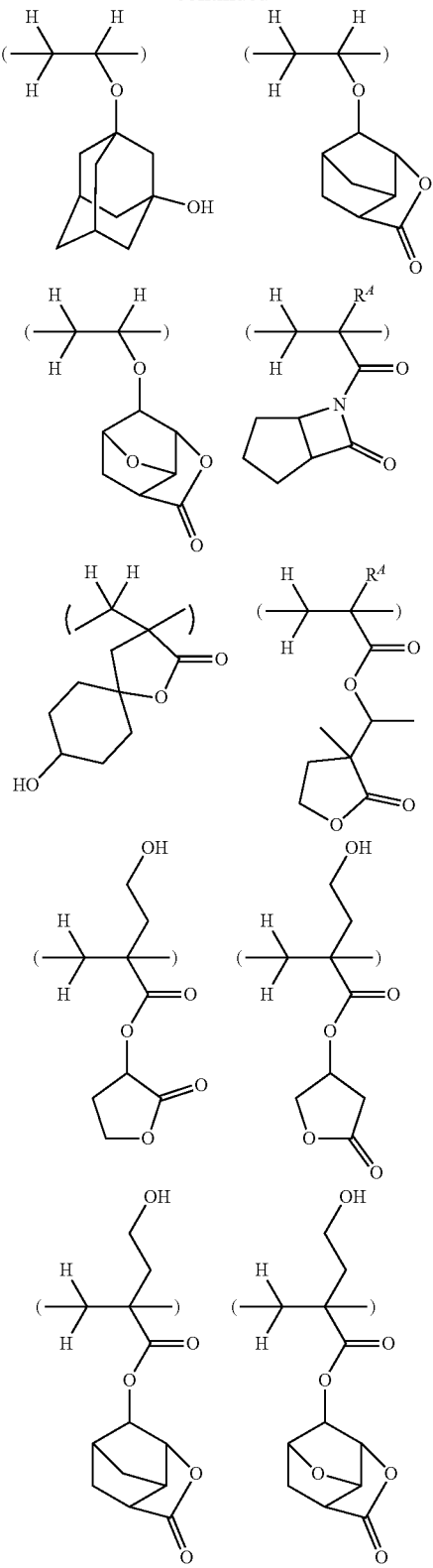
In addition to the foregoing examples, examples of the recurring units (e) include those described in JP-A 2014-225005, paragraphs [0045]-[0053].

Of the foregoing, units having a hydroxyl group or lactone ring are preferred as the recurring unit (e), with preferred examples being shown below. Herein, $R^A$ is as defined above.

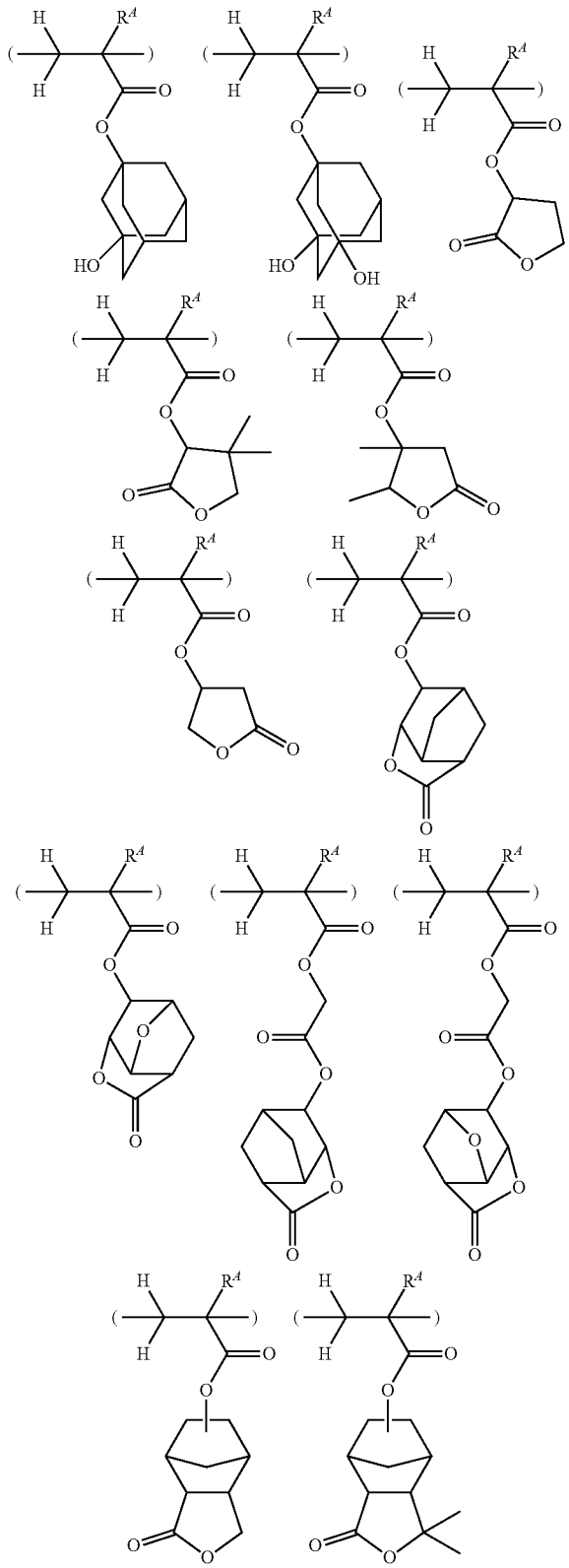

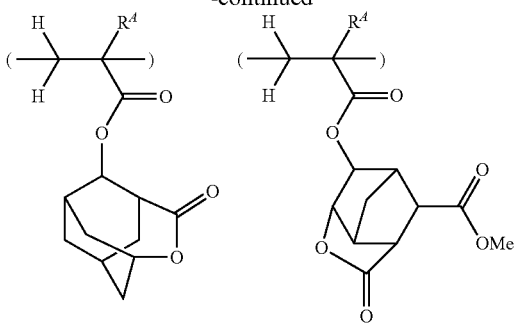

The base polymer may further comprise recurring units of the structure having a hydroxyl group protected with an acid labile group. The recurring unit of the structure having a hydroxyl group protected with an acid labile group is not particularly limited as long as the unit has at least one protected hydroxy structure wherein a hydroxyl group is resumed as a result of decomposition of the protective group under the action of acid. Such recurring units are described in JP-A 2014-225005, paragraphs [0055]-[0065] and JP-A 2015-214634, paragraphs [0110]-[0115].

The base polymer may further comprise other recurring units. Typical of the other recurring units are recurring units having an oxirane or oxetane ring. A polymer comprising recurring units having an oxirane or oxetane ring is cross-linked in exposed regions, leading to improvements in retention and etching resistance of a resist film in exposed regions.

The base polymer may further comprise still other recurring units, for example, units derived from substituted acrylates such as methyl crotonate, dimethyl maleate, and dimethyl itaconate, unsaturated carboxylic acids such as maleic acid, fumaric acid, and itaconic acid, cyclic olefins such as norbornene, norbornene derivatives, tetracyclo[6.2.1.1$^{3,6}$.0$^{2,7}$]dodecene derivatives, unsaturated acid anhydrides such as itaconic anhydride, vinyl aromatics such as styrene, tert-butoxystyrene, vinylnaphthalene, acetoxystyrene, and acenaphthylene, and other monomers.

The base polymer should preferably have a Mw of 1,000 to 500,000, more preferably 3,000 to 100,000, and even more preferably 4,000 to 20.000. A Mw within the range eliminates an extreme drop of etching resistance and provides satisfactory resolution due to a difference in dissolution rate before and after exposure. As used herein, Mw is measured versus polystyrene standards by GPC. Also preferably the polymer has a dispersity (Mw/Mn) of 1.20 to 2.50, more preferably 1.30 to 2.00.

The polymer may be synthesized by any method, for example, by using one or more monomers corresponding to the desired recurring units in an organic solvent, adding a radical polymerization initiator, and heating for polymerization. For the polymerization method, reference should be made to U.S. Pat. No. 9,256,127 (JP-A 2015-214634, paragraphs [0134]-[0137]). The acid labile group that has been incorporated in the monomer may be kept as such, or polymerization may be followed by protection or partial protection.

While the base polymer comprises recurring units derived from monomers, the molar fractions of respective units preferably fall in the following range (mol %), but are not limited thereto:

(I) 10 to 70 mol, more preferably 20 to 65 mol %, even more preferably 30 to 60 mol % of recurring units of at least one type selected from recurring units (a) and (b), (II) 0 to 90 mol %, more preferably 15 to 80 mol %, even more preferably 30 to 60 mol % of recurring units (c) of at least one type, and optionally, (III) 0 to 30 mol %, more preferably 0 to 20 mol %, and even more preferably 0 to 15 mol % of recurring units of at least one type selected from recurring units (d1) to (d4), and optionally, (IV) 0 to 80 mol %, more preferably 0 to 70 mol %, and even more preferably 0 to 50 mol % of recurring units of at least one type selected from recurring units (e) and other recurring units.

The base polymer (A) may be used alone or in a combination of two or more polymers which are different in compositional ratio, Mw and/or Mw/Mn. In addition to the polymer, a hydrogenated product of ring-opening metathesis polymerization (ROMP) polymer may be used. The hydrogenated ROMP polymer is as described in JP-A 2003-066612.

(B) Photoacid Generator

The resist composition should comprise (B) a photoacid generator, which is sometimes referred to as PAG of addition type, when the base polymer does not contain any of recurring units (d1) to (d4). It is noted that a PAG of addition type may be added even when the base polymer contains recurring units of at least one type selected from recurring units (d1) to (d4).

The PAG of addition type may be any compound capable of generating an acid upon exposure to high-energy radiation. Suitable PAGs include sulfonium salts, iodonium salts, sulfonyldiazomethanes, N-sulfonyloxydicarboxyimides, O-arylsulfonyloximes, and O-alkylsulfonyloximes, which may be used alone or in admixture. Suitable examples are described in JP-A 2007-145797, paragraphs [0102]-[0113], JP-A 2008-111103, paragraphs [0122]-[0142], JP-A 2014-001259, paragraphs [0081]-[0092], JP-A 2012-041320, JP-A 2012-153644, JP-A 2012-106986, and JP-A 2016-018007. The PAGs capable of generating partially fluorinated sulfonic acids described in the foregoing patent documents are preferably used in a resist composition because the strength and diffusion length of the generated acid are appropriate in the ArF lithography.

Preferred as the PAG (B) are sulfonium salts having the formula (5A) and iodonium salts having the formula (5B).

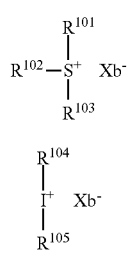

(5A)

(5B)

In formulae (5A) and (5B), $R^{101}$, $R^{102}$, $R^{103}$, $R^{104}$ and $R^{105}$ are each independently a $C_1$-$C_{20}$ hydrocarbyl group which may contain a heteroatom. Examples of the hydrocarbyl group areas exemplified above for $R^{31}$ to $R^{41}$ in formulae (d1) to (d4). Any two of $R^{101}$, $R^{102}$ and $R^{103}$ may bond together to form a ring with the sulfur atom to which they are attached, and $R^{104}$ and $R^{105}$ may bond together to form a ring with the iodine atom to which they are attached. Examples of the ring include those exemplified above for the ring that any two of $R^{M1}$, $R^{M2}$ and $R^{M3}$, taken together, form with the sulfur atom to which they are attached, in formula (M-1), and those exemplified above for the ring that $R^{M4}$ and $R^{M5}$, taken together, form with the iodine atom to which they are attached, in formula (M-2). $R^{101}$ to $R^{105}$ are preferably of a structure containing a phenyl group which is bonded to $S^+$ or $I^+$ in the formula.

The sulfonium cation of the sulfonium salt having formula (5A) is described in JP-A 2014-001259, paragraphs [0082]-[0085]. Exemplary sulfonium cations include those described in JP-A 2007-145797, paragraphs [0027]-[0033], JP-A 2010-113209, paragraph [0059]. JP-A 2012-041320, JP-A 2012-153644, and JP-A 2012-106986, as well as those exemplified above for the sulfonium cation $M^+$ in formula (1).

Preferred examples of the cation of the sulfonium salt having formula (5A) are given below, but not limited thereto.

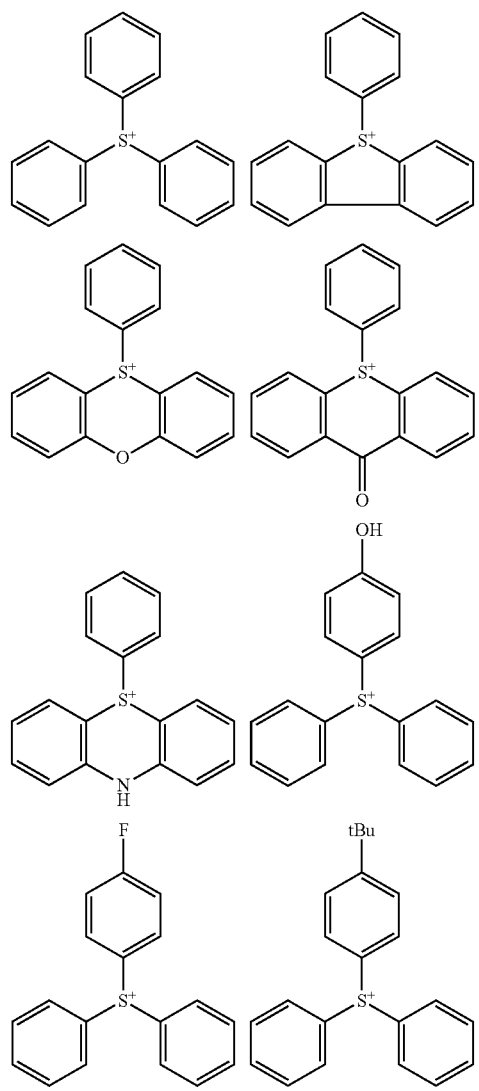

-continued

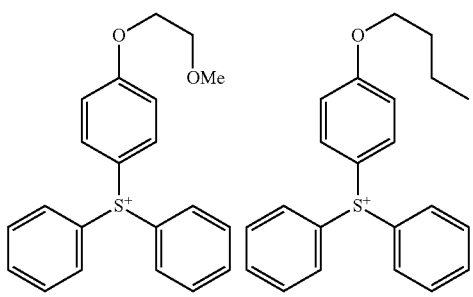
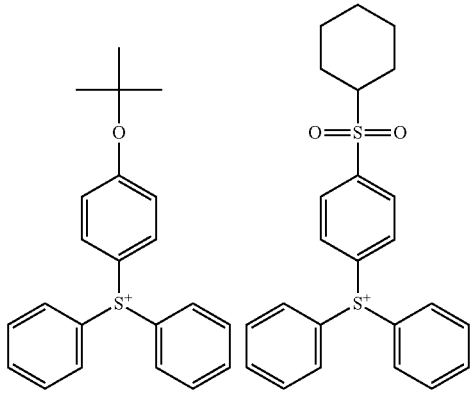
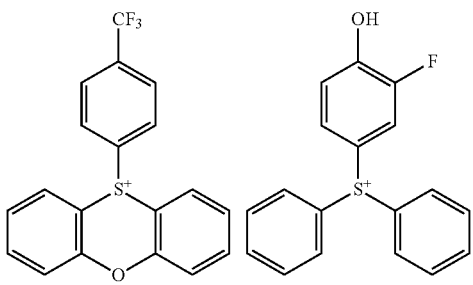
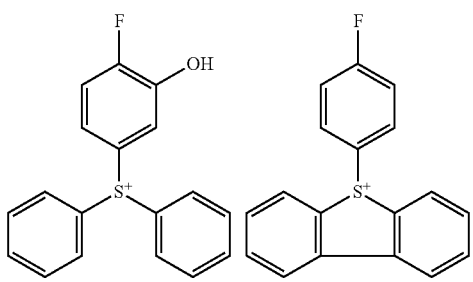
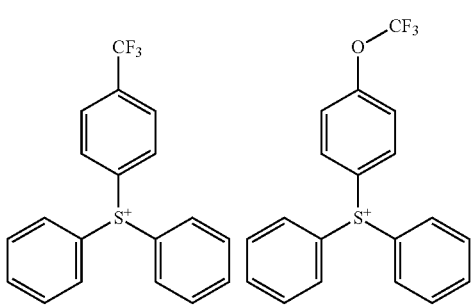

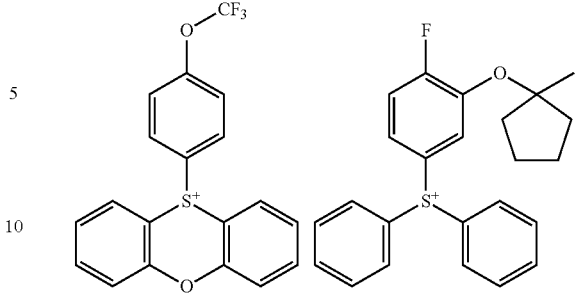

Specific examples of the cation of the sulfonium salt having formula (5A) include triphenylsulfonium, S-phenyldibenzothiophenium, (4-tert-butylphenyl)diphenylsulfonium, (4-fluorophenyl)diphenylsulfonium, and (4-hydroxyphenyl)diphenylsulfonium cations.

Examples of the cation of the iodonium salt having formula (5B) include those exemplified above for the iodonium cation $M^+$ in formula (I), with diphenyliodonium and di-tert-butylphenyliodonium cations being preferred.

In formulae (5A) and (5B), $Xb^-$ is an anion having the formula (6A) or (6B).

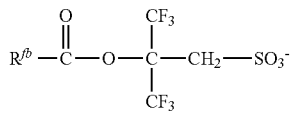

In formulae (6A) and (6B), $R^{fa}$ is fluorine, a $C_1$-$C_{40}$ perfluoroalkyl group, or a $C_1$-$C_{40}$ hydrocarbyl group which may contain a heteroatom, in which —$CH_2$— may be replaced by an ether bond or carbonyl moiety. $R^{fb}$ is a $C_1$-$C_{40}$ hydrocarbyl group which may contain a heteroatom, in which —$CH_2$— may be replaced by an ether bond or carbonyl moiety.

Preferred examples of the anion having formula (6A) include trifluoromethanesulfonate and nonafluorobutanesulfonate anions, and anions having the formula (6A').

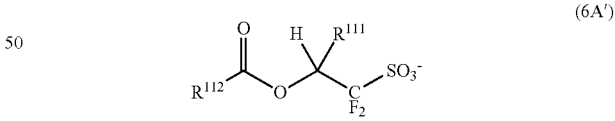

In formula (6A'), $R^{111}$ is hydrogen or trifluromethyl, preferably trifluoromethyl. $R^{112}$ is a $C_1$-$C_{35}$ hydrocarbyl group which may contain a heteroatom, in which —$CH_2$— may be replaced by an ether bond or carbonyl moiety. The anion having formula (6A') is described in JP-A 2007-145797, JP-A 2008-106045. JP-A 2009-007327, JP-A 2009-258695, and JP-A 2012-181306. Examples of the anion having formula (6A) include those described in these patent documents and those exemplified above as the anion having formula (d1-1).

The anion having formula (6B) is described in JP-A 2010-215608 and JP-A 2014-133723. Examples of the anion having formula (6B) include those described in these patent documents and those exemplified above as the anion having formula (d1-2). Notably, the compound having the anion of formula (6B) does not have fluorine at the α-position relative to the sulfo group, but two trifluoromethyl groups at the β-position. For this reason, it has a sufficient acidity to sever the acid labile groups in the base polymer. Thus the compound is an effective PAG.

Preferred examples of the anion $Xb^-$ are shown below, but not limited thereto. Herein $R^{HF}$ is hydrogen or trifluoromethyl.

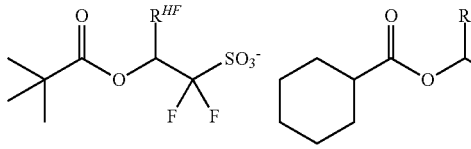

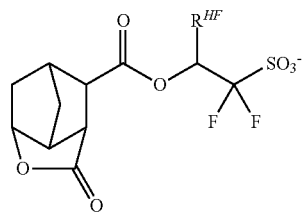

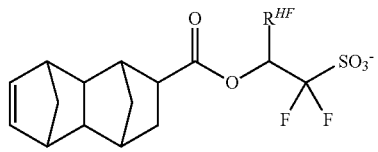

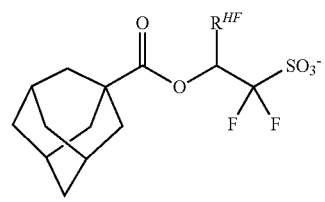

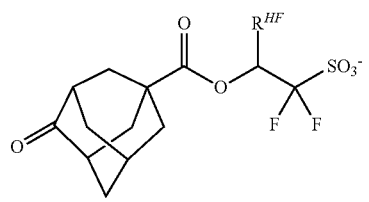

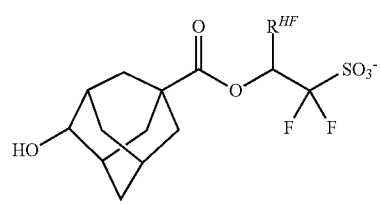

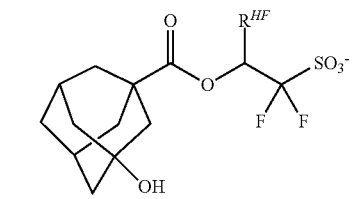

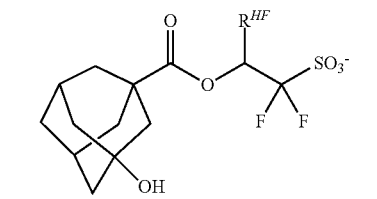

-continued

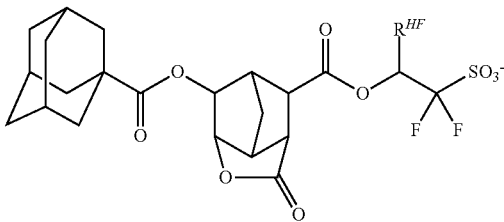

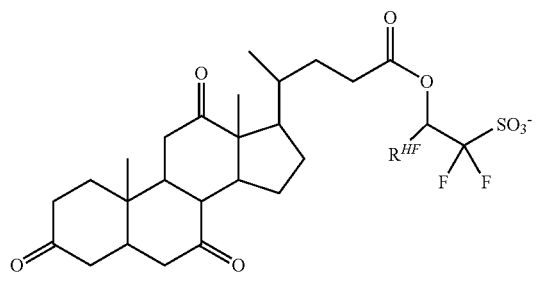

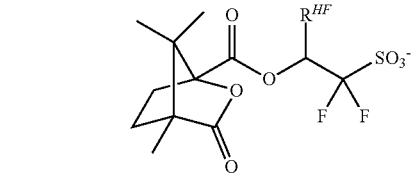

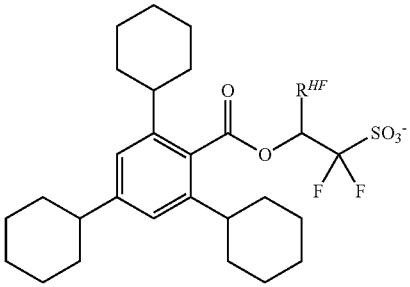

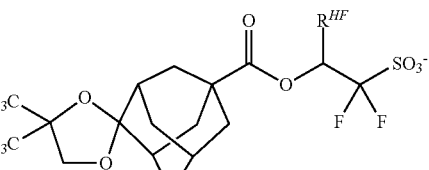

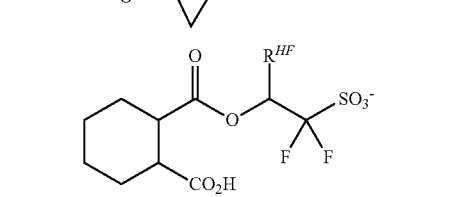

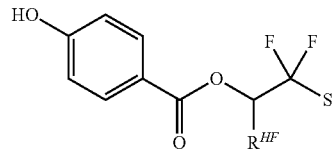

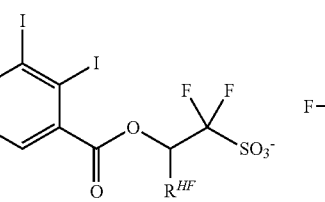 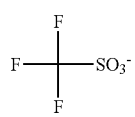

141
-continued
142
-continued
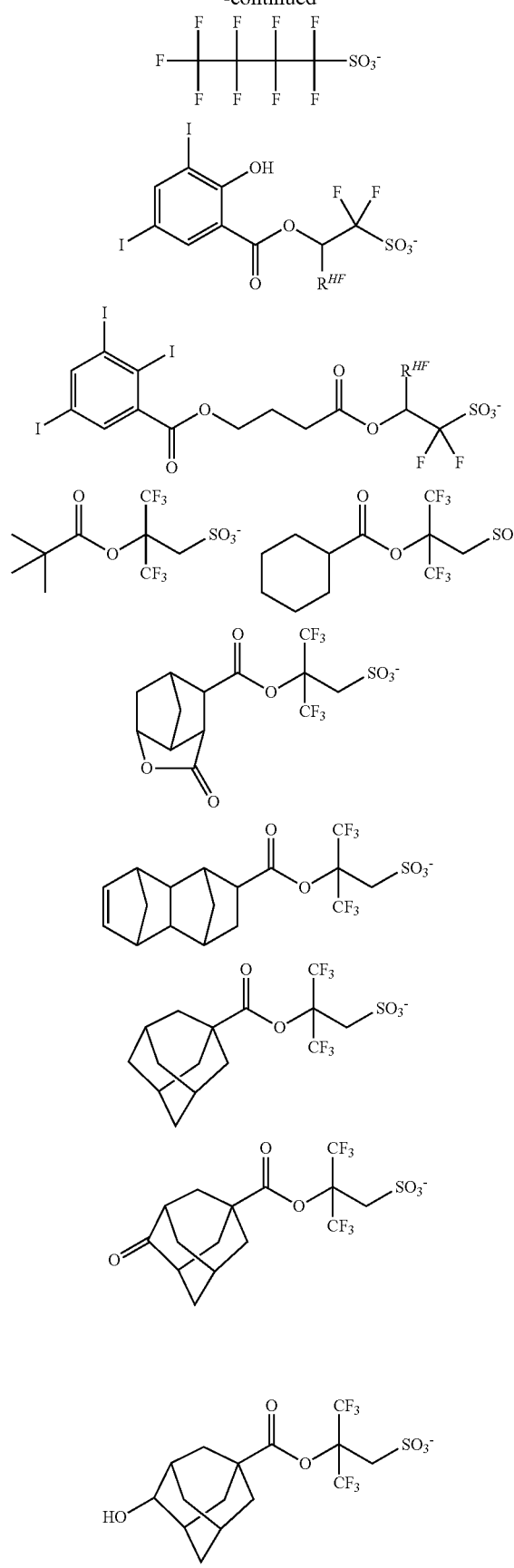
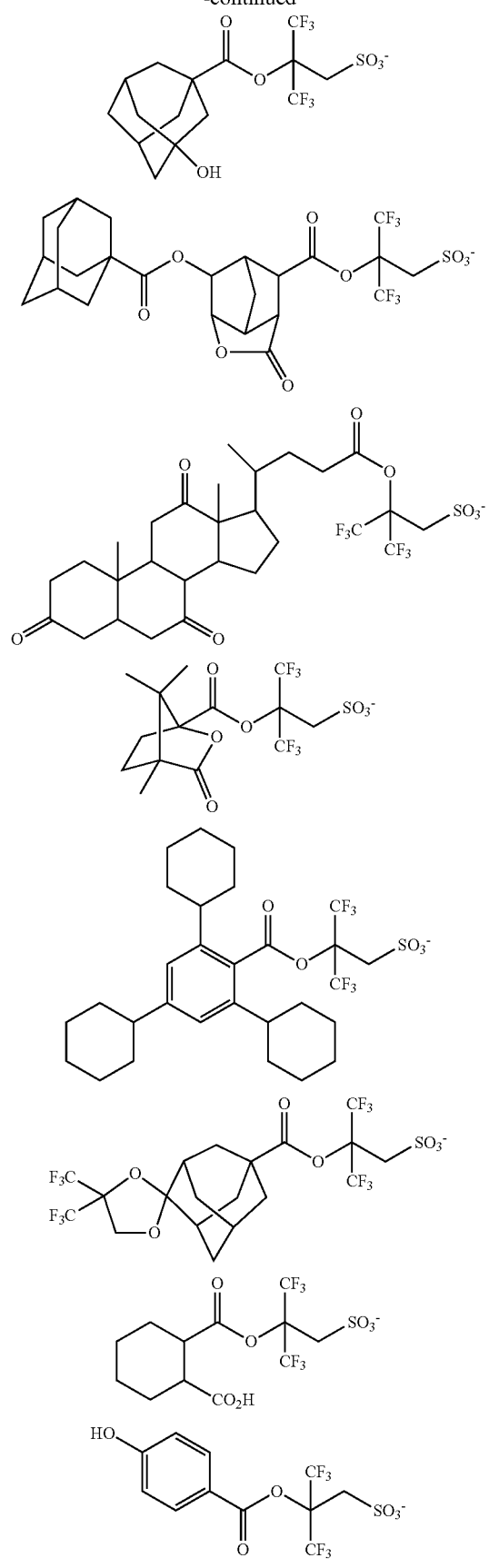

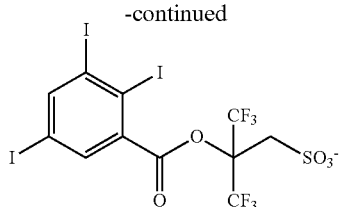

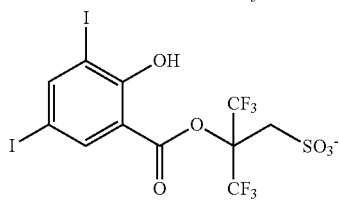

Exemplary structures for the PAG having formula (5A) or (5B) include arbitrary combinations of cations with anions, both as exemplified above, but are not limited thereto.

Another preferred example of the PAG (B) is a compound having the formula (7).

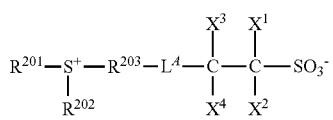

(7)

In formula (7), $R^{201}$ and $R^{202}$ are each independently a $C_1$-$C_{30}$ hydrocarbyl group which may contain a heteroatom. $R^3$ is a $C_1$-$C_{30}$ hydrocarbylene group which may contain a heteroatom. Any two of $R^{201}$, $R^{202}$ and $R^{203}$ may bond together to form a ring with the sulfur atom to which they are attached. $L^A$ is a single bond, ether bond, ester bond, or a $C_1$-$C_{20}$ hydrocarbylene group which may contain a heteroatom, in which —$CH_2$— may be replaced by an ether bond or carbonyl moiety. The constituent —$CH_2$— in the hydrocarbyl group may be one bonding to the carbon atom and/or $R^{203}$ in formula (7). $X^1$, $X^2$, $X^3$ and $X^4$ are each independently hydrogen, fluorine or trifluoromethyl, with at least one thereof being fluorine or trifluoromethyl.

Of the PAGs having formula (7), those having formula (7') are more preferred.

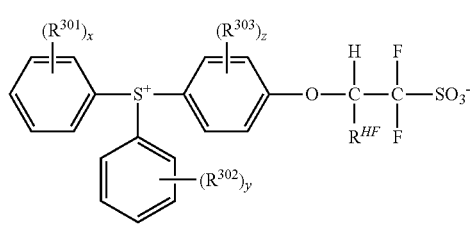

(7')

In formula (7'), $R^{HF}$ is hydrogen or trifluoromethyl, preferably trifluoromethyl. $R^{301}$, $R^{302}$ and $R^{303}$ are each independently a $C_1$-$C_{20}$ hydrocarbyl group which may contain a heteroatom, in which —$CH_2$— may be replaced by an ether bond or carbonyl moiety. The constituent —$CH_2$— in the hydrocarbyl group may be one bonding to a carbon atom in the benzene ring in formula (7'). The subscripts x and y are each independently an integer of 0 to 5, and z is an integer of 0 to 4.

The PAG having formula (7) or (7') is described in JP-A 2011-016746. Examples thereof include those exemplified for the sulfonium salt in the same patent document and those exemplified for the sulfonium salt in JP-A 2015-214634, paragraphs [0149]-[0150].

Specific examples of the PAG having formula (7) are given below, but not limited thereto. Herein $R^{HF}$ is as defined above.

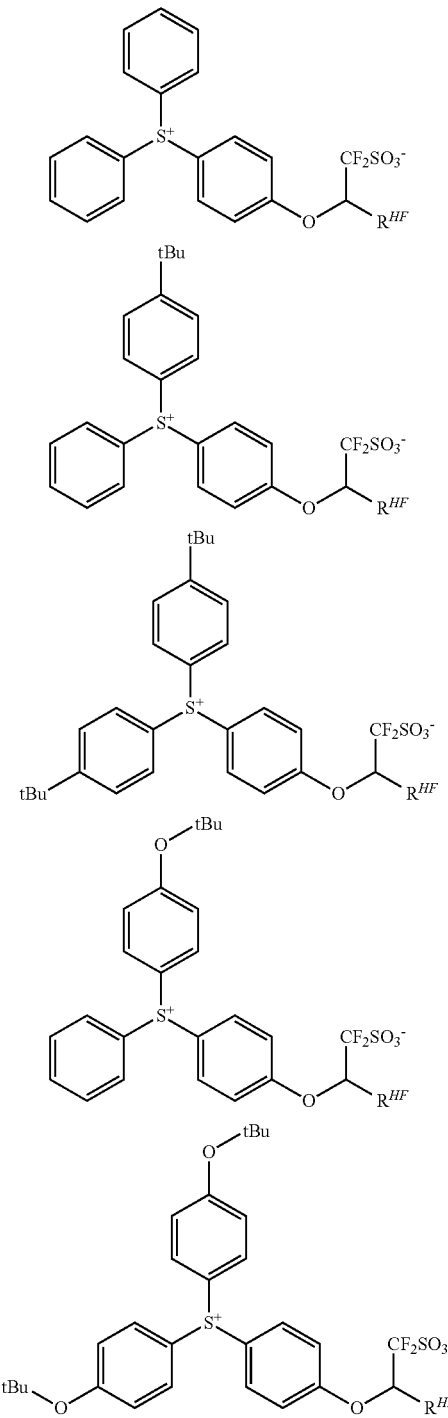

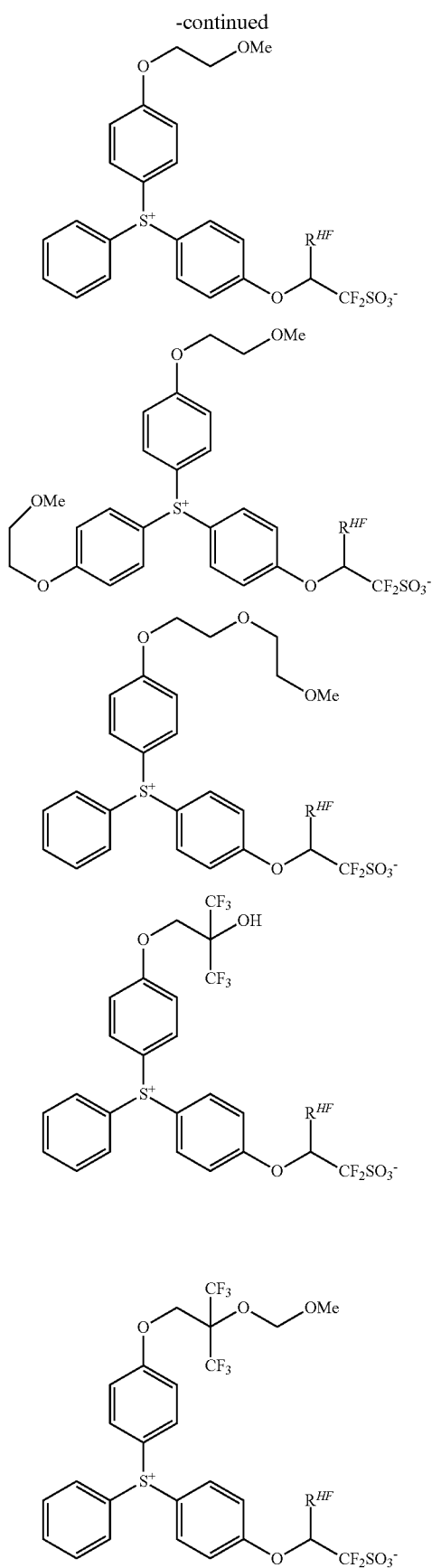
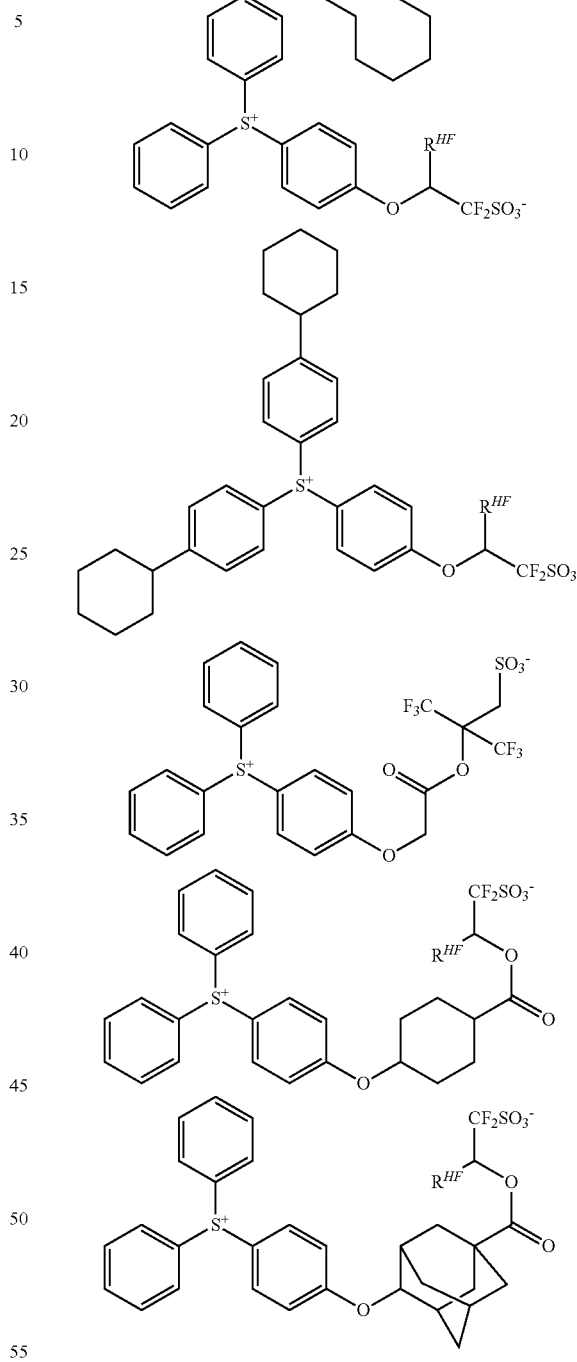

The PAG as component (B) is preferably added in an amount of 1 to 30 parts, more preferably 2 to 25 parts by weight, even more preferably 4 to 20 parts by weight per 100 parts by weight of the base polymer as component (A). The PAG in the range eliminates the problems of degradation of resolution and formation of foreign matter after development or during stripping. The PAG may be used alone or in admixture.

(C) Acid Diffusion Inhibitor

The resist composition further comprises (C) an acid diffusion inhibitor or quencher. Component (C) should contain (C-1) the onium salt compound having formula (1) as an essential component and may contain (C-2) an acid diffusion inhibitor other than the onium salt compound having formula (1). As used herein, the "acid diffusion inhibitor" refers to a compound capable of holding down the diffusion rate when the acid generated by the PAG diffuses in the resist film.

The acid diffusion inhibitor (C-2) is typically selected from amine compounds and onium salts of weak acids such as α-non-fluorinated sulfonic acids and carboxylic acids.

Examples of the amine compound include primary, secondary, and tertiary amine compounds, specifically amine compounds having a hydroxyl group, ether bond, ester bond, lactone ring, cyano group or sulfonate bond. Primary and secondary amine compounds protected with a carbamate group are also included. Such protected amine compounds are effective when the resist composition contains a base labile component. Suitable acid diffusion inhibitors include the compounds described in JP-A 2008-111103, paragraphs [0146]-[0164], and JP 3790649 as well as the following compounds, but are not limited thereto.

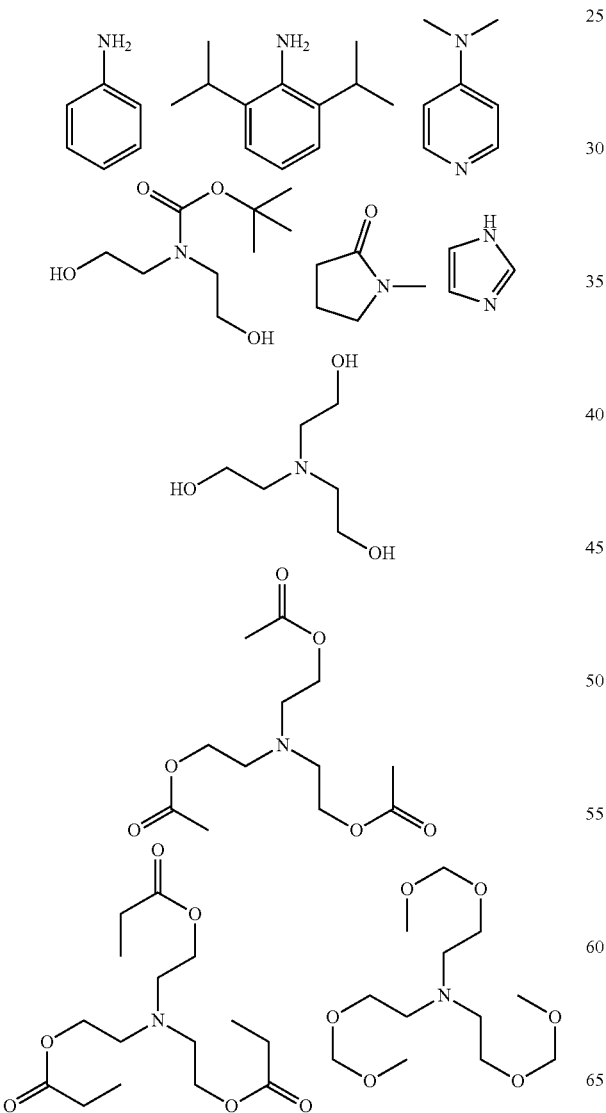

-continued

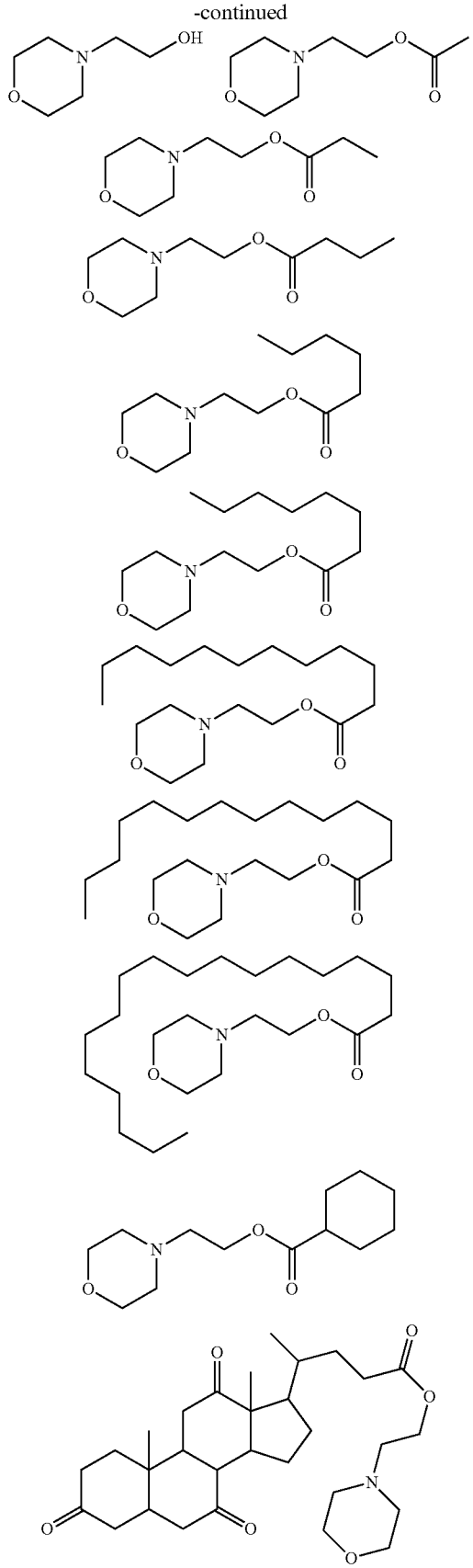

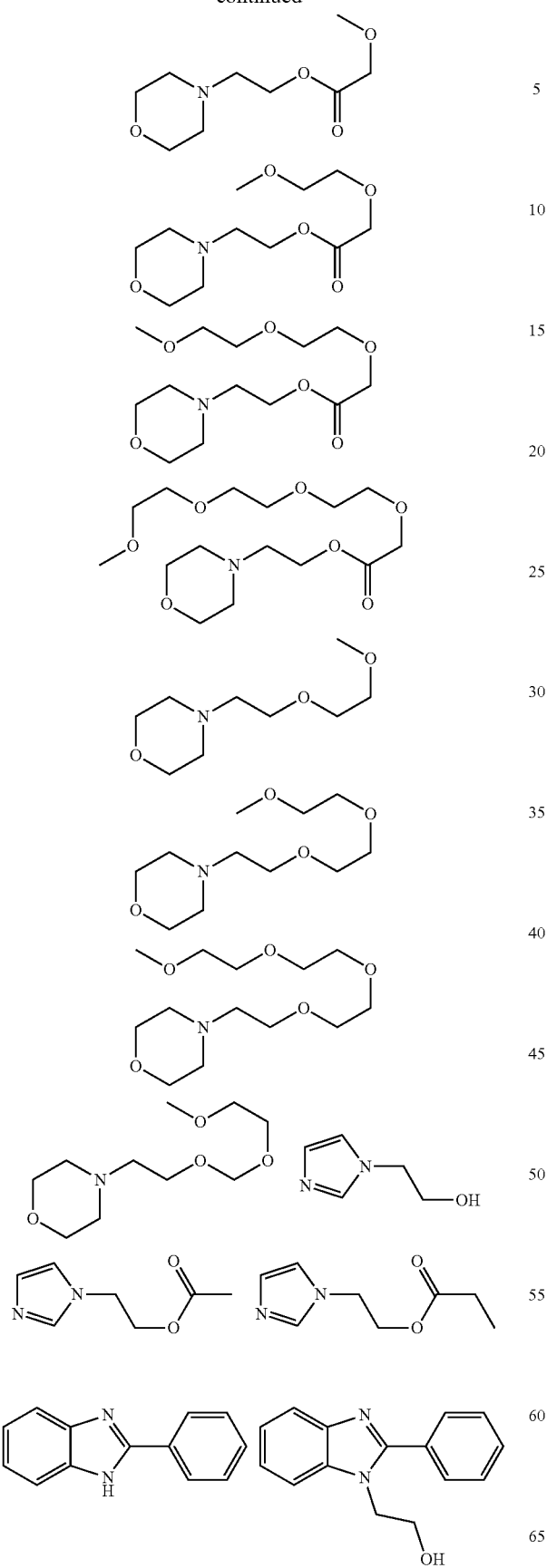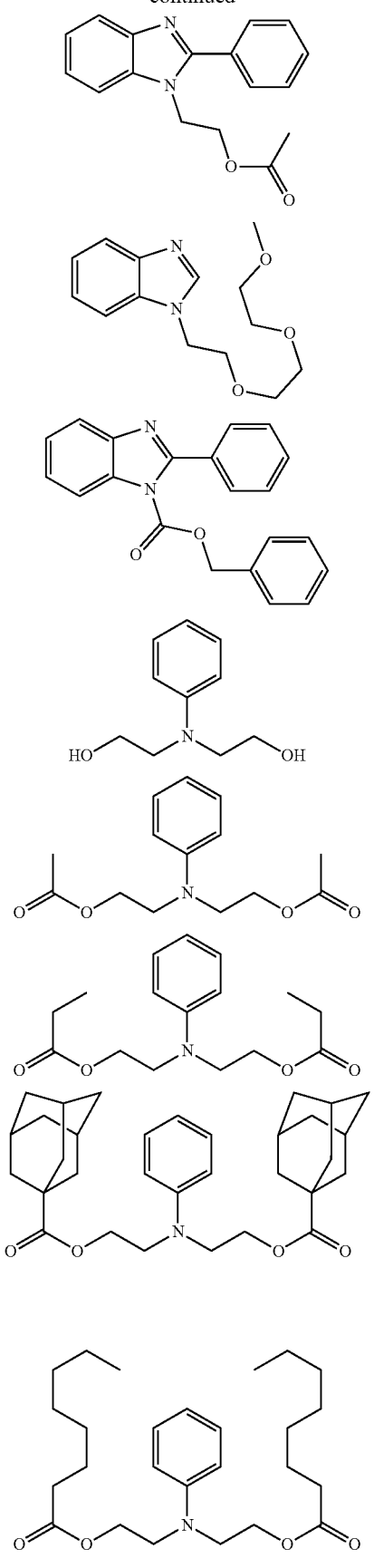

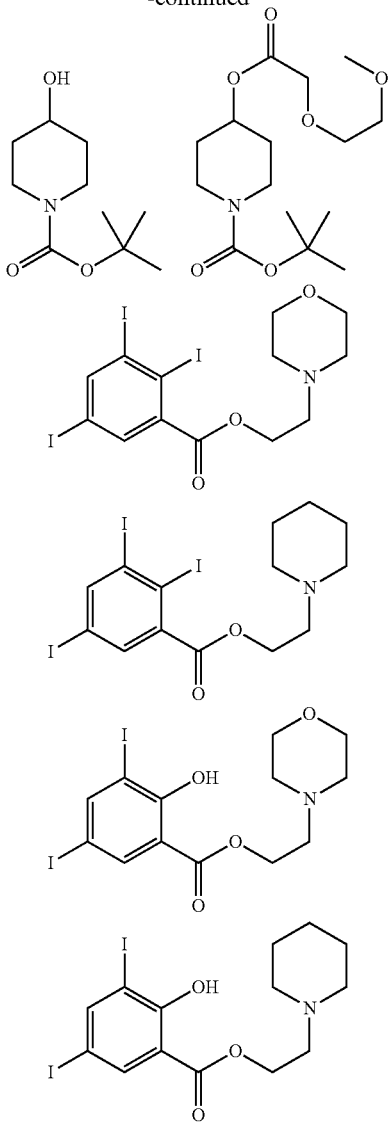

Suitable onium salts of α-no-fluorinated sulfonic acids and carboxylic acids include onium salt compounds having the formulae (8A) and (8B).

In formula (8A), $R^{q1}$ is hydrogen, methoxy, or a $C_1$-$C_{40}$ hydrocarbyl group which may contain a heteroatom, exclusive of the group wherein hydrogen bonded to the carbon atom at α-position relative to the sulfo group is substituted by fluorine or fluoroalkyl.

In formula (8B), $R^{q2}$ is hydrogen, hydroxyl or a $C_1$-$C_{40}$ hydrocarbyl group which may contain a heteroatom.

In formulae (8A) and (8B), $Mq^+$ is an onium cation, which is preferably selected to from cations having the formulae (9A), (9B) and (9C).

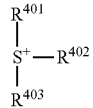

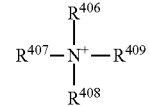

In formulae (9A) to (9C), $R^{401}$ to $R^{409}$ are each independently a $C_1$-$C_{40}$ hydrocarbyl group which may contain a heteroatom. A pair of $R^{401}$ and $R^{402}$, $R^{404}$ and $R^{405}$, or $R^{406}$ and $R^{407}$ may bond together to form a ring with the sulfur, iodine or nitrogen atom to which they are attached.

The optionally heteroatom-containing $C_1$-$C_{40}$ hydrocarbyl group, represented by Re, may be saturated or unsaturated and straight, branched or cyclic. Examples thereof include alkyl groups such as methyl, ethyl, propyl, isopropyl, n-butyl, sec-butyl, tert-butyl, tert-pentyl, n-pentyl, n-hexyl, n-octyl, 2-ethylhexyl, n-nonyl, and n-decyl; cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl; alkenyl groups such as vinyl, allyl, propenyl, butenyl, and hexenyl; cyclic unsaturated hydrocarbyl groups such as cyclohexenyl; aryl groups such as phenyl and naphthyl; heteroaryl groups such as thienyl; hydroxyphenyl groups such as 4-hydroxyphenyl; alkoxyphenyl groups such as 4-methoxyphenyl, 3-methoxyphenyl, 2-methoxyphenyl, 4-ethoxyphenyl, 4-ter-butoxyphenyl, and 3-tert-butoxyphenyl; alkylphenyl groups such as 2-methylphenyl, 3-methylphenyl, 4-methylphenyl, 4-ethylphenyl, 4-tert-butylphenyl, 4-n-butylphenyl, 2,4-dimethylphenyl and 2,4,6-triisopropylphenyl; alkylnaphthyl groups such as methylnaphthyl and ethylnaphthyl; alkoxynaphthyl groups such as methoxynaphthyl, ethoxynaphthyl, n-propoxynaphthyl and n-butoxynaphthyl; dialkylnaphthyl groups such as dimethynaphthyl and diethylnaphthyl; dialkoxynaphthyl groups such as dimethoxynaphthyl and diethoxynaphthyl; aralkyl groups such as benzyl, 1-phenylethyl and 2-phenylethyl; aryloxoalkyl groups, typically 2-aryl-2-oxoethyl groups such as 2-phenyl-2-oxoethyl, 2-(1-naphthyl)-2-oxoethyl, 2-(2-naphthyl)-2-oxoethyl; and combinations thereof.

In the foregoing groups, some hydrogen may be substituted by a moiety containing a heteroatom such as oxygen, sulfur, nitrogen or halogen, and a moiety containing a heteroatom such as oxygen, sulfur or nitrogen may intervene in a carbon-carbon bond, so that the group may contain a hydroxyl moiety, cyano moiety, carbonyl moiety, ether bond, ester bond, sulfonic acid ester bond, carbonate bond, lactone ring, sultone ring, carboxylic anhydride, or haloalkyl moiety.

The optionally heteroatom-containing $C_1$-$C_{40}$ hydrocarbyl group, represented by $R^{q2}$, may be saturated or unsaturated and straight, branched or cyclic. Examples thereof include those exemplified above for $R^{q1}$ and fluorinated alkyl groups such as trifluoromethyl, trifluoroethyl, 2,2,2-trifluoro-1-methyl-1-hydroxyethyl, and 2,2,2-trifluoro-1-(trifluoromethyl)-1-hydroxyethyl and fluorinated aryl groups such as pentafluorophenyl and 4-trifluoromethylphenyl.

The sulfonic acid onium salt having formula (8A) and the carboxylic acid onium salt having formula (8B) are described in JP-A 2008-158339 and JP-A 2010-155824. Examples thereof are as exemplified in these patent documents.

Examples of the anion in the sulfonic acid onium salt having formula (8A) are shown below, but not limited thereto.

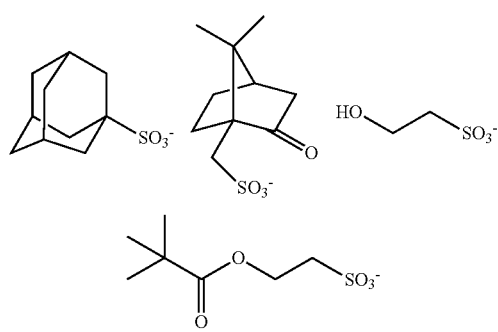
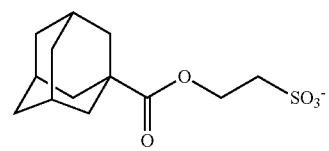
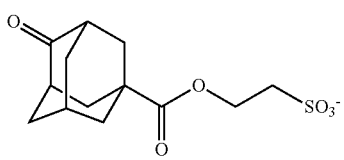
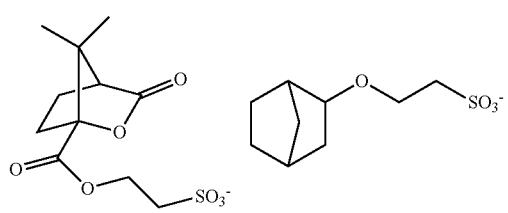
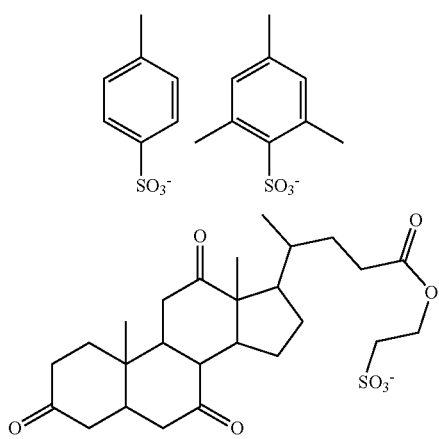
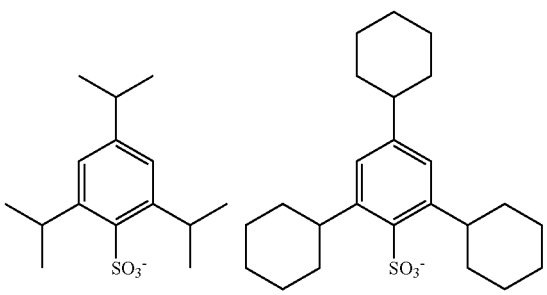
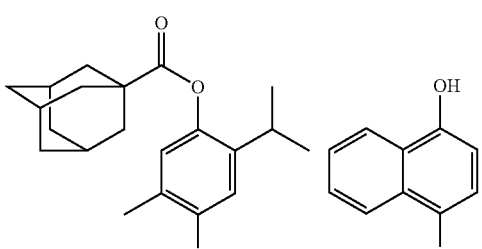
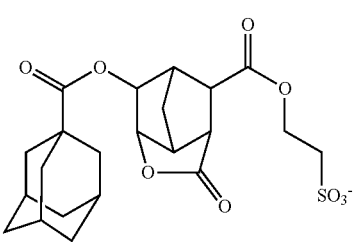

Examples of the anion in the carboxylic acid onium salt having formula (8B) are shown below, but not limited thereto.

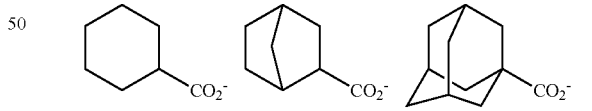
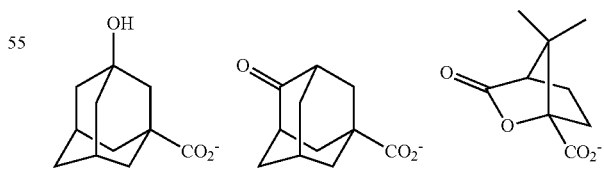
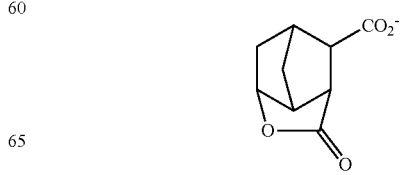

-continued
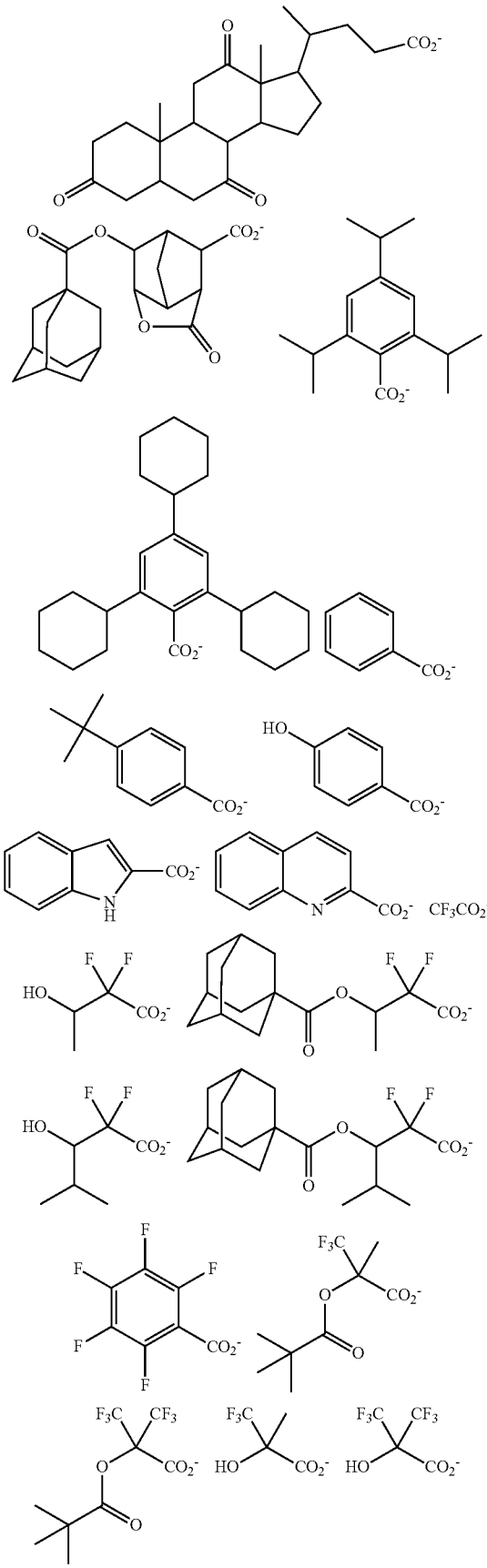
-continued
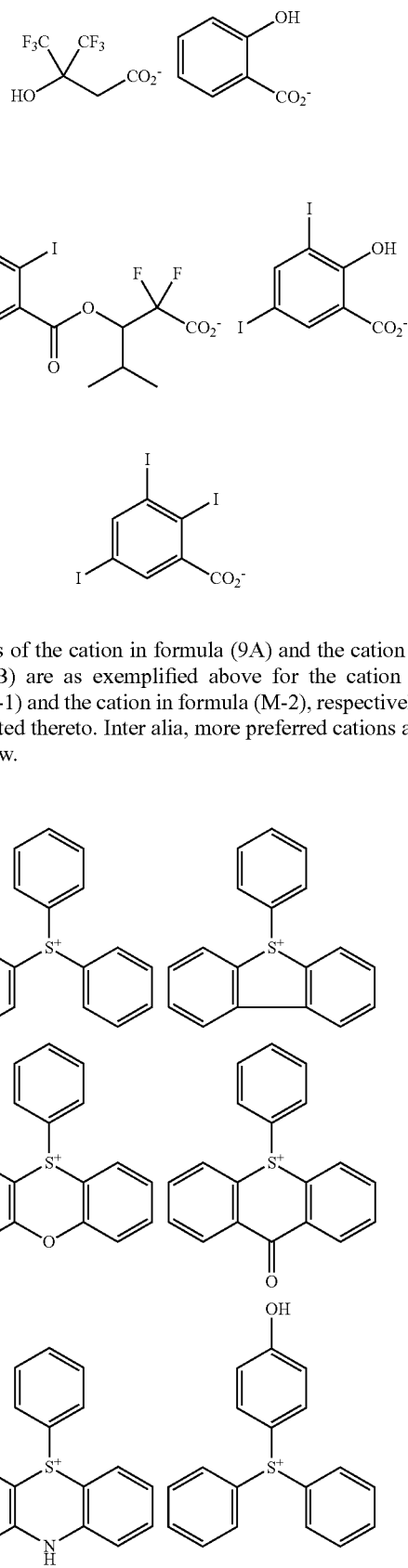
Examples of the cation in formula (9A) and the cation in formula (9B) are as exemplified above for the cation in formula (M-1) and the cation in formula (M-2), respectively, but not limited thereto. Inter alia, more preferred cations are shown below.

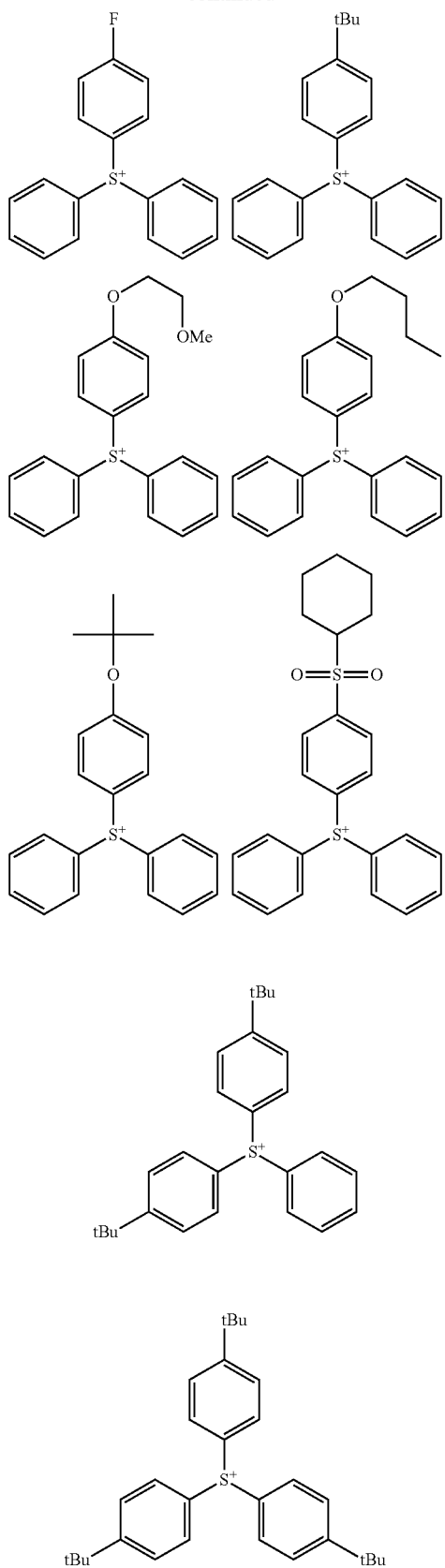
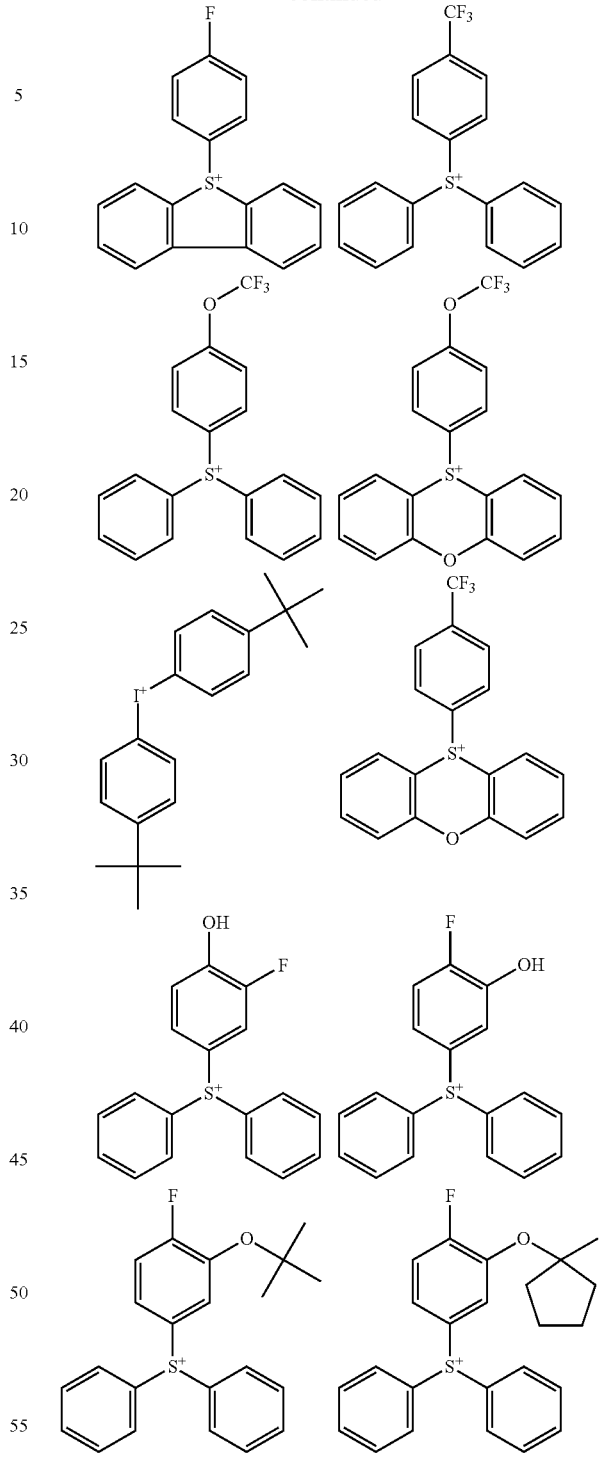

Examples of the sulfonic acid onium salt having formula (8A) and the carboxylic acid onium salt having formula (8B) include arbitrary combinations of anions with cations, both as exemplified above. These onium salts may be readily synthesized by ion exchange reaction according to any well-known organic chemistry technique. For the ion exchange reaction, reference may be made to JP-A 2007-145797, for example.

The onium salt having formula (8A) or (8B) functions as an acid diffusion inhibitor in the resist composition because the counter anion of the onium salt is a conjugated base of a weak acid. As used herein, the weak acid indicates an acidity insufficient to deprotect an acid labile group from an acid labile group-containing unit in the base polymer. The onium salt having formula (8A) or (8B) functions as a quencher when used in combination with an onium salt type PAG having a conjugated base of a strong acid (typically α-fluorinated sulfonic acid) as the counter anion. In a system using a mixture of an onium salt capable of generating a strong acid (e.g., α-fluorinated sulfonic acid) and an onium salt capable of generating a weak acid (e.g., non-fluorinated sulfonic acid or carboxylic acid), if the strong acid generated from the PAG upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

Since the onium salt compound having formula (8A) or (8B) wherein Mq+ is a sulfonium cation (9A) or iodonium cation (9B) is photo-decomposable, the quenching ability is reduced and the concentration of strong acid derived from the PAG is increased in the region with high light intensity. Thus the contrast is improved in the exposed region. As a result, a pattern with improved LWR or CDU can be formed.

In case the acid labile group is an acetal group which is quite sensitive to acid, the acid for eliminating the protective group need not necessarily be an α-fluorinated sulfonic acid, imide acid or methide acid. Sometimes, deprotection reaction can take place even with an α-non-fluorinated sulfonic acid. In this case, an amine compound or carboxylic acid onium salt having formula (8B) is preferably used as the acid diffusion inhibitor.

Besides the onium salt, a betaine type compound of weak acid may also be used as the acid diffusion inhibitor. Suitable betaine type compounds are shown below, but not limited thereto.

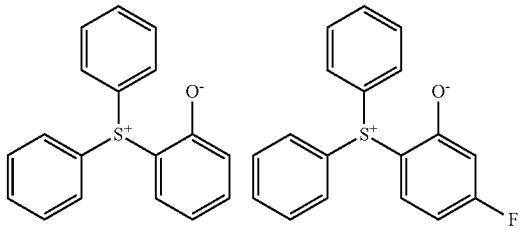

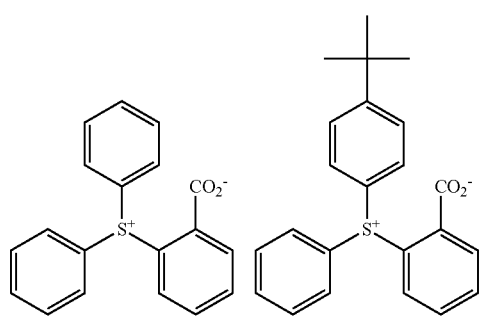

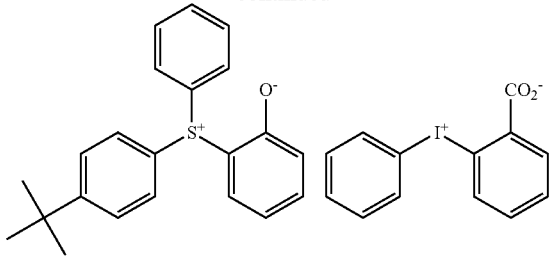

Besides the foregoing compounds, sulfonium or iodonium salts having Cl−, Br− or $NO_3^-$ as the anion may be used as the acid diffusion inhibitor. Examples include triphenylsulfonium chloride, diphenyliodonium chloride, triphenylsulfonium bromide, and triphenylsulfonium nitrate. Since the conjugate acid corresponding to the anion has a low boiling point, the acid created after quenching of strong acid is readily removed from the resist film during PEB or the like. Due to easy removal of acid from within the resist film, acid diffusion is fully suppressed, resulting in an improvement in contrast.

Also a photo-decomposable onium salt having a nitrogen-containing substituent may be used as the acid diffusion inhibitor. The photo-decomposable onium salt functions as an acid diffusion inhibitor in the unexposed region, but as a so-called photo-degradable base in the exposed region because it loses the acid diffusion inhibitory ability due to neutralization thereof with the acid generated by itself. Using a photo-degradable base, the contrast between exposed and unexposed regions can be further enhanced. With respect to the photo-degradable base, reference may be made to JP-A 2009-109595, 2012-046501, and 2013-209360, for example.

Examples of the anion in the photo-degradable onium salt are shown below, but not limited thereto. Herein $R^{HF}$ is hydrogen or trifluoromethyl.

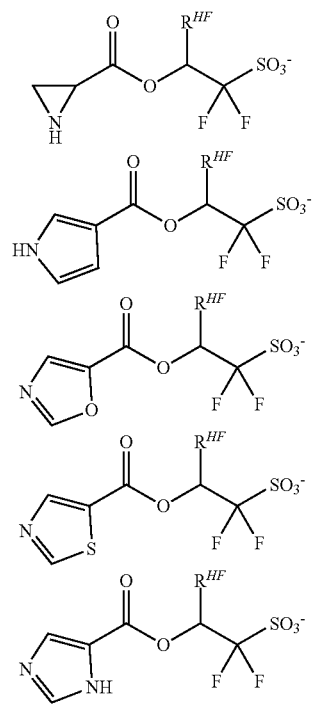

-continued
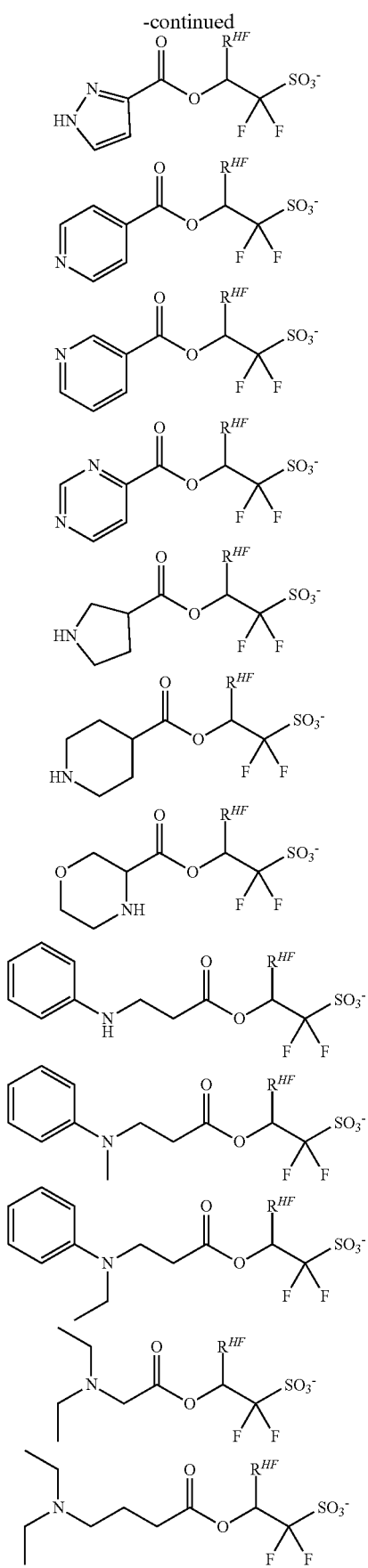
-continued
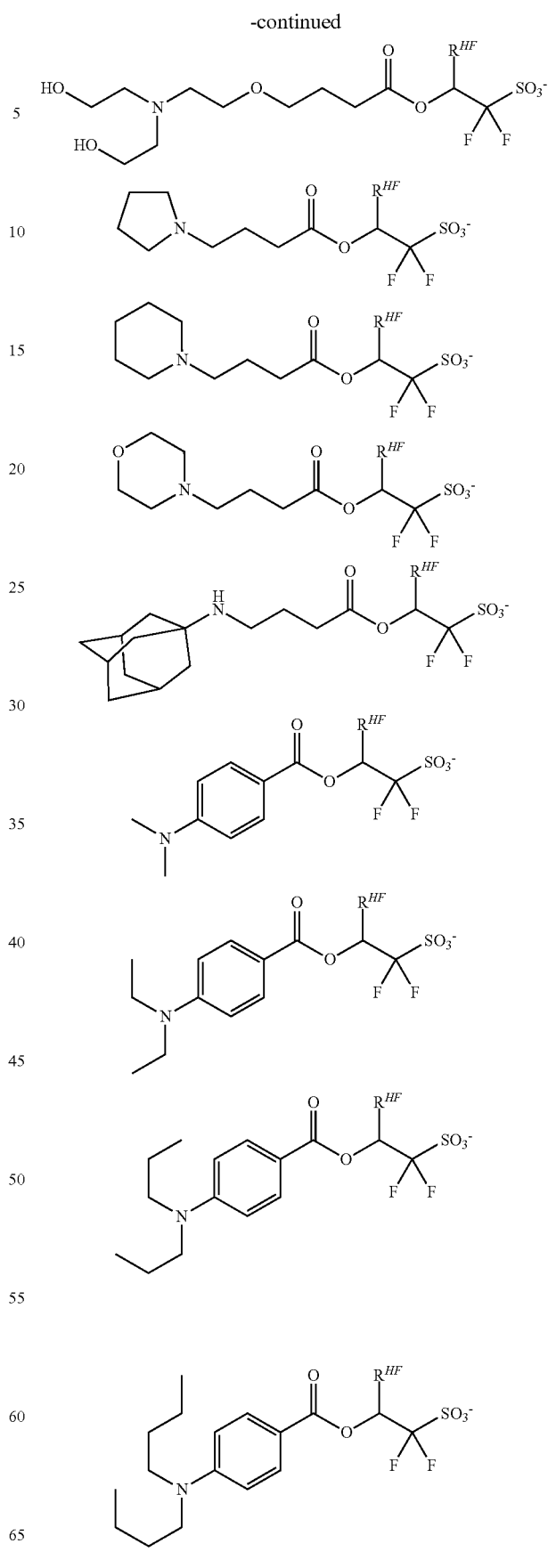

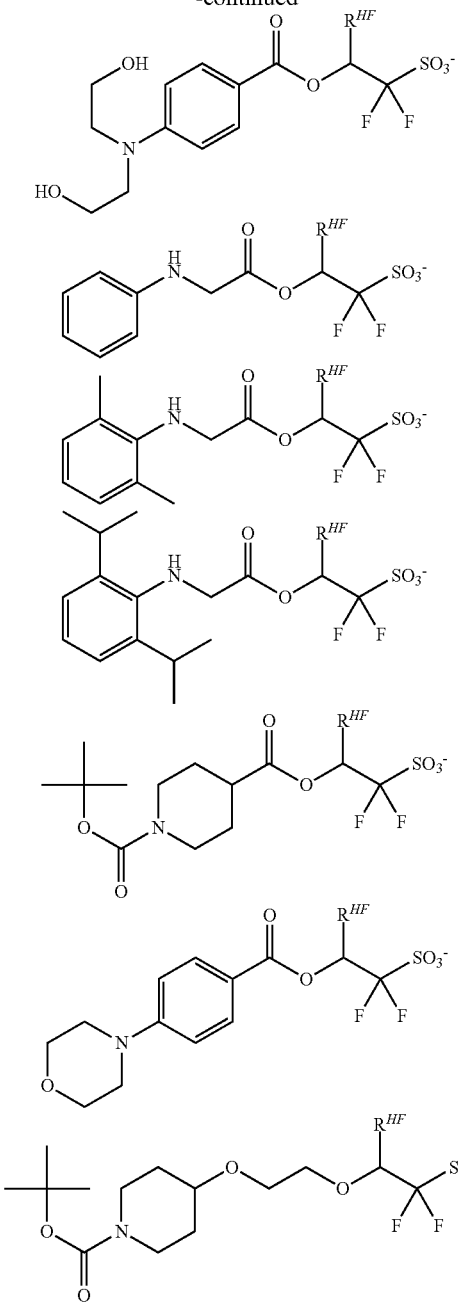
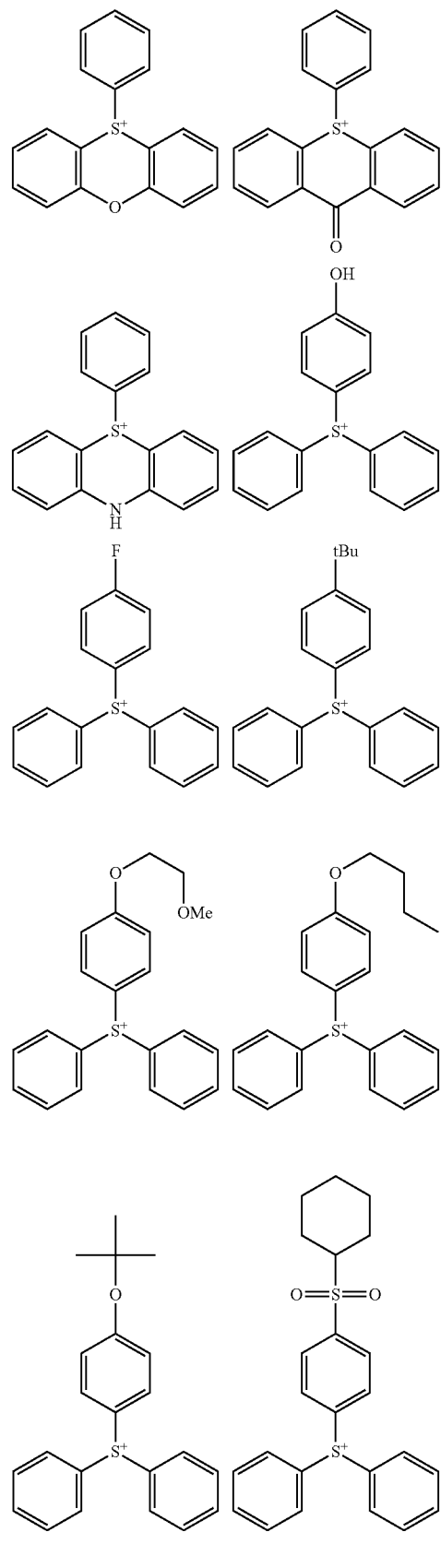
Examples of the cation in the photo-degradable onium salt are as exemplified above for the cation M⁺ in formula (1). Inter alia, the following cations are preferred but not imitative.
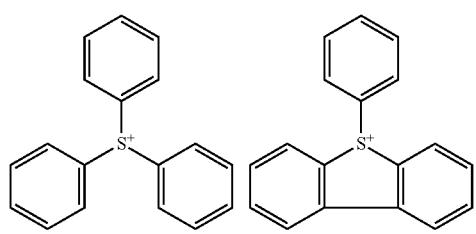

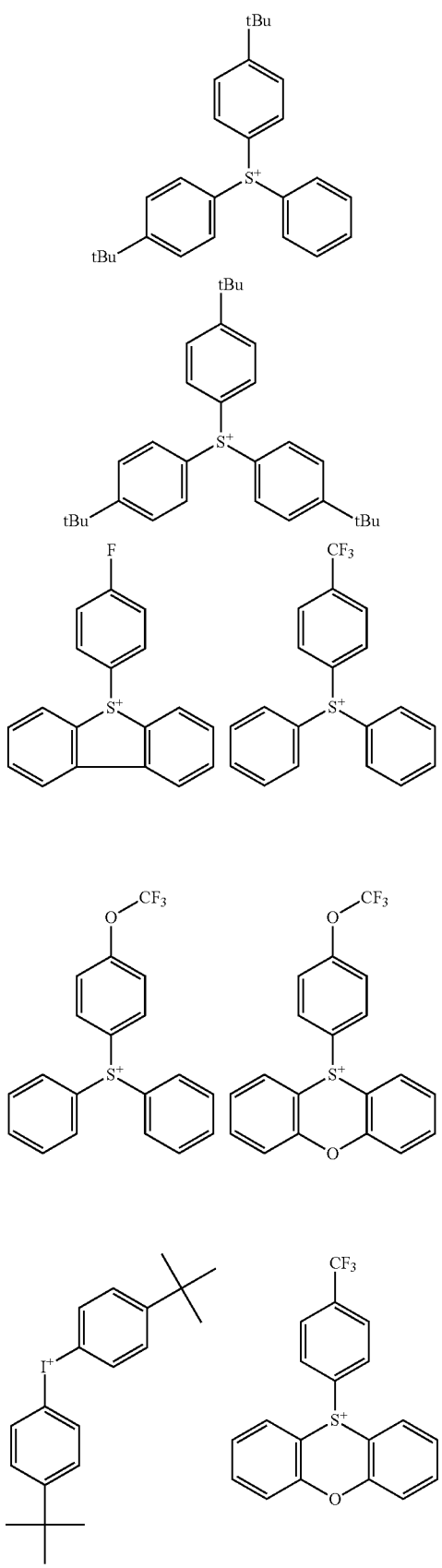

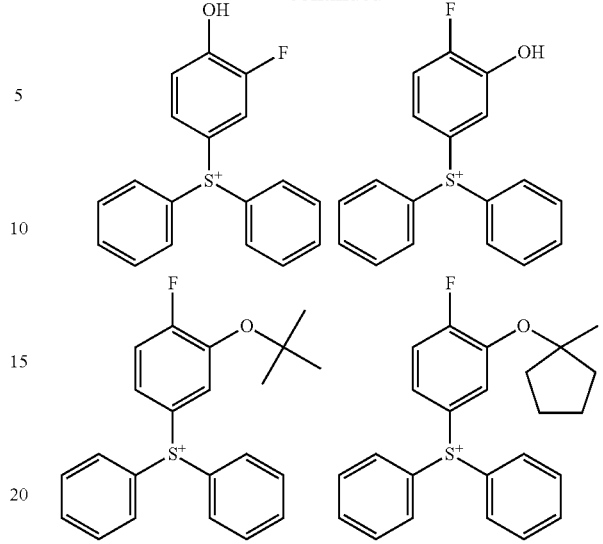

Examples of the photo-decomposable onium salt include arbitrary combinations of cations with anions, both as exemplified above, but are not limited thereto.

Component (C) is preferably used in an amount of 2 to 30 parts by weight, more preferably 2.5 to 20 parts by weight, even more preferably 4 to 15 parts by weight per 100 parts by weight of the base polymer (A). The acid diffusion inhibitor within the range allows for easy adjustment of resist sensitivity, holds down the diffusion rate of acid within the resist film (with improved resolution), suppresses a sensitivity change after exposure, reduces substrate or environment dependency, and improves exposure latitude and pattern profile. Also the addition of the acid diffusion inhibitor is effective for improving substrate adhesion. It is noted that the amount of component (C) is the total amount of the acid diffusion inhibitor in the form of the onium salt compound having formula (1) and the acid diffusion inhibitor other than the onium salt compound having formula (1). In the acid diffusion inhibitor (C), preferably the onium salt compound having formula (1) accounts for 50 to 100% by weight. The acid diffusion inhibitor as component (C) may be used alone or in admixture.

(D) Organic Solvent

The resist composition further comprises (D) an organic solvent. The organic solvent used herein is not particularly limited as long as the foregoing and other components are dissolvable therein. Examples of the organic solvent used herein are described in JP-A 2008-111103, paragraphs [0144]-[0145] (U.S. Pat. No. 7,537,880). Exemplary solvents include ketones such as cyclohexanone (CyHO) and methyl-2-n-pentyl ketone; alcohols such as 3-methoxybutanol, 3-methyl-3-methoxybutanol, 1-methoxy-2-propanol, 1-ethoxy-2-propanol, and diacetone alcohol (DAA); ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether, esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone (GBL), which may be used alone or in admixture. Where an acid labile group of acetal form is used, a high boiling alcohol solvent such as diethylene glycol, propylene glycol, glycerol, 1,4-butanediol or 1,3-butanediol may be added to accelerate deprotection reaction of acetal.

Of these organic solvents, preference is given to 1-ethoxy-2-propanol, PGMEA, DAA, CyHO, and GBL and mixtures thereof because the PAG is highly soluble therein. The preferred solvent system is a mixture of PGMEA as solvent X and at least one of 1-ethoxy-2-propanol, DAA, CyHO, and GBL as solvent Y in a ratio X-Y of from 90:10 to 60:40.

The organic solvent (D) is preferably added in an amount of 100 to 8,000 parts, and more preferably 400 to 6.000 parts by weight per 100 parts by weight of the base polymer (A).

(E) Surfactant

In addition to the foregoing components, the resist composition may comprise (E) a surfactant which is commonly used for facilitating coating operation.

Component (E) is typically a surfactant which is insoluble or substantially insoluble in water and alkaline developer or a surfactant which is insoluble or substantially insoluble in water and soluble in alkaline developer.

For the surfactant which is insoluble or substantially insoluble in water and alkaline developer, reference should be made to JP-A 2010-215608 and JP-A 2011-016746. Suitable surfactants include FC-4430 (3M), Surflon® S-381, KH-20 and KH-30 (AGC Seimi Chemical Co., Ltd.), and Olfine® E1004 (Nisshin Chemical Co., Ltd.). Partially fluorinated oxetane ring-opened polymers having the structural formula (surf-1) are also useful.

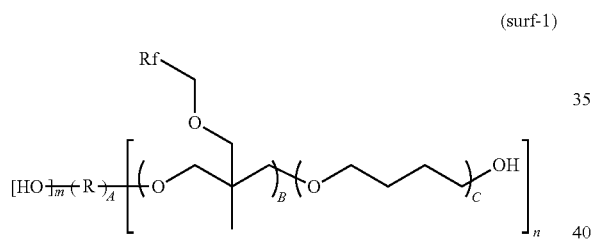
(surf-1)

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

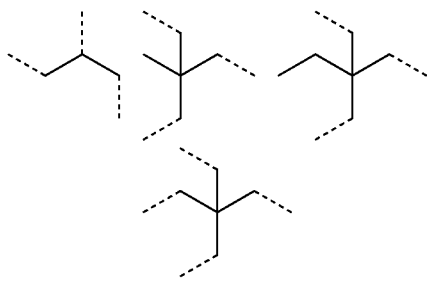

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. "A" is equal to 1, B is an integer of 2 to 25, and C is an integer of 0 to 10. Preferably, B is an integer of 4 to 20, and C is 0 or 1. Note that the above structural formula does not prescribe the arrangement of respective constituent units while they may be arranged either blockwise or randomly. For the preparation of surfactants in the form of partially fluorinated oxetane ring-opened polymers, reference should be made to U.S. Pat. No. 5,650,483, for example.

The surfactant which is insoluble or substantially insoluble in water and soluble in alkaline developer is useful when ArF immersion lithography is applied to the resist composition in the absence of a resist protective film. In this embodiment, the surfactant has a propensity to segregate on the resist film surface for achieving a function of minimizing water penetration or leaching. The surfactant is also effective for preventing water-soluble components from being leached out of the resist film for minimizing any damage to the exposure tool. The surfactant becomes solubilized during alkaline development following exposure and PEB, and thus forms few or no foreign particles which become defects. The preferred surfactant is a polymeric surfactant which is insoluble or substantially insoluble in water, but soluble in alkaline developer, also referred to as "hydrophobic resin" in this sense, and especially which is water repellent and enhances water sliding.

Suitable polymeric surfactants include those containing recurring units of at least one type selected from the formulae (10A) to (10E).

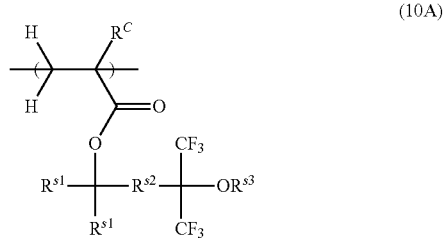
(10A)

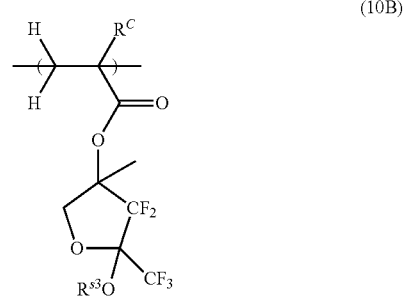
(10B)

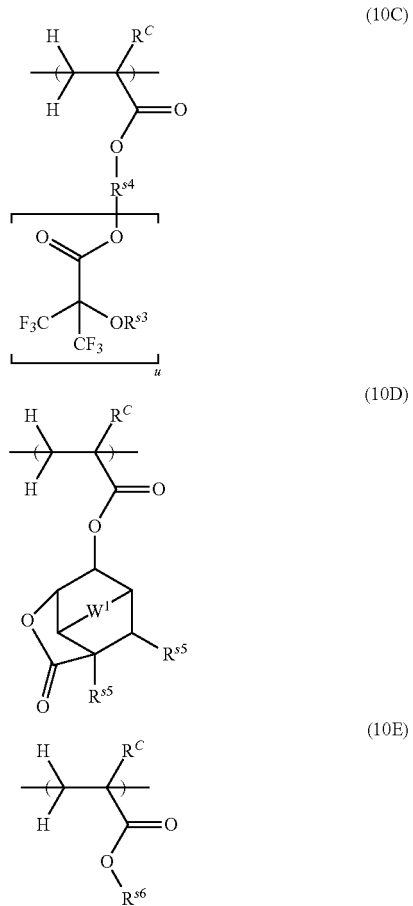

Herein, $R^C$ is each independently hydrogen or methyl. $W^1$ is —$CH_2$—, —$CH_2CH_2$— or —O—, or two separate —H. $R^{s1}$ is each independently hydrogen or a $C_1$-$C_{10}$ hydrocarbyl group. $R^{s2}$ is a single bond or a $C_1$-$C_5$ alkanediyl group. $R^{s3}$ is each independently hydrogen, a $C_1$-$C_{15}$ hydrocarbyl or fluorinated hydrocarbyl group, or an acid labile group. When $R^{s3}$ is a hydrocarbyl or fluorinated hydrocarbyl group, an ether bond (—O—) or carbonyl moiety (—C(=O)—) may intervene in a carbon-carbon bond. $R^{s4}$ is a $C_1$-$C_{20}$ (u+1)-valent hydrocarbon or fluorinated hydrocarbon group, and u is an integer of 1 to 3. $R^{s5}$ is each independently hydrogen or a group having the formula: —C(=O)—O—$R^{s5A}$ wherein $R^{s5A}$ is a $C_1$-$C_{20}$ fluorinated hydrocarbyl group. $R^{s6}$ is a $C_1$-$C_{15}$ hydrocarbyl or fluorinated hydrocarbyl group in which an ether bond or carbonyl moiety may intervene in a carbon-carbon bond.

The polymeric surfactant may further contain recurring units other than the recurring units having formulae (10A) to (10E). Typical other recurring units are those derived from methacrylic acid and α-trifluoromethylacrylic acid derivatives. In the polymeric surfactant, the content of the recurring units having formulae (10A) to (10E) is preferably at least 20 mol %, more preferably at least 60 mol %, most preferably 100 mol % of the overall recurring units.

For the surfactant which is insoluble or substantially insoluble in water and soluble in alkaline developer, reference may be made to JP-A 2008-122932, JP-A 2009-098638, JP-A 2009-191151, JP-A 2009-192784, JP-A 2009-276363, JP-A 2010-107695, JP-A 2010-134012, JP-A 2010-250105, and JP-A 2011-042789.

The amount of component (E) is preferably 0 to 20 parts by weight per 100 parts by weight of the base polymer (A). When added, the amount of component (E) is more preferably 0.001 to 15 parts by weight, even more preferably 0.01 to 10 parts by weight. The surfactant may be used alone or in admixture. The surfactant is also described in JP-A 2007-297590.

(F) Other components

The resist composition may further comprise (F) another component, for example, a compound which is decomposed with an acid to generate another acid (i.e., acid amplifier compound), an organic acid derivative, a fluorinated alcohol, a crosslinker, a compound having a Mw of up to 3,000 which changes its solubility in developer under the action of an acid (i.e., dissolution inhibitor), and an acetylene alcohol. Specifically, the acid amplifier compound is described in JP-A 2009-269953 and JP-A 2010-215608 and preferably used in an amount of 0 to 5 parts, more preferably 0 to 3 parts by weight per 100 parts by weight of the base polymer (A). An extra amount of the acid amplifier compound can make the acid diffusion control difficult and cause degradations to resolution and pattern profile. With respect to the remaining additives, reference should be made to JP-A 2008-122932, paragraphs [0155]-[0182], JP-A 2009-269953 and JP-A 2010-215608.

The chemically amplified resist composition comprising the onium salt compound having formula (1) as an acid diffusion inhibitor, when processed by photolithography using high-energy radiation such as KrF excimer laser, ArF excimer laser, EB or EUV as the energy source, exhibits a high acid diffusion suppressing effect, and forms a pattern at a high contrast and with improved lithography performance factors such as CDU, LWR and sensitivity.

Process

A further embodiment of the invention is a pattern forming process using the chemically amplified resist composition defined above. The process includes the steps of applying the resist composition to form a resist film on a substrate, exposing a selected region of the resist film to high-energy radiation, and developing the exposed resist film in a developer. Any desired steps may be added to the process if necessary.

The substrate used herein may be a substrate for integrated circuitry fabrication, e.g., Si, $SiO_2$, SiN, SiON, TiN, WSi, BPSG, SOG, organic antireflective film, etc. or a substrate for mask circuitry fabrication, e.g., Cr, CrO, CrON, $MoSi_2$, $SiO_2$, etc.

The resist composition is applied onto a substrate by a suitable coating technique such as spin coating. The coating is prebaked on a hot plate preferably at a temperature of 60 to 180° C. for 10 to 600 seconds, more preferably at 70 to 150° C. for 15 to 300 seconds. The resulting resist film preferably has a thickness of 10 to 2,000 nm.

The resist film is then exposed to high-energy radiation. On use of KrF excimer laser, ArF excimer laser or EUV of wavelength 13.5 nm, the resist film is exposed through a mask having the desired pattern in a dose of preferably 1 to 200 m/$cm^2$, more preferably to 100 mJ/$cm^2$. On use of EB, a pattern may be written directly or through a mask having the desired pattern, preferably in a dose of 1 to 300 μC/$cm^2$, more preferably 10 to 200 μC/$cm^2$.

The exposure may be performed by conventional lithography whereas the immersion lithography of holding a liquid between the mask and the resist film may be employed if desired. In the immersion lithography, preferably a liquid having a refractive index of at least 1.0 is held between the resist film and the projection lens. The liquid is typically water, and in this case, a protective film which is insoluble in water may be formed on the resist film.

While the water-insoluble protective film which is used in the immersion lithography serves to prevent any components from being leached out of the resist film and to improve water sliding on the film surface, it is generally divided into two types. The first type is an organic solvent-strippable protective film which must be stripped, prior to alkaline development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

After the exposure, the resist film may be baked (PEB), for example, on a hotplate at 60 to 150° C. for 1 to 5 minutes, preferably at 80 to 140° C. for 1 to 3 minutes.

The resist film is then developed with a developer in the form of an aqueous base solution, for example, 0.1 to 5 wt %, preferably 2 to 3 wt % aqueous solution of tetramethyl-ammonium hydroxide (TMAH) for 0.1 to 3 minutes, preferably 0.5 to 2 minutes by conventional techniques such as dip, puddle and spray techniques. In this way, a desired resist pattern is formed on the substrate.

With respect to the formation of a positive pattern using an alkaline aqueous solution as the developer, reference may be made to U.S. Pat. No. 8,647,808 (JP-A 2011-231312, paragraphs [0138]-[0146]). With respect to the formation of a negative pattern using an organic solvent as the developer, reference may be made to U.S. Pat. No. 9,256,127 (JP-A 2015-214634, paragraphs [0173]-[0183]).

Any desired step may be added to the pattern forming process. For example, after the resist film is formed, a step of rinsing with pure water (post-soaking) may be introduced to extract the acid generator or the like from the film surface or wash away particles. After exposure, a step of rinsing (post-soaking) may be introduced to remove any water remaining on the film after exposure.

Also, a double patterning process may be used for pattern formation. The double patterning process includes a trench process of processing an underlay to a 1:3 trench pattern by a first step of exposure and etching, shifting the position, and forming a 1:3 trench pattern by a second step of exposure, for forming a 1:1 pattern; and a line process of processing a first underlay to a 1:3 isolated left pattern by a first step of exposure and etching, shifting the position, processing a second underlay formed below the first underlay by a second step of exposure through the 1:3 isolated left pattern, for forming a half-pitch 1:1 pattern.

Where a hole pattern is formed by negative tone development using organic solvent developer, exposure by double dipole illuminations of X- and Y-direction line patterns provides the highest contrast light. The contrast may be further increased by combining two dipole illuminations of X- and Y-direction line patterns with s-polarized illumination. These pattern forming processes are described in JP-A 2011-221513.

With respect to the developer in the pattern forming process, examples of the aqueous alkaline solution include TMAH aqueous solutions as mentioned above and aqueous alkaline solutions described in JP-A 2015-180748, paragraphs [0148]-[0149], preferably 2 to 3% by weight TMAH aqueous solutions.

The organic solvent used as the developer is preferably selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, butenyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate. These organic solvents may be used alone or in admixture of two or more.

A hole or trench pattern after development may be shrunk by the thermal flow, RELACS® (resolution enhancement lithography assisted by chemical shrink) or DSA (directed self-assembly) process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

When processed by photolithography, the chemically amplified resist composition comprising the onium salt compound having formula (1) as an acid diffusion inhibitor forms a fine size pattern with improved lithography performance factors such as CDU, LWR and sensitivity.

EXAMPLES

Examples of the invention are given below by way of illustration and not by way of limitation. The abbreviation "pbw" is parts by weight. For all polymers, Mw and Mn are determined by GPC versus polystyrene standards using tetrahydrofuran (ITF) solvent.

Example 1-1

Synthesis of Acid Diffusion Inhibitor Q-I
(1) Synthesis of Compound SM-2

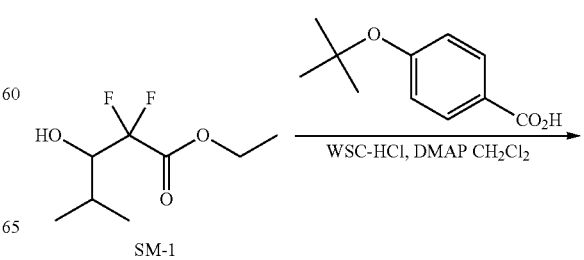

SM-1

-continued

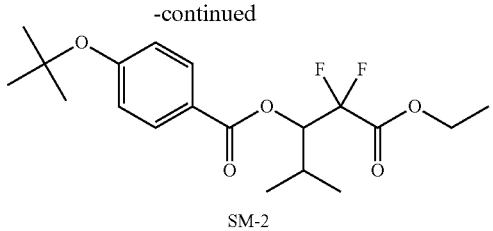

SM-2

To a mixture of 354.7 g of Compound SM-1, 437.2 g of p-tert-butoxybenzoic acid, 66.5 g of N,N-dimethylaminopyridine, and 3,400 g of methylene chloride, 450.9 g of N-(3-dimethylaminopropyl)-N'-ethylcarbodiimide hydrochloride was added, after which stirring was continued at room temperature for 21 hours. Once the completion of reaction was confirmed by $^{19}$F-NMR spectroscopy, 1,600 g of 5 wt % NaHCO$_3$ aqueous solution was added to the reaction solution, which was stirred to quench the reaction. The organic layer was taken out and washed once with 1,600 g of deionized water and 400 g of saturated saline. The organic layer was concentrated under reduced pressure and dissolved in 2,000 g of hexane again. The organic layer was sequentially washed with 1,000 g of deionized water, 1,000 g of 5 wt % hydrochloric acid, and 1,000 g of deionized water. The organic layer was concentrated under reduced pressure. The crude product was distilled under reduced pressure, obtaining the desired Compound SM-2 (amount 601.1 g, yield 89%).

(2) Synthesis of Compound SM-3

To a mixture of 91.8 g of Compound SM-2 and 184 g of dioxane, 93.4 g of 25 wt % TMAH aqueous solution was added dropwise. After overnight stirring at 35° C., the reaction solution was concentrated under reduced pressure. To the concentrate were added 500 g of methylene chloride, 200 g of deionized water, and 50 g of benzyltrimethylammonium chloride. After 10 minutes of stirring, the organic layer was taken out. The organic layer was washed with 200 g of 10 wt % benzyltrimethylammonium chloride aqueous solution and 200 g of deionized water. The organic layer was concentrated under reduced pressure. To the concentrate, 300 g of diisopropyl ether was added. During stirring, crystals precipitated out. The solid was filtered and washed with diisopropyl ether. The resulting solid was dried in vacuum, obtaining the desired Compound SM-3 (amount 104.7 g, yield 88%).

(3) Synthesis of Acid Diffusion Inhibitor Q-1

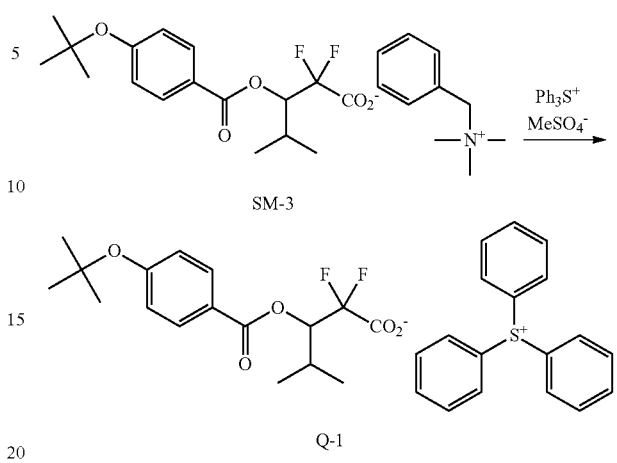

To 186.6 g of Compound SM-3, 1,200 g of methylene chloride and 80 g of methanol were added and stirred. To the mixture, 156 g of triphenylsulfonium methylsulfate and 400 g of deionized water were added. After 30 minutes of stirring, the organic layer was taken out. To the organic layer, a mixture of 14.2 g of triphenylsulfonium methylsulfate, 2.2 g of 29 wt % aqueous ammonia, and 400 g of deionized water was added, performing two cycles of additional salt exchange. The organic layer was washed 5 times with 400 g of deionized water, and 3 times with 20 wt % methanol aqueous solution. The organic layer was concentrated under reduced pressure, obtaining the target acid diffusion inhibitor Q-I as oily matter (amount 210.5 g, yield 91.8%). The spectral data of Q-1 are shown below.

$^1$H-NMR (500 MHz, DMSO-d$_6$):
δ=0.87 (3H, d), 0.92 (3H, d), 1.36 (9H, s), 2.12 (1K m), 5.45 (1H, m), 7.10 (2H, m), 7.76-7.91 (17H, m) ppm $^{19}$F-NLR (500 MHz, DMSO-d$_6$):
δ=−115.2 (1F, dd), −107.5 (1F, dd) ppm IR (D-ATR):
v=3061, 2975, 2953, 2878, 1716, 1658, 1604, 1505, 1477, 1448, 1392, 1369, 1315, 1269, 1257, 1212, 1158, 1098, 1036, 997, 927, 897, 850, 805, 751, 701, 685, 504 cm$^{-1}$ Time-of-flight mass spectrometry (TOFMS; MALDI)
Positive M$^+$ 263.1 (corresponding to C$_{18}$H$_{15}$S$^+$)
Negative M$^-$ 343.1 (corresponding to C$_{17}$H$_{21}$F$_2$O$_5^-$)

Example 1-2

Synthesis of Acid Diffusion Inhibitor Q-22
(1) Synthesis of Compound SM-5

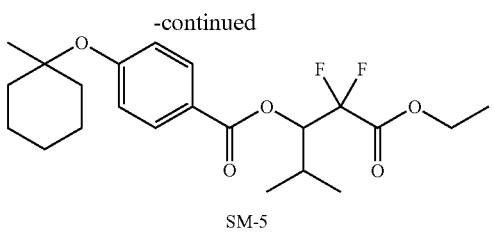

SM-5

To a mixture of 11.8 g of Compound SM-1, 14.8 g of Compound SM-4, 0.73 g of N,N-dimethylaminopyridine, and 70 g of methylene chloride, 13.8 g of N-(3-dimethylaminopropyl)-N'-ethylcarbodiimide hydrochloride was added, after which stirring was continued at room temperature for 60 hours. Once the completion of reaction was confirmed by $^{19}$F-NMR spectroscopy, 40 g of deionized water was added to the reaction solution, which was stirred to quench the reaction. The organic layer was taken out and washed with 40 g of 2 wt % hydrochloric acid. The organic layer was further washed once with a mixture of 40 g of deionized water and 40 g of saturated sodium hydrogencarbonate aqueous solution, once with 40 g of deionized water, and once with 40 g of saturated saline. The organic layer was combined with 1.2 g of activated carbon and stirred for 60 hours, after which the activated carbon was filtered off. The filtrate was concentrated under reduced pressure, obtaining the desired Compound SM-5 (amount 23.6 g, yield 95%).

(2) Synthesis of Compound SM-6

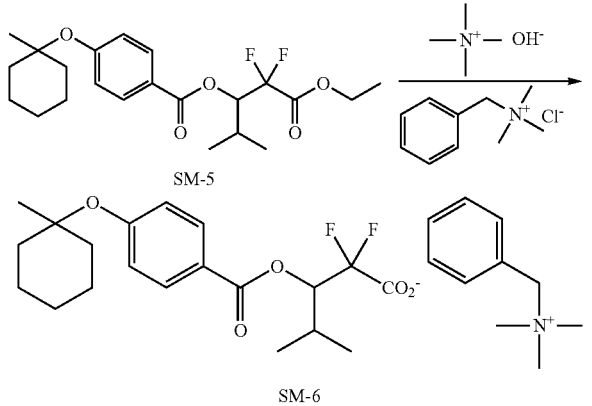

To a mixture of 23.5 g of Compound SM-5 and 24 g of dioxane, 19.8 g of 25 wt % TMAH aqueous solution was added dropwise. After overnight stirring at 30° C., the completion of reaction was confirmed by $^{19}$F-NMR spectroscopy. The reaction solution was concentrated under reduced pressure. To the concentrate were added 70 g of methylene chloride, 35 g of deionized water, and 15.9 g of benzyltrimethylammonium chloride. After 10 minutes of stirring, the organic layer was taken out. The organic layer was washed once with 40 g of 10 wt % benzyltrimethylammonium chloride aqueous solution and twice with 40 g of 10 wt % methanol aqueous solution. The organic layer was concentrated under reduced pressure. The concentrate was dissolved in 60 g of methanol, and the solution was combined with 1.5 g of activated carbon and stirred overnight. After the activated carbon was filtered off, the filtrate was concentrated under reduced pressure. To the concentrate, 100 mL of hexane was added for crystallization. The solid was filtered and dried in vacuum, obtaining the desired Compound SM-6 (amount 26.7 g, yield 87%).

(3) Synthesis of Acid Diffusion Inhibitor Q-22

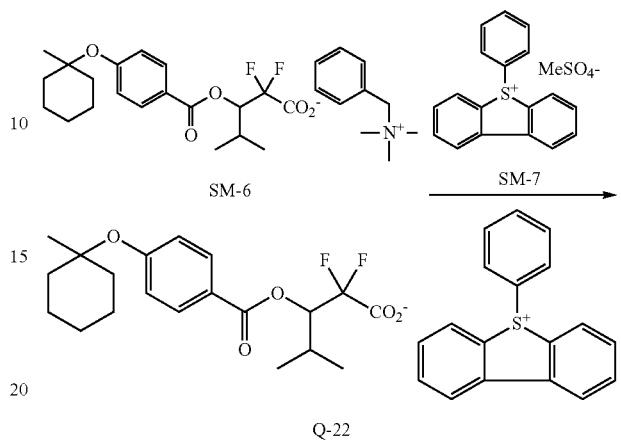

A reactor was charged with 8.0 g of Compound SM-6, 6.7 g of Compound SM-7, 50 g of methylene chloride, and 50 g of deionized water, which were stirred for 10 minutes. The organic layer was taken out. To the organic layer, a mixture of 0.6 g of Compound SM-7 and 60 g of deionized water was added, performing two cycles of additional salt exchange. The organic layer was washed 5 times with 60 g of deionized water. The organic layer was concentrated under reduced pressure. The concentrate was dissolved in 50 g of methylene chloride, and the solution was combined with 0.5 g of activated carbon and stirred overnight. After the activated carbon was filtered off the filtrate was concentrated under reduced pressure. To the concentrate was added 100 mL of diisopropyl ether. After stirring, the supernatant was removed. To the remainder, 100 mL of hexane was added and stirred for precipitation. The precipitate was filtered and dried in vacuum, obtaining the target acid diffusion inhibitor Q-22 as solid (amount 9.1 g, yield 92.5%). The spectral data of Q-22 are shown below.

$^{1}$H-NMR (500 MHz, DMSO-$d_6$):
δ=0.87 (3H, d), 0.93 (3H, d), 1.27 (1H, m), 1.32 (3H, s), 1.37-1.61 (7H, m), 1.89 (2H, m), 2.13 (1H, m), 5.46 (1H, m), 7.10 (2H, m), 7.55-7.63 (4, m), 7.68 (1H, tt), 7.74 (2H, dt), 7.89 (2H, m), 7.94 (2H, dt), 8.39 (2, d), 8.52 (2H, dd) ppm $^{19}$F-NR (500 MHz, DMSO-$d_6$):
δ=−115.2 (1F, dd), −107.6 (1F, dd) ppm IR (D-ATR):
ν=3369, 3086, 2966, 2935, 2860, 1718, 1653, 1603, 1505, 1475, 1464, 1448, 1429, 1389, 1341, 1313, 1265, 1243, 1153, 1098, 1036, 1012, 998, 964, 896, 849, 798, 767, 739, 708, 680, 526, 489 cm$^{-1}$ TOFMS; MALDI
Positive M$^+$261.1 (corresponding to $C_{18}H_{13}S^+$)
Negative M$^-$ 383.2 (corresponding to $C_{20}H_{25}F_2O_5^-$)

Examples 1-3 to 1-22

Synthesis of Acid Diffusion Inhibitors Q-2 to Q-21

A series of acid diffusion inhibitors Q-2 to Q-21 as shown below were synthesized in accordance with Examples 1-1 and 1-2.

177
Q-2
Q-3
Q-4
Q-5
178
-continued
Q-6
Q-7
Q-8
Q-9
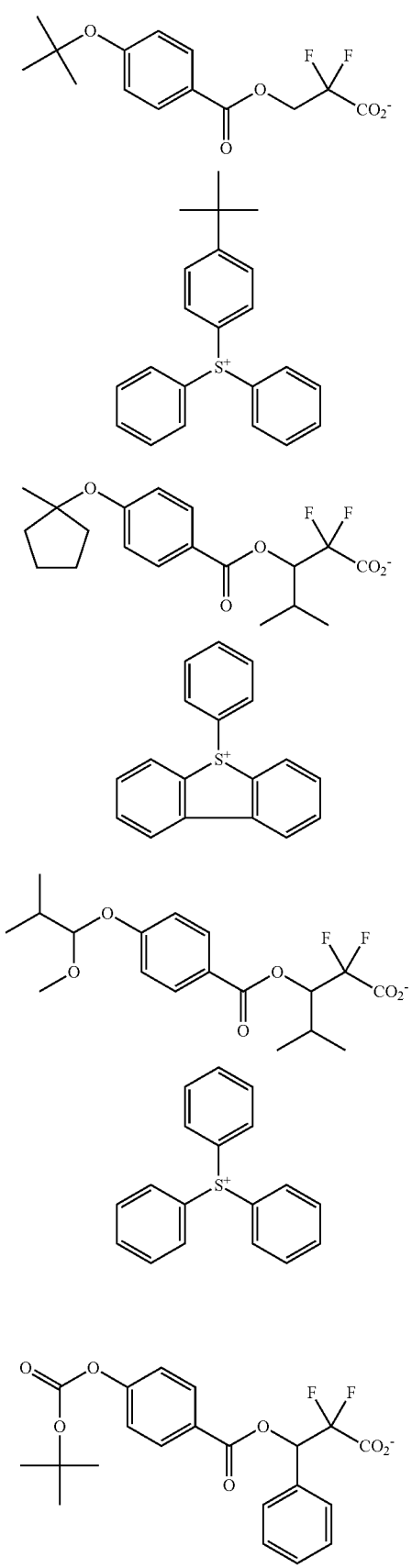
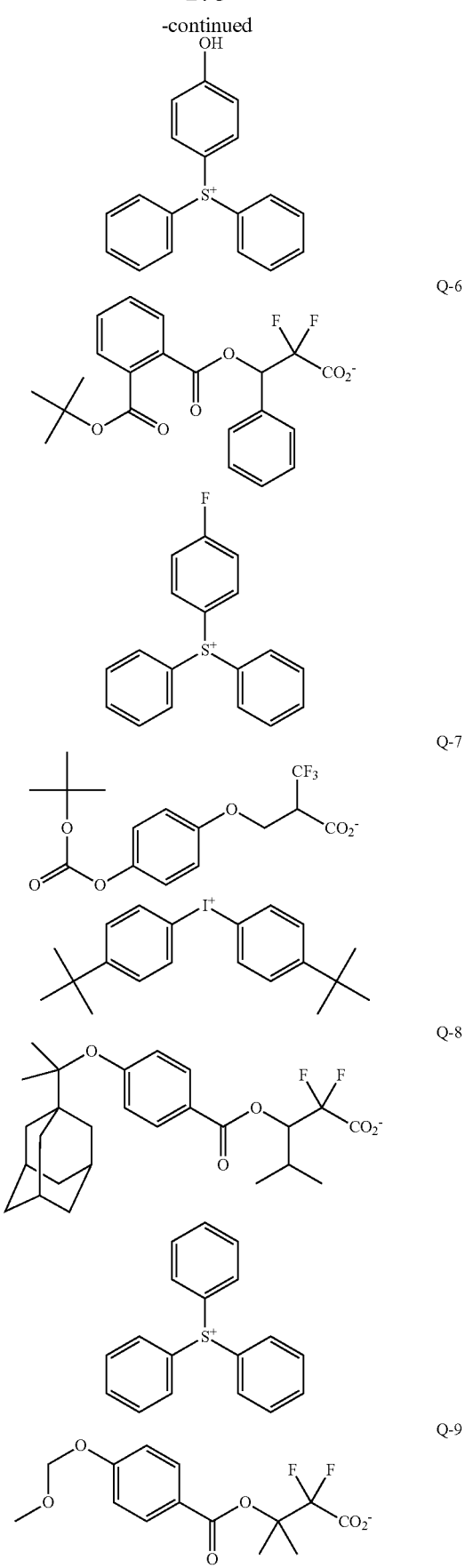

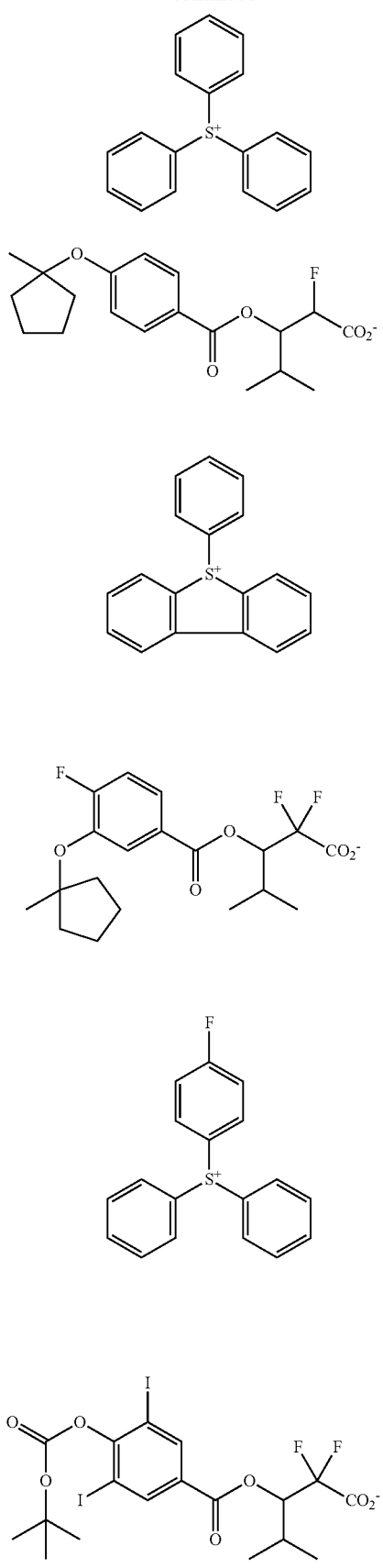
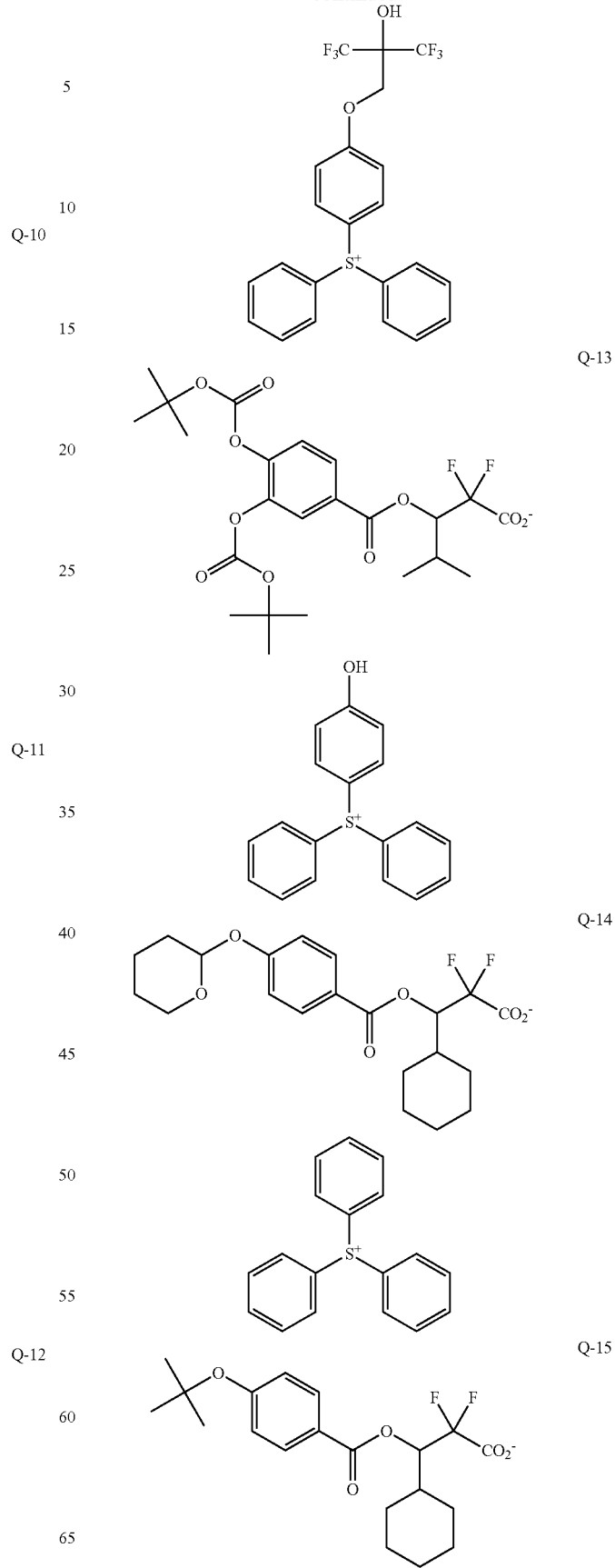

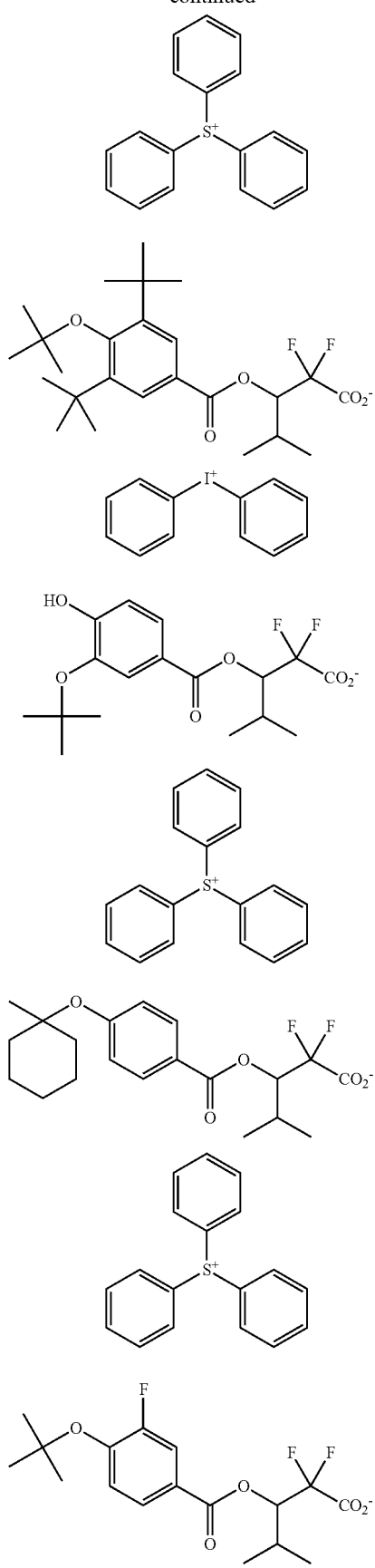

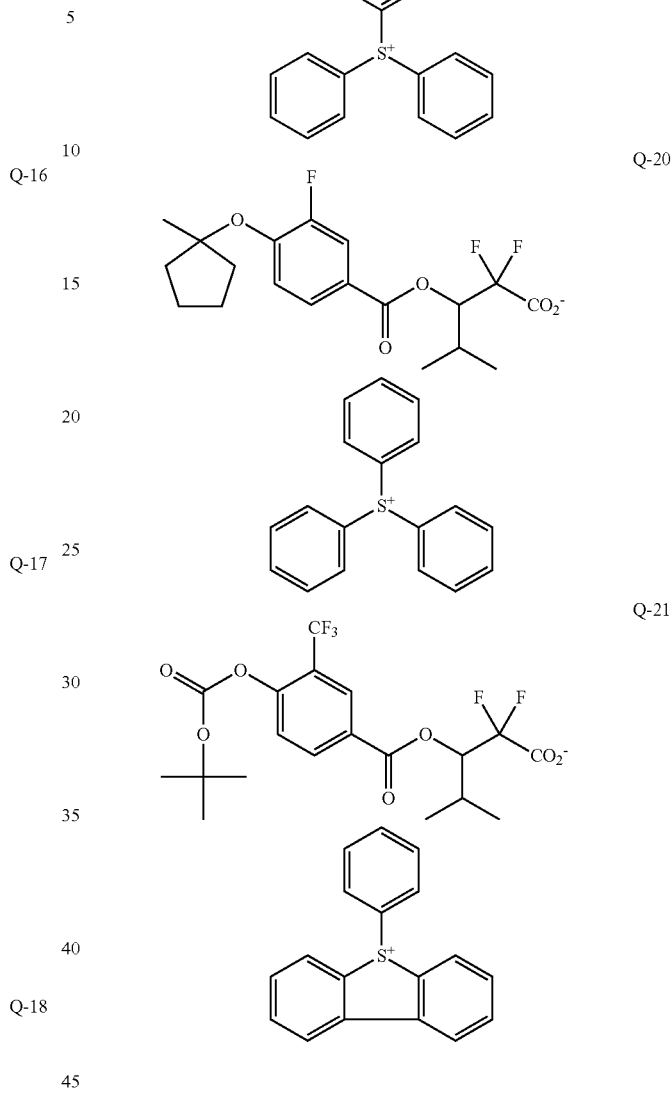

Synthesis Example 1

Synthesis of Polymer P-1

In nitrogen atmosphere, 22 g of 1-tert-butylcyclopentyl methacrylate, 17 g of 2-oxotetrahydrofuran-3-yl methacrylate, 0.48 g of dimethyl 2,2'-azobis(2-methylpropionate) (V-601 by Wako Pure Chemical Industries, Ltd.), 0.41 g of 2-mercaptoethanol, and 50 g of methyl ethyl ketone were combined to form a monomer/initiator solution. A flask in nitrogen atmosphere was charged with 23 g of methyl ethyl ketone, which was heated at 80° C. with stirring. With stirring, the monomer/initiator solution was added dropwise to the flask over 4 hours. After the completion of dropwise addition, the polymerization solution was continuously stirred for 2 hours while maintaining the temperature of 80° C. The polymerization solution was cooled to room temperature, whereupon it was added dropwise to 640 g of methanol with vigorous stirring. The precipitate was collected by filtration, washed twice with 240 g of methanol, and vacuum dried at 50° C. for 20 hours, obtaining Polymer P-1 in white powder form (amount 36 g. yield 90%). Polymer P-1 had a Mw of 8,200 and a dispersity Mw/Mn of 1.63.

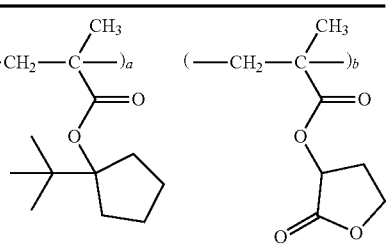

Synthesis Examples 2 to 4

Synthesis of Polymers P-2 to P4

Polymers P-2 to P-4 were synthesized by the same procedure as in Synthesis Example 1 aside from changing the type and amount of monomers.

Examples 2-1 to 2-55 and Comparative Examples 1-1 to 1-20

Preparation of Chemically Amplified Resist Compositions

Resist compositions were prepared by dissolving the components shown in Tables 1 to 5 in a solvent containing 0.01 wt % of surfactant Polyfox 636 (Onnova Solutions, Inc.), and filtering the solution through a Teflon® filter with a pore size of 0.2 μm.

The photoacid generators PAG-1 to PAG-4, solvents, comparative acid diffusion inhibitors Q-A to Q-J, and alkali-soluble surfactant SF-1 in Tables 1 to 5 are identified below.

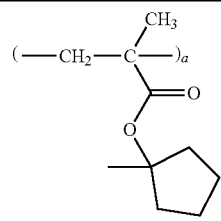
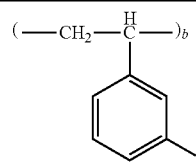
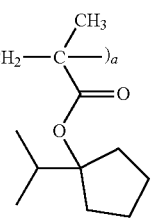
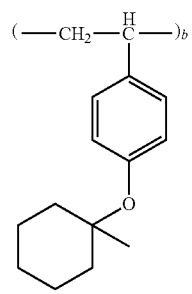
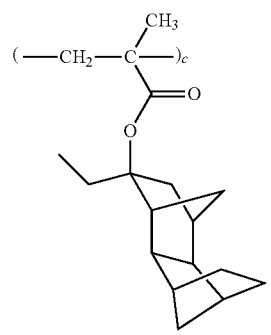 [SMILES: CCC(C)(C)C(=O)OC1(CC)CC2CC1C1C3CCC(C3)C21]
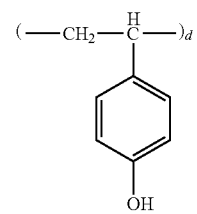
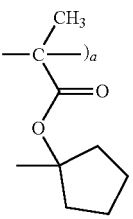
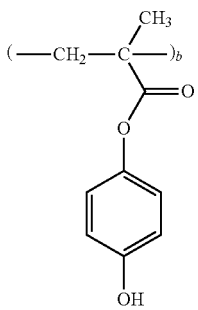
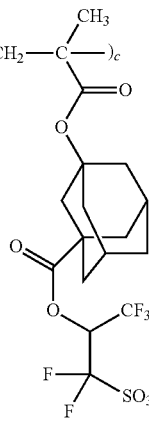
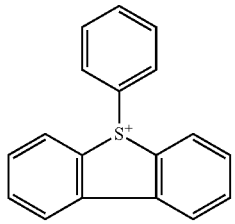

Photoacid Generators PAG-1 to PAG-4:
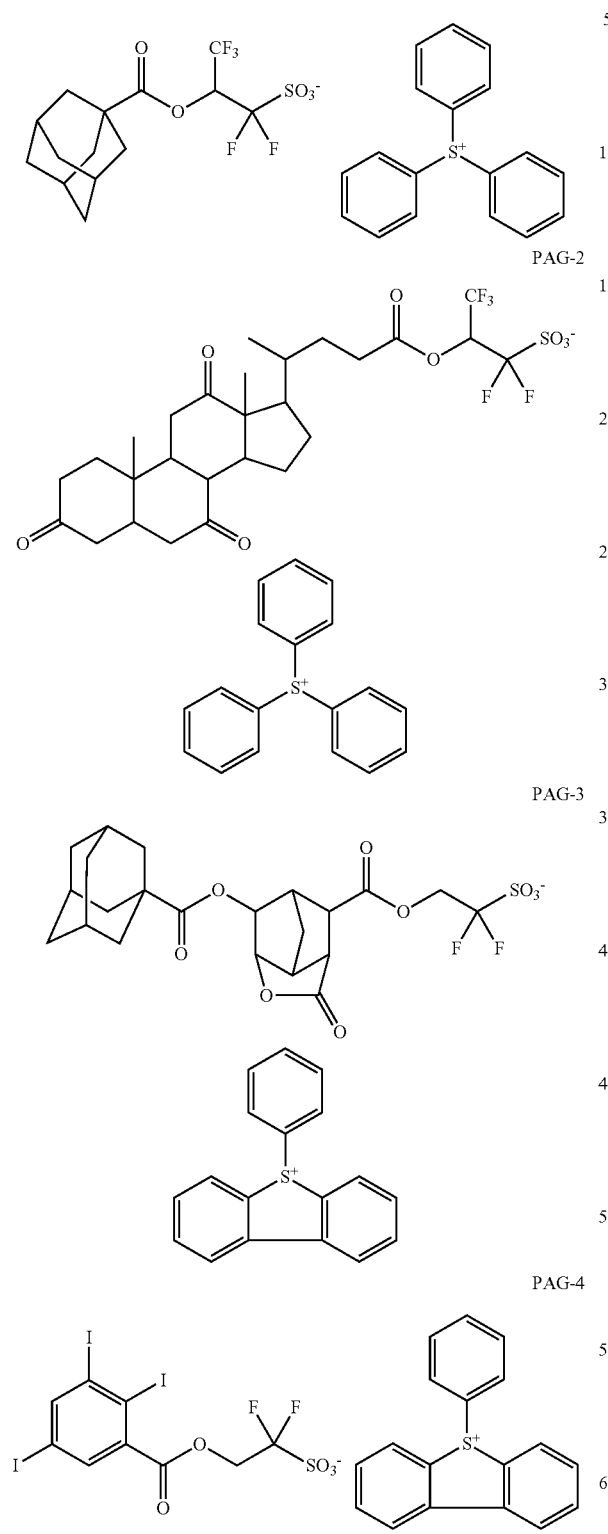
Solvent:
　PGMEA=propylene glycol monomethyl ether acetate
　GBL=γ-butyrolactone
　CyHO=cyclohexanone
　DAA=diacetone alcohol
Acid Diffusion Inhibitors Q-A to Q-J:
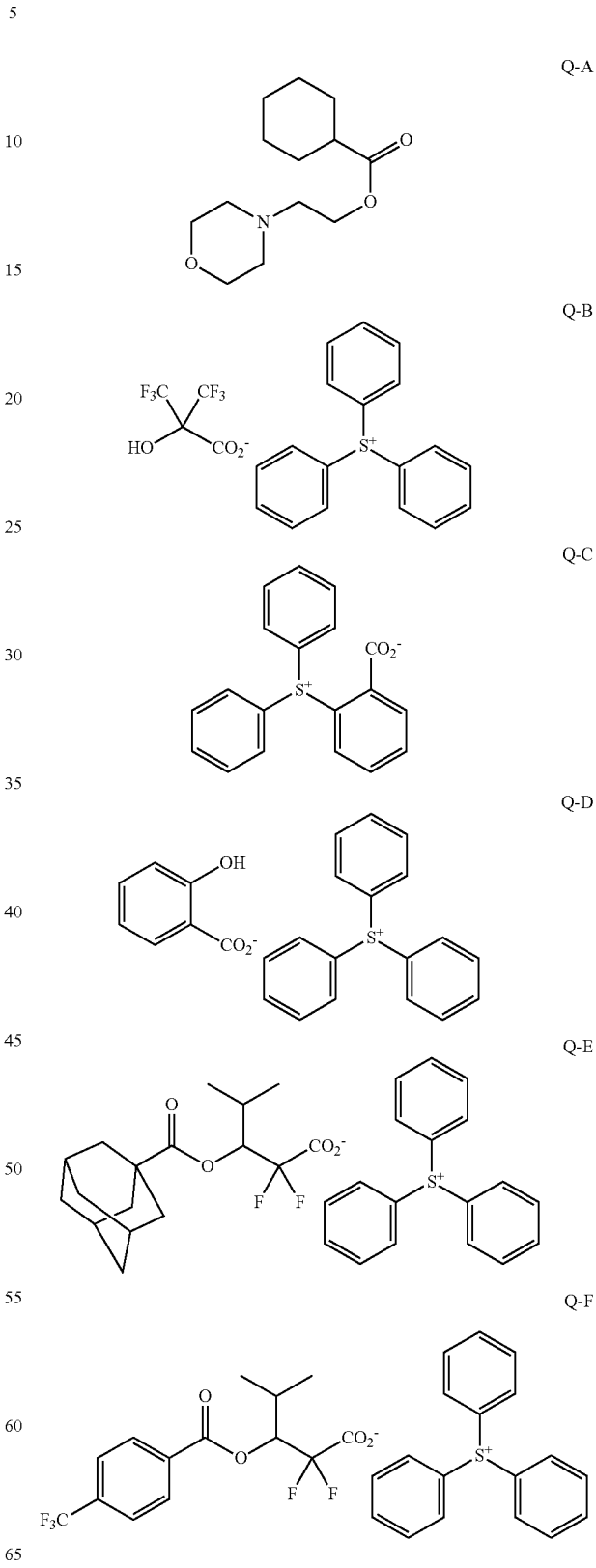

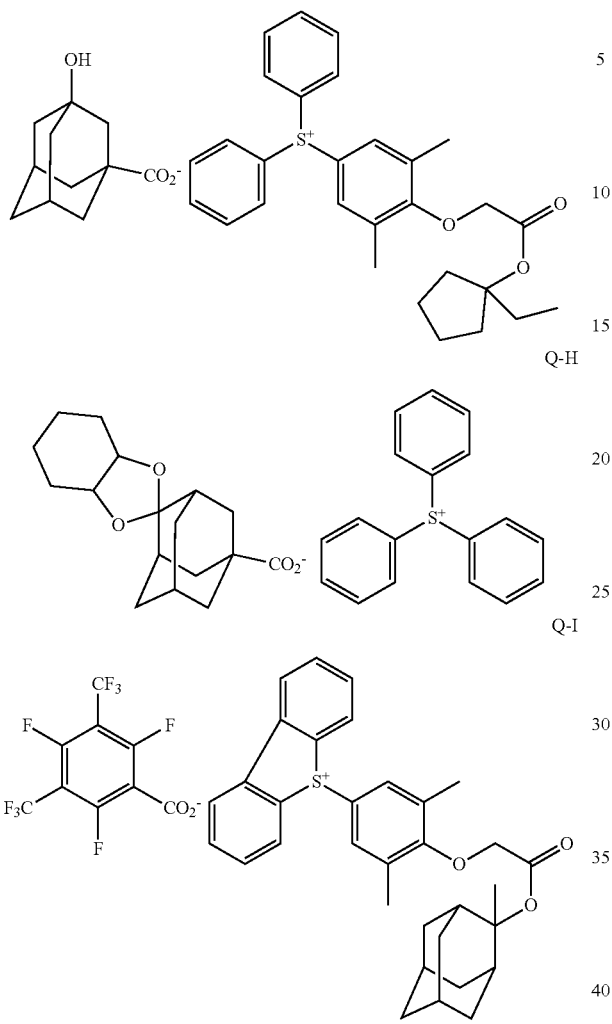

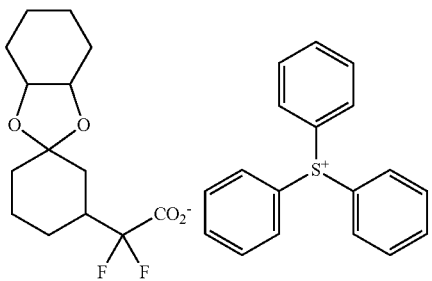

Alkali-Soluble Surfactant SF-1:
poly(2,2,3,3,4,4,4-heptafluoro-1-isobutyl-1-butyl methacrylate/9-(2,2,2-trifluoro-1-trifluoroethyloxycarbonyl)-4-oxatricyclo[4.2.1.0$^{3,7}$]nonan-5-on-2-yl methacrylate)

Mw=7,700
Mw/Mn=1.82

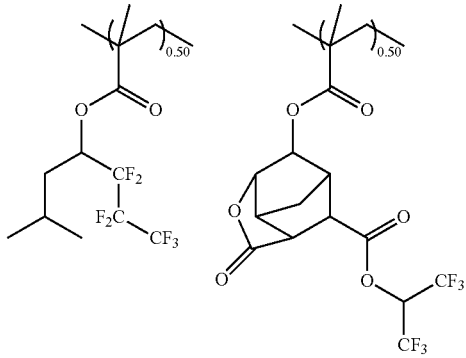

TABLE 1

| Example | Resist composition | Polymer (pbw) | Photoacid generator (pbw) | Acid diffusion inhibitor (pbw) | Surfactant (pbw) | Solvent (pbw) |
|---|---|---|---|---|---|---|
| 2-1 | R-1 | P-1 (100) | PAG-1 (8.0) | Q-1 (5.0) | SF-1 (3.0) | PGMEA/GBL (1,920/480) |
| 2-2 | R-2 | P-1 (100) | PAG-1 (8.0) | Q-2 (5.0) | SF-1 (3.0) | PGMEA/GBL (1,920/480) |
| 2-3 | R-3 | P-1 (100) | PAG-1 (8.0) | Q-3 (5.0) | SF-1 (3.0) | PGMEA/GBL (1,920/480) |
| 2-4 | R-4 | P-1 (100) | PAG-1 (8.0) | Q-4 (5.0) | SF-1 (3.0) | PGMEA/GBL (1,920/480) |
| 2-5 | R-5 | P-1 (100) | PAG-1 (8.0) | Q-5 (4.9) | SF-1 (3.0) | PGMEA/GBL (1,920/480) |
| 2-6 | R-6 | P-1 (100) | PAG-1 (8.0) | Q-6 (4.8) | SF-1 (3.0) | PGMEA/GBL (1,920/480) |
| 2-7 | R-7 | P-1 (100) | PAG-1 (8.0) | Q-7 (5.0) | SF-1 (3.0) | PGMEA/GBL (1,920/480) |
| 2-8 | R-8 | P-1 (100) | PAG-1 (8.0) | Q-8 (5.0) | SF-1 (3.0) | PGMEA/GBL (1,920/480) |
| 2-9 | R-9 | P-1 (100) | PAG-1 (8.0) | Q-9 (5.0) | SF-1 (3.0) | PGMEA/GBL (1,920/480) |
| 2-10 | R-10 | P-1 (100) | PAG-1 (8.0) | Q-10 (5.0) | SF-1 (3.0) | PGMEA/GBL (1,920/480) |

TABLE 1-continued

| Example | Resist composition | Polymer (pbw) | Photoacid generator (pbw) | Acid diffusion inhibitor (pbw) | Surfactant (pbw) | Solvent (pbw) |
|---|---|---|---|---|---|---|
| 2-11 | R-11 | P-1 (100) | PAG-1 (8.0) | Q-11 (5.0) | SF-1 (3.0) | PGMEA/GBL (1,920/480) |
| 2-12 | R-12 | P-1 (100) | PAG-1 (8.0) | Q-12 (4.5) | SF-1 (3.0) | PGMEA/GBL (1,920/480) |
| 2-13 | R-13 | P-1 (100) | PAG-1 (8.0) | Q-13 (4.7) | SF-1 (3.0) | PGMEA/GBL (1,920/480) |
| 2-14 | R-14 | P-1 (100) | PAG-1 (8.0) | Q-14 (5.0) | SF-1 (3.0) | PGMEA/GBL (1,920/480) |
| 2-15 | R-15 | P-1 (100) | PAG-1 (8.0) | Q-15 (5.0) | SF-1 (3.0) | PGMEA/GBL (1,920/480) |
| 2-16 | R-16 | P-1 (100) | PAG-1 (8.0) | Q-16 (4.9) | SF-1 (3.0) | PGMEA/GBL (1,920/480) |
| 2-17 | R-17 | P-1 (100) | PAG-1 (8.0) | Q-17 (5.0) | SF-1 (3.0) | PGMEA/GBL (1,920/480) |
| 2-18 | R-18 | P-1 (100) | PAG-1 (8.0) | Q-18 (5.0) | SF-1 (3.0) | PGMEA/GBL (1,920/480) |
| 2-19 | R-19 | P-1 (100) | PAG-1 (8.0) | Q-19 (5.0) | SF-1 (3.0) | PGMEA/GBL (1,920/480) |
| 2-20 | R-20 | P-1 (100) | PAG-1 (8.0) | Q-20 (5.0) | SF-1 (3.0) | PGMEA/GBL (1,920/480) |
| 2-21 | R-21 | P-1 (100) | PAG-1 (8.0) | Q-21 (5.0) | SF-1 (3.0) | PGMEA/GBL (1,920/480) |

TABLE 2

| Example | Resist composition | Polymer (pbw) | Photoacid generator (pbw) | Acid diffusion inhibitor (pbw) | Surfactant (pbw) | Solvent (pbw) |
|---|---|---|---|---|---|---|
| 2-22 | R-22 | P-2 (100) | PAG-2 (20.0) | Q-1 (10.0) | SF-1 (3.0) | PGMEA/DAA (2,100/900) |
| 2-23 | R-23 | P-3 (100) | PAG-3 (20.0) | Q-1 (10.0) | SF-1 (3.0) | PGMEA/DAA (2,100/900) |
| 2-24 | R-24 | P-4 (100) | — | Q-1 (10.0) | SF-1 (3.0) | PGMEA/DAA (2,100/900) |
| 2-25 | R-25 | P-2 (100) | PAG-3 (20.0) | Q-2 (10.0) | SF-1 (3.0) | PGMEA/DAA (2,100/900) |
| 2-26 | R-26 | P-2 (100) | PAG-3 (20.0) | Q-3 (10.0) | SF-1 (3.0) | PGMEA/DAA (2,100/900) |
| 2-27 | R-27 | P-4 (100) | — | Q-3 (10.0) | SF-1 (3.0) | PGMEA/DAA (2,100/900) |
| 2-28 | R-28 | P-2 (100) | PAG-3 (20.0) | Q-4 (10.0) | SF-1 (3.0) | PGMEA/DAA (2,100/900) |
| 2-29 | R-29 | P-4 (100) | PAG-2 (6.0) | Q-4 (10.0) | SF-1 (3.0) | PGMEA/DAA (2,100/900) |
| 2-30 | R-30 | P-2 (100) | PAG-3 (20.0) | Q-5 (10.0) | SF-1 (3.0) | PGMEA/DAA (2,100/900) |
| 2-31 | R-31 | P-4 (100) | — | Q-5 (9.7) | SF-1 (3.0) | PGMEA/DAA (2,100/900) |
| 2-32 | R-32 | P-2 (100) | PAG-3 (20.0) | Q-6 (7.2) Q-A (2.0) | SF-1 (3.0) | PGMEA/DAA/CyHO (2,100/600/300) |
| 2-33 | R-33 | P-3 (100) | PAG-3 (20.0) | Q-7 (10.0) | SF-1 (3.0) | PGMEA/DAA (2,100/900) |
| 2-34 | R-34 | P-2 (100) | PAG-3 (20.0) | Q-8 (10.0) | SF-1 (3.0) | PGMEA/DAA (2,100/900) |
| 2-35 | R-35 | P-2 (100) | PAG-3 (20.0) | Q-9 (10.0) | SF-1 (3.0) | PGMEA/DAA (2,100/900) |
| 2-36 | R-36 | P-2 (100) | PAG-3 (20.0) | Q-10 (10.0) | SF-1 (3.0) | PGMEA/DAA (2,100/900) |
| 2-37 | R-37 | P-2 (100) | PAG-3 (20.0) | Q-11 (10.0) | SF-1 (3.0) | PGMEA/DAA (2,100/900) |
| 2-38 | R-38 | P-4 (100) | — | Q-11 (10.0) | SF-1 (3.0) | PGMEA/DAA (2,100/900) |
| 2-39 | R-39 | P-2 (100) | PAG-3 (20.0) | Q-12 (8.0) Q-B (2.0) | SF-1 (3.0) | PGMEA/DAA/CyHO (2,100/600/300) |
| 2-40 | R-40 | P-3 (100) | PAG-3 (20.0) | Q-13 (9.6) | SF-1 (3.0) | PGMEA/DAA (2,100/900) |

TABLE 2-continued

| Example | Resist composition | Polymer (pbw) | Photoacid generator (pbw) | Acid diffusion inhibitor (pbw) | Surfactant (pbw) | Solvent (pbw) |
|---|---|---|---|---|---|---|
| 2-41 | R-41 | P-2 (100) | PAG-3 (20.0) | Q-14 (10.0) | SF-1 (3.0) | PGMEA/DAA (2,100/900) |
| 2-42 | R-42 | P-2 (100) | PAG-3 (20.0) | Q-15 (10.0) | SF-1 (3.0) | PGMEA/DAA (2,100/900) |
| 2-43 | R-43 | P-2 (100) | PAG-3 (20.0) | Q-16 (7.3) Q-C (2.8) | SF-1 (3.0) | PGMEA/DAA/CyHO (2,100/600/300) |

TABLE 3

| Example | Resist composition | Polymer (pbw) | Photoacid generator (pbw) | Acid diffusion inhibitor (pbw) | Surfactant (pbw) | Solvent (pbw) |
|---|---|---|---|---|---|---|
| 2-44 | R-44 | P-3 (100) | PAG-4 (20.0) | Q-17 (10.3) | SF-1 (3.0) | PGMEA/DAA (2,100/900) |
| 2-45 | R-45 | P-2 (100) | PAG-3 (20.0) | Q-18 (10.0) | SF-1 (3.0) | PGMEA/DAA (2,100/900) |
| 2-46 | R-46 | P-4 (100) | PAG-3 (6.0) | Q-18 (10.0) | SF-1 (3.0) | PGMEA/DAA (2,100/900) |
| 2-47 | R-47 | P-2 (100) | PAG-3 (20.0) | Q-19 (10.0) | SF-1 (3.0) | PGMEA/DAA (2,100/900) |
| 2-48 | R-48 | P-4 (100) | PAG-3 (6.0) | Q-19 (10.0) | SF-1 (3.0) | PGMEA/DAA (2,100/900) |
| 2-49 | R-49 | P-2 (100) | PAG-4 (20.0) | Q-20 (10.0) | SF-1 (3.0) | PGMEA/DAA (2,100/900) |
| 2-50 | R-50 | P-4 (100) | — | Q-20 (10.0) | SF-1 (3.0) | PGMEA/DAA (2,100/900) |
| 2-51 | R-51 | P-2 (100) | PAG-3 (20.0) | Q-21 (10.1) | SF-1 (3.0) | PGMEA/DAA (2,100/900) |
| 2-52 | R-52 | P-4 (100) | PAG-3 (6.0) | Q-1 (10.0) | SF-1 (3.0) | PGMEA/DAA (2,100/900) |
| 2-53 | R-53 | P-4 (100) | PAG-4 (6.0) | Q-1 (10.0) | SF-1 (3.0) | PGMEA/DAA (2,100/900) |
| 2-54 | R-54 | P-1 (100) | PAG-1 (8.0) | Q-22 (5.0) | SF-1 (3.0) | PGMEA/GBL (1,920/480) |
| 2-55 | R-55 | P-4 (100) | PAG-3 (6.0) | Q-22 (10.0) | SF-1 (3.0) | PGMEA/DAA (2,100/900) |

TABLE 4

| Comparative Example | Resist composition | Polymer (pbw) | Photoacid generator (pbw) | Acid diffusion inhibitor (pbw) | Surfactant (pbw) | Solvent (pbw) |
|---|---|---|---|---|---|---|
| 1-1 | CR-1 | P-1 (100) | PAG-1 (8.0) | Q-A (2.8) | SF-1 (3.0) | PGMEA/GBL (1,920/480) |
| 1-2 | CR-2 | P-1 (100) | PAG-1 (8.0) | Q-B (5.0) | SF-1 (3.0) | PGMEA/GBL (1,920/480) |
| 1-3 | CR-3 | P-1 (100) | PAG-1 (8.0) | Q-C (4.8) | SF-1 (3.0) | PGMEA/GBL (1,920/480) |
| 1-4 | CR-4 | P-1 (100) | PAG-1 (8.0) | Q-D (4.8) | SF-1 (3.0) | PGMEA/GBL (1,920/480) |
| 1-5 | CR-5 | P-1 (100) | PAG-1 (8.0) | Q-E (5.0) | SF-1 (3.0) | PGMEA/GBL (1,920/480) |
| 1-6 | CR-6 | P-1 (100) | PAG-1 (8.0) | Q-F (5.0) | SF-1 (3.0) | PGMEA/GBL (1,920/480) |
| 1-7 | CR-7 | P-1 (100) | PAG-1 (8.0) | Q-G (4.7) | SF-1 (3.0) | PGMEA/GBL (1,920/480) |
| 1-8 | CR-8 | P-1 (100) | PAG-1 (8.0) | Q-H (4.7) | SF-1 (3.0) | PGMEA/GBL (1,920/480) |
| 1-9 | CR-9 | P-1 (100) | PAG-1 (8.0) | Q-I (5.0) | SF-1 (3.0) | PGMEA/GBL (1,920/480) |
| 1-10 | CR-10 | P-1 (100) | PAG-1 (8.0) | Q-J (5.0) | SF-1 (3.0) | PGMEA/GBL (1,920/480) |

TABLE 5

| Comparative Example | Resist composition | Polymer (pbw) | Photoacid generator (pbw) | Acid diffusion inhibitor (pbw) | Surfactant (pbw) | Solvent (pbw) |
|---|---|---|---|---|---|---|
| 1-11 | CR-11 | P-2 (100) | PAG-3 (20.0) | Q-A (6.0) | SF-1 (3.0) | PGMEA/DAA (2,100/900) |
| 1-12 | CR-12 | P-2 (100) | PAG-3 (20.0) | Q-B (10.0) | SF-1 (3.0) | PGMEA/DAA (2,100/900) |
| 1-13 | CR-13 | P-2 (100) | PAG-3 (20.0) | Q-C (9.5) | SF-1 (3.0) | PGMEA/DAA (2,100/900) |
| 1-14 | CR-14 | P-2 (100) | PAG-3 (20.0) | Q-D (9.8) | SF-1 (3.0) | PGMEA/DAA (2,100/900) |
| 1-15 | CR-15 | P-2 (100) | PAG-3 (20.0) | Q-E (10.0) | SF-1 (3.0) | PGMEA/DAA (2,100/900) |
| 1-16 | CR-16 | P-2 (100) | PAG-3 (20.0) | Q-F (10.0) | SF-1 (3.0) | PGMEA/DAA (2,100/900) |
| 1-17 | CR-17 | P-2 (100) | PAG-3 (20.0) | Q-G (9.5) | SF-1 (3.0) | PGMEA/DAA (2,100/900) |
| 1-18 | CR-18 | P-2 (100) | PAG-3 (20.0) | Q-H (9.7) | SF-1 (3.0) | PGMEA/DAA (2,100/900) |
| 1-18 | CR-19 | P-2 (100) | PAG-3 (20.0) | Q-I (10.0) | SF-1 (3.0) | PGMEA/DAA (2,100/900) |
| 1-20 | CR-20 | P-2 (100) | PAG-3 (20.0) | Q-J (10.0) | SF-1 (3.0) | PGMEA/DAA (2,100/900) |

Examples 3-1 to 3-22 and Comparative Examples 2-1 to 2-10

ArF Lithography Test

On a silicon substrate, an antireflective coating solution (ARC-29A by Nissan Chemical Corp.) was coated and baked at 180° C. for 60 seconds to form an ARC of 100 nm thick. On the ARC, each of the resist compositions (R-1 to R-21, R-54, CR-1 to CR-10) was spin coated and baked on a hotplate at 100° C. for 60 seconds to form a resist film of 90 nm thick.

Using an ArF excimer laser scanner (NSR-S610C by Nikon Corp., NA 1.30, σ 0.94/0.74, dipole 35 deg, illumination, 6% halftone phase shift mask), the resist film was exposed by the immersion lithography. Water was used as the immersion liquid. After exposure, the resist film was baked (PEB) at 90° C. for 60 seconds and developed in 2.38 wt % TMAH aqueous solution for 60 seconds to form a line-and-space (LS) pattern.

The LS pattern was observed under CD-SEM (CG-5000 by Hitachi High-Technologies Corp.) and evaluated for sensitivity. LWR and defect density by the following methods. The results are shown in Table 6.

Evaluation of Sensitivity

The optimum dose (Eop) is a dose (mJ/cm$^2$) which provides a LS pattern having a line width of 40 nm at a pitch of 80 nm and reported as sensitivity. A smaller value indicates a higher sensitivity.

Evaluation of LWR

On the L/S pattern formed by exposure in the optimum dose Eop, the line width was measured at longitudinally spaced apart 10 points, from which a 3-fold value (3σ) of standard deviation (σ) was determined and reported as LWR. A smaller value of 3σ indicates a pattern having a lower roughness and more uniform line width. A pattern with a LWR value of 2.5 nm or less is acceptable while a pattern with a LWR value in excess of 2.5 nm is rejected.

Evaluation of Defect Density

Defects in the pattern as developed were inspected by a flaw detector KLA2905 (KLA-Tencor). A defect density (count/cm$^2$) was computed by dividing the total number of detected defects by a detection area. The defect inspection conditions included light source UV, inspected pixel size 0.22 μm, and array mode. In this test, the sample was rated good for a defect density of less than 0.03 defect cm$^2$, moderate for a density of 0.03 to less than 0.05 defect/cm$^2$, and NG for a density of equal to or more than 0.05 defect cm$^2$.

TABLE 6

|  |  | Resist composition | Eop (mJ/cm$^2$) | LWR (nm) | Defect density |
|---|---|---|---|---|---|
| Example | 3-1 | R-1 | 32 | 2.1 | good |
|  | 3-2 | R-2 | 30 | 2.4 | good |
|  | 3-3 | R-3 | 31 | 21 | good |
|  | 3-4 | R-4 | 32 | 2.3 | good |
|  | 3-5 | R-5 | 34 | 2.4 | good |
|  | 3-6 | R-6 | 34 | 24 | good |
|  | 3-7 | R-7 | 36 | 2.3 | good |
|  | 3-8 | R-8 | 33 | 2.3 | good |
|  | 3-9 | R-9 | 31 | 23 | good |
|  | 3-10 | R-10 | 32 | 21 | good |
|  | 3-11 | R-11 | 32 | 2.2 | good |
|  | 3-12 | R-12 | 35 | 2.5 | good |
|  | 3-13 | R-13 | 34 | 2.4 | good |
|  | 3-14 | R-14 | 32 | 23 | good |
|  | 3-15 | R-15 | 33 | 2.4 | good |
|  | 3-16 | R-16 | 34 | 23 | good |
|  | 3-17 | R-17 | 33 | 21 | good |
|  | 3-18 | R-18 | 31 | 21 | good |
|  | 3-19 | R-19 | 31 | 2.2 | good |
|  | 3-20 | R-20 | 37 | 23 | good |
|  | 3-21 | R-21 | 33 | 2.4 | good |
|  | 3-22 | R-54 | 33 | 21 | good |
| Comparative Example | 2-1 | CR-1 | 43 | 3.3 | NG |
|  | 2-7 | CR-2 | 35 | 2.7 | moderate |
|  | 2-3 | CR-3 | 47 | 2.9 | NG |
|  | 2-4 | CR-4 | 43 | 3.0 | NG |
|  | 2-5 | CR-5 | 34 | 2.7 | moderate |
|  | 2-6 | CR-6 | 35 | 2.9 | NG |
|  | 2-7 | CR-7 | 45 | 2.8 | moderate |
|  | 2-8 | CR-8 | 47 | 3.2 | NG |
|  | 2-9 | CR-9 | 38 | 3.1 | NG |
|  | 2-10 | CR-10 | 35 | 2.9 | moderate |

As is evident from Table 6, the chemically amplified resist compositions containing onium salt compounds within the scope of the invention exhibit satisfactory values of sensitivity and LWR and are effective in reducing defects. The resist compositions are useful as the ArF immersion lithography material.

Examples 4-1 to 4-33 and Comparative Examples 3-1 to 3-10

EUV Lithography Test

Each of the resist compositions (R-22 to R-53, R-55, CR-11 to CR-20) was spin coated on a silicon substrate having a 20-mu coating of silicon-containing spin-on hard mask SHB-A940 (silicon content 43 wt %, Shin-Etsu Chemical Co., Ltd.) and prebaked on a hotplate at 105° C. for 60 seconds to form a resist film of 50 nm thick. Using an EUV scanner NXE3300 (ASML, NA 0.33, σ 0.9/0.6, quadrupole illumination), the resist film was exposed to EUV in a dose of 20 to 40 mJ/cm² through a mask bearing a hole pattern having a pitch 46 nm+20% bias (on-wafer size). The resist film was baked (PEB) on a hotplate at 85° C. for 60 seconds and developed in a 2.38 wt % TMAH aqueous solution for 30 seconds to form a hole pattern having a size of 23 nm.

The hole pattern as developed was observed under CD-SEM (CG-5000 by Hitachi High-Technologies Corp.) and evaluated for sensitivity, CDU and defect density by the following methods. The results are shown in Tables 7 and 8.

Evaluation of Sensitivity

The optimum dose (Eop) is a dose (mJ/cm²) which provides a hole pattern having a hole size of 23 nm and reported as sensitivity. A smaller value indicates a higher sensitivity.

Evaluation of CDU

For the hole pattern at the optimum dose (Eop), the size of 50 holes within the same dose shot was measured, from which a size variation (3σ) was computed and reported as CDU. A smaller value of CDU indicates better dimensional uniformity of hole pattern. The sample was rated good for a CDU value of up to 3.0 nm and NG for a CDU value in excess of 3.0 nm.

Evaluation of Defect Density

Defects in the pattern were inspected by a flaw detector KLA2905 (KLA-Tencor).

A defect density (count/cm²) was computed by dividing the total number of detected defects by a detection area. The defect inspection conditions included light source UV, inspected pixel size 0.22 μm, and array mode. In this test, the sample was rated good for a defect density of less than 0.04 defect/cm², moderate for a density of 0.04 to less than 0.06 defect/cm², and NG for a density of equal to or more than 0.06 defect/cm².

TABLE 7

|  |  | Resist composition | Eop (mJ/cm²) | CDU (nm) | Defect density |
|---|---|---|---|---|---|
| Example | 4-1 | R-22 | 17 | 2.9 | good |
|  | 4-2 | R-23 | 28 | 2.8 | good |
|  | 4-3 | R-24 | 25 | 2.5 | good |
|  | 4-4 | R-25 | 17 | 2.8 | good |
|  | 4-5 | R-26 | 28 | 2.8 | good |
|  | 4-6 | R-27 | 25 | 2.5 | good |
|  | 4-7 | R-28 | 28 | 2.7 | good |
|  | 4-8 | R-29 | 23 | 2.5 | good |
|  | 4-9 | R-30 | 27 | 2.8 | good |
|  | 4-10 | R-31 | 24 | 2.6 | good |
|  | 4-11 | R-32 | 29 | 2.9 | good |
|  | 4-12 | R-33 | 27 | 2.6 | good |
|  | 4-13 | R-34 | 27 | 2.8 | good |
|  | 4-14 | R-35 | 28 | 27 | good |
|  | 4-15 | R-36 | 77 | 2.8 | good |
|  | 4-16 | R-37 | 77 | 2.7 | good |
|  | 4-17 | R-38 | 24 | 2.4 | good |
|  | 4-18 | R-39 | 30 | 2.6 | good |

TABLE 7-continued

|  | Resist composition | Eop (mJ/cm²) | CDU (nm) | Defect density |
|---|---|---|---|---|
| 4-19 | R-40 | 29 | 3.0 | good |
| 4-20 | R-41 | 27 | 2.9 | good |
| 4-21 | R-42 | 28 | 2.8 | good |
| 4-22 | R-43 | 29 | 2.7 | good |
| 4-23 | R-44 | 28 | 2.7 | good |
| 4-24 | R-45 | 28 | 2.7 | good |
| 4-25 | R-46 | 23 | 2.5 | good |
| 4-26 | R-47 | 77 | 2.8 | good |
| 4-27 | R-48 | 23 | 2.5 | good |
| 4-28 | R-49 | 26 | 2.6 | good |
| 4-29 | R-50 | 25 | 2.4 | good |
| 4-30 | R-51 | 79 | 2.7 | good |
| 4-31 | R-52 | 24 | 2.4 | good |
| 4-32 | R-53 | 23 | 2.3 | good |
| 4-33 | R-55 | 25 | 2.4 | good |

TABLE 8

|  |  | Resist composition | Eop (mJ/cm²) | CDU (nm) | Defect density |
|---|---|---|---|---|---|
| Comparative Example | 3-1 | CR-11 | 38 | 3.6 | NG |
|  | 3-7 | CR-12 | 31 | 3.1 | moderate |
|  | 3-3 | CR-13 | 40 | 3.3 | NG |
|  | 3-4 | CR-14 | 38 | 3.4 | NG |
|  | 3-5 | CR-15 | 30 | 3.1 | NG |
|  | 3-6 | CR-16 | 34 | 3.4 | NG |
|  | 3-7 | CR-17 | 37 | 3.4 | moderate |
|  | 3-8 | CR-18 | 41 | 3.3 | NG |
|  | 3-9 | CR-19 | 33 | 3.5 | NG |
|  | 3-10 | CR-20 | 33 | 3.3 | NG |

As is evident from Tables 7 and 8, the chemically amplified resist compositions containing onium salt compounds within the scope of the invention exhibit satisfactory values of sensitivity and CDU and are effective in reducing defects. The resist compositions are useful as the EUV lithography material.

Japanese Patent Application No. 2019-209432 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An onium salt compound having the formula (1):

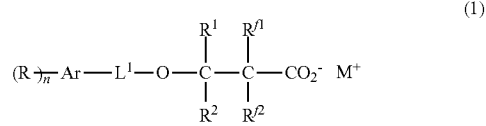

wherein $R^1$ and $R^2$ are each independently hydrogen or a $C_1$-$C_{10}$ hydrocarbyl group which may contain a heteroatom, $R^1$ and $R^2$ may bond together to form a ring with the carbon atom to which they are attached, $R^{f1}$ and $R^{f2}$ are each independently hydrogen, fluorine or trifluoromethyl, at least one thereof being fluorine or trifluoromethyl, $L^1$ is a single bond or carbonyl group, Ar is a (n+1)-valent $C_3$-$C_{15}$ aromatic group which may have a substituent, n is an integer of 1 to 5,
M⁺ is an ammonium, sulfonium or iodonium cation,
R is a group having the following formula (R-1), (R-2), (R-3), (R-4) or (R-5):

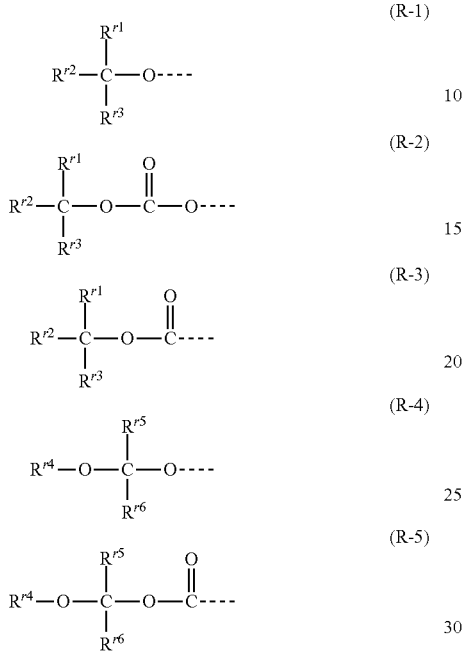

wherein $R^{r1}$, $R^{r2}$, $R^{r3}$ and $R^{r4}$ are each independently a $C_1$-$C_{10}$ hydrocarbyl group, $R^{r1}$ and $R^{r2}$ may bond together to form a ring with the carbon atom to which they are attached,
$R^{r5}$ and $R^{r6}$ are each independently hydrogen or a $C_1$-$C_5$ hydrocarbyl group, any two of $R^{r4}$, $R^{r5}$ and $R^{r6}$ may bond together to form a ring with the atom to which they are attached,
the broken line designates a valence bond to Ar in formula (1).

2. The onium salt compound of claim 1, having the formula (2):

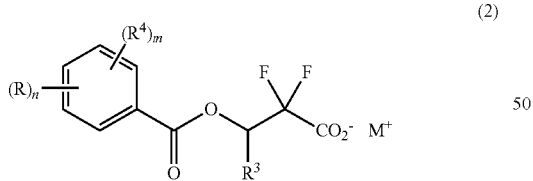

wherein R and M⁺ are as defined in claim 1,
n is an integer of 1 to 5, m is an integer of 0 to 4, n+m is 5,
$R^3$ is hydrogen or a $C_1$-$C_{10}$ hydrocarbyl group which may contain a heteroatom,
$R^4$ is hydrogen, fluorine, iodine, hydroxyl, or a $C_1$-$C_{10}$ hydrocarbyl group which may contain a heteroatom, a constituent —$CH_2$— in the hydrocarbyl group may be replaced by an ether bond or carbonyl moiety, with the proviso that when m is 2 or more, a plurality of $R^4$ may be the same or different, or two $R^4$ may bond together to form a ring with the carbon atoms to which they are attached.

3. The onium salt compound of claim 2 wherein $R^3$ is hydrogen, isopropyl, adamantyl or optionally substituted phenyl.

4. The onium salt compound of claim 1 wherein R is a group having formula (R-1) or (R-2).

5. The onium salt compound of claim 1 wherein M⁺ is a cation having any one of the following formulae (M-1) to (M-4):

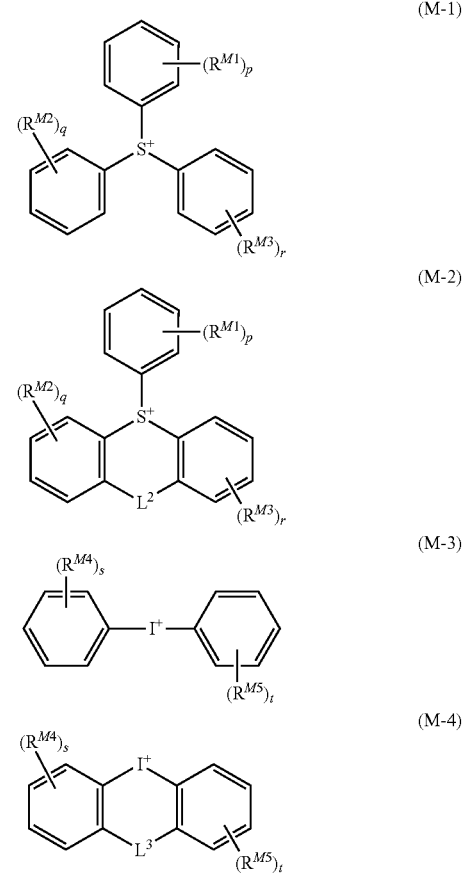

wherein $R^{M1}$, $R^{M2}$, $R^{M3}$, $R^{M4}$, and $R^{M5}$ are each independently hydrogen, halogen, hydroxyl, or a $C_1$-$C_{15}$ hydrocarbyl group which may contain a heteroatom, —$CH_2$— in the hydrocarbyl group may be replaced by an ether bond, carbonyl moiety or sulfonyl moiety,
$L^2$ and $L^3$ are each independently a single bond, methylene group, ether bond, thioether bond, carbonyl group, sulfinyl group, sulfonyl group or —N($R^N$)—, $R^N$ is hydrogen or a $C_1$-$C_{10}$ hydrocarbyl group which may contain a heteroatom, —$CH_2$— in the hydrocarbyl group may be replaced by an ether bond, carbonyl moiety or sulfonyl moiety,
p, q, r, s and t are each independently an integer of 0 to 5,
when p is 2 or more, a plurality of $R^{M1}$ may be the same or different, and two $R^{M1}$ may bond together to form a ring with the carbon atoms on the benzene ring to which they are attached, when q is 2 or more, a plurality of $R^{M2}$ may be the same or different, and two $R^{M2}$ may bond together to form a ring with the carbon atoms on the benzene ring to which they are attached, when r is 2 or more, a plurality of $R^{M3}$ may be the same or different, and two $R^{M3}$ may bond together to form a ring with the carbon atoms on the benzene ring to which they are attached, when s is 2 or more, a plurality of $R^{M4}$ may be the same or different, and two $R^{M4}$ may bond together to form a ring with the carbon atoms on the benzene ring to which they are attached, when t is 2 or more, a plurality of $R^{M5}$ may be the same or different, and two $R^{M5}$ may bond together to form a ring with the carbon atoms on the benzene ring to which they are attached.

6. The onium salt compound of claim 5, having the following formula (3) or (4):

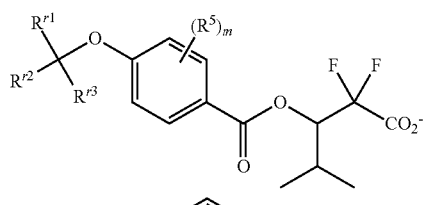

(3)

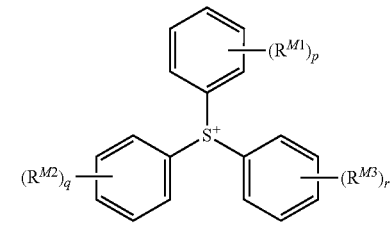

(4)

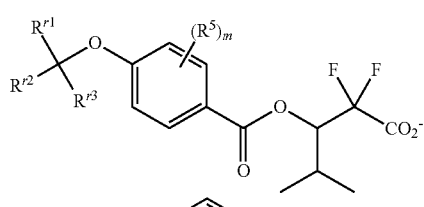

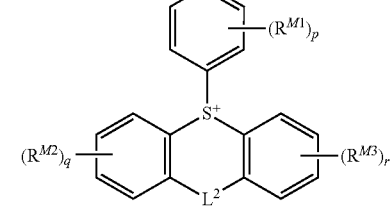

wherein $R^{r1}$, $R^{r2}$, $R^{r3}$, $R^{M1}$, $R^{M2}$, $R^{M3}$, $L^2$, p, q r, and m are as defined in claim 5, $R^5$ is hydrogen, fluorine, hydroxyl, or a $C_1$-$C_5$ hydrocarbyl group in which —$CH_2$— may be replaced by an ether bond or carbonyl moiety, and when m is 2 or more, a plurality of $R^5$ may be the same or different, and two $R^5$ may bond together to form a ring with the carbon atoms to which they are attached.

7. An acid diffusion inhibitor comprising the onium salt compound of claim 1.

8. A chemically amplified resist composition comprising (A) a base polymer adapted to change its solubility in a developer under the action of an acid, (B) a photoacid generator, (C) an acid diffusion inhibitor comprising the onium salt compound of claim 1, and (D) an organic solvent.

9. A chemically amplified resist composition comprising (A') a base polymer adapted to change its solubility in a developer under the action of an acid, the base polymer comprising recurring units having a function of generating an acid upon exposure to light, (C) an acid diffusion inhibitor comprising the onium salt compound of claim 1, and (D) an organic solvent.

10. The resist composition of claim 8 wherein the base polymer comprises recurring units having the formula (a) or recurring units having the formula (b):

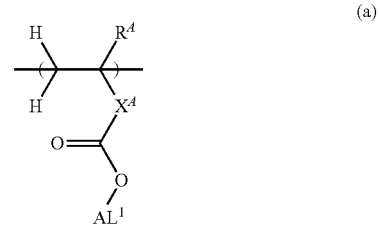

(a)

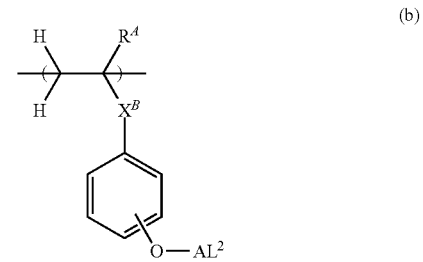

(b)

wherein $R^A$ is each independently hydrogen or methyl, $X^A$ is a single bond, phenylene group, naphthylene group or (backbone)-C(=O)—O—$X^{A1}$—, $X^{A1}$ is a $C_1$-$C_{15}$ hydrocarbylene group which may contain a hydroxyl moiety, ether bond, ester bond or lactone ring, $X^B$ is a single bond or ester bond, $AL^1$ and $AL^2$ are each independently an acid labile group.

11. The resist composition of claim 10 wherein the acid labile group has the formula (L1), (L2) or (L3):

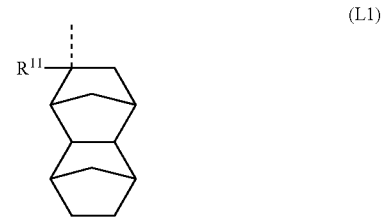

(L1)

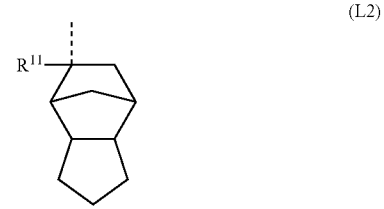

(L2)

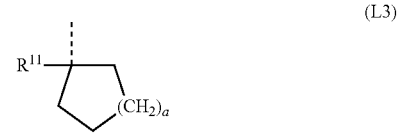

(L3)

wherein $R^{11}$ is each independently a $C_1$-$C_7$ hydrocarbyl group in which —$CH_2$— may be replaced by an ether bond, a is 1 or 2, and the broken line designates a valence bond.

12. The resist composition of claim 8 wherein the base polymer comprises recurring units having the formula (c):

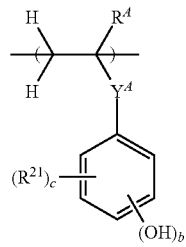
(c)

wherein $R^A$ is hydrogen or methyl, $Y^A$ is a single bond or ester bond, $R^{21}$ is fluorine, iodine or a $C_1$-$C_{10}$ hydrocarbyl group in which —$CH_2$— may be replaced by an ether bond or carbonyl moiety, b is an integer of 1 to 5, c is an integer of 0 to 4, and b+c is 1 to 5.

13. The resist composition of claim 9 wherein the recurring units having a function of generating an acid upon exposure to light are units of at least one type selected from the formulae (d1) to (d4):

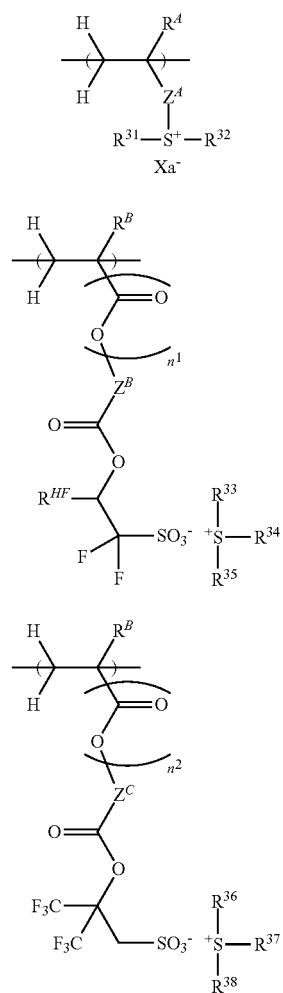
(d1)
(d2)
(d3)

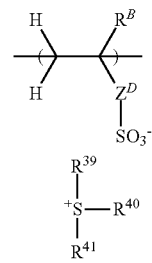
(d4)

wherein $R^B$ is each independently hydrogen, fluorine, methyl or trifluoromethyl, $Z^A$ is a single bond, phenylene group, —O—$Z^{41}$—, —C(=O)—O—$Z^{41}$— or —C(=O)—NH—$Z^{41}$—, $Z^{41}$ is a $C_1$-$C_{20}$ hydrocarbylene group which may contain a heteroatom, $Z^B$ and $Z^C$ are each independently a single bond or a $C_1$-$C_{20}$ hydrocarbylene group which may contain a heteroatom, $Z^D$ is a single bond, methylene, ethylene, phenylene, fluorinated phenylene, —C(=O)—O—$Z^{D1}$— or —C(=O)—NH—$Z^{D1}$—, $Z^{D1}$ is an optionally substituted phenylene group, $R^{31}$ to $R^{41}$ are each independently a $C_1$-$C_{20}$ hydrocarbyl group which may contain a heteroatom, any two of $Z^A$, $R^{31}$ and $R^{32}$ may bond together to form a ring with the sulfur atom to which they are attached, any two of $R^{33}$, $R^{34}$ and $R^{35}$, any two of $R^{36}$, $R^{37}$ and $R^{38}$, and any two of $R^{39}$, $R^{40}$ and $R^{41}$ may bond together to form a ring with the sulfur atom to which they are attached, $R^{HF}$ is hydrogen or trifluoromethyl, $n^1$ is 0 or 1, $n^1$ is 0 when $Z^B$ is a single bond, $n^2$ is 0 or 1, $n^2$ is 0 when $Z^C$ is a single bond, and Xa⁻ is a non-nucleophilic counter ion.

14. A pattern forming process comprising the steps of applying the chemically amplified resist composition of claim 8 to form a resist film on a substrate, exposing a selected region of the resist film to KrF excimer laser, ArF excimer laser, EB or EUV, and developing the exposed resist film in a developer.

15. The pattern forming process of claim 14 wherein the developing step uses an alkaline aqueous solution as the developer, thereby forming a positive pattern in which an exposed region of the resist film is dissolved away and an unexposed region of the resist film is not dissolved.

16. The pattern forming process of claim 14 wherein the developing step uses an organic solvent as the developer, thereby forming a negative pattern in which an unexposed region of the resist film is dissolved away and an exposed region of the resist film is not dissolved.

17. The pattern forming process of claim 16 wherein the organic solvent is at least one solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

18. The onium salt compound of claim 1 wherein both $R^{f1}$ and $R^{f2}$ are fluorine.

19. The onium salt compound of claim 1 wherein one of $R^1$ and $R^2$ is hydrogen.

* * * * *